US012697392B2

(12) United States Patent
Bernardes et al.

(10) Patent No.: US 12,697,392 B2
(45) Date of Patent: Aug. 4, 2026

(54) QUINONE PROTECTED FORMS AND CONJUGATES

(71) Applicant: CAMBRIDGE ENTERPRISE LIMITED, Cambridge (GB)

(72) Inventors: Gonçalo Bernardes, Torres Vedras (PT); Lavinia Couturier, Cambridge (GB); Julie Becher, Boston, MA (US); Enrique Gil De Montes Rojas, London (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 0 days.

(21) Appl. No.: 18/869,122

(22) PCT Filed: May 25, 2023

(86) PCT No.: PCT/EP2023/064139
§ 371 (c)(1),
(2) Date: Nov. 25, 2024

(87) PCT Pub. No.: WO2023/227757
PCT Pub. Date: Nov. 30, 2023

(65) Prior Publication Data
US 2025/0170252 A1 May 29, 2025

(30) Foreign Application Priority Data
May 25, 2022 (GB) ..................................... 2207691

(51) Int. Cl.
*A61K 47/64* (2017.01)
*C07C 49/553* (2006.01)
(Continued)

(52) U.S. Cl.
CPC ............ *A61K 47/64* (2017.08); *C07C 49/553* (2013.01); *C07D 307/92* (2013.01);
(Continued)

(58) Field of Classification Search
CPC combination set(s) only.
See application file for complete search history.

(56) References Cited

U.S. PATENT DOCUMENTS 4,816,567 A 3/1989 Cabilly et al.

FOREIGN PATENT DOCUMENTS

CN 114195814 B * 7/2023 .............. C07F 5/025
EP 1986636 A2 * 11/2008 ............. A61K 31/05
(Continued)

OTHER PUBLICATIONS

Awad HM, Boersma MG, Boeren S, Van Bladeren PJ, Vervoort J, Rietjens IM. Quenching of quercetin quinone/quinone methides by different thiolate scavengers: stability and reversibility of conjugate formation. Chem Res Toxicol. Jul. 2003;16(7):822-31. doi: 10.1021/tx020079g. PMID: 12870884. (Year: 2003).*
(Continued)

*Primary Examiner* — Jeffrey Stucker
*Assistant Examiner* — Laura Ann Essex
(74) *Attorney, Agent, or Firm* — Leason Ellis LLP

(57) ABSTRACT

The invention provides protected ortho-quinone compounds comprising a group represented by:

(Continued)

where —Ar— is optionally substituted phenylene,
—X is selected from —$NH_2$, —OH and —SH, and the protected forms of each,
—W— is optionally substituted methylene, such as methylene, and
d is a double or single bond, and the salts and solvates thereof.

24 Claims, 19 Drawing Sheets

(51) Int. Cl.
*C07D 307/92* (2006.01)
*C07D 311/80* (2006.01)
*C07D 311/92* (2006.01)
*C07D 471/04* (2006.01)
*C07H 15/26* (2006.01)
*C07J 73/00* (2006.01)

(52) U.S. Cl.
CPC .......... *C07D 311/80* (2013.01); *C07D 311/92* (2013.01); *C07D 471/04* (2013.01); *C07H 15/26* (2013.01); *C07J 73/003* (2013.01); *C07C 2602/02* (2017.05); *C07C 2603/26* (2017.05)

(56) References Cited

FOREIGN PATENT DOCUMENTS

| | | | |
|---|---|---|---|
| WO | 2007085930 | A1 | 8/2007 |
| WO | 2012003955 | A1 | 1/2012 |
| WO | 2017186894 | A1 | 11/2017 |
| WO | 2019011078 | A1 | 1/2019 |
| WO | 2020146182 | A1 | 7/2020 |

OTHER PUBLICATIONS

English Translation of Zhang (CN114195814.B) (Year: 2022).*
Dunsmore L, et al. Controlled masking and targeted release of redox-cycling ortho-quinones via a C—C bond-cleaving 1,6-elimination. Nat Chem. Jul. 2022;14(7):754-765. doi: 10.1038/s41557-022-00964-7. Epub Jun. 27, 2022. PMID: 35764792; PMCID: PMC9252919. (Year: 2022).*
Yang, Shun-Chieh et al., "Identifying HER2 Inhibitors from Natural Products Database", PLOS One, Dec. 2011, pp. 1-9 2011.
Rodrigues, Tiago et al., "Counting on natural products for drug design", nature chemistry, Jun. 2016, pp. 531-541 2016.
Lichota, Anna et al., "Anticancer Activity of Natural Compounds from Plant and Marine Environment", Int. J. Mol. Sci, Nov. 2018, vol. 19, pp. 1-38 2018.
Pardee, Arthur B. et al., "Cancer Therapy with ß-Lapachone", Curr. Cancer Drug Targets, 2002, pp. 227-242 2002.
Chonsut, Piriya et al., "Ethoxy mansonone G as an anticancer agent in estrogen receptor-positive and endocrine-resistant breast cancer", J. Pharm. Pharmacol., Sep. 2019,, pp. 1839-1853 2019.
Bian, Jinlei et al., "Synthesis and evaluation of (±)-dunnione and its ortho-quinone analogues as substrates for NAD (P)H:quinone oxidoreductase 1 (NQO1)", Bioorg. Med. Chem. Lett, Jan. 2015, pp. 1244-1248 2015.
Burmaoğlu, Serdar et al, "Syntheses and evaluation of multicaulin and miltirone-like compounds as antituberculosis agents", J. Enzyme Inhib. Med. Chem, Jun. 2017, pp. 878-884 2017.
Deng, Fei et al., "Synthesis and antitumor activity of novel salvicine analogues", Chin. Chem. Lett, Apr. 2010, pp. 25-28 2010.
Saruul, Erdenebileg et al., "An antibacterial ortho-quinone diterpenoid and its derivatives from Caryopteris mongolica", Bioorg. Med. Chem. Lett., Apr. 2015, pp. 2555-2558 2015.
Castellanos, J. Rubén Gómez et al., "Red Lapacho (*Tabebuia impetiginosa*)—A global ethnopharmacological commodity?", J. Ethnopharmacol., Nov. 2008 pp. 1-13 2008.
Planchon, Sarah, et al., "ß-Lapachone-mediated Apoptosis in Human Promyelocytic Leukemia (HL-60) and Human Prostate Cancer Cells: A p53-independent Response", Cancer Res., Sep. 1995, pp. 3706-3711 1995.
Yang Yang et al., "β-lapachone suppresses tumour progression by inhibiting epithelialto-mesenchymal transition in NQO1-positive breast cancers", Sci. Rep., Apr. 2017 pp. 1-13 2017.
Bey, Erik A. et al., "An NQO1- and PARP-1-mediated cell death pathway induced in non-small-cell lung cancer cells ß-lapachone" Proc. Natl. Acad. Sci. U.S.A., Mar. 2007, pp. 11832-11837 2007.
Ough, Matthew et al., "Efficacy of beta-lapachone in pancreatic cancer treatment: Exploiting the novel, therapeutic target NQO1", , Cancer Biol. Ther, Nov. 2004, pp. 95-102 2004.
Pink, John J. et al., "NAD(P)H:Quinone Oxidoreductase Activity Is the Principal Determinant of ß-Lapachone Cytotoxicity", J. Biol. Chem., Dec. 1999 pp. 5416-5424 1999.
Gopinath, Pushparathinam et al., "Understanding and predicting the potency of ROS-based enzyme inhibitors, exemplified by naphthoquinones and ubiquitin specific protease-2", Chem. Sci, 2016, pp. 7079-7086 2016.
Bolton, Judy L. et al., "Formation and Biological Targets of Quinones: Cytotoxic versus Cytoprotective Effects", Chem. Res. Toxicol, 2016, pp. 13-37 2016.
Powis, Garth, "Free Radical Formation By Antitumor Quinones", Radic. Biol. Med., 1989, pp. 63-101 1989.
Shapiro, G.I., et al., "Phase I trial of ARQ 501, an Activated Checkpoint Therapy (ACT) agent, in patients with advanced solid tumors", Jun. 2005, pp. 3042 2005.
Gerber, David E.et al., "Phase 1 study of ARQ 761, a β-lapachone analogue that promotes NQO1-mediated programmed cancer cell necrosis", Br. J. Cancer, Sep. 2018, pp. 928-936 2018.
Penning, Trevor M., "Genotoxicity of ortho-quinones: reactive oxygen species versus covalent modification", Toxicol. Res., Sep. 2017, pp. 740-754 2017.
Li, Xiaoguang, et al., "NQO1 targeting prodrug triggers innate sensing to overcome checkpoint blockade resistance", Nature Commun., Jul. 2019, pp. 1-13 2019.
Bolton,Judy L., "Formation and Biological Targets of Quinones: Cytotoxic versus Cytoprotective Effects", Chem. Res. Toxicol., 2017, pp. 13-37 2017.
Li, Chiang J. et al., "Potent inhibition of tumor survival in vivo by ß-lapachone plus taxol: Combining drugs imposes different artificial checkpoints", Proc. Natl. Acad. Sci. U. S. A., Aug. 1999, pp. 13369-13374 1999.
Huang, Xiumei et al., "Leveraging an NQO1 Bioactivatable Drug for Tumor-Selective Use of Poly(ADP-ribose) Polymerase Inhibitors", Cancer Cell, 2016, pp. 940-952 2016.
Sborov, Douglas W., "Investigational cancer drugs targeting cell metabolism in clinical development", Expert Opin. Investig. Drugs, 2015, pp. 79-94 2015.
Fulda, Simone et al., "Targeting mitochondria for cancer therapy", Nat. Rev. Drug Discov, Jun. 2010, pp. 447-464 2010.
Cui, Qingbin et al., "Modulating ROS to overcome multidrug resistance in cancer", Drug Resist. Updat., 2018, pp. 1-25 2018.
Rooseboom, Martijn et al., "Enzyme-Catalyzed Activation of Anticancer Prodrugs", Pharmacol. Rev., 2004, pp. 53-102 2004.
Beck, Alain et al., "Strategies and challenges for the next generation of antibody-drug conjugates", Nat. Rev. Drug Discov, 2017, pp. 315-337 2017.
Cragg, Gordon M. et al., "New Horizons for Old Drugs and Drug Leads", J. Nat. Prod., Feb. 2014, pp. 703-723 2014.
Cragg, Gordon M. et al., "Natural Products as a Vital Source for the Discovery of Cancer Chemotherapeutic and Chemopreventive Agents", Med. Princ. Pract., Dec. 2015, pp. 41-59 2015.
Ma, Xinpeng et al., "Esterase-activatable β-lapachone prodrug micelles for NQO1-targeted lung cancer therapy", J. Control. Release, 2015, pp. 201-211 2015.
Zhou, Yinjian et al., "Lysosome-oriented, dual-stage pH-responsive polymeric micelles for ß-lapachone delivery", J. Mater. Chem. B, 2016, pp. 7429-7440 2016.

(56) References Cited

OTHER PUBLICATIONS

Blencowe, Christopher et al., "Self-immolative linkers in polymeric delivery systems", Polym. Chem., 2011, pp. 773-790 2011.
Caculitan, Niña G. et al., "Cathepsin B Is Dispensable for Cellular Processing of Cathepsin B-Cleavable Antibody-Drug Conjugates", Cancer Res., 2017, pp. 7027-7037 2017.
Jeffrey, Scott C., "Development and Properties of â-Glucuronide Linkers for Monoclonal Antibody-Drug Conjugates", Bioconjugate Chem, Mar. 2006, pp. 831-840 2006.
Jeffrey, Scott C., "Minor groove binder antibody conjugates employing a water soluble ß-glucuronide linker", Bioorg. Med. Chem Lett., Jan. 2007, pp. 2278-2280 2007.
Jeffrey, Scott C. et al., "Expanded Utility of the β-Glucuronide Linker: ADCs That Deliver Phenolic Cytotoxic Agents", Med. Chem. Lett, Jun. 2010, pp. 277-280 2010.
Renoux, Brigitte et al., "A β-glucuronidase-responsive albumin-binding prodrug programmed for the double release of monomethyl auristatin E", Med. Chem. Commun., Oct. 2018 pp. 2068-2071 2018.
Tranoy-Opalinski, Isabelle et al., "ß-Glucuronidase-responsive prodrugs for selective cancer chemotherapy: An update", Euro. J. Med. Chem., Jan. 2014, pp. 302-313 2014.
Wellington, K. W et al., "Understanding cancer and the anticancer activities of naphthoquinones—a review", RSC Adv, Feb. 2015, pp. 20309 20338 2015.
Gong et al., "A comprehensive review on ß-lapachone: Mechanisms, structural modifications, and therapeutic potentials", European Journal of Medicinal Chemistry, 2021, pp. 1-27 2021.
Zorzi et al., "Non-covalent albumin-binding ligands for extending the circulating half-life of small biotherapeutics", Medchemcomm, Jun. 2019, pp. 1068 1081 2019.
Olesen et al., "Molecular, Macromolecular, and Supramolecular Glucuronide Prodrugs: Lead Identified for Anticancer Prodrug Monotherapy", Angew. Chem. Int. Ed, 2020 pp. 7390 7396 2020.
Jansen et al., "Extended Structure-Activity Relationship and Pharmacokinetic Investigation of (4-Quinolinoyl)glycyl-2-cyanopyrrolidine Inhibitors of Fibroblast Activation Protein (FAP)", J. Med. Chem., Mar. 2014, pp. 3053-3074 2014.
Millul et al., "An ultra-high-affinity small organic ligand of fibroblast activation protein for tumor-targeting applications", Proc. Natl. Acad. Sci. USA., 2021, pp. 1-10 2021.
Miller et al., "Design, Construction, and In Vitro Analyses of Multivalent Antibodies", Jour. of Immunology, May 2003, pp. 4854 4861 2003.
Kohler et al., "Continuous cultures of fused cell secreting antibody of predefined specificity", Nature, Aug. 1975, p. 495-497 1975.
Clackson et al., "Making antibody fragments using phage display libraries", Nature, Aug. 1991, pp. 624 628 1991.
Marks et al., "By-passsing Immunization Human Antibodies from V-gene Libraries Displayed on Phage", J. Mol. Biol., Sep. 1991, pp. 581-597.
Lonberg, "Fully human antibodies from transgenic mouse and phage display platforms", Curr. Opinion, Jul. 2008, pp. 450-459.
Tang et al., "A Human Single-Domain Antibody Elicits Potent Antitumor Activity by Targeting an Epitope in Mesothelin Close to the Cancer Cell Surface", Mol Cancer Ther, Apr. 2013, pp. 416 426.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chemistry, Apr. 2002, pp. 855-869.
Stieger, Angew. "Diethynyl Phosphinates for Cysteine-Selective Protein Labeling and Disulfide Rebridging", Chemie Int. Ed., 2021, pp. 153599-15364.
Walsh, A general approach for the site-selective modification of native proteins, enabling the generation of stable and functional antibody-drug conjugates:, Chem. Sci., 2019, pp. 694-700.
Walsh, "General dual functionalisation of biomacromolecules via a cysteine bridging strategy", Org. Biomol. Chem., May 2020, pp. 4224 4230.
Badescu, "Bridging Disulfides for Stable and Defined Antibody Drug Conjugates", Bioconjug. Chem., May 2014, pp. 1124-1136.
Koniev, "Reduction-rebridging strategy for the preparation of ADPN-based antibody-drug conjugates", Medchemcomm, Apr. 2018,, pp. 827-830.
Robinson, "Pyridazinediones deliver potent, stable, targeted and efficacious antibody-drug conjugates (ADCs) with a controlled loading of 4 drugs per antibody", RSC Adv., Jan. 2017, pp. 907-9077.
Behrens, "Antibody-Drug Conjugates (ADCs) Derived from Interchain Cysteine Cross-Linking Demonstrate Improved Homogeneity and Other Pharmacological Properties over Conventional Heterogeneous ADCs", Mol. Pharm., Sep. 2015, pp. 3986-3998.
Schechter et al., "N-[(2-Sulfo)-9-fluorenylmethoxycarbonyl]3-gentamicin C1 Is a Long-Acting Prodrug Derivative", J. Med Chem, Jan. 2002, p. 4264-4270.
Shamis et al., "Single-Triggered AB Self-Immolative Dendritic Amplifiers", , Chem. Eur. J, 2007, pp. 4523-4528.
Chau et al., "Involvement of Hydrogen Peroxide in Topoisomerase Inhibitor B-Lapachone-Induced Apoptosis and Differentiation in Human Leukemia Cells", Free Radic. Biol. Med., 1998, pp. 660-670.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem, 2002, pp. 855-869.
Poole et al., "Effect of Weak Bases on the Intralysosomal pH in Mouse Peritoneal Macrophages", J. Cell Biol., Sep. 1981, pp. 665-669.
Tamali et al, "In Vitro and In Vivo Inhibition of Cysteine Proteinases By Est, A New Analog of E-64", J. Pharmacobiodyn, 1986, pp. 672-677.
Yu et al., "Lysosome Dysfunction Enhances Oxidative Stress-Induced Apoptosis Through Ubiquitinated Protein Accumulation in Hela Cells", Anat. Rec, 2013, pp. 31-39.
Porceba, "Protease-activated prodrugs: strategies, challenges, and future directions", FEBS J, Jan. 2020, pp. 1936-1969.
Aggarwal et al., "Cathepsin B: Multiple roles in cancer", Proteomics Clin. Appl, 2014, pp. 427-437.
Cairns et al., "Regulation of cancer cell metabolism", Nat. Rev. Cancer, Feb. 2011, pp. 85-95.
Kell, "Considerations and challenges for patients with refractory andrelapsed acute myeloid leukaemia", , Leuk. Res, Jun. 2016, pp. 149-160.
Saultz et al., "Acute Myeloid Leukemia: A Concise Review", J. Clin. Med., Mar. 2016, pp. 1-17.
Vetrie et al., "The leukaemia stem cell: similarities, differences and clinical prospects in CML and AML", Nat. Rev. Cancer, Mar. 2020, pp. 158-173.
Prieto-Bermejo et al., "Reactive oxygen species in haematopoiesis: leukaemic cells take a walk on the wild side", J. Exp. Clin. Cancer Res, 2018 (18 pages.
Miller et al., "Mechanisms of Action of Arsenic Trioxide", Cancer Res, Jul. 2002, pp. 3893-3903.
Sinha et al., "Is Metabolic Activation of Topoisomerase II Poisons Important in the Mechanism of Cytotoxicity?", J. Drug Metab. Toxicol., 2015 (15 pages).
Rodrigues, "Machine intelligence decrypts b-lapachone as an allosteric 5-lipoxygenase inhibitor", Chem. Sci, Jul. 2018, pp. 6899-6903.
Roos et al., "5-Lipoxygenase Is a Candidate Target for Therapeutic Management of Stem Cell-like Cells in Acute Myeloid Leukemia", Cancer Res., Sep. 2014, pp. 5244-5255.
Chen et al., "Loss of the Alox5 gene impairs leukemia stem cells and prevents chronic myeloid leukemia", Nat. Genet, Jul. 2009, pp. 783-792.
Johnston et al., "Development of a 384-Well Colorimetric Assay to Quantify Hydrogen Peroxide Generated by the Redox Cycling of Compounds in the Presence of Reducing Agents", Assay Drug Dev. Technol., Nov. 2008, pp. 505-518.
Ingaki et al., "Synthesis, Characterization, and Antileukemic Properties of Naphthoquinone Derivatives of Lawsone", ChemMedChem, 2015, pp. 1413-1423.

(56) References Cited

OTHER PUBLICATIONS

International Search Report for corresponding PCT Application No. PCT/EP2023/064139 dated Jul. 14, 2023 (4 pages).
Bian et al., "Lewis acid mediated highly regioselective intramolecular cyclization for the synthesis of b-lapachone", Tet. Lett., Jan. 2014, pp. 1475-1478.
Houba et al., "Characterization of Novel Anthracycline Prodrugs Activated by Human 13-glucuronidase for Use in Antibody-Directed Enzyme Prodrug Therapy", Biochem. Pharma., 1996, pp. 455-463.
Shao, Si-Yuan et al, "Phenanthrenequinone enantiomers with cytotoxic activities from the tubers of Pleione bulbocodioides", Organic & Biomolecular Chemistry, vol. 17, 2019, pp. 567-572.
Rubin, Mordecai B. et al, "Polar effects in free radical reactions. The mechanism of photochemical addition of ethers and substituted toluenes to 9,10-phenanthrenequinone", Tetrahedron Letters, Amsterdam , NL, 1965, pp. 2453-2457.
Dunsmore, Lavinia et al, "Controlled masking and targeted release of redox-cycling ortho-quinones via a C—C bond-cleaving 1,6-elimination", Nature Chemistry, Nature Publishing Group Uk, London, vol. 14, Jul. 2022, pp. 754-773.

* cited by examiner

4 - PhQ
6 - Boc-PAB-PhQ
7 - PAB-PhQ
8 - PhQ-HQ

1 - BL

11 - HBL

12 - DN

13 - CTN

9 - Boc-PAB-BL
14 - Boc-PAB-HBL
15 - Boc-PAB-DN
16 - Boc-PAB-CTN

10 - PAB-BL
17 - PAB-HBL
18 - PAB-DN
19 - PAB-CTN

21 - 2-phenylacetyl-PhQ
22 - 2-phenylacetyl-BL
23 - 2-phenylacetyl-DN

7 - PAB-PhQ
10 - PAB-BL
18 - PAB-DN

4 - PhQ
1 - BL
12 - DN i ii

1

24

25

29

1

XX = -Val-Cit- 26, -Val-Ala- 27, -Phe-Cit- 28 a)

Lowering pKa
Stabilizing TS
Optimized Derivative

| | 37a | 37b | 37c | 37d | 37e | 37f |
|---|---|---|---|---|---|---|
| *pKa* | ~ 9.4 | ~ 6.8 | ~ 5.5 | ~ 9.2 | ~ 9.3 | ~ 9.0 |

b)

*Fig.* 9
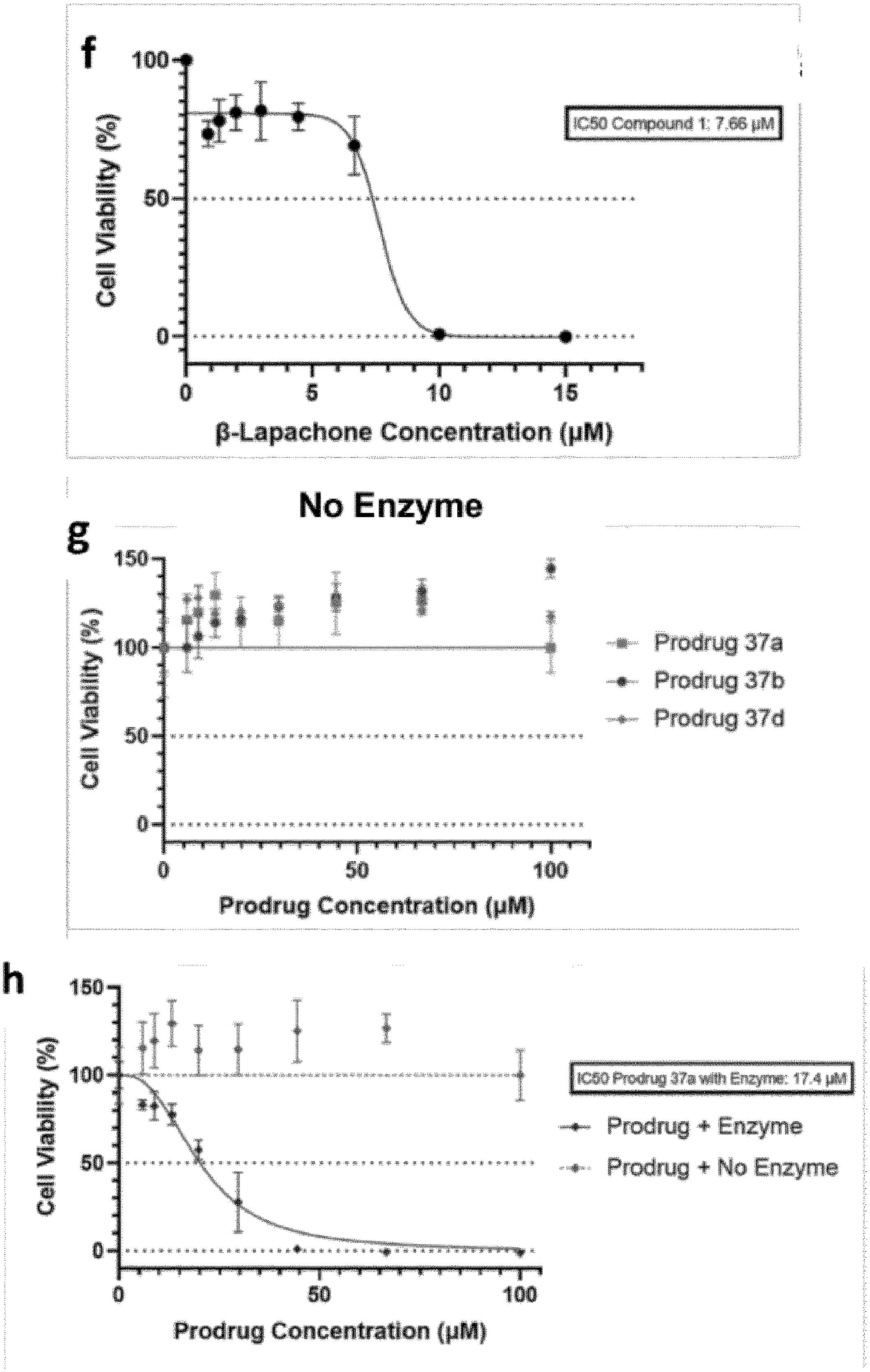

*Fig.* 9
i
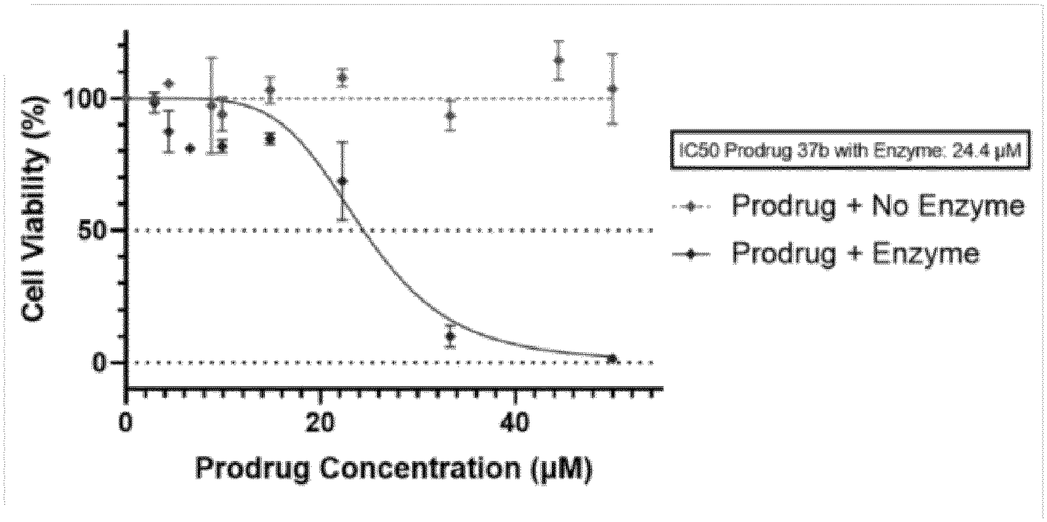
j
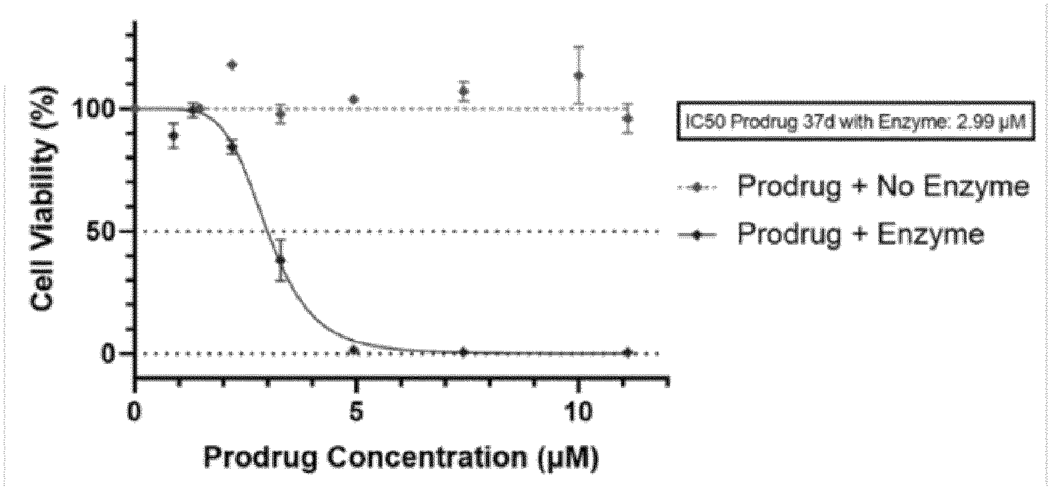

QUINONE PROTECTED FORMS AND CONJUGATES

RELATED APPLICATION

This application is a U.S. National Stage Application under 35 U.S.C. § 371 of International Patent Application No. PCT/EP2023/064139, filed May 25, 2023, which claims priority to, and the benefit of GB 2207691.3 filed May 25, 2022, the contents of which are hereby incorporated by reference in their respective entireties.

FIELD OF THE INVENTION

The invention provides a conjugate of an ortho-quinone for use in methods of treatment and diagnosis, such as for use in methods of treating cancer. Also provided is a protected ortho-quinone and methods of preparing an ortho-quinone, and methods for preparing the conjugate from the ortho-quinone.

BACKGROUND

The application of new chemical entities with innovative mechanisms of action is necessary for the development of next-generation therapeutics. Natural products are often a source of anticancer agents or act as inspiration for rational molecular design (*PLoS ONE,* 2007, 12, 1-12; Nat. Chem., 2006, 8, 531-541). However, many natural products identified with medicinal value in vitro remain underexploited due to dose-limiting toxicity in vivo (Int. J. Mol. Sci., 2018, 19, 3533).

One underused family of cytotoxic natural products are ortho-quinones. Several low molecular weight compounds that contain an ortho-quinone group, such as β-lapachone (Curr. Cancer Drug Targets, 2002, 2, 227-242), tanshinones (I, IIA, IIB, and crypto) (Cancer Epidemiol. Biomarkers & Prev., 2006, 15, A118), mansonones A-G (J. Pharm. Pharmacol. 71, 2019, 1839-1853), dunnione (Bioorg. Med. Chem. Lett., 2015, 25, 1244-1248), miltirone (J. Enzyme Inhib. Med. Chem., 2017, 32, 878-884), salvicine (Chin. Chem. Lett., 2011, 22, 25-28), and caryopteron A (Bioorg. Med. Chem. Lett., 2015, 25, 2555-2558), display wide anti-proliferative effects in vitro. For example, β-lapachone (1, FIG. 1*a*), a natural product from Brazilian Lapacho tree bark (J. Ethnopharmacol., 2009, 121, 1-13) exhibits good efficacy against leukaemias (Cancer Res., 1995, 55, 3706-3711) and NQO1+ cancers, such as breast (Sci. Rep., 2017, 7, 1-13), non-small-cell lung (Proc. Natl. Acad. Sci. U.S.A., 2007, 104, 11832-11837) and pancreatic (Cancer Biol. Ther., 2005, 4, 95-102). However, untargeted ortho-quinones have dose-limiting toxicity and metabolic liabilities because of their NQO1-dependent redox-cycling behaviour that results in the formation of reactive oxygen species (ROS; FIG. 1*a*) (J. Biol. Chem., 2000, 275, 5416-5424). ROS disrupt the function of proteins (Chem. Sci., 2016, 7, 7079-7086) and can lead to irremediable DNA oxidation, PARP1 hyperactivation and cell death (Chem. Res. Toxicol., 2017, 30, 13-37; Free Radic. Biol. Med., 1989, 6, 63-101). Although this mechanism is of use against cancer cells, systemic propagation of ROS is undesirable and may lead to anaemia and methaemoglobinemia, as observed in clinical trials of β-lapachone (J. Clin. Oncol., 2005, 23, 3042-3042; Br. J. Cancer, 2018, 119, 928-936). Additional ortho-quinone toxicity can result from their ability to react as electrophiles with critical cellular proteins, peptides, nucleic acids, or glutathione, which interferes with redox homeostasis (Toxicol. Res., 2017, 6, 740-754).

Some tumour selectivity of β-lapachone has been reported, as overexpression of oxidoreductase enzymes (e.g. NQO1) can increase redox-cycling rates selectively in the tumour (Nature Commun., 2019, 10, 3251). However, no therapeutic ortho-quinone has yet reached the clinic due to generalised ROS-mediated systemic toxicity. In contrast, para-quinones, such as doxorubicin (Adriamycin), geldanamycin, mitoxantrone and mitomycin C, have lower redox-cycling rates and are successfully used in the clinic (Chem. Res. Toxicol., 2017, 30, 13-37). If the side-effects of ortho-quinones could be prevented through selective protection and targeting strategies, this may lead to new cancer treatment options.

SUMMARY OF THE INVENTION

The invention relates to a modular strategy that uses self-immolative benzyl linkers for protection and controlled release of ortho-quinones. The self-immolative 1,6-elimination of, for example, a para-aminobenzyl linker or a para-hydroxybenzyl linker, attached at the quinone carbon as a benzyl ketol, enables release of a hydroquinone (HQ). The released HQ then oxidises spontaneously to give the desired ortho-quinone. Beneficially, the strategy is compatible with known peptide linkers, such as those activated by the cysteine protease cathepsin B. The strategy is also compatible with known glucosides, such as those activated by β-glucuronidase.

In a general aspect, the invention provides a protected ortho-quinone for use in methods of treatment and diagnosis. The protecting group for the ortho-quinone is cleavable under physiological conditions, and beneficially at the site of action, to give the active ortho-quinone.

The invention uses ortho-quinones protected in their α-hydroxy keto form (ketol). Here, the protecting group is attached to the ring α-carbon (the ring carbon having the hydroxy substituent). The protecting group is a substituted benzyl group connected through the benzylic carbon to the α-carbon of the ortho-quinone ring. The formation of the protected ketol form therefore comprises the step of forming a carbon-carbon bond between the ortho-quinone and a benzylic carbon. The release of the protecting group occurs through cleavage of the carbon-carbon bond.

The protected ortho-quinone may form part of a conjugate, together with a polypeptide such as an antibody. Here, the protected ortho-quinone is covalently connected to the polypeptide via a linker. The linker may be cleavable, such as in vivo. Thus, the protected ortho-quinone may be covalently connected to the polypeptide via a linker which can be selectively cleaved in vivo. This cleavage will result in the removal of the protecting group and subsequently release of the ortho-quinone. The invention also provides for other connections between the protected ortho-quinone and the antibody, using such techniques and chemistries that are familiar to those working in the field.

Advantageously, release of the protection from the ortho-quinone may occur in cancer cells, thus the ortho-quinone may be made available from the conjugate and from the protected ortho-quinone in such cells.

The quinone may have anticancer activity, and thus the protected ortho-quinone and the conjugate may be for use in methods of treating cancer.

In a first aspect of the invention there is provided a protected ortho-quinone comprising a group:

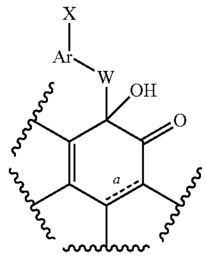

where —Ar— is optionally substituted phenylene,

—X is selected from —$NH_2$, —OH and —SH, and the protected forms of each,

—W— is optionally substituted methylene, such as methylene, and a is a double or single bond, such as a double bond, and the salts and solvates thereof.

In a second aspect of the invention there is provided a conjugate of formula:

$$Z\text{-}(L\text{-}D)_p$$

where:

—Z is a polypeptide, such as an antibody,

-L- is a linker,

-D is a protected quinone compound, as defined herein, and p is an integer from 1 to 8.

In a third aspect of the invention there is provided a pharmaceutical composition comprising the conjugate or the protected ortho-quinone according to the invention, optionally together with one or more pharmaceutically acceptable excipients.

In a fourth aspect of the invention there is provided a conjugate, a protected ortho-quinone or a pharmaceutical composition of the invention for use in a method of treatment or diagnosis.

In a fifth aspect of the invention there is provided a conjugate, a protected ortho-quinone or a pharmaceutical composition of the invention for use in a method of treating cancer.

In other aspects of the invention, there is provided a conjugate, a protected ortho-quinone or a pharmaceutical composition of the invention for use in a method of treating a microbial infection, such as a bacterial infection, and also for use in methods of treating parasitic infections.

In a further aspect there is provided a method of preparing a protected ortho-quinone, the method comprising the step of reacting an ortho-quinone with a compound containing a benzyl halide.

These and other aspects and embodiments of the invention are described in further detail herein.

DETAILED DESCRIPTION OF THE INVENTION

The present inventors have understood that ortho-quinones, if delivered to target cells without systemic side effects, may have significant potential as a mono-therapy or in combination with mainstay anti-cancer agents (Proc. Natl. Acad. Sci. U.S.A, 1999, 96, 13369-13374; Cancer Cell, 2016, 30, 940-952). Their metabolic interference may be a potential new avenue to tackle malignancies (Expert Opin. Investig. Drugs, 2015, 24, 79-94; Nat. Rev. Drug Discov., 2010, 9, 447-464), and a strategy to overcome cancer drug resistance (Drug Resist. Updat., 2018, 41, 1-25).

Toxicity arising from low cancer-cell specificity, off-target reactivity, or built-in metabolic reactivity can be addressed with prodrug strategies that can mask pharmacophores to prevent secondary pharmacology or accelerated metabolism and can widen the therapeutic window (Pharmacol. Rev., 2004, 56, 53-102). Drug targeting strategies can also be useful. For example, antibody-mediated delivery for cancer cell discrimination has facilitated the use of auristatins, maytansinoids and calicheamicins (Nat. Rev. Drug Discov., 2017, 16, 315-337). However, some medicinal compounds contain a reactive moiety that cannot be effectively protected by existing chemistry or prodrug strategies. Furthermore, only highly functionalised molecules that contain amine- or hydroxyl-groups tend to be suitable for conjugation to carriers. Toxic molecules that do not contain such amenable functional groups are often discarded if a carrier cannot be attached without laborious synthetic derivatisation. Therefore, improvements to protect new functionalities and attachment of drug carriers to alternative functional groups will extend treatment options with already-discovered compounds (J. Nat. Prod., 2014, 77, 703-723; Med. Princ. Pract., 2016, 25, 41-59).

Prodrug approaches to mask redox activity and limit side effects of ortho-quinones, such as β-lapachone, have previously been described.

Boothman and co-workers developed a number of approaches, including formation of esterase cleavable hydroquinone alkyl esters (J. Control. Release, 2015, 200, 201-211), and pH-sensitive aryl imine, acyl hydrazone, ketal (J. Mater. Chem. B, 2016, 4, 7429-7440), aminoalkyl alcohol, and amino aromatic phenol prodrugs (WO 2012/03955). However, the disadvantages of these strategies have prevented their widespread adoption. For example, esters and hydrazones are often too labile under physiological conditions for effective targeting, whereas ketals are not sufficiently labile in tumours (J. Mater. Chem. B, 2016, 4, 7429-7440). Modern prodrug strategies and linkers, including those that connect targeting antibodies and their payloads, use enzymatically-activatable trigger groups and release drug functionality by means of self-immolative spacers. For example, para-aminobenzyl carbamate linkers release amines and para-aminobenzyl ether linkers release alcohols upon specific protease-triggered hydrolysis (Polym. Chem., 2011, 2, 773-790).

Figure 1:
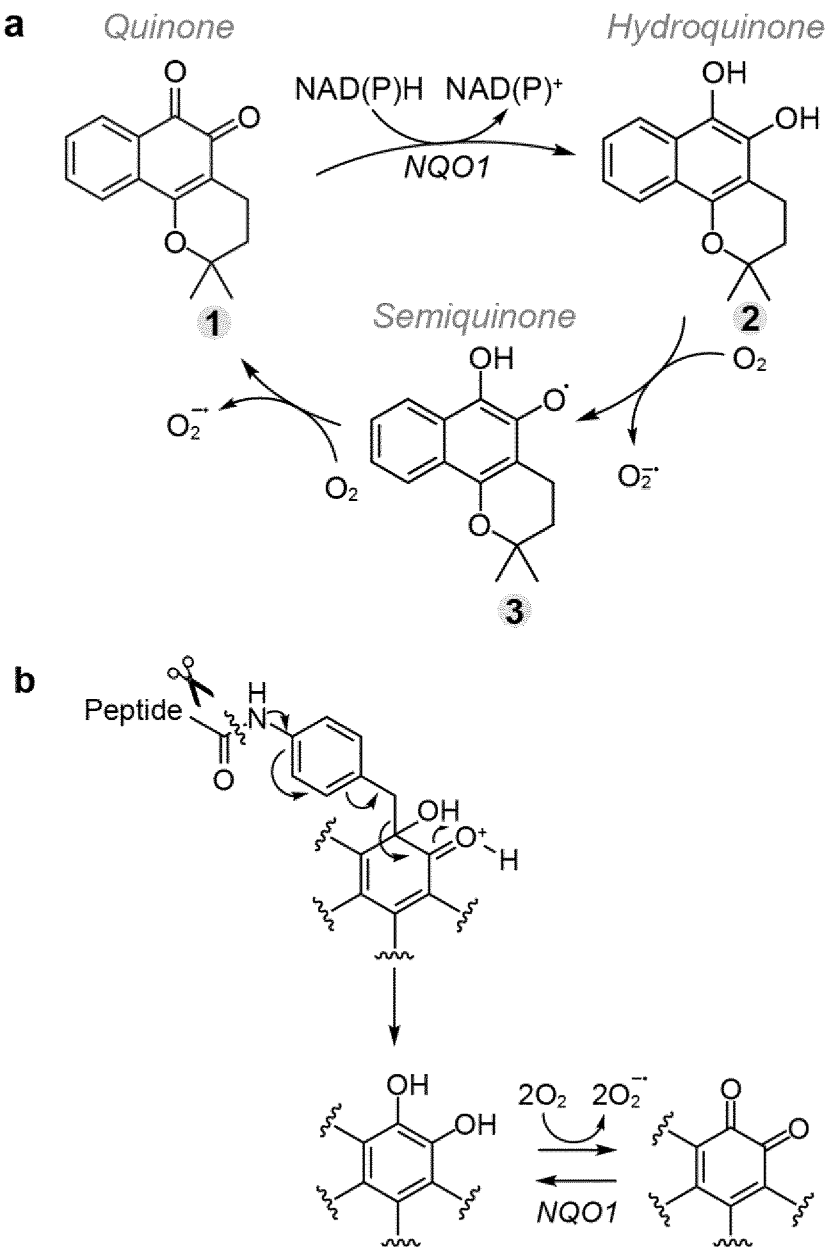
FIG. 1 shows the protection strategy for ortho-quinone containing compounds, where a, shows metabolism of ortho-quinones, like β-lapachone, 1, which redox-cycles between hydroquinone 2 and semi-quinone 3 forms; and b, shows an embodiment of the present work: acid-dependent self-immolative release of ortho-quinones following enzymatic peptide cleavage. 1,6-elimination of an aminobenzyl linker results in cleavage of a C—C bond to release an unstable hydroquinone intermediate, which auto-oxidises into an ortho-quinone.

Described herein is the use of a trigger group for ortho-quinone compounds. The invention provides a modular strategy that uses self-immolative benzyl linkers for protection and controlled release of ortho-quinones. The self-immolative 1,6-elimination of, for example, a para-aminobenzyl group or a para-hydroxybenzyl group attached at the quinone carbon as a benzyl ketol enables release of a hydroquinone (HQ). The released HQ then oxidises spontaneously to give the desired ortho-quinone by using the redox-cycling ability of the payload (FIG. 1*b*). Beneficially the strategy is compatible with peptide linkers, such as those activated by the cysteine protease cathepsin B (Cancer Res., 2017, 77, 7027-7037), and known glucosides, such as those activated by β-glucuronidase (Bioconjugate Chem., 2006, 17, 831-840; Bioorg. Med. Chem Lett., 2007, 17, 2278-2280; Med. Chem. Lett., 2010, 1, 277-280; Med. Chem. Commun., 2018, 9, 2068-2071; and Euro. J. Med. Chem., 2014, 74, 302-313).

Protected forms of ortho-quinones are known, but the protecting groups generally do not protect the ortho-quinone in its ketol form. Furthermore, these known protecting groups strategies does not involve the formation and cleavage of a carbon-carbon bond between a carbon ring atom—such as the α-carbon—of the ortho-quinone and a carbon atom of the protecting group. Rather, the prior art strategies usually involve the formation of bonds between the carbon ring atom and a heteroatom of the protecting group. Other strategies use the diol form of the ortho-quinone, and trap one or more of the hydroxy groups, for example in the form of a phosphate group, a monoester or a diester.

An example of protecting group using the ketol form is known within ARQ-761 (ArQule Inc.), but here the ring α-carbon connects to sulfur, which is a component of a sulfonic acid group protection. Thus, the addition and release of the protecting group involves carbon-sulfur bond formation and cleavage.

Elements of the work described in this application have previously been made available within an abstract relating to the thesis entitled Strategy for Controlled Protection of Redox-Cycling Ortho-Quinones with Self-Immolative Linkers in the name of one of the present inventors (Cambridge University 2022). The abstract does not provide a detailed description of the methods for preparing the protected ortho-quinone compounds of the invention.

Ortho-Quinone

In the present case, an ortho-quinone is a compound having a 1,2-benzoquinone group present. The 1,2-benzoquinone group may be fused with other cyclic groups, such as one or more aromatic groups. Each cyclic group, such as each aromatic group, is optionally substituted. The 1,2-benzoquinone group may also be substituted with groups other than a fused cyclic group.

Example ortho-quinone compounds for use in the present invention include those ortho-quinone compounds having biological, such as therapeutic, activity. For example, the ortho-quinone compounds may have anticancer activity, such as activity against leukaemia cells, including against acute myeloid leukaemia (AML).

The ortho-quinone is provided in a protected form for use, and as described in further detail below, and the ortho-quinone is releasable and released from its protected form, such as intracellularly and such as in vivo.

An ortho-quinone compound is a compound having a 1,2-benzoquinone group within its structure, as shown below:

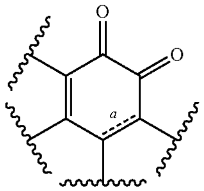

where a is a double or single bond.

In certain embodiments, a is a double bond. Thus, the ortho-quinone compound is a compound having a 1,2-benzoquinone group within its structure, as shown below:

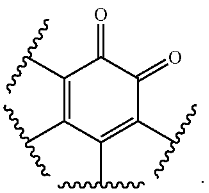 [SMILES: *C1=C(*)C(*)=C(*)C(=O)C1=O]

The 3-, 4-, 5- and 6-positions of the benzoquinone ring are optionally substituted. Typically, the ortho-quinone ring is fused with one or two rings. A first ring may be fused at the 3- and 4-positions. A second ring may be fused at the 5- and 6-positions. Alternatively, a bicyclic ring may be fused with the ortho-quinone at the 3-, 4- and 5-positions. If a ring position is not substituted, then hydrogen is present at the position.

Where a ring atom of the ortho-quinone group is not part of a fused ring, it may be optionally substituted, for example where each optional substituent is a group —$R^S$.

Preferably, at least three of these positions are substituted. Where only three positions are substituted, it is preferably the 5-position that is unsubstituted.

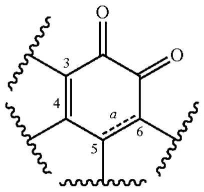

Each of the ring 3-, 4-, 5- and 6-positions, as shown above, may be substituted, or two or more neighbouring ring atoms may be contained within a further cyclic group that is fused to the ortho-quinone.

The 1,2-benzoquinone group may be fused with one or two cyclic groups. A cyclic group may be fused at the benzoquinone 3- and 4-positions. A cyclic group may be fused at the benzoquinone 5- and 6-positions. A cyclic group may be fused at both the benzoquinone 3- and 4-positions and the 5- and 6-positions. A cyclic group may be fused at the benzoquinone 3-, 4- and 5-positions.

A cyclic group fused to the 1,2-benzoquinone may be selected from carboaromatic, cycloalkene, heteroaromatic and heterocycloalkene.

Preferably, a cyclic group fused to the 1,2-benzoquinone is selected from $C_{6-10}$ carboaromatic, $C_{5-10}$ cycloalkenene, $C_{5-10}$ heteroaromatic and $C_{5-10}$ heterocycloalkene. Each cyclic group may be optionally substituted, such as optionally substituted at a carbon ring atom, for example with one or more groups —$R^c$.

For the avoidance of doubt, the index "$C_{x-y}$" in terms such as "$C_{5-10}$ heterocycloalkene", and the like, refers to the number of ring atoms, which may be carbon atoms or heteroatoms (e.g., N, O, S). For example, tetrahydropyran is an example of a $C_6$heterocycloalkene group. Where a cyclic group is fused to the ortho-quinone, the ring atoms include the ring atoms shared with the ortho-quinone to which it is fused.

The term "heterocycloalkene" means a group (1) which has one or more heteroatoms (e.g., N, O, S) forming part of a ring system, wherein the ring system comprises one ring or two or more fused rings, wherein at least one ring of the ring system is a non-aromatic ring, and (2) which is attached to the rest of the molecule by a non-aromatic ring atom (i.e., a ring atom that is part of a non-aromatic ring that is part of the ring system). For example: 2,3-dihydrofuran and 3,4-dihydro-2H-pyran are examples of a $C_5$ and $C_6$ heterocycloalkene group respectively; 2,3-dihydrobenzofuran is an example of a $C_9$heterocycloalkene group; and isochromane is an example of a $C_{10}$heterocycloalkene group.

2,3-hydro-furan

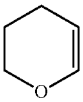
3,4-dihydro-2H-pyran

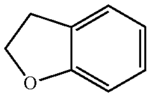
2,3-dihydrobeno-furan

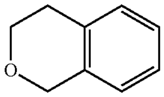
isochromane

In one embodiment, where a heterocycloalkene group contains two or more fused rings, each ring is non-aromatic.

In one embodiment, the heterocycloalkene group has one ring.

For the avoidance of doubt, "heteroaromatic" refers to a group (1) which has one or more heteroatoms (e.g., N, O, S) forming part of a ring system, wherein the ring system comprises one ring or two or more fused rings, wherein at least one ring of the ring system is an aromatic ring, and (2) which is attached to the rest of the molecule by an aromatic ring atom (i.e., a ring atom that is part of an aromatic ring that is part of the ring system). For example: pyridine is an example of a $C_6$heteroaromatic group; isoquinoline is an example of a $C_{10}$ heteroaromatic group; and 1,2,3,4-tetrahydro-isoquinoline is an example of a $C_{10}$ heteroaromatic group, when attached via the aromatic ring.

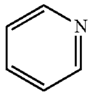
pyridine

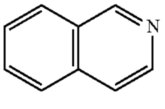
isoquinoline

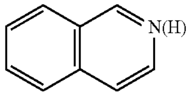
1,2,3,4-tertra-hydroisoquinoline

In one embodiment, where a heteroaromatic comprises two or more fused rings, each ring is an aromatic ring.

In one embodiment, the heteroaromatic group comprises one aromatic ring.

A heteroaromatic group may also include a pyridone group, which may be regarded as a structure corresponding to a pyridine group having a 2- or 4-hydroxyl substituent.

In one embodiment, a heteroaromatic group is not a pyridone group.

Similarly, "carboaromatic" refers to a group (1) which has a ring system comprising one ring or two or more fused rings, wherein at least one ring of the ring system is an aromatic ring, and (2) which is attached to the rest of the molecule by an aromatic ring atom (i.e., a ring atom that is part of an aromatic ring that is part of the ring system). For example: benzene is an example of a Ce carboaromatic group; and tetralin is an example of a $C_{10}$ carboaromatic group, when attached via the aromatic ring.

benzene

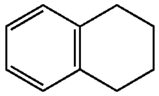
tetralin

In one embodiment, where a carboaromatic comprises two or more fused rings, each ring is an aromatic ring.

Where a non-aromatic ring is present, that ring may be a carbocycle (such as shown above for tetralin), or the ring may be a heterocycle, as shown below for the group dihydrobenzo[b][1,4]dioxine.

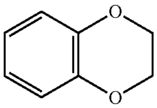
dihydronezo[b][1,4]dioxane

For the avoidance of doubt, "cycloalkene" refers to a group (1) which has at least one double bond, (2) which has a ring system comprising one ring or two or more fused rings, wherein one ring of the fused ring system may be an aromatic ring, and (3) which is attached to the rest of the molecule by a non-aromatic ring atom (i.e., a ring atom that is part of a non-aromatic ring that is part of the ring system). For example: cyclohexene is a $C_6$ cycloalkene group.

Where an aromatic ring is present, it may be optionally substituted. In one embodiment, where the cycloalkene comprises two or more fused rings, each ring is non-aromatic. In one embodiment, the cycloalkene group comprises one ring.

In one embodiment, at least one cyclic ring fused to the 1,2-quinone is an aromatic group. Each aromatic group is optionally substituted. The aromatic group may be a carboaromatic group or a heteroaromatic group.

Similarly, "cycloalkane" refers to a group (1) which has a ring system comprising one ring or two or more fused rings, wherein one ring of the fused ring system may be an aromatic ring, and (2) which is attached to the rest of the molecule by a non-aromatic ring atom (i.e., a ring atom that is part of a non-aromatic ring that is part of the ring system). For example: cyclohexane is an example of a Ce cycloalkane group; and tetralin is an example of a $C_{10}$ cycloalkane group, when attached via the non-aromatic ring.

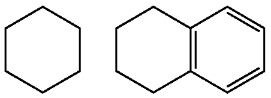

cyclo-hexane tetralin

A carboaromatic group may be, together with the ring atoms of the quinone to which it is fused, a $C_{6-10}$ carboaromatic group. The carboaromatic group has at least one aromatic ring and this ring is fused with the quinone.

The carboaromatic group may be selected from optionally substituted benzene, naphthalene and tetralin.

The heteroaromatic group may be, together with the ring atoms of the quinone to which it is fused, a $C_{5-10}$ heteroaromatic group.

The heteroaromatic group may be selected from optionally substituted furan, pyrrole, pyridine and benzofuran.

In one embodiment, at least one cyclic ring fused to the 1,2-quinone is a cycloalkene group. This group is partially or fully saturated, and is not aromatic.

The cycloalkene group may be selected from cyclohexene.

Each or both of the cyclic groups may be a carbocyclic ring. Thus, each or both of the cyclic groups does not contain a ring heteroatom, such as a ring heteroatom selected from O, S and N(H).

In one embodiment, at least one cyclic ring fused to the 1,2-quinone is a heterocycloalkene group. This group is partially or fully saturated, and is not aromatic.

The heterocycloalkene group may be selected from dihydrofuran and dihydropyran.

Where two cyclic groups are fused with the 1,2-benzoquinone, and these cyclic groups are fused with one another, the two cyclic groups may together be an isochromane or isochromene group. Examples of such ortho-quinones include Mansonone E and F.

In certain embodiments, the ortho-quinone compound is a compound having a 1,2-benzoquinone group, as shown below:

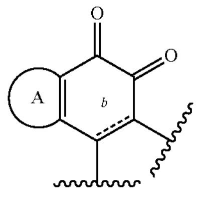

where:

b is a double or single bond;

Ring A is selected from optionally substituted $C_{6-10}$ carboaromatic, $C_{6-10}$ cycloalkene and $C_{5-10}$ heteroaromatic; and each of the 5- and 6-positions may be substituted or fused to another cyclic group, as defined above.

In certain embodiments, b is a double bond.

Preferably, Ring A is selected from an optionally substituted benzene, naphthalene, cyclohexene, benzofuran, tetralin, pyridine and tetrahydronaphthalene. More preferably, Ring A is selected from an optionally substituted benzene, naphthalene, cyclohexene, benzofuran, tetralin and pyridine.

It will be appreciated that when Ring A is tetralin, the tetralin ring may be attached to the 1,2-benzoquinone group by an aromatic ring atom (i.e., a ring atom that is part of the aromatic ring of tetralin).

It will also be understood that when Ring A is an optionally substituted tetrahydronaphthalene, this covers groups of the following formula:

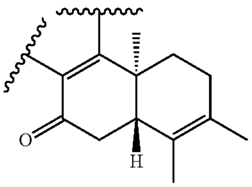 [SMILES: *C1=C(*)[C@@]2(C)CCC(C)=C(C)[C@@H]2CC1=O]

where the optional substituent groups, —$R^c$, on the tetrahydronaphthalene may, for example, be selected from carbonyl and methyl.

In certain preferred embodiments, Ring A is selected from an optionally substituted benzene and cyclohexene, preferably an optionally substituted benzene.

Ring A may be optionally substituted, for example with one or more —$R^c$ groups, as defined herein.

Benzoquinones Fused at the 3- and 4-Positions

In one embodiment, a cyclic group is fused at the benzoquinone 3- and 4-positions. Here, the 5- and 6-positions may be optionally substituted, for example where each optional substituent is a group —$R^S$. The 5-position may be unsubstituted. The 6-position may be substituted, for example substituted with $C_{1-10}$ alkyl.

Preferably, the cyclic group fused at the benzoquinone 3- and 4-positions is selected from $C_{6-10}$ carboaromatic, $C_{6-10}$ cycloalkene and $C_{5-10}$ heteroaromatic, each of which may be optionally substituted. More preferably, the cyclic group fused at the benzoquinone 3- and 4-positions is selected from optionally substituted benzene, $C_{5-9}$ cycloalkene and $C_9$ heteroaromatic. Even more preferably, the cyclic group fused at the benzoquinone 3- and 4-positions is optionally benzene, optionally substituted cyclohexene or optionally substituted 2,3-dihydrobenzofuran. Most preferably, the cyclic group fused at the benzoquinone 3- and 4-positions is optionally substituted benzene.

The cyclic group fused at the benzoquinone 3- and 4-positions may be optionally substituted with one or more-Re groups as defined below.

Thus, in certain embodiments, the ortho-quinone compound is a compound having a 1,2-benzoquinone group, as shown below:

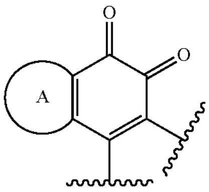

where:

Ring A is selected from an optionally substituted $C_{6-10}$ carboaromatic, $C_{6-10}$ cycloalkene and $C_{5-10}$ heteroaromatic; and each of the 5- and 6-positions may be substituted, for example with a group —$R^S$.

In certain embodiments, Ring A is selected from an optionally substituted benzene, cyclohexene, and $C_{6-9}$ heteroaryl. Preferably, Ring A is selected from optionally substituted benzene, cyclohexene and 2,3-dihydrobenzofuran, and most preferably Ring A is optionally substituted benzene.

In certain embodiments, —$R^S$ is $C_{1-10}$ alkyl, such as $C_{1-6}$ alkyl, such as $C_{1-4}$ alkyl. The alkyl group may also be linear or branched. The alkyl group is preferably methyl, ethyl or isopropyl.

Ring A may be optionally substituted, for example with one or more-Re groups, as defined herein.

In some embodiments, —$R^c$ is selected from $C_{16}$ alkyl (e.g. methyl, ethyl or isopropyl) and $C_{1-6}$ hydroxyalkyl.

Example ortho-quinones that are unsubstituted at the 5-position and substituted at the 6-position, whilst also having a cyclic group fused to the benzoquinone 3- and 4-positions, include Mansonone A, C and D, and Salvicine.

Benzoquinones Fused at the 3- and 4-Positions and the 5- and 6-Positions

In one embodiment, a cyclic group is fused at the benzoquinone 3- and 4-positions and a cyclic group is fused at the benzoquinone 5- and 6-positions.

Thus, in certain embodiments, the ortho-quinone compound is a compound having a 1,2-benzoquinone group, as shown below:

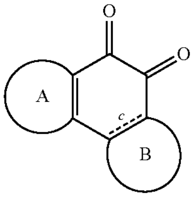

wherein:

c is a double or single bond;

Ring A is selected from $C_{6-10}$ carboaromatic, $C_{6-10}$ cycloalkene and $C_{5-10}$ heteroaromatic;

Ring B is selected from $C_{5-6}$ heterocycloalkene, $C_{5-6}$ heteroaromatic, $C_{5-10}$ cycloalkene, $C_{6-10}$ carboaromatic and $C_{5-10}$ cycloalkane; and Ring A and Ring B are optionally substituted with one or more —$R^c$ groups.

In certain preferred embodiments, c is a double bond.

Preferably, Ring A is selected from an optionally substituted $C_{6-10}$ carboaromatic and $C_6$ heteroaromatic. More preferably, Ring A is selected from an optionally substituted benzene, optionally substituted naphthlene, optionally substituted tetralin and optionally substituted pyridine. The optional substituent may be alkyl, alkenyl, hydroxyalkyl, alkoxy, carboxy and hydroxyl, preferably $C_{1-4}$ alkyl, $C_{2-4}$ alkenyl, $C_{1-4}$ hydroxyalkyl, $C_{1-4}$ alkoxy, carboxy and hydroxyl.

Preferably, Ring B is selected from an optionally substituted $C_{5-6}$ heterocycloalkene (e.g. dihydrofuran and dihydropyran) or an optionally substituted $C_{5-6}$ heteroaromatic (e.g. furan or pyrrole), where each optional substituent is a group —$R^c$, such as $C_{1-4}$ alkyl, $C_{2-4}$ alkenyl or carboxy.

Example ortho-quinones of this type include β-lapachone and Dunnione.

Benzoquinones Fused at the 3-, 4- and 5-Positions

A cyclic group may be fused at the benzoquinone 3-, 4- and 5-positions.

In one embodiment, two cyclic groups may be fused with the 1,2-benzoquinone, and may be fused with one another. Thus, a bicyclic ring may be fused with the 1,2-benzoquinone at the 3-, 4- and 5-positions. Example ortho-quinones of this type include Biflorin, and Mansonone E and F.

Thus, in certain embodiments, the ortho-quinone compound is a compound having a 1,2-benzoquinone group, as shown below:

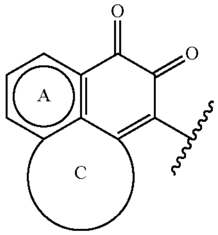

wherein:

Ring A is benzene;

Ring C is selected from a $C_{5-6}$ heterocycloalkene, $C_{5-10}$ cycloalkene and $C_{5-10}$ cycloalkene; and and wherein Ring A and Ring C are each independently optionally substituted with one or more-Re groups.

Preferably, Ring C is a $C_{5-6}$heterocycloalkene. More preferably, Ring C is a $C_6$ heterocycloalkene. Most preferably, Ring C is a $C_6$heterocycloalkene comprising oxygen (e.g. tetrahydropyran).

It will be understood that Rings A and C are fused with the 1,2-benzoquinone and with one another. Thus, it will be appreciated that Rings A and C together define various bicyclic rings that may be fused with the 1,2-benzoquinone at the 3-, 4- and 5-positions. That is, Rings A and C define bicyclic rings formed from the fusion of the rings defined by each of Rings A and C independently.

For example, isochromane is an example of a bicyclic ring formed from the fusion of a benzene of Ring A and a $C_6$heterocycloalkene (e.g. tetrahydropyran) of Ring C.

Preferably, Rings A and C are such that the bicyclic ring fused with the 1,2-benzoquinone, is an isochromane or isochromene group. Examples of such ortho-quinones include Mansonone E and F.

—$R^S$ and —$R^c$ groups

As outlined above, —$R^S$ represents the substituent group which may be substituted on the ortho-quinone group, such as at the 5- or 6-position of the ortho-quinone group.

The group —$R^c$ is a substituent group which may be present on the cyclic rings which are fused to ortho-quinone group, as defined above. This is typically a substituent to a carbon atom.

The group —$R^S$ is selected from —$R^{S1}$, —$OR^{S1}$, —$NR^{S1}R^{S2}$, halo, $C_{1-10}$ haloalkyl, $C_{1-10}$ haloalkoxy, $C_{1-10}$ aminoalkyl, $C_{1-10}$ hydroxyalkyl, $C_{1-10}$ azidoalkyl, cyano, hydroxyl, carboxy, carbamoyl, sulfamoyl and mercapto, wherein —$R^{S1}$ is selected from hydrogen, $C_{1-10}$ alkyl, $C_{2-10}$ alkenyl, $C_{2-10}$ alkynyl and $C_{3-6}$ cycloalkyl, and —$R^{S2}$ is selected from hydrogen and —$R^{S1}$, and wherein —$R^s$ is not hydrogen.

Preferably, —$R^S$ is selected from $C_{1-10}$ alkyl, $C_{2-10}$ alkenyl, $C_{2-10}$ alkynyl, $C_{3-6}$ cycloalkyl, halo, $C_{1-10}$ haloalkyl, $C_{1-10}$ haloalkoxy, $C_{1-10}$ alkoxy, $C_{1-10}$ aminoalkyl, $C_{1-10}$ hydroxyalkyl, $C_{1-10}$ azidoalkyl, cyano, —$NR^{S3}R^{S4}$, —$OR^{S3}$ and carboxy, where —$R^{S3}$ and —$R^{S4}$ are independently selected from hydrogen or $C_{1-4}$alkyl (e.g. methyl).

More preferably, —$R^S$ is selected from $C_{1-6}$ alkyl, $C_{3-6}$ cycloalkyl, halo, $C_{1-6}$ haloalkyl, $C_{1-6}$ alkoxy, $C_{1-6}$ aminoalkyl, —$NH_2$, cyano and hydroxyl.

Even more preferably, —$R^S$ is selected from $C_{1-6}$ alkyl, $C_{3-6}$ cycloalkyl (e.g. cyclopropyl), halo, cyano and hydroxyl.

Most preferably, —$R^S$ is selected from $C_{1-3}$ alkyl (e.g. methyl and isopropyl), cyclopropyl, methyl-cyclopropyl and hydroxyl.

The group —$R^c$ is selected from —$R^{C1}$, —$OR^{C1}$, —$NR^{C1}R^{C2}$, halo, $C_{1-10}$ haloalkyl, $C_{1-10}$ haloalkoxy, $C_{1-10}$ aminoalkyl, $C_{1-10}$ hydroxyalkyl, $C_{1-10}$ azidoalkyl, cyano, hydroxyl, carboxy, carbamoyl, carbonyl, sulfamoyl and mercapto, wherein —$R^{C1}$ is selected from hydrogen, $C_{1-10}$ alkyl, $C_{2-10}$ alkenyl, $C_{2-10}$ alkynyl, $C_{3-6}$ cycloalkyl, $C_{5-10}$ carboaryl, $C_{5-10}$ heteroaryl and $C_{5-10}$ heterocyclyl and $R^{C2}$ is selected from hydrogen or —$R^{C1}$, and wherein-Re is not hydrogen.

When —$R^c$ is carbonyl, it will be appreciated that the carbon of the carbonyl group (—C(═O)—) may form part of the cyclic ring to which —$R^c$ is attached. That is, —$R^c$ being carbonyl will be understood to cover groups such as the tetrahydronaphthalene ring with the following substitution:

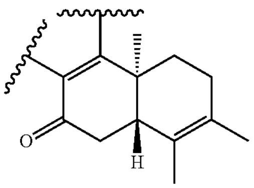 [SMILES: *C1=C(*)[C@@]2(C)CCC(C)=C(C)[C@@H]2CC1=O]

Preferably, —$R^c$ is selected from $C_{1-10}$ alkyl, $C_{2-10}$ alkenyl, $C_{2-10}$ alkynyl, $C_{3-6}$ cycloalkyl, halo, $C_{1-10}$ haloalkyl, $C_{1-10}$ haloalkoxy, $C_{1-10}$ alkoxy, $C_{1-10}$ aminoalkyl, $C_{1-10}$ hydroxyalkyl, $C_{1-10}$ azidoalkyl, cyano, —$NR^{C3}R^{C4}$, —$OR^{C3}$, carboxy, and carbonyl, where —$R^{C3}$ and —$R^{C4}$ are independently selected from hydrogen or $C_{1-4}$ alkyl (e.g. methyl).

More preferably, —$R^c$ is selected from $C_{1-10}$ alkyl, $C_{2-6}$ alkenyl, $C_{2-6}$ alknyl, $C_{3-6}$ cycloalkyl (e.g. cyclopropyl), halo, $C_{1-6}$ alkoxy, $C_{1-6}$ aminoalkyl, $C_{1-6}$ hydroxyalkyl, $C_{1-6}$ azidoalkyl, —$NH_2$, cyano, hydroxyl, carboxy and carbonyl.

Most preferably, —$R^c$ is selected from $C_{16}$ alkyl (e.g. methyl, ethyl or isopropyl), $C_{2-6}$ alkenyl (e.g. propylenyl), $C_{1-6}$ alkoxy (e.g. methoxy), $C_{1-6}$ hydroxyalkyl, hydroxyl, carboxy and carbonyl.

It will be appreciated that any $C_{1-10}$ alkyl, $C_{2-10}$ alkenyl, $C_{2-10}$ alknyl or $C_{3-6}$ cycloalkyl may be optionally substituted, for example, with one or more groups selected from $C_{1-4}$ alkyl, halo, $C_{1-4}$ alkoxy, —$NH_2$, cyano, hydroxyl and carboxy. Preferably, any $C_{3-6}$ cycloalkyl is optionally substituted with a group further selected from $C_{1-4}$ alkyl (e.g. methyl).

The term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "$C_{1-6}$ alkyl" includes $C_{1-4}$ alkyl, $C_{1-3}$ alkyl, propyl, isopropyl, t-butyl, ethyl and methyl.

The term "alkenyl" will be understood to include both straight and branched hydrocarbon groups comprising one or more carbon-carbon double bonds. Reference to, for example, "$C_{2-6}$ alkenyl" will be understood to refer to alkene groups containing from 2 to 6 carbon atoms and may includes, for example, hexenyl, pentenyl, butenyl, propenyl and ethylenyl.

The term "alkynyl" will be understood to include both straight and branched hydrocarbon groups comprising one or more carbon-carbon triple bonds. Again, reference to "$C_{2-6}$ alkynyl" groups will be understood to refer to alkyne groups containing from 3 to 6 carbon atoms and may includes, for example hexynyl, pentynyl, butynyl, propynyl and acetylenyl. The alkynyl group may be $C_{2-10}$ alkynyl, such as $C_{2-6}$ alkynyl, such as $C_{2-4}$ alkynyl. The alkynyl may be 1-butyne or 1-pentyne, and preferably 1-butyne.

The term "$C_{3-6}$ cycloalkyl" will be understood to include unsaturated hydrocarbon ring containing from 3 to 6 carbon atoms, for example, cyclopropyl, cyclobutyl, cyclopentyl and cyclohexyl. Preferably, the $C_{3-6}$ cycloalkyl is cyclopropyl. The $C_{3-6}$ cycloalkyl may be optionally substituted with a $C_{1-4}$alkyl (e.g. methyl).

A cyano group is —CN.

A hydroxyl group is —OH.

A carboxy group is —C(O)OH.

A carbamoyl group is —$C(O)NH_2$.

Additionally or alternatively, the carbamoyl group is —$C(O)NR^{cx}H$ or —$C(O)NR^{cx}{}_2$, where $R^{cx}$ is selected from $C_{1-6}$ alkyl (e.g. methyl, ethyl or isopropyl), $C_{2-6}$ alkenyl (e.g. propylenyl), $C_{2-6}$ alkynyl (e.g. butynyl), $C_{1-6}$ alkoxy (e.g. methoxy), $C_{1-6}$ aminoalkyl, $C_{1-6}$ hydroxyalkyl and $C_{1-6}$ azidoalkyl, and preferably Rex is selected from $C_{1-6}$ alkyl (e.g. methyl, ethyl or isopropyl), $C_{2-6}$ alkynyl (e.g. butynyl) and $C_{1-6}$ azidoalkyl (e.g. n-propyl azide).

A sulfamoyl group is —$S(O)_2NH_2$.

Additionally or alternatively, the sulfamoyl group is —$S(O)_2NR^{sx}H$ or —$S(O)_2NR^{sx}{}_2$, where $R^{sx}$ is selected from $C_{1-6}$ alkyl (e.g. methyl, ethyl or isopropyl), $C_{2-6}$ alkenyl (e.g. propylenyl), $C_{2-6}$ alkynyl (e.g. butynyl), $C_{1-6}$ alkoxy (e.g. methoxy), $C_{1-6}$ aminoalkyl, $C_{1-6}$ hydroxyalkyl and $C_{1-6}$ azidoalkyl, and preferably $R^{sx}$ is selected from $C_{16}$ alkyl (e.g. methyl, ethyl or isopropyl), $C_{2-6}$ alkynyl (e.g. butynyl) and $C_{1-6}$ azidoalkyl (e.g. n-propyl azide).

A mercapto group is —SH.

A halo group may be selected from the group consisting of F, Cl, Br and I, such as F, Cl, and I.

The term "carboaryl" will be understood to be a radical of the carboaromatic group defined above. That is, the term carboaryl includes any of the carboaromatic groups defined above where a hydrogen radical from the carboaromatic is formally replaced with a covalent bond to the group on which the carboaryl is attached. For example, phenyl is an example of the radical form derived from the carboaromatic group, benzene. Preferably, the carboaryl is $C_{6-10}$ carboaryl, and most preferably a $C_6$ carboaryl (e.g. phenyl). Examples of carboaryl groups include, but are not limited to, phenyl, biphenyl, naphthyl, and the like. In particular embodiment, a carboaryl is phenyl.

The term "heteroaryl" will be understood to be a radical of the heteroaromatic group defined above. That is, the term heteroaryl includes any of the heteroaromatic groups defined above where a hydrogen radical from the heteroaromatic is formally replaced with a covalent bond to the group on which the heteroaryl is attached. Preferably, the heterooaryl is a $C_{5-10}$ heterooaryl, and most preferably a $C_{5-6}$ heterooaryl (e.g. pyridyl). Examples of heteroaryl groups include, but are not limited to, pyridyl, furanyl, and the like. In particular embodiment, a heteroaryl is a $C_{5-6}$ heteroaryl, such as furanyl and pyridyl.

The term "heterocyclyl" will be understood to be a radical of a non-aromatic saturated or partially saturated monocyclic, fused, bridged, or spiro bicyclic heterocyclic rings. Thus, the term "heterocyclyl" will be understood to be a group which has one or more heteroatoms (e.g., N, O, S) forming part of a ring system, wherein the ring system comprises one ring or two or more fused rings, wherein at least one ring of the ring system is a non-aromatic ring. Preferably, the "heterocyclyl" is a $C_{5-10}$ heterocyclyl, most suitably a $C_{5-6}$ heterocyclyl. Examples of heterocyclyl groups include, but are not limited to 2,3-dihydrofuran, 3,4-dihydro-2H-pyran, pyrrolidine, tetrahydrofuran and tetrahydropyran.

The $C_{1-10}$ aminoalkyl group may be a $C_{1-10}$ alkyl group having at least one amino (—$NH_2$) group. The $C_{1-10}$ aminoalkyl group may be a $C_{1-4}$ alkyl group comprising at least one amino (—$NH_2$) group, such as 3-aminopropan-1-yl shown below:

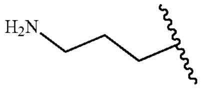 [SMILES: *CCCN]

The $C_{1-10}$ hydroxyalkyl group may be a $C_{1-10}$ alkyl group having at least one hydroxy (—OH) group. The $C_{1-10}$ hydroxyalkyl group may be a $C_{1-4}$ alkyl group comprising at least one hydroxy (—OH) group, such as 3-hydroxypropan-1-yl shown below:

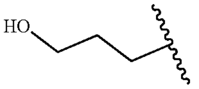 [SMILES: *CCCO]

The $C_{1-10}$ azidoalkyl group may be a $C_{1-10}$ alkyl group having at least one azide (—$N_3$) group. The $C_{1-10}$ azidoalkyl group may be a $C_{1-4}$ alkyl group comprising at least one azido (—$N_3$) group, such as 3-azidopropan-1-yl, shown below:

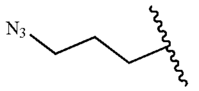 [SMILES: *CCCN=[N+]=[N-]]

The $C_{1-10}$ haloalkyl group may be a $C_{1-10}$ alkyl group having at least one halo (—F, —Cl, —Br— and —I) group. The $C_{1-10}$ haloalkyl group may be a $C_{1-4}$ alkyl group comprising at least one fluoro (—F) group, such as —$CF_3$.

The $C_{1-10}$ haloalkoxy group may be a $C_{1-10}$ alkoxy group having at least one halo (F, Cl, Br— and I) group. The $C_{1-10}$ haloalkoxy group may be a $C_{1-4}$ alkoxy group comprising at least one fluoro (F) group, such as —$OCF_3$.

In one embodiment, the ortho-quinone is selected from the group consisting of β-lapachone, Rhinacanthone, Dunnione, Biflorin, Tanshinone I, Tanshinone IIA. Tanshinone IIB, Dihydrotanshinone I, Cryptotanshinone, Mansonone A, C, D, E, F, and G, Miltirone, Salvicine, Caryopteron A, Lantalucratin A, B and C, pyrroloquinolone quinone and HBL (3-hydroxy-β-lapachone). These ortho-quinones are known, naturally occurring ortho-quinones. The structures of these ortho-quinones are given below, for reference.

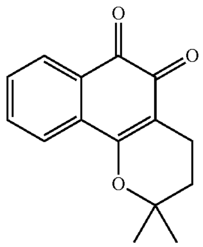

β-lapachone

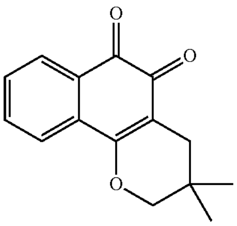

Rhinacanthone

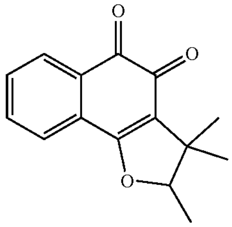

Dunnione

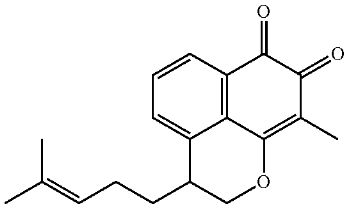

Biforin

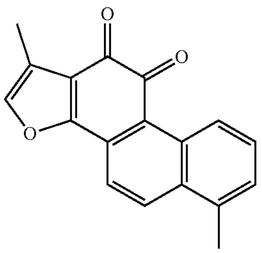

Tanshinone I

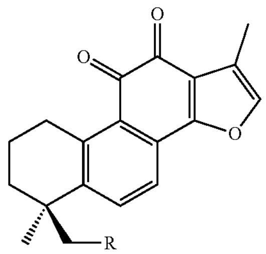

Tanshinone
IIA-R = H
IIB-R = OH

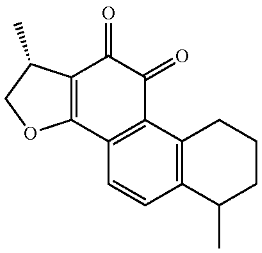

Dihydrotanshinone I

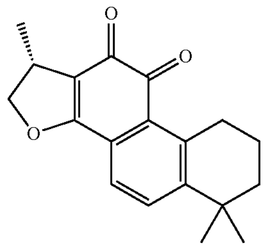

Cryptotanshinone

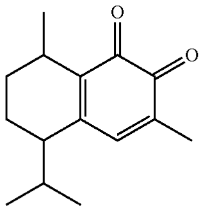

Mansonone A

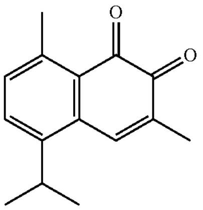

Mansonone C

-continued

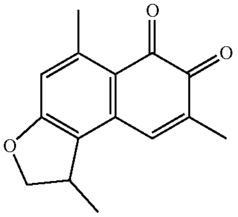

Mansonone D

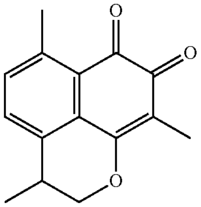

Mansonone E

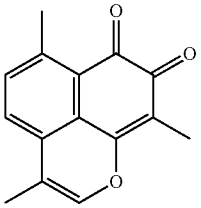

Mansonone F

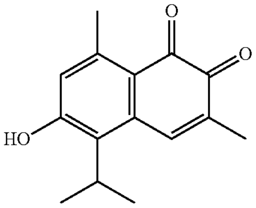

Mansonone G

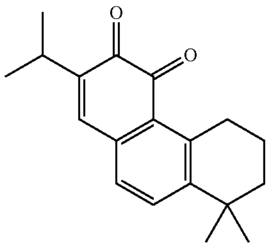

Miltirone

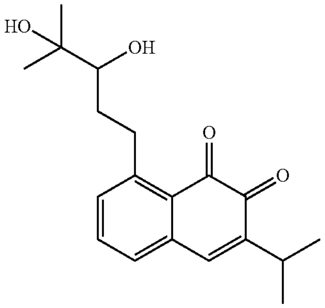

Salvicine

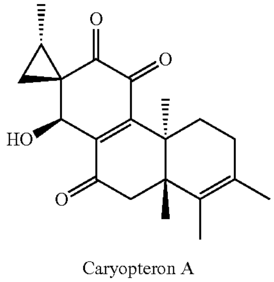

Caryopteron A

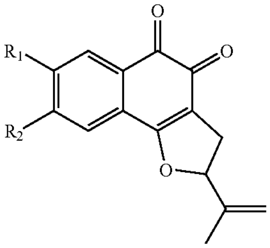

Lantalucratin

A-$R_1$ = OMe, $R_2$ = H

B-$R_1$ = OH, $R_2$ = H

C-$R_1$ = H, $R_2$ = OH

-continued

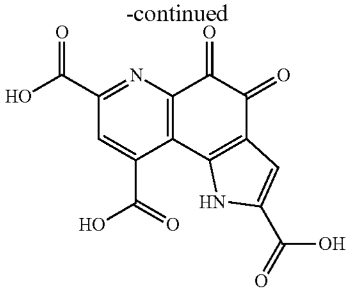

Pyrroloquinolone quinone

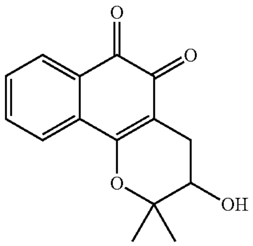

3-hydroxy-β-lapachone (HBL)

Each of these ortho-quinones is also reported as having anticancer activity, such as having an inhibitory activity, determined as $IC_{50}$, in the range 0.1 to 10 μM (see for example, Wellington, K. W. et al, RSC Adv., 2015, 5, 20309-20338).

Further β-Lapachone derivatives are described in Gong et al (2021), European Journal of Medicinal Chemistry, 210, 112962, the contents of which is incorporated herein by reference.

In one embodiment, the ortho-quinone is selected from the group consisting of β-lapachone, HBL Dunnione and Cryptotanshinone.

In one embodiment, the ortho-quinone is β-lapachone. The use of β-lapachone to form protected ortho-quinones, as may be used in a conjugate, is exemplified in the present case. β-lapachone is also known to have activity against acute myeloid leukaemia cell lines, as also demonstrated herein, and is therefore suitable for use in methods of treating leukaemia and other cancers.

An ortho-quinone for use in the present invention may be an ortho-quinone having activity against a cancerous cell line.

The $IC_{50}$ value for an ortho-quinone may be known, or may be established according to the viability tests as described herein against an appropriately selected cell line, which may include cell lines selected from leukaemia, breast, colon, and cervical cancer, amongst others. The $IC_{50}$ value for the ortho-quinone may be 100 μM or less, such as 10 μM or less, such as 1 μM or less, such as 100 nM or less, such as 10 nM or less.

For example, β-lapachone has measured $IC_{50}$ values of 1.1 μM against HCT-116 (colon cancer cell line), 1.4 μM against HL-60 (leukaemia cell line), 2.8 μM against SKBR3 (breast cancer cell line), 1.9 μM against MCF-7 (breast cancer cell line) and 4.2 μM against HeLa (cervical cancer cell line).

An ortho-quinone for use in the present invention may be an ortho-quinone having activity against a HCT-116 (colon cancer) cell line, HL-60 (leukaemia) cell line, SKBR3 (breast cancer) cell line, MCF-7 (breast cancer) cell line and HeLa (cervical cancer) cell line. Preferably, an ortho-quinone for use in the present invention is an ortho-quinone having activity against a HL-60 (leukaemia) cell line.

An ortho-quinone for use in the present invention may be an ortho-quinone having activity against a bacterium.

The MIC value for an ortho-quinone against a particular bacterium may be known, or may be established according to standard procedures. An ortho-quinone may have a MIC against a bacterium of 100 μg/mL or less, such as 10 μg/mL or less, such as 1 μg/mL or less, such as 1 μg/mL or less.

An ortho-quinone for use in the present invention may be an ortho-quinone having activity against a parasite.

The MIC value for an ortho-quinone against a particular parasite may be known, or may be established according to standard procedures. An ortho-quinone may have a MIC against a parasite of 100 μg/mL or less, such as 10 μg/mL or less, such as 1 μg/mL or less, such as 1 μg/mL or less.

An ortho-quinone compound for use in the present invention is typically a compound where pKa for one hydroquinone alcohol in the corresponding ortho-diol form is 9.2 or less, such as 9.0 or less, such as 8.5 or less, where the pKa for the hydroquinone alcohols may be determined, for example, with the PerkinElmer CambridgeSoft Chem3D software.

As described in further detail below, the cytotoxicity of the ortho-quinone is significantly reduced when it is provided in its ketol protected form, and as might be present in a conjugate. Thus, significant biological activity is achieved only once the protection is removed, and the ortho-quinone form is generated.

A reference to an ortho-quinone is also a reference to its corresponding ortho-diol form. As discussed in further detail below, the removal of the protecting group from the protected quinone is believed to generate the diol form. In practice, this form is believed to rapidly auto-oxidise to give the ortho-quinone.

Typically, the ortho-quinone compound has a molecular weight of at most 1,000, such as at most 500, such as at most 400, such as at most 300.

Protected Ortho-Quinone

The invention provides protected quinone compounds, and more specifically protected ortho-quinone compounds.

The ortho-quinone compound is protected in its α-hydroxy keto form (ketol form), with a protecting group connecting to the α-carbon atom. Thus, the protecting group is connected via a ring carbon atom, and the connection is not formed via the oxygen atom of the hydroxy group within the α-hydroxy keto form. When the protecting group is removed, a bond to the ring carbon atom is cleaved, ultimately revealing the ortho-quinone form.

The protecting group is connected by a carbon-carbon bond to the α-carbon atom.

For convenience, the ketol form may be regarded as having the ketone group at the 1-position on the ring, and the α-hydroxy group at the 2-position. It follows that the protecting group is connected to the ring 2-position. The protected form is shown below, where PG is the protecting group connecting to the ring 2-position (the α-carbon to the keto group), and a is a double or single bond:

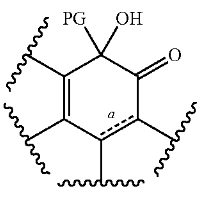

The protecting group may be an aminobenzyl group or hydroxybenzyl group connected by the benzylic carbon to the α-carbon of the α-hydroxy keto form of the quinone. The aminobenzyl group and the hydroxybenzyl group are the self-immolative components of the protected quinone and the conjugate.

The protected ortho-quinone may have significantly reduced biological activity compared with the ortho-quinone itself.

The $IC_{50}$ value for a protected ortho-quinone, when compared with the ortho-quinone against the same cell line, may be at least 10 times greater, such as 25 times greater, such as 50 times greater than that of the ortho-quinone.

In the present case, model protected forms of β-lapachone were determined to have $IC_{50}$ values of greater than 30 μM, and more typically greater than 50 μM. In comparison, β-lapachone was determined to have $IC_{50}$ values in the range 1.1. to 4.2 μM against the same panel of cells.

The removal of the protection from the protected ortho-quinone may occur at or close to the site of action.

A protected ortho-quinone may contain a group represented thus:

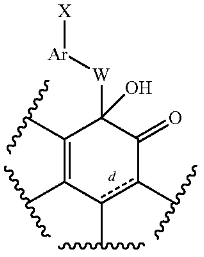

where —Ar— is optionally substituted phenylene,

—X is selected from $—NH_2$, —OH and —SH, and the protected forms of each,

—W— is optionally substituted methylene, such as methylene, and d is a double or single bond, and the salts and solvates thereof.

The 3-, 4-, 5- and 6-positions may be optionally substituted, as described for the ortho-quinone compounds above. The embodiments and preferences for the ortho-quinone compounds also apply to the protected forms, as appropriate.

The protected ortho-quinone may also be represented as X—Ar—W-Q, where —X, —Ar— and —W—have the same meanings as above, and -Q is the ketol from of the ortho-quinone, with the optionally substituted methylene group (—W—) connected via a carbon-carbon bond to the a-carbon of the ketol.

In certain embodiments, —W— is a methylene group ($—CH_2—$). This is the case, for example, where the conjugate of the invention has a polypeptide connected via the group —X.

In other embodiments, —W— is a methylene group substituted with one or two groups, such as substituted with one group, selected from $C_{1-10}$ alkyl, $C_{2-10}$ alkenyl, $C_{2-10}$ alknyl, $C_{3-6}$ cycloalkyl, halo, $C_{1-10}$ haloalkyl, $C_{1-10}$ haloalkoxy, $C_{1-10}$ aminoalkyl, $C_{1-10}$ hydroxyalkyl, $C_{1-10}$ azidoalkyl, $—NR^{W1}R^{W2}$, $—OR^{W1}$, cyano, carboxy, carbamoyl, sulfamoyl and mercapto, where $—R^{W1}$ and $—R^{W2}$ are independently selected from hydrogen and $C_{1-4}$ alkyl (e.g. methyl).

Each of these substituent groups have the meaning given hereinabove.

Thus, the methylene group may be provided with substituents.

Preferably, —W— is a methylene group substituted with one or two groups, such as substituted with one group, selected from $C_{1-10}$ alkyl, $C_{2-10}$ alkenyl, $C_{2-10}$ alknyl, halo, $C_{14}$ haloalkyl, $C_{1-4}$ alkoxy, $C_{1-10}$ aminoalkyl, $C_{1-10}$ hydroxyalkyl, $C_{1-10}$ azidoalkyl, —$NR^{W1}R^{W2}$, —$OR^{W1}$, cyano, carboxy and carbamoyl, where —$R^{W1}$ and —$R^{W2}$ are independently selected from hydrogen or $C_{1-4}$ alkyl (e.g. methyl). More suitably, —W— is methylene optionally substituted with one or more groups selected from $C_{1-10}$ alkyl, $C_{2.10}$ alkenyl, $C_{2-10}$ alknyl, and $C_{1-10}$ azidoalkyl.

In certain embodiments, —W— is a methylene group substituted with one or two groups, such as substituted with one group, selected from $C_{1-10}$ alkyl, halo, $C_{1-4}$ haloalkyl, $C_{1-4}$ alkoxy and hydroxyl, preferably $C_{1-6}$alkyl such as methyl and ethyl.

In other embodiments, —W— is a methylene group optionally substituted with one or two groups, as substituted with one group, selected from $C_{2-10}$ alknyl, $C_{1-10}$ aminoalkyl, $C_{1-10}$ hydroxyalkyl, $C_{1-10}$ azidoalkyl and carboxy, preferably $C_{2-10}$ alknyl and $C_{1-10}$ azidoalkyl (e.g. $C_{1-6}$ azidoalkyl), and most preferably $C_{2-10}$ alknyl (e.g. 1-butyne).

It will be appreciated that in certain embodiments a substituent group on the methylene group may serve to connect, such as covalently connect, the protected quinone compound to a targeting moiety, such as a polypeptide (e.g. an antibody), either directly or via a linker group, -L-, wherein the linker group -L- is as defined below.

One suitable means for connecting the protected ortho-quinone compound to a polypeptide via the substituent group on the methylene group is using click chemistry, such as the reaction between an alkyne and an azide to form a triazole ring. Thus, in certain embodiments, the methylene group connecting —Ar— to the ortho-quinone is substituted with a group comprising an alkyne, such as 1-butyne, or a $C_{1-10}$ azidoalkyl, such as 3-azidopropan-1-yl.

The group —Ar— may be phenyl-1,4-ene. Thus, the amino or hydroxy group, or their protected forms, may be provided at the 4-position of the ring relative to the benzylic group (the methylene group connecting to the α-carbon).

The group —Ar— may be phenylene that is not substituted.

The group —Ar— may also be substituted phenylene. The phenylene may have one, two, three of four substituents, such as one, two or four substituents.

Where one substituent is present it may be at the 3-position. This is preferred. Alternatively, where one substituent is present it may be at the 2-position.

Where two substituents are present they may be at the 3- and 5-positions.

Where three substituents are present they may be at the 2-, 3- and 5-positions.

Where four substituents are present they may be at the 2-, 3-, 5- and 6-positions.

Where two or more substituents are present, these may be the same or different, and preferably the substituents are the same.

Each substituent on the group —Ar— may be independently selected from alkyl, alkoxy, —$NR^{A1}R^{A2}$, halo, $C_{2-10}$ alknyl, $C_{1-10}$ aminoalkyl, $C_{1-10}$ hydroxyalkyl, $C_{1-10}$ azidoalkyl and carboxy, and amido, where —$R^{A1}$ and —$R^{A2}$ are independently selected from hydrogen or $C_{1-4}$ alkyl.

Preferably, each substituent on the group —Ar— may be independently selected from alkyl, alkoxy, —$NR^{A1}R^{A2}$, halo, carboxy, and amido, where —$R^{A1}$ and —$R^{A2}$ are independently selected from hydrogen or $C_{1-4}$ alkyl.

When —X is —$NH_2$, preferably each substituent on the group —Ar— is independently selected from alkyl, alkoxy, nitro, and amido.

When —X is OH, preferably each substituent on the group —Ar— is independently selected from halo (e.g. fluoro), alkoxy (e.g. $C_{1-2}$ alkoxy), and $NH_2$.

It will be appreciated that in certain embodiments a substituent group on the group Ar may serve to connect, such as covalently connect, the protected quinone compound to a targeting moiety, such as a polypeptide (e.g. antibody), either directly or via a linker group, -L-, wherein the linker group -L- is as defined below.

One suitable means for connecting the protected ortho-quinone compound to a polypeptide via the substituent group on the group —Ar— is using amide coupling chemistry, such as the reaction between an amine and a carboxylic acid to form an amide bond. Thus, in certain embodiments, the group —Ar— is substituted with amine (—$NH_2$) for participation in such coupling reactions.

Each substituent may alternatively be independently selected from a substituent group comprising an alkyne, azide, carboxylic acid or amine functional group. For example, each substituent may be independently selected from an alkyl group comprising an alkyne, azide, carboxylic acid or amine group. In certain embodiments, each substituent is independently selected from an alkynyl and azidoalkyl.

The alkyl group may be $C_{1-10}$ alkyl, such as $C_{1-6}$ alkyl, such as $C_{1-4}$ alkyl. The alkyl group may be methyl or ethyl, and preferably methyl. An alkyl group may be linear or branched.

The alkoxy group may be $C_{1-10}$ alkoxy, such as $C_{1-6}$ alkoxy, such as $C_{14}$ alkoxy. The alkoxy group may be methoxy or ethoxy, and preferably methoxy. An alkoxy group may be linear or branched.

The alkynyl group may be $C_{2-10}$ alkynyl, such as $C_{2-6}$ alkynyl, such as $C_{2-4}$ alkynyl. The alkynyl group may be 1-butyne or 1-pentyne, and preferably 1-butyne.

An amido group is a group —$NR^{N1}C(O)R^{N2}$ where —$R^{N1}$ is selected from hydrogen and alkyl, and —$R^{N2}$ is selected from hydrogen and alkyl. The alkyl group may be as defined above. The group —$R^{N1}$ may be hydrogen.

The group —$R^{N2}$ may be alkyl.

Preferably, the amido group is aminoacetyl (—NHC(O)Me).

In one embodiment, the protected ortho-quinone is selected from the group consisting of:

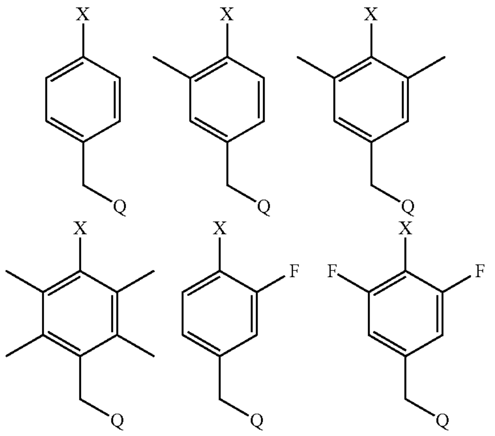

-continued

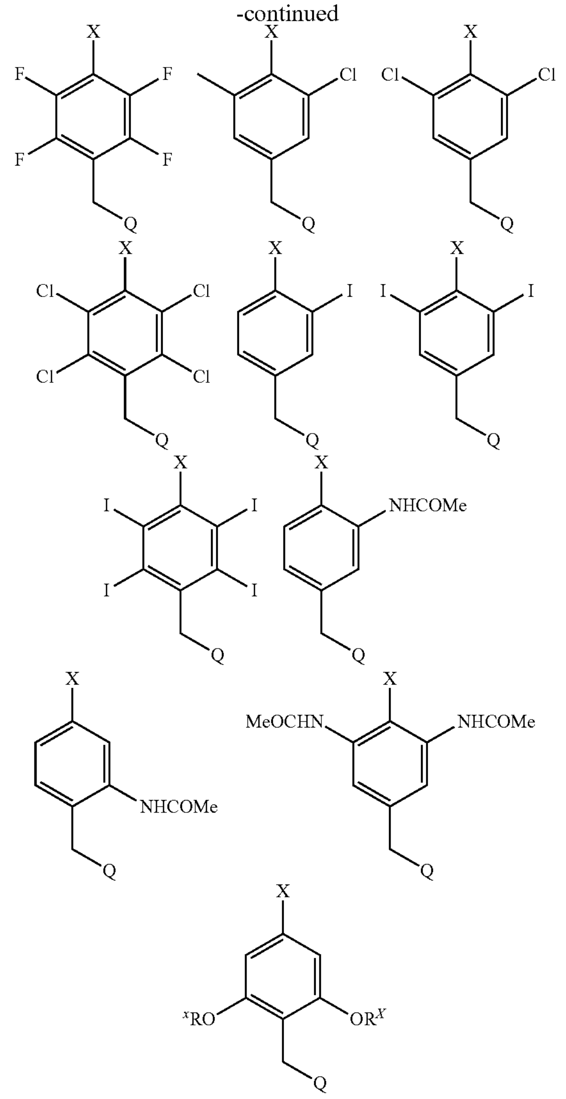

where —X and -Q are as defined previously and each $-R^x$ is $C_{1-4}$ alkyl.

Alternatively, in other embodiments, the protected ortho-quinone is selected from the group consisting of:

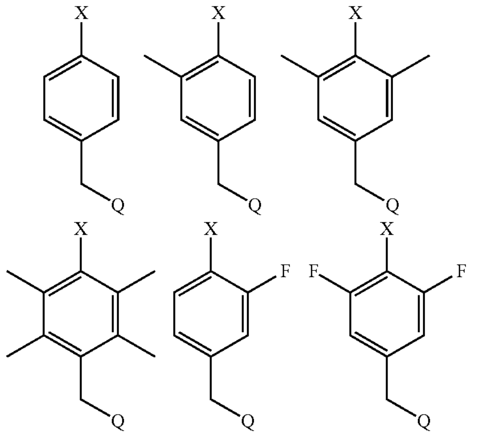

-continued

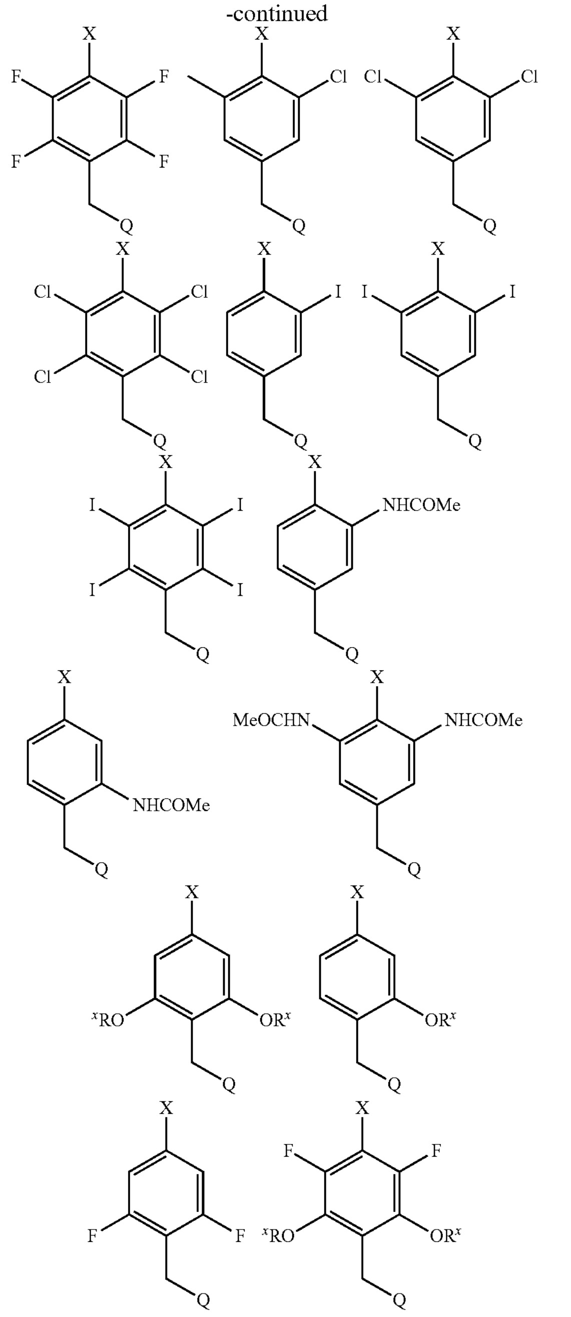

where —X and -Q are as defined previously and each $-R^x$ is $C_{1-4}$ alkyl.

When —X is amino or a protected form thereof, it is preferred the phenylene may be unsubstituted. In the worked examples of the present case para-aminobenzyl is exemplified as the protecting group for the ortho-quinone. Here, the phenylene is unsubstituted.

When —X is hydroxy or a protected form thereof, the phenylene may be unsubstituted or substituted. In one embodiment, the phenylene is unsubstituted.

The group —X may be $-NH_2$, —OH or —SH, such as $-NH_2$ or —OH.

In one embodiment —X is $-NH_2$.

In one embodiment, —X is —OH.

In the protected form of the ortho-quinone, the group —X may itself be a protected. Thus, —X may be a protected amino group, a protected hydroxy group or a protected thiol group.

Thus, the group —X may be selected from —$NH_2$, —NHBoc, —$NBn_2$, —NHCBz, —NHC(O)Bn, —NHFmoc, —OH, —OTBDMS, —OTMS, —OTOM, —OTIPS, —OBz, —OAc, —OTrt, —OTHP and —SH.

For example, the group —X may be selected from —$NH_2$, —NHBoc, —NHC(O)Bn, —OH, and —OTBDMS.

Where the group —X is a protected amino, hydroxyl or thiol group, the group may be selected from —NHBoc, —$NBn_2$, —NHCBz, —NHC(O)Bn, —NHFmoc, —OTBDMS, —OTMS, —OTOM, —OTIPS, —OBz, —OAc, and —OTrt. Such groups may be converted to the amino, hydroxyl or thiol forms using standard conditions, such as those described herein.

In certain embodiments, the group —X is a protected amino, hydroxyl or thiol group, preferably a protected hydroxyl group, and the protecting group is a glycan.

Thus, the protected ortho-quinone may be regarded as being glycosylated with the glycan.

Typically, the ortho-quinone is connected through an O-glycoside bond to the anomeric position of a sugar group with the glycan. For example, the ortho-quinone may be connected through an O-glycoside bond between group —X and the anomeric position of a sugar group.

The bond between the glycan and the protected ortho-quinone is cleavable, and preferably enzymatically cleavable. Typically, the bond is cleavable by a glycoside hydrolase.

The glycan may be a saccharide, such as monosaccharide or a polysaccharide, for example as a disaccharide.

The saccharide may be a sugar acid. Thus, the saccharide may possess a carboxylic acid functionality, which may be beneficially used as the site for connection to the group -$L^Q$-, as described below.

The saccharide may be glucuronic acid (e.g. B-glucuronic acid).

In one embodiment, the saccharide is glucuronic acid, connecting to the ortho-quinone at the anomeric position ($C_1$). The glucuronic acid may be β-glucuronic acid.

Where the saccharide is glucuronic acid, the bond between the glucuronic acid and the protected ortho-quinone is cleavable with glucuronidase, such as B-glucuronidase.

In certain embodiments, the group used as the protecting group for —X may form part of a linker for connecting the protected ortho-quinone to a targeting moiety, such as a polypeptide. Thus, the linker may be connected to the protected ortho-quinone via the group —X, which in turn serves to protect group —X, as described below.

In other embodiments, the protected ortho-quinone is not connected to a targeting moiety via group —X. Thus, when the targeting moiety is connected to the protected ortho-quinone, via a linker, at a position other than —X, it will be appreciated that —X may be protected using one of the groups described above, such as a glucuronic acid.

Typically, the protection for the amino, hydroxy and thiol groups is removable to give the amino, hydroxy and thiol groups. Once revealed, self-immolation may occur to remove the protection from the protected ortho-quinone.

In certain embodiments, the protected ortho-quinone comprises an albumin-binding motif.

Preferably, the protected ortho-quinone comprises an albumin-binding motif when the group —X is a protected amino, hydroxyl or thiol group, preferably a protected hydroxyl group, and the protecting group is a glycan, such as glucuronic acid (e.g. β-glucuronic acid).

Albumin-binding motifs are small molecule groups which non-covalently bind to albumin. Such chemical groups are well-known in the art as a means for improving the circulating half-life of therapeutic agents.

Examples of known albumin-binding motifs are described in Zorzi et al., *Medchemcomm.* 2019, 10(7), 1068-1081 and Olesen et al., *Angew. Chem. Int. Ed,* 2000, 59, 7390-7396, the contents of which are incorporated herein by reference.

It will be appreciated that the albumin-binding motif may be attached to the protected ortho-quinone via the group —Ar—, or the group —W— of the protected ortho-quinone.

Thus, for example, the albumin-binding motif may be connected to the protected ortho-quinone through an amide bond formed between an amino (—$NH_2$) substituent group associated with groups —Ar or —W— and a carboxy (—C(O)OH) group of the albumin-binding motif.

Similarly, the albumin-binding motif may be connected to the protected ortho-quinone through a triazole bond formed between an alkynyl substituent group associated with groups —Ar— or —W— and an azide (—$N_3$) group of the albumin-binding motif.

In certain embodiments, the protected ortho-quinone comprises a fibroblast activating protein (FAP)-binding motif.

Preferably, the protected ortho-quinone comprises a FAP-binding motif when the group —X is a protected amino, hydroxyl or thiol group, preferably a protected hydroxyl group, and the protecting group is a glycan, such as glucuronic acid (e.g. β-glucuronic acid).

FAP-binding motifs are small molecule groups which non-covalently bind to FAP. Such chemical groups are well-known in the art as a means for targeting solid tumours.

Examples of known FAP-binding motifs are described in Jansen et al., *J. Med. Chem.,* 2014, 57(7), 3053-3074 and Millul et al., *Proc. Natl. Acad. Sci. USA.,* 2021, 118(16), e2101852118, the contents of which are incorporated herein by reference.

It will be appreciated that the FAP-binding motif may be attached to the protected ortho-quinone via the group —Ar—, or the group —W— of the protected ortho-quinone.

Thus, for example, the FAP-binding motif may be connected the protected ortho-quinone through an amide bond formed between an amino (—$NH_2$) substituent group associated with groups —Ar— or —W— and a carboxy (—C(O)OH) group of the FAP-binding motif, or a sulfamoyl bond formed between a sulfonyl chloride substituent group associated with groups —Ar— or —W— and an amino (—$NH_2$) substituent group of the FAP-binding motif.

Similarly, the FAP-binding motif may be connected to the protected ortho-quinone through a triazole bond formed between an alkynyl substituent group associated with groups —Ar— or —W— and an azide (—$N_3$) group of the FAP-binding motif.

Conjugate

In one aspect of the present invention, there is provided a conjugate comprising a polypeptide, such as a protein, a linker and at least one protected ortho-quinone compound.

The linker serves to connect, such as covalently connect, the at least one protected ortho-quinone compound to the polypeptide. The linker may be cleavable, to release a protected ortho-quinone. Under the local conditions, such as in vivo, the protected ortho-quinone may self-immolate to give the ortho-quinone.

The conjugate may comprise a protein, such as an antibody, that is provided for targeting the protected ortho-quinone, and therefore the ortho-quinone also, to a desired location in vivo. The protein may be selected for its selectivity for certain cell types, such as cancer cells.

The conjugate may have the formula:

$$Z\text{-}(L\text{-}D)_p$$

where:

—Z is a polypeptide,

-L- is a linker,

-D is a protected ortho-quinone compound, as defined herein, and p is an integer from 1 to 8, and the salts, solvates and protected forms thereof.

In certain embodiments, the protected ortho-quinone compound is connected to the linker -L- through the group —X. Here, a hydrogen radical from the —$NH_2$, —OH or —SH groups is formally replaced with a covalent bond to the linker -L-.

In other embodiments, the protected ortho-quinone compound is connected to the linker -L- through either a substituent to the group —Ar—, such as an alkynyl group or $NH_2$, or a substituent to the group —W—, such as an alkynyl group.

Where the protected ortho-quinone compound is connected to the linker -L- through an alkynyl substituent to the group —Ar— or —W—, it will be appreciated that this means via reaction with the alkynyl group, such as via a click reaction between the alkynyl group and a corresponding azide group on the linker to form a triazole linkage.

It will be appreciated that the protected ortho-quinone compound may be connected to the linker -L- through a reaction between other suitable substituent groups to the group —Ar— or —W—, and substituent groups on the linker. For example, through an amide coupling reaction between a substituent to the group —Ar— or —W— and a corresponding amino (—$NH_2$) substituent group on the linker, and vice versa. Here, for example, a hydrogen radical from the —$NH_2$, group is formally replaced with a covalent bond to the linker -L-.

The integer p sets the number of protected ortho-quinone forms that may be connected to a single polypeptide, such as a single antibody. Within the art it is not unusual for a polypeptide to be connected to a plurality of suitably protected active agents, and similarly in the present case, a plurality of protected ortho-quinones may be connected to the polypeptide.

In certain embodiments, p is an integer from 1 to 4. Preferably, p is 1 or 2.

In some embodiments, the conjugate may comprise more than one polypeptide attached to the linker. For example, the conjugate may comprise 2 or more polypeptides attached to the linker.

Polypeptides

A polypeptide may be a protein, as described in further detail below.

In one embodiment, a polypeptide is a linear or cyclic peptide comprising 2-50, preferably 4-30, and more preferably 6-20, contiguous amino acid residues.

Protein

In the context of the present invention, the term "protein" should be construed to cover any protein which has targeting capabilities and so has the ability to deliver a payload to a specific target tissue. Accordingly, "proteins" include antibodies and fragments thereof, albumin and transferrin, as well as any other alternatives known for use in conjugates. Proteins suitable for use in the present invention may be globular proteins.

Additionally, it will also be appreciated that the term "protein" should be construed to cover both natural and non-natural (synthetic) proteins which have targeting capabilities and thus the ability to deliver a payload to a specific target tissue. This will include, for example, de novo designed proteins at the like.

In certain preferred embodiments, the protein is an antibody or a fragment thereof.

The protein or peptide may specifically bind to a target molecule. In some embodiments, they may be a fragment of an antibody that contains at least one target molecule-binding site, lymphokines, hormones, growth factors, or any other cell binding molecule or substance that can specifically bind to a target.

The terms "specifically binds" and "specific binding" refer to the binding of an antibody or other protein, polypeptide or peptide to a predetermined molecule (e.g., an antigen).

Typically, the antibody or other molecule binds with an affinity of at least about $1\times10^7$ $M^{-1}$, and binds to the predetermined molecule with an affinity that is at least two-fold greater than its affinity for binding to a non-specific molecule (e.g., BSA, casein) other than the predetermined molecule or a closely-related molecule.

Antibody

The term "antibody" herein is used in the broadest sense and specifically covers monoclonal antibodies, polyclonal antibodies, dimers, multimers, multispecific antibodies (e.g., bispecific antibodies), multivalent antibodies, antibody fragments and single-domain antibodies (so-called nanobodies), so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cells or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full-length antibody, generally the antigen binding or variable region thereof. Examples of antibody fragments include Fab, Fab', $F(ab')_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

In certain embodiments, the antibody is a monoclonal antibody.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20 (4): 450-459).

The monoclonal antibodies herein specifically include chimeric antibodies, humanized antibodies and human antibodies.

Examples of cell binding agents include those agents described for use in WO 2007/085930, which is incorporated herein.

Tumour-associate antigens and cognate antibodies for use in embodiments of the present invention are listed below, and are described in more detail on pages 14 to 86 of WO 2017/186894, which is incorporated herein.

In one embodiment the antibody is for an antigen target selected from the group consisting of CEA (carcinoembryonic antigen), CD20 (β-lymphocyte antigen CD20), CD44 including CD44v6, CD45 (lymphocyte common antigen), Tenascin including Tenascin-C, MUC1 (Mucin 1), A3 such as melanoma-associated antigen 3 (MAGE-A3), Fibronectin EDA and EDB, VEGF (vascular endothelial growth factor) including VEGF-A, G250 antigen, MC1, GD2, HER2 (human epidermal growth factor receptor 2), CD33 (Siglec-3), CD30 (TNFRSF8), CD22 (cluster of differentiation-22; Siglec-2), CD79b (immunoglobulin-associated beta), Nectin-4 (nectin cell adhesion molecule 4), Trop-2 (Tumor-associated calcium signal transducer 2) and BCMA (B-cell maturation antigen).

Alternatively, in certain embodiments, the antibody is a single-domain antibody (a so-called nanobody). For example, the antibody may be a mesothelin-targeting nanobody, such as those described in Tang et al (2013) Mol Cancer Ther., 12 (4), 416-426 and WO 2020/146182 A2.

Linker

The linker, -L-, is a group that attaches the polypeptide (e.g. antibody), —Z, to one or more protected ortho-quinones, -D.

It will be appreciated that any suitable linker may be used to connect the polypeptide —Z, to the protected quinone, -D.

In certain embodiments, the linker -L- comprises one or more groups that are susceptible to enzymatic cleavage (e.g. proteolytic or peptidase cleavage, such as cathepsin cleavage, sulfatase cleavage or galactosidase cleavage). Thus, in some embodiments, the linker -L- comprises one or more amino-acid residues, dipeptide residues or tripeptide residues, one or more aryl sulfates, one or more aryl galactosides or combinations thereof. Suitably, the linker -L- comprises one or more amino-acid residues, dipeptide residues or tripeptide residues, wherein the amino-acid residues, dipeptide residues or tripeptide residues are as described below.

In certain embodiments, the linker -L- is or comprises one or more groups that are susceptible to chemical cleavage (e.g. a disulfide or a hydrazone).

The linker may also be a non-cleavable linker. Such non-cleavable linkers are well known in the art of antibody drug conjugates.

Thus, in some embodiments, the linker -L- is or comprises one or more groups selected from a $C_1$-$C_{20}$ alkylene, an alkylenediamine moiety, a (poly)ethylene glycol moiety, an amino acid residue and combinations thereof.

In certain embodiments, the linker -L- comprises an albumin-binding motif. Examples of albumin-binding motifs are described above.

Additionally, in some embodiments, the linker -L- comprises a FAP-binding motif. Examples of FAP-binding motifs are described above.

In certain embodiments, the linker is or comprises a group of formula V:

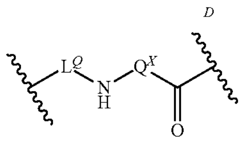

wherein:

-$L^Q$- is a selected from a bond, $C_1$-$C_{10}$ alkylene and $C_2$-$C_{10}$ alkylene containing O or N(H) in the backbone;

-$Q^X$- is an amino-acid residue, a dipeptide, or a tripeptide; and

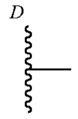

indicates the position where the group of Formula V is attached to a protected ortho-quinone, -D.

The group $L^Q$ may connect directly to the polypeptide —Z. However, preferably it does not do so, and instead forms a connection with a spacer and a binding moiety, which binding moiety provides the connection to the polypeptide. The spacer and the binding moiety are described in further detail below.

Within the linker of formula (V), the group —N(H)— forms part of the amino functionality of an amino acid residue present in -$Q^X$-. The group —C(O)— forms part of the carboxy functionality of an amino acid residue prese in -$Q^X$-.

Where the ortho-quinone is protected with an aminobenzyl group (for example, where —X is $NH_2$), an amide bond is formed between the amino group and the carbonyl of the linker. Where the ortho-quinone is protected with a hydroxybenzyl group (for example, where —X is OH), an ester bond is formed between the hydroxyl group and the carbonyl of the linker. Where the ortho-quinone is protected with a thiobenzyl group (for example, where —X is —SH), a thioester bond is formed between the thio group and the carbonyl of the linker.

The bond connecting the linker to the protected ortho-quinone may be cleavable, and is preferably enzymatically cleavable.

A $C_1$-$C_{10}$ alkylene group may be a linear or branched alkylene, and is preferably linear. The alkylene group is a saturated group.

A $C_1$-$C_{10}$ alkylene group may be $C_{1-6}$ alkylene, such as $C_{1-4}$ alkylene, such as methylene or ethylene.

A $C_1$-$C_{10}$ alkylene group may be $C_{2-6}$ alkylene, such as $C_{2-4}$ alkylene, such as ethylene.

A $C_2$-$C_{10}$ alkylene group alkylene containing O or N(H) in the backbone may be a linear or branched alkylene wherein one or more methylene (—$CH_2$—) groups are replaced with an O or N(H). For example, a $C_4$ alkylene group containing O in the background will be understood to cover groups such as:

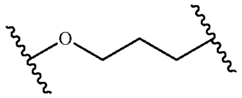
and
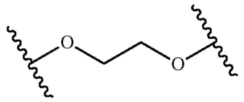

Similarly, a $C_4$ alkylene group containing N(H) in the background will be understood to cover groups such as:

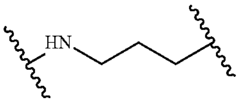
and
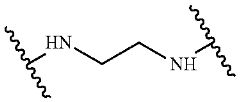

Where two or more heteroatoms are present these are separated by one carbon atom, and preferably two or three carbon atoms.

Suitably, -$L^Q$- is a selected from a bond, $C_1$-$C_{10}$ alkylene and $C_2$-$C_{10}$ alkylene containing O in the backbone.

In some embodiments, -$L^Q$- is a selected from a bond. In other embodiments, -$L^Q$- is a $C_1$-$C_{10}$alkylene or a $C_2$-$C_{10}$alkylene containing O in the backbone. Suitably, -$L^Q$- is a $C_2$-$C_{10}$alkylene containing O in the backbone.

In certain embodiments, the linker is or comprises a group of formula Va:

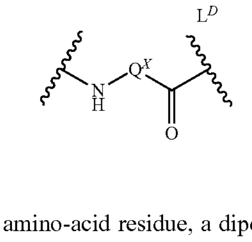

wherein:

-$Q^X$- is an amino-acid residue, a dipeptide or a tripeptide;

-$L^D$- is a group for attachment to the protected quinone, D; and

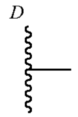

indicates the position where the group of Formula Va is attached to a protected ortho-quinone, -D.

The groups -$Q^X$- and -$L^D$- have the same meanings as for the linkers of formula V.

-$Q^X$—

In one embodiment, -$Q^X$- is an amino acid residue. The amino acid may be a natural amino acid or a non-natural amino acid.

In one embodiment, -$Q^X$- is selected from: Phe, Lys, Val, Ala, Cit, Leu, Ile, Arg, and Trp, where Cit is citrulline.

In one embodiment, -$Q^X$- is a dipeptide residue. The amino acids in the dipeptide may be any combination of natural amino acids and non-natural amino acids. In some embodiments, the dipeptide comprises natural amino acids.

Where the linker is a cathepsin labile linker, the dipeptide is the site of action for cathepsin-mediated cleavage. The dipeptide then is a recognition site for cathepsin.

In one embodiment, -$Q^X$- is selected from the group consisting of:

$^{NH}$-Phe-Lys-$^{C=O}$,
$^{NH}$Val-Ala-$^{C=O}$,
$^{NH}$Val-Lys-$^{C=O}$,
$^{NH}$Ala-Lys-$^{C=O}$,
$^{NH}$-Val-Cit-$^{C=O}$,
$^{NH}$-Phe-Cit-$^{C=O}$,
$^{NH}$-Leu-Cit-$^{C=O}$,
$^{NH}$-Ile-Cit-$^{C=O}$,
$^{NH}$-Phe-Arg-$^{C=O}$, and
$^{NH}$-Trp-Cit-$^{C=O}$;

where Cit is citrulline, and NH and C═O are the amino and carboxy terminals of the amino acid residues, which are present as —N(H)— and —C(O)— in the linker of formula V.

Preferably, -$Q^X$- is selected from the group consisting of:

$^{NH}$-Phe-Lys-$^{C=O}$,
$^{NH}$-Val-Ala-$^{C=O}$,
$^{NH}$-Val-Lys-$^{C=O}$,
$^{NH}$-Ala-Lys-$^{C=O}$, and
$^{NH}$-Val-Cit-$^{C=O}$.

Most preferably, -$Q^X$- is selected from $^{NH}$-Phe-Lys-$^{C=O}$, $^{NH}$-Val-Cit-$^{C=O}$ or $^{NH}$-Val-Ala-$^{C=O}$.

Other dipeptide combinations of interest include:

$^{NH}$-Gly-Gly-$^{C=O}$,
$^{NH}$-Pro-Pro-$^{C=O}$, and
$^{NH}$-Val-Glu-$^{C=O}$.

Other dipeptide combinations may be used, including those described by Dubowchik et al., *Bioconjugate Chemistry,* 2002, 13, 855-869, which is incorporated herein by reference.

In some embodiments, -$Q^X$- is a tripeptide residue. The amino acids in the tripeptide may be any combination of natural amino acids and non-natural amino acids. In some embodiments, the tripeptide comprises natural amino acids.

Where the linker is a cathepsin labile linker, the tripeptide is the site of action for cathepsin-mediated cleavage. The tripeptide then is a recognition site for cathepsin.

References to amino acids and amino acid residues are generally intended as references to α-amino acids.

An amino acid side chain may be chemically protected, where appropriate. Protected amino acid sequences may be enzymatically cleavable. For example, a dipeptide sequence comprising a Boc side chain-protected Lys residue is cleavable by cathepsin.

Protecting groups for the side chains of amino acids are well known in the art and are described in the Novabiochem Catalog.

-L-

It will be understood that the linker, -L-, preferably comprises a "protein binding moiety", $-L^1-$ and a "protected ortho-quinone binding moiety", $-L^2$—. The protein binding moiety, $-L^1-$, being the part of the linker that attaches to the polypeptide (e.g. antibody) and the "protected ortho-quinone binding moiety", $-L^2-$ being the part of the linker that attaches to the protected ortho-quinone. The "protein binding moiety", $-L^1-$ and the "protected ortho-quinone binding moiety", $-L^2-$ are preferably separated by a spacer, —S—.

Thus, the linker, -L-, preferably is of formula:

$$-L^1\text{-}S\text{-}L^2-$$

wherein:

$-L^1-$ is a polypeptide (e.g. antibody) binding moiety;

$-L^2-$ is a protected ortho-quinone binding moiety; and

—S— is a spacer.

Preferably, $-L^2-$ is a group of formula V, as defined above, where the group $-L^Q-$ within the group of formula V is connected to the spacer —S—.

It will be appreciated that the spacer, —S—, may be any group that is capable of linking together, and spacing apart, the protein binding moiety, $-L^1-$, and the protected ortho-quinone binding moiety, $-L^2-$.

Additionally, it will be appreciated that when the conjugate comprises 2 or more protected ortho-quinones, -D, each protected ortho-quinone, -D, may be attached via the protected ortho-quinone binding moiety, $-L^2-$. Similarly, if the conjugate comprises 2 or more polypeptides, Z, each polypeptide, Z, may be attached via the polypeptide (e.g. antibody) binding moiety, $-L^1-$.

In certain embodiments, the spacer, —S—, is a bond.

In other embodiments, the spacer, —S—, is or comprises one or more groups selected from $C_1$-$C_{20}$ alkylene, an alkylenediamine moiety, a (poly)ethylene glycol moiety, an amino acid residue, and combinations thereof.

It will be understood that $-L^1-$, the polypeptide (e.g. antibody) binding moiety, can be any functional group that is capable of linking the polypeptide (e.g. antibody) to the linker. The polypeptide (e.g. antibody) binding moiety $L^1$ is thus a functional grouping that is capable of forming a covalent attachment to sulfur atoms present on the polypeptide (e.g. antibody). Suitably, the sulfur atoms are sulfur atoms from cysteine residues on an antibody, and more suitably, sulfur atoms from cysteine residues from reduced interchain disulfide bonds of an antibody.

Functional linking groups capable of linking the polypeptide (e.g. antibody) to the linker in this way are well known in the art. Thus, the skilled person will be able to select suitable functional linking groups to use with the invention. Examples of suitable functional linking groups, $-L^1-$, include, for instance, those described in, for example, Xu 2021 (ChemRxiv. Cambridge: Cambridge Open Engage; 2021, 1-17), Stieger 2021 (Angew. Chemie Int. Ed., 2021, 60, 1-7), Walsh 2019 (Chem. Sci., 2019, 10, 694-700), Walsh 2020 (Org. Biomol. Chem., 2020, 18, 4224-4230), Badescu 2014 (Bioconjug. Chem., 2014, 25, 1124-1136), Koniev 2018 (Medchemcomm, 2018, 9, 827-830), Robinson 2017 (RSC Adv., 2017, 7, 9073-9077), Behrens 2015 (Mol. Pharm., 2015, 12, 3986-3998) and WO2019/011078.

It will be understood that $-L^1-$ may form one or more covalent attachments to the polypeptide (e.g. antibody).

In certain embodiments, $-L^1-$ is selected from one of the functional linking groups shown below:

Formula Xa

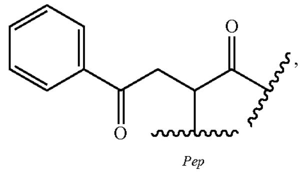

Formula Xb

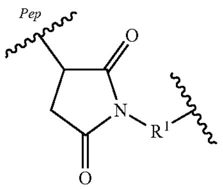

Formula Xc

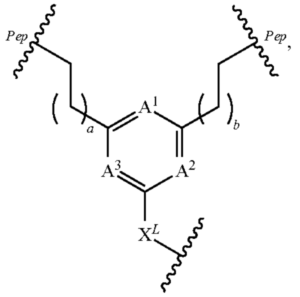

Formula Xd

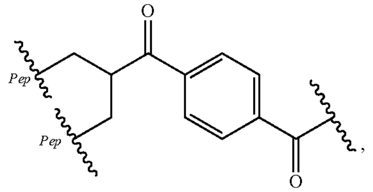

Formula Xe

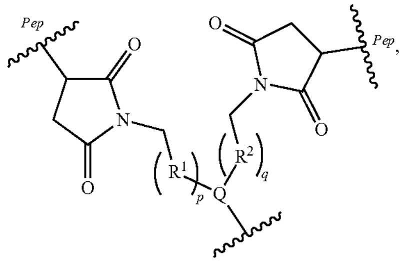

Formula Xf

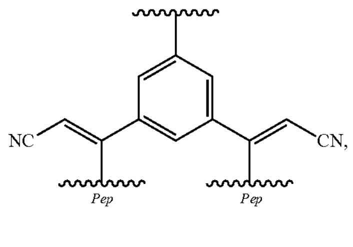

-continued

Formula Xg

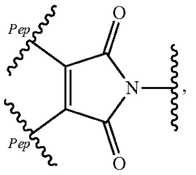

Formula Xh

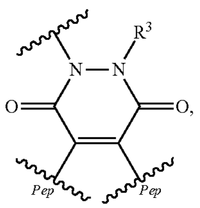

Formula Xi

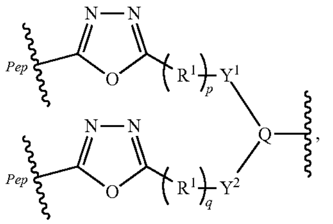

Formula Xj

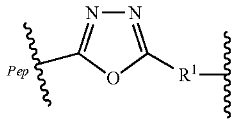

Formula Xk

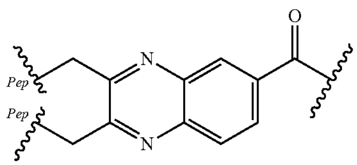

wherein:

- one or two of $A^1$, $A^2$ and $A^3$ are N and the other one or two of $A^1$, $A^2$ and $A^3$ are CH, or all three of $A^1$, $A^2$ and $A^3$ are N or C;
- a and b are integers selected from 0 or 1; —$X^L$— is selected from —N(H)—, —N($R^N$)—, —O— and —S—, wherein —$R^N$ is $C_{1-2}$ alkyl;
- —$R^1$— and —$R^2$— are independently selected from $C_{1-6}$ alkylene and $C_{1-6}$ alkylene containing O in the backbone;
- —$R^3$ is selected from hydrogen and $C_{1-4}$ alkyl;
- —$Y^1$— and —$Y^2$— are independently absent (covalent bond) or selected from —O—, —N($R^4$)—, —C(═O)—, —C(═O)N($R^4$)— and —N($R^5$)C(═O)—;
- p and q are independently integers selected from 0 or 1;
- Q is $CR^6$, N or aryl;
- —$R^4$, —$R^5$ and —$R^6$ are independently selected from hydrogen and $C_{1-4}$ alkyl; and

indicates the position where the moiety is linked to the polypeptide (e.g. antibody), either directly or indirectly.

In certain embodiments, two of A1, A2 and A3 are N (e.g. A1 and A2 are N) and the other of A1, A2 and A3 is CH (e.g. A3 is CH). Suitably, in this embodiment, integers a and b are 1.

In other embodiments, all three of A1, A2 and A3 are N. Suitably, in this embodiment, integers a and b are 1.

In some embodiments, one of $A^1$, $A^2$ and $A^3$ is N (e.g. $A^3$ is N) and the other two of $A^1$, $A^2$ and $A^3$ are CH (e.g. $A^1$ and $A^2$ are CH). Suitably, in this embodiment, integers a and b are 0.

Suitably, —$X^L$— is —N(H)— or —O—. Most suitably, —$X^L$— is —N(H)—.

In certain embodiments, —$R^1$ and —$R^2$ are independently selected from $C_{1-6}$ alkylene. Suitably, —$R^1$ and —$R^2$ are each independently $C_{1-4}$ alkylene.

In some embodiments, —$R^3$ is a $C_{1-4}$ alkyl (e.g. a methyl group).

In some embodiments, —$Y^1$— and —$Y^2$— are independently absent or selected from —O—, —N($R^4$)— and —C(═O)—. Suitably, —$Y^1$— and —$Y^2$— are independently absent.

Suitably, Q is $CR^6$ or N. In some embodiments, Q is $CR^6$. In other embodiments, Q is N.

In some embodiments, —$R^4$, —$R^5$ and —$R^6$ are independently selected from hydrogen and methyl. Suitably, —$R^4$, —$R^5$ and —$R^6$ are each hydrogen.

In certain preferred embodiments, -$L^1$- is selected from one of the functional linking groups shown below:

Formula Xa

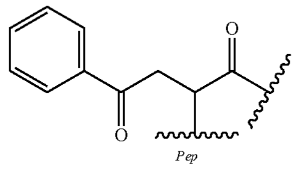

Formula Xb

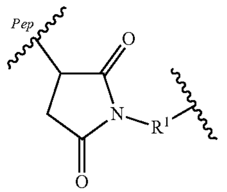

Formula Xc

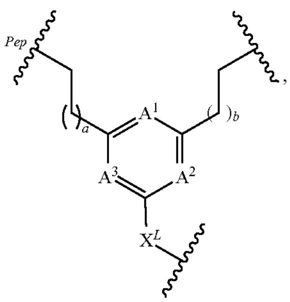

-continued

Formula Xd

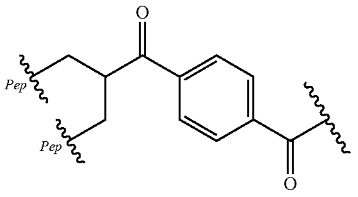

wherein —$R^1$, $A^1$, $A^2$, $A^3$, —$X^L$—, a, b, and

are as defined above.

Preferably, -$L^1$- is a functional linking groups of Formula Xa or Xb.

Most preferably, -$L^1$- is a functional linking groups of Formula Xa.

Thus, in certain preferred embodiments, the linker, -L, is a group of formula Vc shown below:

Formula Vc

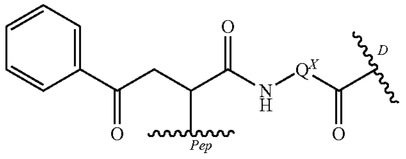

wherein:

each of -$Q^X$—,

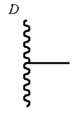

and

are as defined above.

-$L_2$- is a protected ortho-quinone binding moiety. Thus, it will be understood that -$L_2$- is a moiety (functional group) formed from reaction of the group —X or a substituent to the group —Ar— or —W— and the spacer, —S—.

Additional Active Agents

In certain embodiments, a conjugate of the protected ortho-quinone and a polypeptide, such as an antibody, may also comprise one or more other active agents, such as one or more drug molecules.

Examples of drug molecules include a cytotoxic payload or a therapeutic compound, peptide or polypeptide. In particular, the drug is a cytotoxin.

Preferably the cytotoxin is a biologically active cytotoxic material. The cytotoxin may be selected from the group comprising exatecan (in particular exatecan mesylate), auristatins, maytansinoids, tubulysins, calicheamicins, duocarmycins, pyrrolobenzodiazepines (in particular pyrrolobenzodiazepine dimers), camptothecin analogues and doxorubicin.

In certain embodiments, the cytotoxin is exatecan.

However, additionally or alternatively, the cytotoxin could also be selected from other known cytotoxins including ricin subunits and other peptide based cytotoxic materials, although such materials are less commonly utilised in the field of the art.

It will be appreciated that the one or more active agents may be connected to, such as covalently connected to, the polypeptide via the linker or via the protected ortho-quinone.

Thus, it will be understood that the one or more active agents may be connected to, such as covalently connected to via the group —X, the group —Ar—, or the group —W— of the protected ortho-quinone.

Thus, for example, the one or more active agents (such as exatecan) may be connected through an amide bond formed between a carboxy substituent group associated with groups —Ar— or —W— via an amide coupling reaction with an amino (—$NH_2$) group associated with the one or more active agents (such as the —$NH_2$ group in exatecan).

Covalently attaching active agents, such as those mentioned above, to such conjugate molecules is well-known and routine in the art. Thus, the skilled person would readily be able to select appropriate conditions for covalently attaching the one or more active agents to the polypeptide via either the linker or via the protected ortho-quinone.

In certain embodiments, the one or more active agents are connected to the polypeptide via the linker.

Methods for Preparing a Protected Quinone

The present invention also provides a method for preparing a protected ortho-quinone.

The method involves reacting an ortho-quinone, as described herein, with a protecting group:

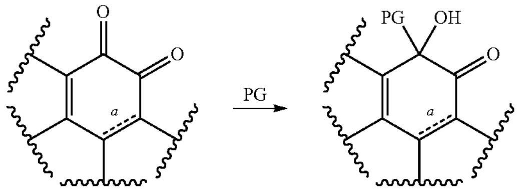

where a is a double bond and PG is a protecting group, as described above.

In certain embodiments, the protecting group is a para-aminobenzyl group or a para-hydroxybenzyl group. Thus, in some embodiments, the method involves reacting an ortho-quinone, as described herein, with a para-(halomethyl)aminobenzene group, a para-(halomethyl) hydroxybenzene group or a protected form thereof:

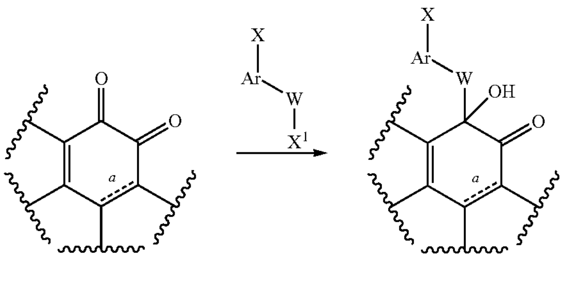

where —Ar, —X, —W— and a are each as defined herein, and —$X^1$ is a halo group.

In certain embodiments, —$X^1$ is —O-GL, where GL is a glycan, such as a glucuronic acid (e.g. β-glucuronic acid).

Methods for Preparing a Conjugate

The present invention also provides a method for preparing a conjugate.

The method involves reacting a protected ortho-quinone with a linker group, -L-, before reacting the product of this reaction with a targeting agent, such as a polypeptide (e.g. antibody).

Thus, the method involves attaching, such as covalently attaching, the protected ortho-quinone to a targeting agent (e.g. polypeptide) via a linker group, -L-. More specifically, the method involves attaching, such as covalently attaching, the protected ortho-quinone to a targeting agent (e.g. polypeptide) via thiol groups (sulfur atoms) of a cysteine residue in the targeting agent (e.g. polypeptide).

In certain embodiments, the method involves attaching, such as covalently attaching, the protected ortho-quinone to a targeting agent (e.g. polypeptide) via thiol groups (sulfur atoms) of a cysteine residue in the targeting agent (e.g. polypeptide) that are involved in the interchain disulfide bonds.

The linker, -L- and polypeptide may be any linker or polypeptide as defined herein.

Functional linking groups capable of linking the polypeptide (e.g. antibody) to the linker in this way are well known in the art. Thus, the skilled person will be able to select suitable functional linking groups to use with the invention. Examples of suitable functional linking groups, -$L^1$-, include, for instance, those described in, for example Xu 2021 (ChemRxiv. Cambridge: Cambridge Open Engage; 2021, 1-17), Stieger 2021 (Angew. Chemie Int. Ed., 2021, 60, 1-7), Walsh 2019 (Chem. Sci., 2019, 10, 694-700), Walsh 2020 (Org. Biomol. Chem., 2020, 18, 4224-4230), Badescu 2014 (Bioconjug. Chem., 2014, 25, 1124-1136), Koniev 2018 (Medchemcomm, 2018, 9, 827-830), Robinson 2017 (RSC Adv., 2017, 7, 9073-9077), Behrens 2015 (Mol. Pharm., 2015, 12, 3986-3998) and WO2019/011078.

Methods for the preparation of a conjugate are well known in the art. Thus, the skilled person will be able to readily select the appropriate reaction conditions and choice of linker, -L-, to use when forming a conjugate.

Thus, in the description of the synthetic methods described herein and in any referenced synthetic methods that are used to prepare the protected ortho-quinone or conjugate of the invention, it is to be understood that all proposed reaction conditions, including choice of solvent, reaction atmosphere, reaction temperature, duration of the experiment and workup procedures, can be selected by a person skilled in the art.

It is also understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

Salts, Solvates and Other Forms

Examples of salts of the compounds (e.g. protected ortho-quinone compounds or conjugates) of the invention include all pharmaceutically acceptable salts, such as, without limitation, acid addition salts of strong mineral acids such as HCl and HBr salts and addition salts of strong organic acids such as a methanesulfonic acid salt. Further examples of salts include sulphates and acetates such as trifluoroacetate or trichloroacetate.

A reference to a compound described herein, is also a reference to a solvate of that compound. Examples of solvates include hydrates.

A compound described herein, includes a compound where an atom is replaced by a naturally occurring or non-naturally occurring isotope. In one embodiment the isotope is a stable isotope. Thus a compound described here includes, for example deuterium containing compounds and the like. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Certain compounds, may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, $OCH_3$, is not to be construed as a reference to its structural isomer, a hydroxymethyl group, $CH_2OH$. Similarly, a reference to ortho-chlorophenyl is not to be construed as a reference to its structural isomer, meta-chiorophenyl. However, a reference to a class of structures may well include structurally isomeric forms falling within that class (e.g., $C_{16}$alkyl includes n-propyl and iso-propyl; butyl includes n, iso-, sec-, and tert-butyl; methoxyphenyl includes ortho-, meta-, and para-methoxyphenyl).

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

One aspect of the present invention pertains to compounds in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Protected Forms

Compounds of the invention, such as the conjugate of the invention, may be provided in a protected form. Here, reactive functionality, such as amino functionality, may be masked in order to prevent its reaction during a synthesis step. A protecting group is provided to mask the reactive functionality, and this protecting groups may be removed at a later stage of the synthesis to reveal the original reactive functionality.

For example, amino, hydroxyl, carboxyl and thiol functionality present in the conjugate may be protected with a protecting group, such as described herein.

In one embodiment, the protected form is a compound where amino, hydroxyl, thiol, and/or carboxyl functionality is protected (masked) by a protecting group. In one embodiment, the protected form is a compound where the side chain functionality of the amino acids residues with the compound are protected.

Protecting groups, such as those for amino acid residues, are well known and well described in the art.

Amino acids having side group protection, optionally together with amino and carboxy protection, are commercially available. Thus, a protected conjugate compound may be prepared from appropriately protected amino acid starting materials.

Where a protecting group is used it is removable under conditions that do not substantially disrupt the structure of the conjugate, for example conditions that do not alter the stereochemistry of the amino acid residues, or do not cause release of the protected ortho-quinone.

In one embodiment, the protecting groups are acid-labile, base labile, or are removable under reducing conditions.

Example protecting groups for amino functionality include Boc (tert-butoxycabonyl), Bn (benzyl, Bzl), CbZ (Z), 2-CL-Z (2-chloro), Dde (1-[4,4-dimethyl-2,6-dioxocylcohex-1-ylidene]-3-methylbutyl), Fmoc (fluorenylmethyloxycarbonyl), $HSO_3$-Fmoc (sulfonylated Fmoc, such as 2-sulfo-Fmoc, as described in e.g. Schechter et al, *J. Med Chem* 2002, 45 $(19)_{4264}$), ivDde (1-[4,4-dimethyl-2,6-dioxocylcohex-1-ylidene]ethyl), Mmt (4-methoxytrityl), Mtt (4-methyltrityl), Nvoc (6-nitroveratroyloxycarbonyl), and Tfa (trifluroacetyl).

Example protecting groups for aromatic nitrogen functionality includes Boc, Mtt, Trt and Dnp (dinitrophenyl).

In one embodiment, the protecting group for amino functionality is selected from Boc, CbZ, Bn and Fmoc and $HSO_3$-Fmoc.

In one embodiment, the protecting group for amino functionality is Boc, Fmoc or CbZ.

Example protecting groups for hydroxyl functionality include Trt (trityl), Bn (benzyl), tBu (tert-butyl), and 2-acetamido-2-deoxy-3,4,6-tri-O-acetyl-a-galactopyranosyl.

In one embodiment, the protecting group for amino functionality is Trt.

Further example protecting groups include silyl ether protecting groups, such as TMS, TES, TBS, TIPS, TBDMS, and TBDPS, and ethers such as THP. Such protecting groups are removable with TBAF, for example.

Example protecting groups for carboxyl functionality include Bn (benzyl, Bz), tBu (tert-butyl), TMSET (trimethylsilylethyl) and Dmab ({1-[4,4-dimethyl-2,6-dioxocylcohex-1-ylidene]-3-methylbutyl}amino benzyl).

Example protecting groups for aromatic nitrogen functionality includes Boc, Mtt, Trt and Dnp (dinitrophenyl).

In some embodiments, only some types of functionality are protected. For example, only amino groups may be protected, such as amino groups in the side chain of an amino acid residue.

In one embodiment, amino groups and hydroxyl groups are protected.

Pharmaceutical Composition

In another aspect of the present invention, there is provided a pharmaceutical composition comprising a protected ortho-quinone or a conjugate as defined herein.

Pharmaceutical compositions according to the present invention, and for use in accordance with the present invention, may comprise, in addition to the active ingredient, i.e. a protected ortho-quinone or a conjugate of the invention, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Thus, the present invention provides a pharmaceutical composition comprising a protected ortho-quinone or a conjugate and a carrier, excipient or diluent.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Methods of Treatment and Diagnosis

The invention provides a protected ortho-quinone, a conjugate and a composition for use in a method of treatment or diagnosis.

It will be understood that the method of treatment comprises administering to a subject in need of treatment a therapeutically-effective amount of a protected ortho-quinone, a conjugate or a composition according to the invention.

The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A protected ortho-quinone, a conjugate or a composition of the present invention may be administered alone or in combination with other treatments, either simultaneously or sequentially dependent upon the condition to be treated. Examples of treatments and therapies include, but are not limited to, chemotherapy (the administration of active agents, including, e.g. drugs); surgery; and radiation therapy.

The protected ortho-quinone, conjugate and composition of the invention can be used to treat proliferative disease, amongst others.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukaemias, psoriasis, bone diseases, fibroproliferative disorders (e.g. of connective tissues), and atherosclerosis. Other cancers of interest include, but are not limited to, haematological; malignancies such as leukaemias and lymphomas, such as non-Hodgkin lymphoma, and subtypes such as DLBCL, marginal zone, mantle zone, and follicular, Hodgkin lymphoma, AML, and other cancers of B or T cell origin. Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Of particular relevance to the present invention are methods for the treatment of a cancer selected from the group consisting of leukaemia, hepatocellular carcinoma, colon, breast, lung, pancreatic and prostate cancers. Of specific relevance to the present invention are methods for the treatment of a cancer selected from the group consisting of leukaemia, breast, lung (e.g. non-small cell lung cancer), pancreatic and prostate cancers.

The present invention also provides for the treatment of a cancer selected from colon, breast, lung such as non-small cell lung (NSCLC), prostate, liver, such as hepatocellular carcinoma, and pancreatic, such as pancreatic adenocarcinoma.

The present invention also provides the use of a protected ortho-quinone, conjugate or composition in a method of treating a disease associated with over-expression of NAD(P)H: Quinone Oxidoreductase 1 (NQO1).

In one embodiment the protected ortho-quinone, a conjugate and a composition are for use in the treatment of leukaemia, such as acute myeloid leukaemia (AML).

A leukaemia for treatment may be selected from a lymphoblastic leukaemia or a myeloid leukaemia, such as selected from the group consisting of acute lymphoblastic leukaemia, chronic myeloid leukaemia, chronic lymphocytic leukaemia and acute myeloid leukaemia (AML).

In one embodiment the leukaemia is acute myeloid leukaemia (AML).

Alternatively, in other embodiments, the protected quinone, a conjugate and a composition are for use in the treatment of pancreatic cancer, such as pancreatic ductal adenocarcinoma (PDAC).

In certain embodiments, protected ortho-quinones, conjugates and compositions of the invention can be used to treat microbial infections, such as bacterial infections. For example, the conjugates can be used to treat bacterial diseases, such as tuberculosis (TB) and methicillin-resistant *Staphylococcus aureus* (MRSA).

The present invention also provides for the use of the protected ortho-quinones, conjugates and compositions in methods of treating parasitic infections.

It will also be understood that features, including optional, suitable, and preferred features in relation to any one of the aspects of the present invention detailed above (e.g. the protected quinones, conjugates and compositions of the present invention) may also be features, including optional, suitable and preferred features in relation to any other aspects of the invention (e.g. the uses of the protected quinones, conjugates and compositions of the present invention).

The present case is not limited to the use of the conjugates and protected ortho-quinones to methods of treatment.

The conjugates and protected ortho-quinones may also be used in methods of diagnosis. Here, an ortho-quinone may be spectroscopically active, and is preferably spectroscopically active as an ortho-quinone whilst its protected ortho-quinone form is not.

Dosage

Generally, the methods of the invention may comprise administering to a subject an effective amount of a conjugate or a protected ortho-quinone.

It will be appreciated by one of skill in the art that appropriate dosages of the conjugate or the protected ortho-quinone, and compositions comprising the conjugate or the protected ortho-quinone, can vary from patient to patient. Determining the optimal dosage will generally involve the balancing of the level of therapeutic benefit against any risk or deleterious side effects. The selected dosage level will depend on a variety of factors including, but not limited to, the activity of the particular conjugate, the protected ortho-quinone or the ortho-quinone itself, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of the conjugate or the protected ortho-quinone and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Kits

One aspect of the invention pertains to a kit comprising (a) the conjugate or the protected ortho-quinone, or a composition comprising the conjugate or the protected ortho-quinone, e.g., preferably provided in a suitable container and/or with suitable packaging; and (b) instructions for use, e.g., written instructions on how to administer the compound or composition.

The written instructions may also include a list of indications for which the conjugate or the protected ortho-quinone is a suitable treatment.

Routes of Administration

A conjugate or a protected ortho-quinone, or a pharmaceutical composition comprising the conjugate or the protected ortho-quinone may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orang-utan, gibbon), or a human. Furthermore, the subject/patient may be any of its forms of development, for example, a foetus.

In one preferred embodiment, the subject/patient is a human.

It is also envisaged that the invention may be practised on a non-human animal having a microbial infection. A non-human mammal may be a rodent. Rodents include rats, mice, guinea pigs, chinchillas and other similarly-sized small rodents used in laboratory research.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described. Where technically appropriate embodiments may be combined and thus the disclosure extends to all permutations and combinations of the embodiments provided herein.

Certain aspects and embodiments of the invention will now be illustrated by way of example and with reference to the figures described above.

Results

Synthesis of Self-Immolative Quinone Models

Figure 2A:
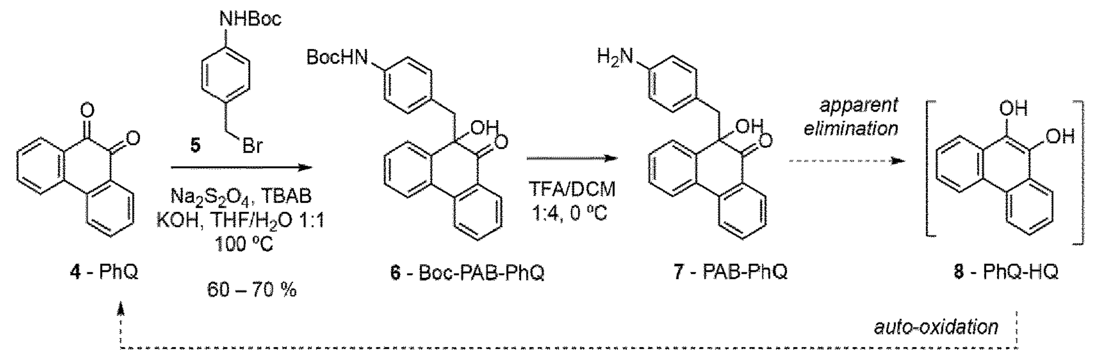
FIG. 2 shows the synthesis of para-aminobenzyl phenanthrene-ketol and its elimination characteristics and protection of medicinally-relevant ortho-quinones as para-aminobenzyl ketols. a, Sodium-dithionite-mediated reductive alkylation of 9,10-phenanthrenequinone (PhQ), 4, with Boc-para-aminobenzyl bromide 5 in a two-phase water/THF system generates benzyl ketol product 6 in 60-70% yield. Upon deprotection of N-Boc, compound 7 is unstable and eliminates to release quinone 4 and a linker by-product via the hydroquinone intermediate 8. b, and c, kinetics of consumption of 7 and formation of 4 were measured by $^1H$ NMR spectroscopy in moderately acidic solution (ca. pH 6). d, Structures of β-lapachone 'BL' 1, 3-hydroxy-β-lapachone 'HBL' 11, dunnione 'DN' 12 and cryptotanshinone 'CTN' 13. e, Protection of ortho-quinones 1, 11, 12 and 13 as benzyl ketol derivatives. Upon deprotection the derivatives eliminate to reform the quinones.
Figure 2B:
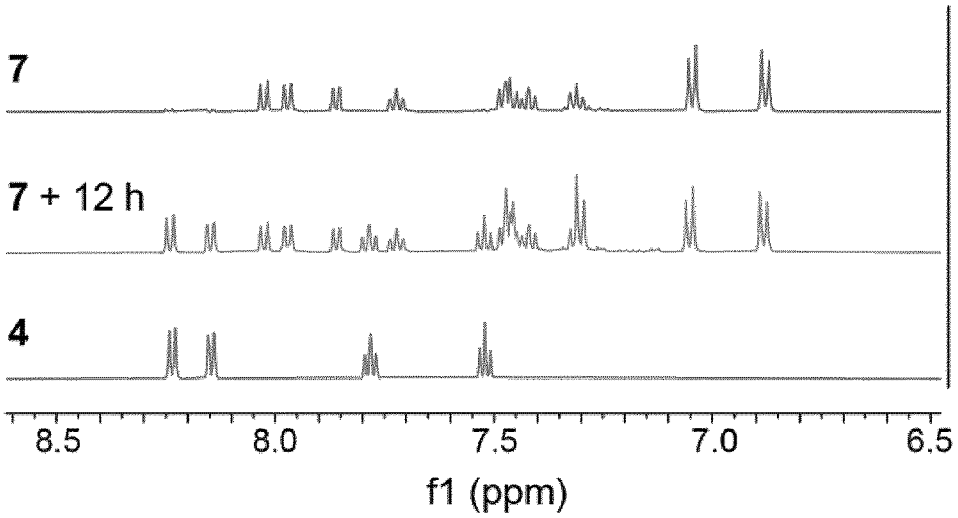

The synthesis of model derivatives of quinones that fragment upon removal of a protecting group was investigated using 9,10-phenanthrenequinone ('PhQ') 4 (FIG. 2*a*). The stability of 6 was tested following N-Boc deprotection to give para-aminobenzyl phenanthrene-ketol ('PAB-PhQ'), 7, and as it was consumed, formation of quinone 4 was observed (FIG. 2*b*).

Figure 2C:
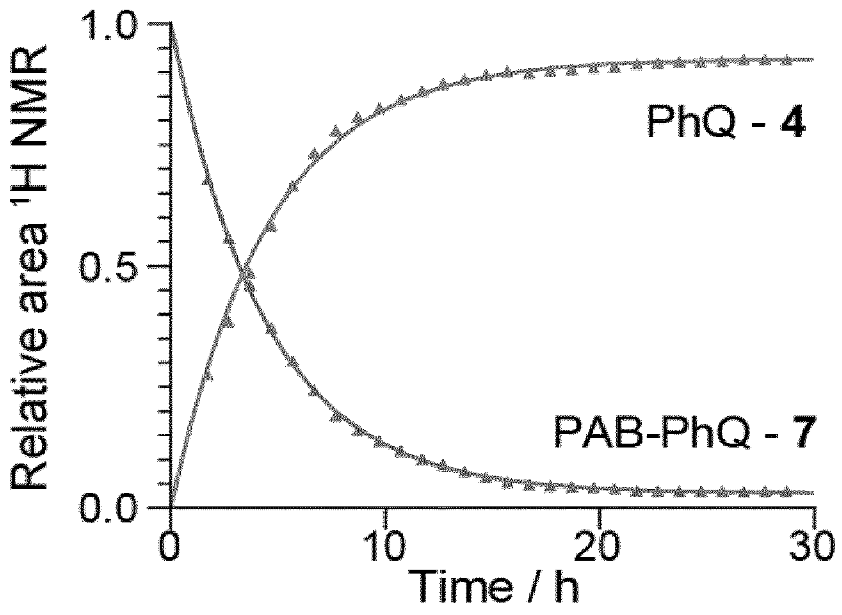

Complete consumption of 7 and formation of 4 was confirmed by $^1H$ NMR spectroscopy. Appearance of 4 proceeded with a half-life ($t_{1/2}$) of 2.94±0.08 h at 25° C. in a moderately acidic methanolic solution with complete release within 20 h. Data fitting suggested that release followed first-order kinetics and the rate of consumption of 7 ($K_{obs}$=6.18±0.12×$10^{-5}$ $s^{-1}$) was consistent with the rate of formation of product 4 ($K_{obs}$=6.55±0.22×$10^{-5}$ $s^{-1}$, FIG. 2*c*).

Generality of C—C Bond Elimination Reaction to Ortho-Quinones

Figure 2D:
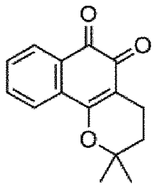
Figure 2D:
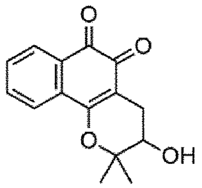
Figure 2D:
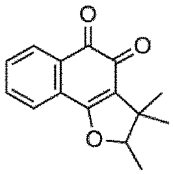
Figure 2D:
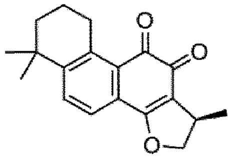

The work above was also applied to additional ortho-quinones (FIG. 2*d,e*). From β-lapachone 1, (FIGS. 1*a*, 2*e*)N-Boc-protected para-aminobenzyl β-lapa-ketol ('Boc-PAB-BL') 9 could be synthesised under identical conditions in similar yield. N-Boc deprotection of 9 gave ('PAB-BL') 10, which was observed to be unstable under acidic conditions and eliminated to reform 1 via hydroquinone intermediate 2 (FIG. 2*e*).

Figure 2E:
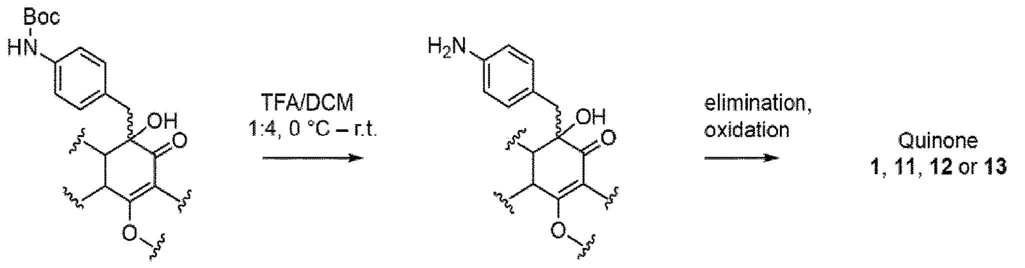

Three additional medicinal ortho-quinones, (±)-3-hydroxy-β-lapachone ('HBL') 11, (±)-Dunnione ('DN') 12, and cryptotanshinone ('CTN') 13 (FIG. 2*d*), were also successfully converted into their corresponding PAB-ketol analogues as diastereoisomeric mixtures (14-16, FIG. 2*e*). In the case of HBL, an intermediate hydroxyl protection and the use of an indium (0) mediated Barbier reaction were required to achieve Boc-PAB-HBL 11. In all cases, the removal of the Boc protecting group in acidic media led to reformation of their respective ortho-quinone precursors (17-19 to 11-13, FIG. 2*e*). These investigations validated the generality of the methodology for a number of medicinally relevant ortho-quinones with structural similarity to 4.

Figure 3A:
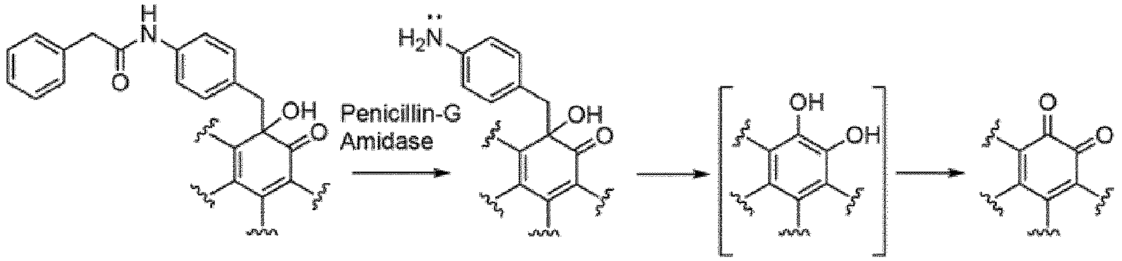
FIG. 3 shows the experimental analysis of the kinetics and pH-rate dependence of elimination. a, Amidase releasable models to test elimination kinetics in buffered aqueous solution of protected and unprotected benzyl ketol species. b, i, Formation rate of 4 from 21 with and without Penicillin-G amidase incubation at pH 7.4 and 37° C. Data are presented as mean values±SEM, n=3, from one representative experiment. ii, Example HPLC trace showing 7 and 4 after 21 was treated with Penicillin-G amidase at pH 7.4 and 37° C. Time=0 h timepoint taken 5 min after enzyme addition. c, Experimental elimination rate $K_{obs}$VS PH dependence of elimination of PAB-PhQ 7, PAB-BL 10 and PAB-DN 18, with data presented as calculated $K_{obs}$ value from representative experiment ±95% Cl.

Determination of pH-Dependent Elimination Profiles of Benzyl Ketol Derivatives by Reaction Kinetics To experimentally determine the rate-pH dependence of the elimination and the critical reaction parameters in aqueous solution, models protected with a Penicillin-G amidase cleavable phenylacetamide group were synthesised (Chem. Eur. J., 2007, 13, 4523-4528). Addition of Penicillin-G amidase to the protected models triggered amide hydrolysis and formation of the desired para-aminobenzyl ketol in neutral aqueous solution (FIG. 3*a*).

Figure 3B:
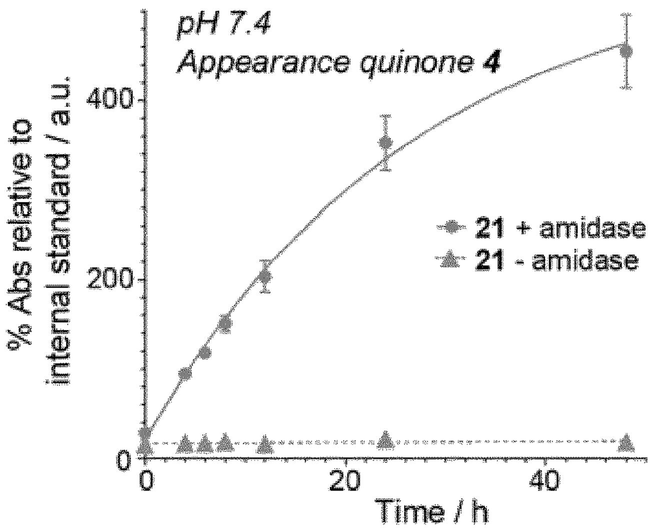
Figure 3B:
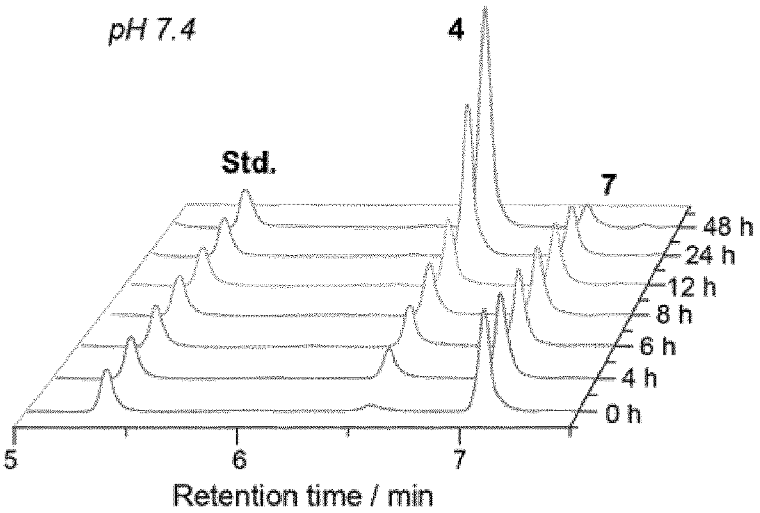

With this strategy, it was shown that at physiological pH and temperature (pH 7.4, 37° C.), formation of PhQ 4 occurred at rate $K_{obs}$=1.15 (±0.66)×$10^{-5}$ $s^{-1}$ following addition of the enzyme to 21. Intermediate 7, PAB-PhQ, could be identified (FIG. 3*b*) and elimination of 7 occurred at rate $K_{obs}$=9.72 (±2.88)×$10^{-6}$ $s^{-1}$. Without added enzyme, 21 was stable and formation of 4 negligible. HQ 8 was not observed by $^{1}$H-NMR spectroscopic analysis of non-degassed solutions, suggesting that in oxygenated aqueous solution the intermediate has a very short $t_{1/2}$ relative to that of species 7.

Figure 3C:
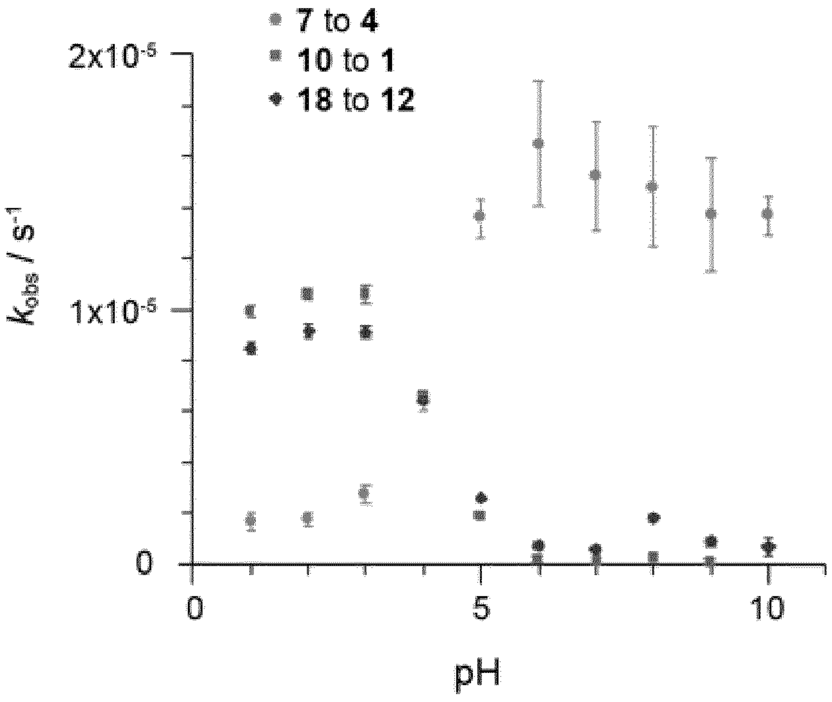

As enzyme-mediated amide hydrolysis was fast (<5 min), immediate kinetic analysis of the subsequent elimination rate was possible without use of acidic or basic deprotection reagents, thus allowing control of pH. Focusing on the phenanthrenequinone, β-lapachone and dunnione derivatives, elimination from 7, 10 and 18 generated enzymatically from 21, 22 and the (R,R/S,S) pair of enantiomers of 23 respectively, was followed across a range of pH values at 37° C. (FIG. 3*c*).

Compound 7 tended to show acid-promoted elimination, which peaks at pH 5-6. The elimination rate of PAB-BL 10 was even more acid-dependent relative to 7 (FIG. 3*c*). Negligible elimination resulting in formation of 1 occurred at pH ≥6 within 72 h, and the rate peaked at pH 3. For the PAB-DN derivative 18, elimination displayed a very similar rate to that of PAB-BL 10, FIG. 3*c*).

C-Benzylation Prevents Quinone Redox Activity

The toxicity of the benzyl ketol pharmacophore generated upon quinone derivatisation was investigated to determine the usefulness of the protection strategy for prodrug generation.

Redox activity of a stable, non-releasable model of benzyl β-lapa-ketol, 24, which lacks a para-amino-group necessary for self-immolative release, was compared to parent drug 1, and control non-redox cycling protected 1,4-dioxine derivative, 25.

Figure 4A:
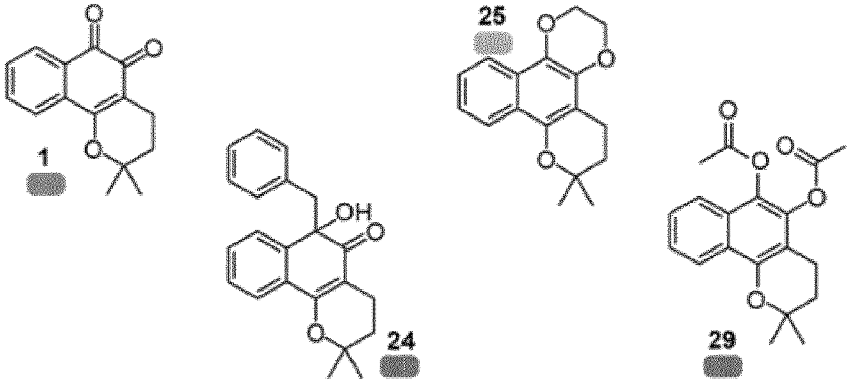
FIG. 4 shows that C-benzylation prevents redox-cycling of β-lapachone and shows cathepsin B-cleavable β-lapachone prodrugs. a, In vitro redox-cycling capability of 1, 24 and 25 measured by horse-radish peroxidase/phenol-red reporter assay. Relative increase in redox-cycling ability calculated by $(A-A_0)/A_0$, where A is absorbance at 610 nm for the test compound and $A_0$ is absorbance at 610 nm for a sample with PBS added only. The redox activity of 1 saturates the assay above 10 μM concentration, but 24 and 25 show no measurable redox activity up to 25 μM concentrations. b, Generalised ROS production by compounds 1, 24 and 25 in HL-60 cells measured with the dye 2',7'-dichlorodi-hydrofluorescein diacetate. c, Toxicity to AML cell line HL-60 with and without ROS quencher N-acetyl cysteine (NAC, 600 mM). $IC_{50}$ of 24 decreased slightly from 13.6±1.3 μM to 10.5±0.9 μM due to NAC. $IC_{50}$ of 1 doubled from 0.47±0.26 μM to 1.18±0.18 μM with NAC. d, In vitro methaemoglobin generation measured by absorbance at 630 nm after 1 h incubation with test compounds. e, Cathepsin B-activatable prodrugs release β-lapachone by linker elimination following enzymatic amide-bond cleavage. f, Release of 1 from 26 at 254 nm after in vitro dipeptide cleavage by protease cathepsin B (MES 20 mM buffer, pH 5). Peaks for PAB-BL 10 and β-lapachone 1 overlap. g, Concentration-dependent methaemoglobin generation by dipeptide prodrugs after 4 h incubation in ovine blood. Methaemoglobin was measured by absorbance at 630 nm following treatment with compounds relative to DMSO control. For a-d and g, data shows mean±SEM from one representative experiment (n=3).
Figure 4A:
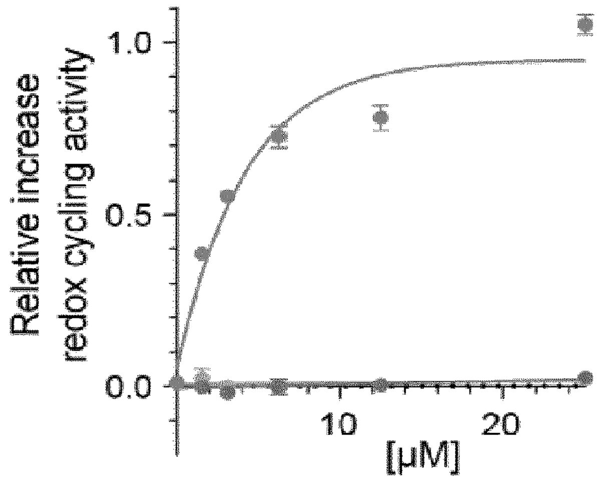
Figure 4B:
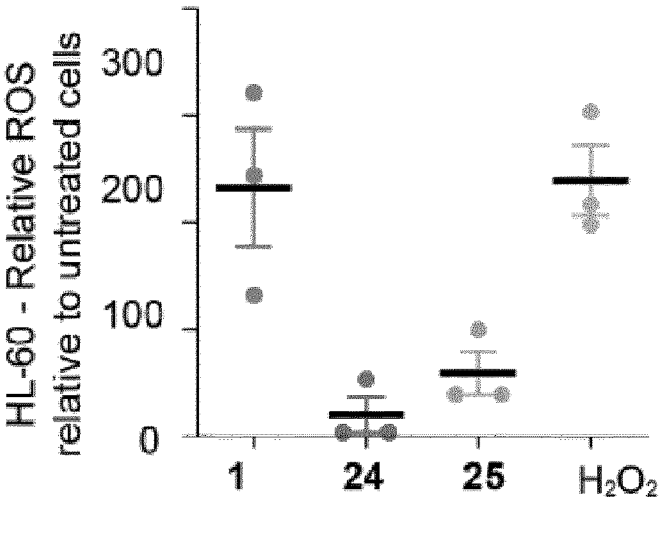
Figure 4C:
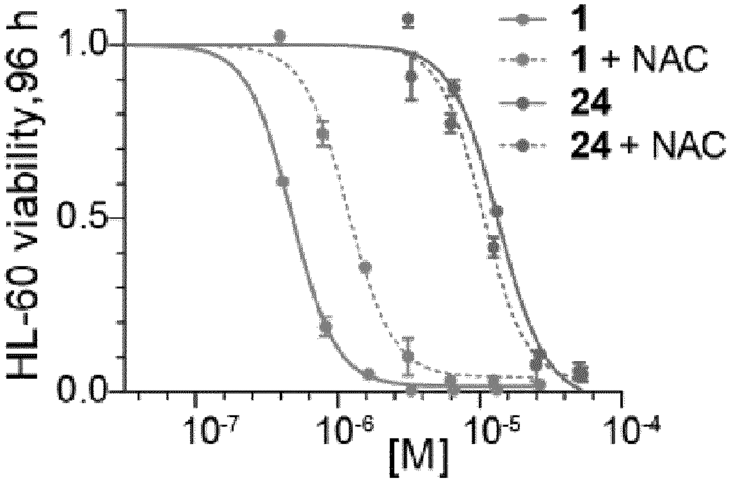
Figure 5A:
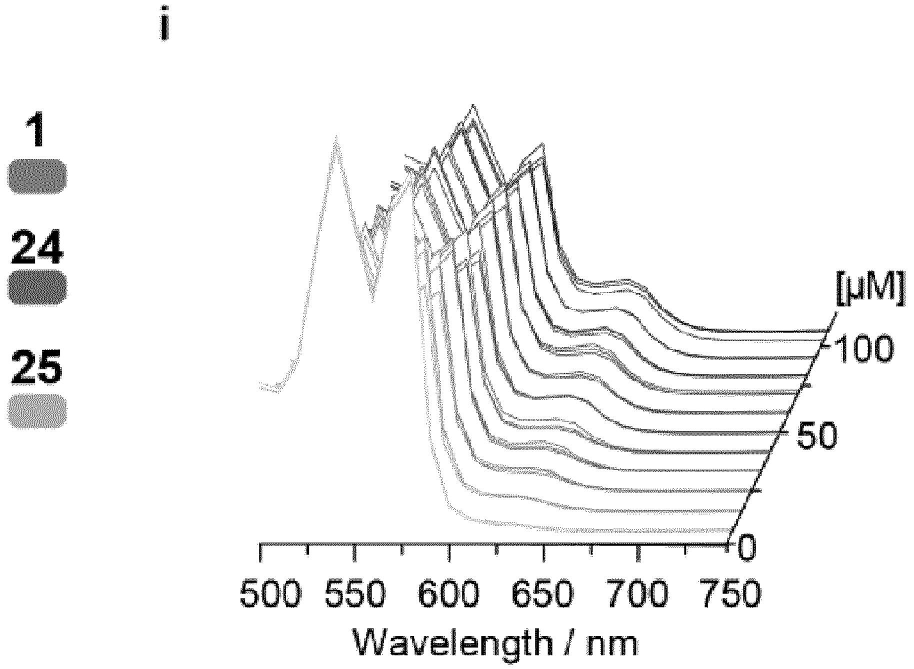
FIG. 5 shows additional in vitro assays of the benzyl ketol protection unit. a, (i) Concentration-dependent in vitro methaemoglobin generation by 1, (ii) appearance of methaemoglobin peak at 630 nm for samples at 100 μM. Line represents mean values, with dotted borders representing ±SEM (n=3). This experiment was repeated once with similar results. b, Toxicity of 1, 24 and 25 to cancer cell lines: HL-60 (acute myeloid leukaemia), HeLa (endocervical adenocarcinoma) and HCT-116 (colon carcinoma). Data are presented as mean values fit to 4-PL model with error bars representing ±SEM (n=3). These experiments were replicated once with similar results. c, Viability of leukaemia cell line MOLM-13 at 24 h timepoints following treatment with peptide prodrugs at 5 μM compared to compounds 1 and 29. Values are mean normalised cell viability from three biological replicates ±SEM (n=9). d, Lysosome deacidification and inhibition assay in HL-60 over 24 h. Significant difference marked: paired two-tailed t test for 26, untreated vs. $NH_4Cl$ 30 mM treated viability: p=0.0199. Bar height displays mean values from one representative experiment with error bar displaying ±SEM (n=3).
Figure 5A:
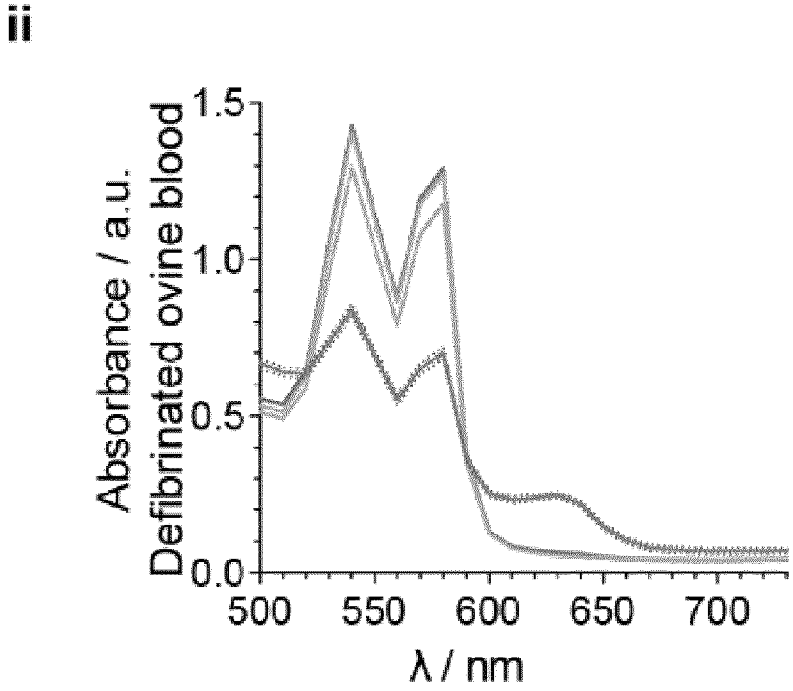
Figure 5B:
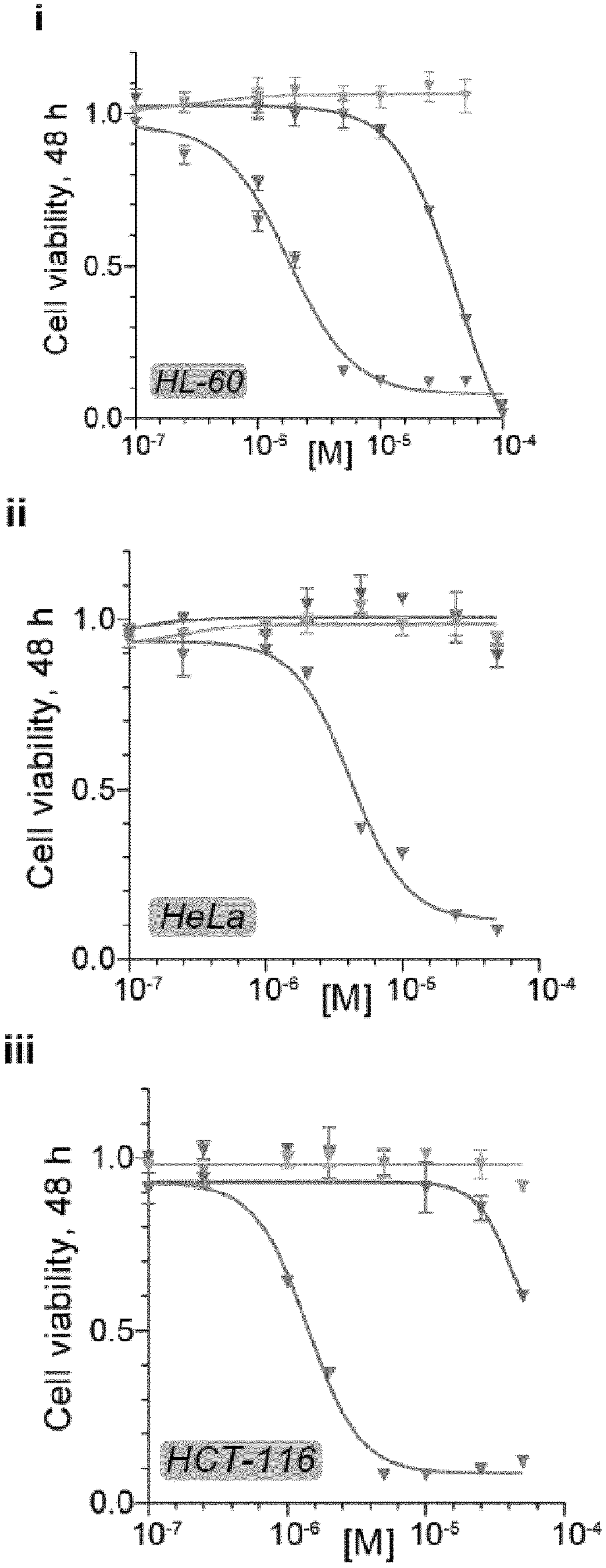

Compound 24 was found to be non-redox active in an in vitro redox cycling assay (FIG. 4*a*) and, unlike 1, did not generate detectable ROS in AML cell line HL-60, a cell line in which $H_2O_2$ generation by 1 has been previously reported (FIG. 4*b*) (Free Radic. Biol. Med., 1998, 24, 660-670). Compound 24 displayed decreased toxicity by >20-fold to a range of cancer cell lines, including leukaemia, breast, colon, and cervical cancer (FIG. 5*b*). The $IC_{50}$ of 24 against HL-60 was unchanged by addition of antioxidant N-acetyl cysteine (NAC; FIG. 4*c*). This is in stark contrast to 1, for which the $IC_{50}$ value more than doubled upon NAC addition as NAC alleviated ROS-mediated toxicity. These results together confirm that 24 does not redox cycle.

Figure 4D:
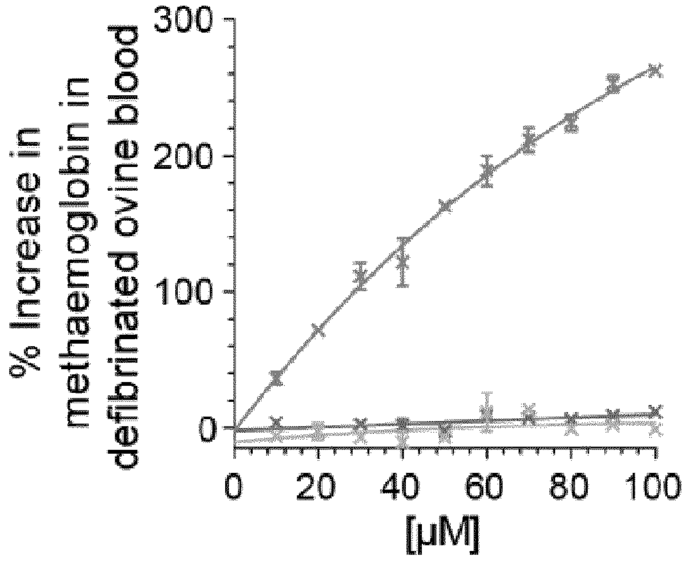

Methaemoglobin formation, a major side-effect of ortho-quinones in vivo, did not occur for the protected compounds 24 and 25 in an in vitro ovine blood model. In contrast, β-lapachone 1 caused dose-dependent methaemoglobin formation detectable at dose concentrations as low as 10 μM after 1 h of incubation (FIGS. 4*d*, 5*a*). Haemolysis of haemoglobin, related to anaemic side effects, was also lower for the protected models 24 and 25. These promising results indicated that the benzyl protection unit, while intact, has the capacity to mitigate the blood-borne redox-mediated side effects of quinones.

Cathepsin B Can Trigger the Release of β-Lapachone from Dipeptide Prodrugs

Figure 4E:
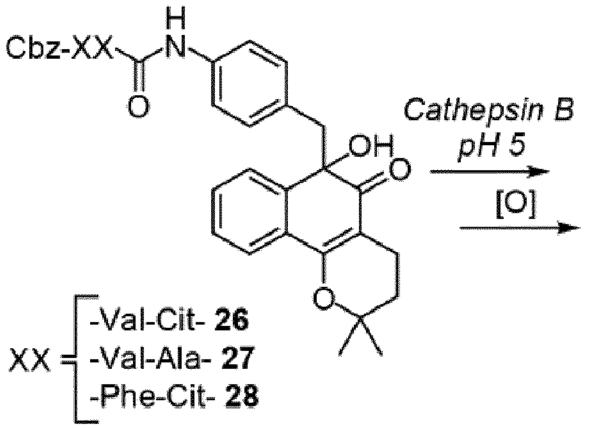
Figure 4F:
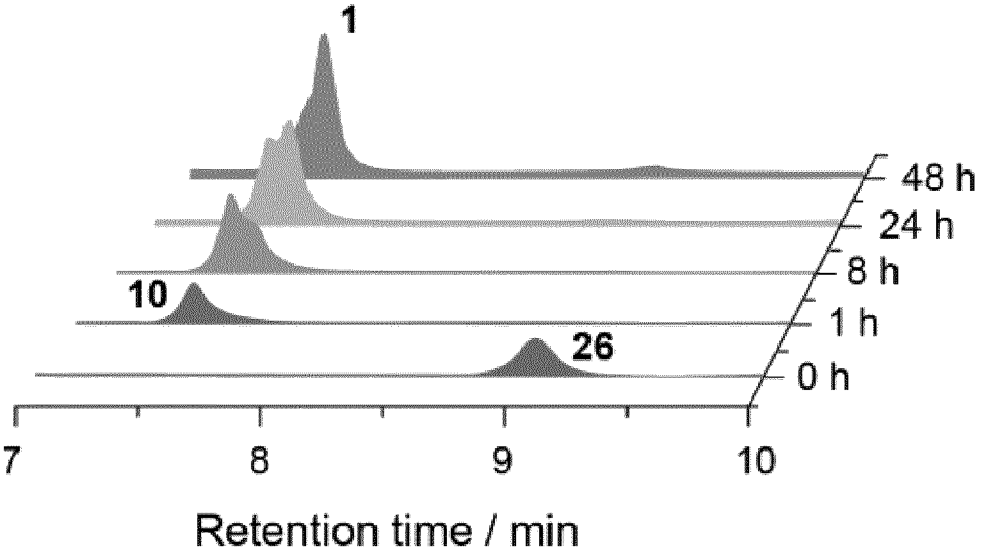
Figure 4G:
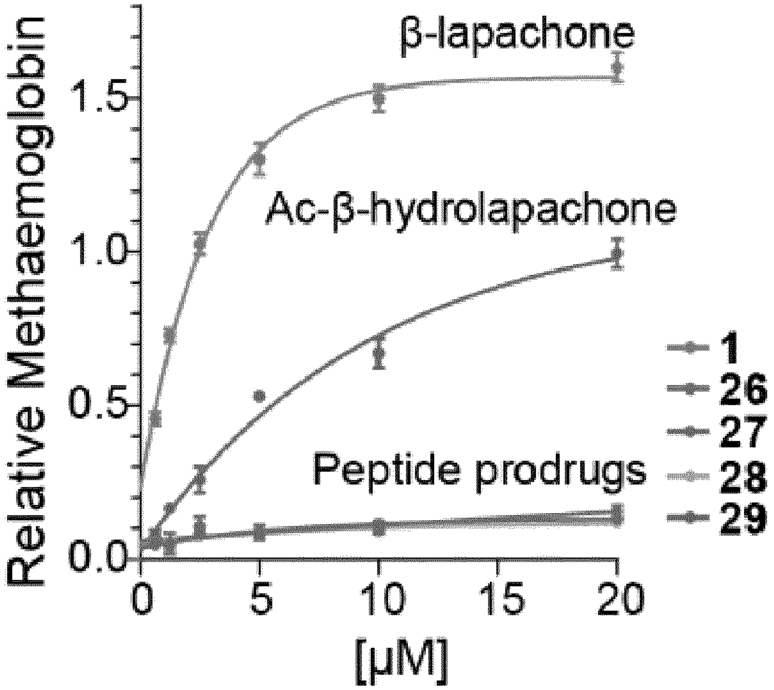

It was next investigated whether the self-immolative linker strategy was compatible with enzymatic cleavage of cathepsin-B labile dipeptides. Dipeptide units Cbz-Val-Cit-, Cbz-Val-Ala- and Cbz-Phe-Cit-were added by sequential amide coupling from deprotected aniline intermediate 10 (26-28, FIG. 4*e*) (Bioconjugate Chem., 2002, 13, 855-869). After incubation of 26-28 with cathepsin B (FIG. 4*f*), compound 1 was observed. Aniline 10 was identified as a common intermediate and release of 1 from 10 occurred as previously observed. The Cbz group was not necessary for cathepsin B action. This demonstrated that the dipeptide-para-aminobenzyl ketols are compatible with cathepsin-B, in an identical manner to dipeptide-para-aminobenzyl alcohol and carbamate linkers. Like benzyl model 24, dipeptide prodrugs 26-28 generated less methaemoglobin in blood in an in vitro model relative to 1 (FIG. 4*g*). Additionally, they generated less methaemoglobin than an acyl-hydroquinone β-lapachone-prodrug 29, previously described by Ma et al (J. Control. Release, 2015, 200, 201-211) due to the increased stability of the dipeptide over labile ester bonds.

Figure 5C:
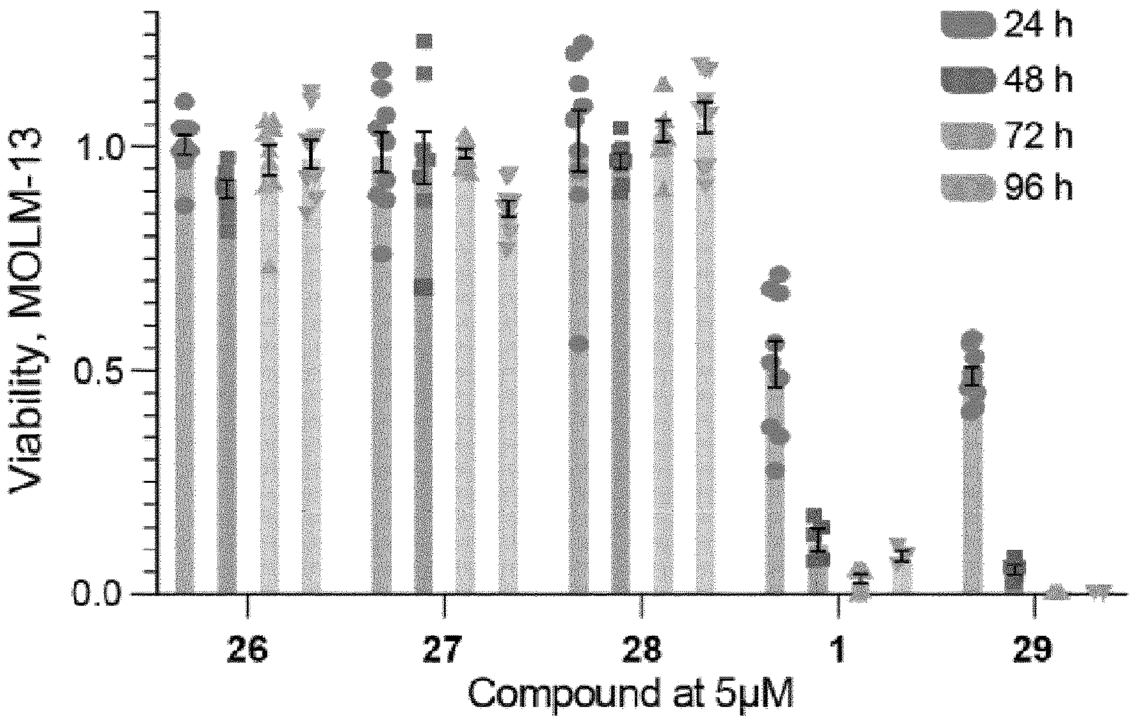
Figure 5D:
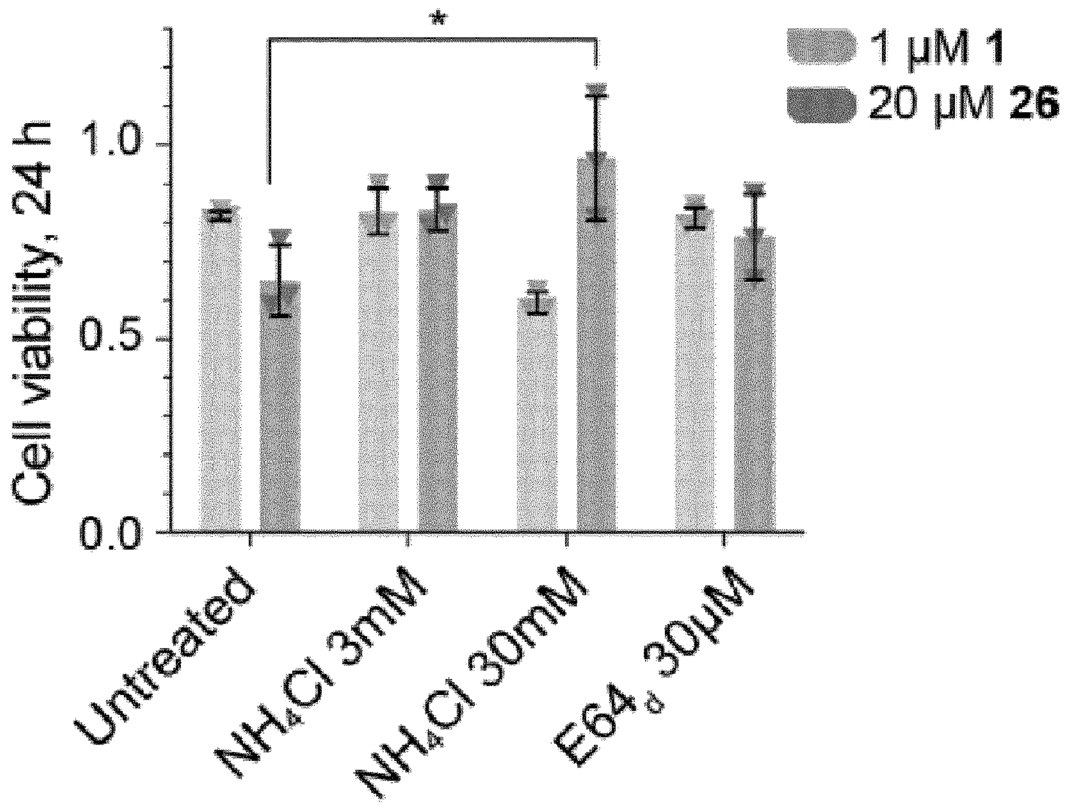

Cbz dipeptide prodrugs 26-28 were fully stable in human serum and did not exhibit toxicity to AML cell line MOLM-13 at 5 μM concentration, unlike 1 and derivative 29 (FIG. 5*c*) that achieved complete cell death at this concentration. Compound 26 exhibited 10-fold higher $IC_{50}$ relative to 1 in AML cell lines HL-60 and MOLM-13. After lysosomal deacidification ($NH_4Cl$) (J. Cell Biol., 1981, 90, 665-669) or inhibition (E64d) (J. Pharmacobiodyn., 1986, 9, 672-677), 26 was less toxic, suggesting that acidic compartments help promote toxicity of the prodrug (FIG. 5*d*). It was interesting that with $NH_4Cl$ at 30 mM, an increase in toxicity of 1 was seen, a result previously described for menadione (Anat. Rec., 2013, 296, 31-39). Prodrugs 26-28 may have suitability for treatment of NQO1+ solid tumours with concurrent overexpression of proteases, e.g. cathepsins (FEBS J., 2020, 287, 1936-1969; Proteomics Clin. Appl., 2014, 8, 427-437) and acidic pH (Nat. Rev. Cancer, 2011, 11, 85-95) in the extracellular malignant environment.

β-Lapachone for Use in the Treatment of AML

AML is the most common form of acute leukaemia among adults (Leuk. Res., 2016, 47, 149-160). It is characterised by immature myeloid cell proliferation and bone marrow failure and is a cancer for which new treatments are urgently needed. AML has a poor 5-year survival rate of ~20% and a large proportion of patients relapse (J. Clin. Med., 2016, 5). Interference in redox homeostasis is an appealing treatment angle for AML (Nat. Rev. Cancer, 2020, 20, 158-173). Recent observations note that despite differences between the mechanisms of action of clinically-used AML therapeutics, most share oxidative stress as a mediator of the cytotoxic effect (J. Exp. Clin. Cancer Res., 2018, 37, 125). For example, anthracyclines and arsenic trioxide induce rapid ROS accumulation (Cancer Res, 2002, 62, 3893-3903; J. Drug Metab. Toxicol., 2015, 6, 186).

Quinone 1 also has relevant protein targets in AML. As mentioned above, in previous work (Chem. Sci., 2018, 9, 6899-6903), it has been shown that β-lapachone strongly inhibits enzyme 5-LO, an enzyme which is a candidate target for therapeutic targeting of the stem cell-like blasts in AML (Cancer Res., 2014, 74, 5244-5255; Nat. Genet., 2009, 41, 783-792). Both redox-sensitivity and 5-LO target relevance made β-lapachone a valuable experimental drug for AML treatment. For AML, the data strongly supports the development of an intracellular targeting strategy to enable application of the quinone prodrugs.

Antibody-Drug Conjugates (ADCs) for Release of β-Lapachone in AML Cells

Antibody conjugation can enable targeting and assisted delivery of payloads inside AML target cells. It has been shown herein that an ortho-quinone protection strategy can eliminate redox toxicity from 1, and indeed, protection should therefore prevent any potential redox damage to the antibody carrier.

Cell killing should depend on effective cellular trafficking of a conjugate, particularly one based on a para-aminobenzyl protecting group, to a low pH cellular compartment inside target cells because pH 4-5 is required for the efficient release of 1 in vitro. Furthermore, in the system described, the slow release of 1 from the quinone protection unit PAB-BL 10 at physiological pH should limit release of drug systemically, i.e. any linker deconjugated from the antibody while in circulation should not release drug, even if a protecting dipeptide unit is broken. This can limit the toxicity profile of the ortho-quinone to that produced by non-specific cell uptake.

In useful contrast, the para-hydoxybenzyl protecting groups may be trafficked to a higher pH cellular compartment inside target cells because conditions that are less acidic than pH 4-5, or conditions that are basic, are more suited for the efficient release of the ortho-quinone.

Alternative payload-classes are an important strategy to identify new treatments and combat drug resistance in the fight against cancer. Here, novel prodrug chemistry and antibody-mediated delivery are leveraged to develop a method for intracellular targeting and release of ortho-quinones from a protected redox-inactive form.

As an example of the application of the ortho-quinone protection strategy, we synthesised cathepsin-B cleavable prodrugs of β-lapachone, and conjugates may be prepared using the protection chemistry.

For β-lapachone, 1, minimal release of the payload from the quinone-protection unit occurs at physiological pH even after peptide deprotection, which for an ADC, means the chemistry offers a built-in protection against premature in-circulation drug release upon linker deconjugation.

The protection strategy described herein is applicable to other ortho-quinones.

EXPERIMENTAL

Compound Numbering

The compound numbers used herein correspond to those shown below:

1

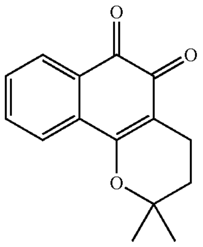

β-Lapachone

4

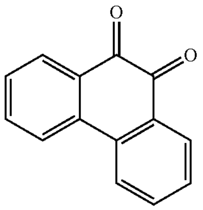

phenanthrene-9,10-dione

5

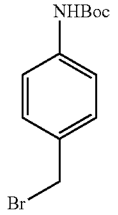

tert-butyl (4-(bromomethyl) phenyl)carbamate

6

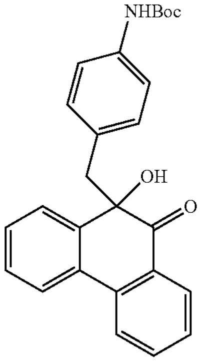

Boc-para-aminobenzyl phenantrene-ketol

10

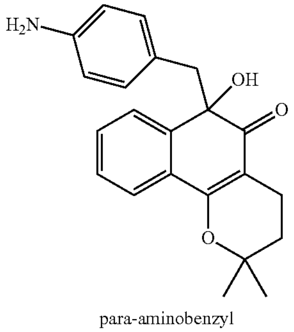

para-aminobenzyl β-lapa-ketol

11

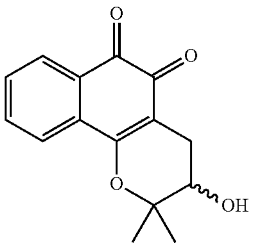

3-Hydroxy β-lapachone

-continued
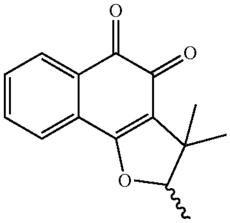
Dunnione
12
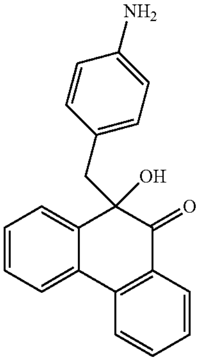
para-aminobenzyl
phenantrene-ketol
7
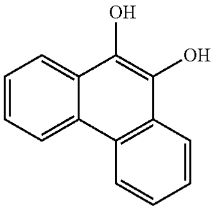
9,10-phenanthrenediol
8
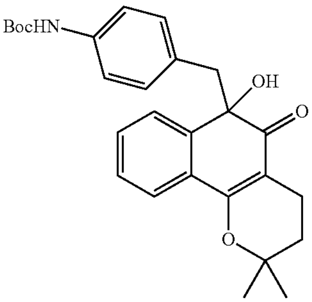
Boc-para-aminobenzyl
β-lapa-ketol
9
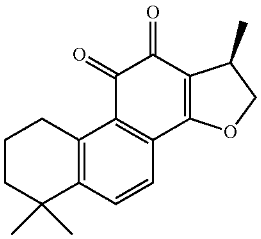
Cryptotanshinone
13
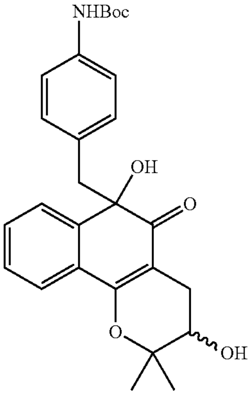
Boc-para-aminobenzyl
3-hydroxy β-lapa-ketol
14

-continued
15
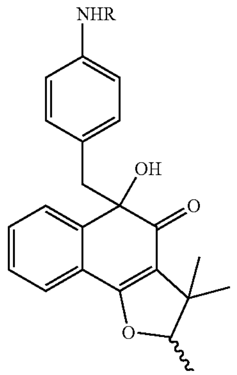
Boc-para-aminobenzyl
dunni-ketol
16
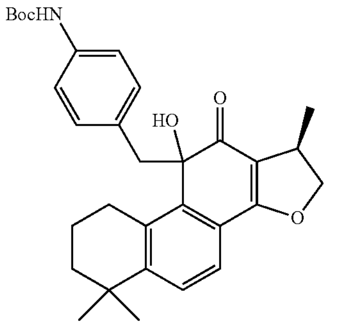
Boc-para-aminobenzyl
cryptoanshi-ketol
17
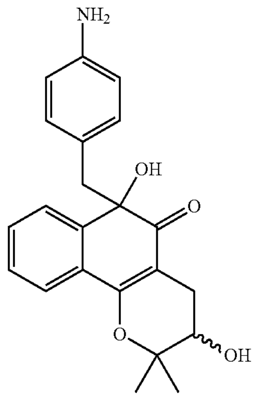
para-aminobenzyl
3-hydrox-β-lapa-ketol
18
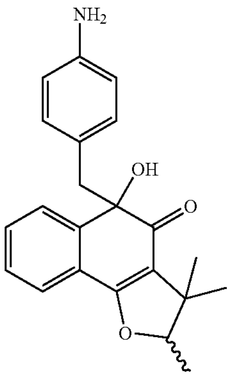
para-aminobenzyl
dunni-ketol
19
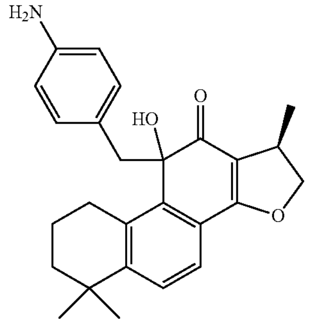
para-aminobenzyl
cryptotanshi-ketol
21
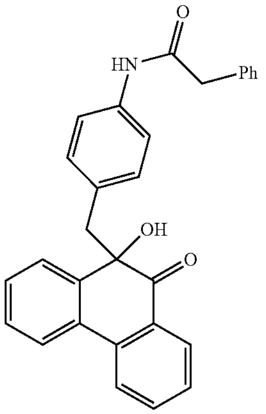
2-phenyl-acetyl
para-aminobenzyl
phenantrene-ketol -continued
22
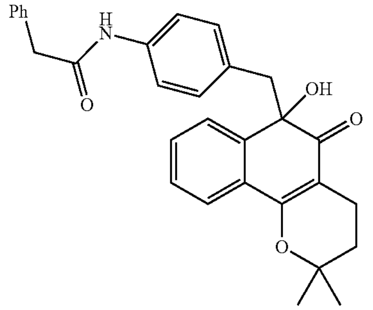
2-phenyl-acetyl
para-aminobenzyl
β-lapa-ketol
23
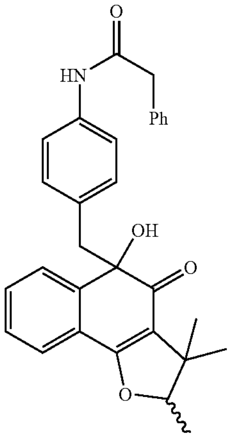
2-phenyl-acetyl
para-aminobenzyl dunni-ketol
24
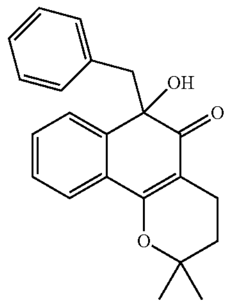
Benzyl-β-lapa-ketol
25
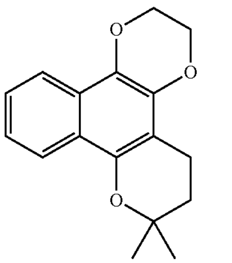
β-lapa-hydroquinone
1,4-dioxine
26
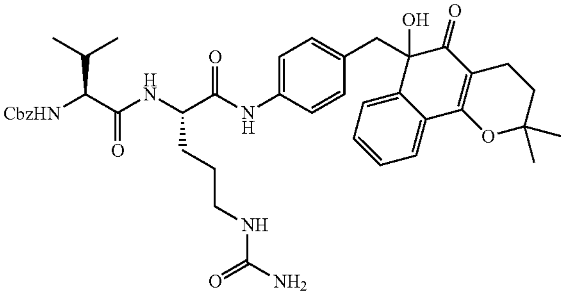
Cbz-Val-Cit-para-aminobenzyl
β-lapa-ketol
27
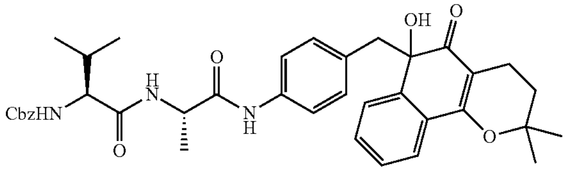
Cbz-Val-Ala-para-aminobenzyl
β-lapa-ketol
28
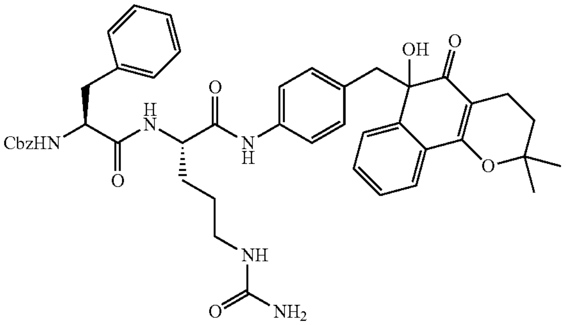
Cbz-Phe-Cit-para-aminobenzyl
β-lapa-ketol
29
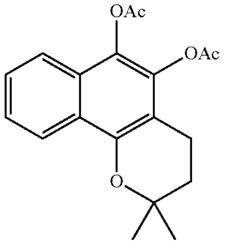
2,2-dimethyl-3,4-dihydro-
2H-benzo[h]chromene-5,6-
diyl diacetate -continued
30
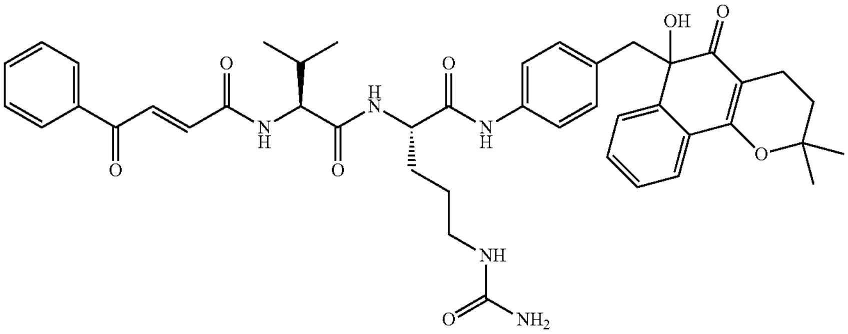
BAA-Val-Cit-para-aminobenzyl β-lapa-ketol
31
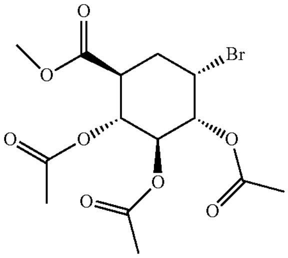
Aceto-a-bromo-glucuronic acid methyl ester
32a
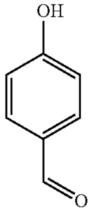
4-Hydroxy benzaldehyde
32b
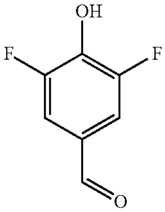
3,5-Difluoro-4-hydroxy benzaldehyde
33a
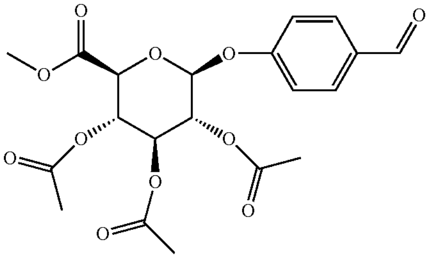
Aceto-b-glucuronic acid methyl ester para-hydroxybenzaldehyde
34a
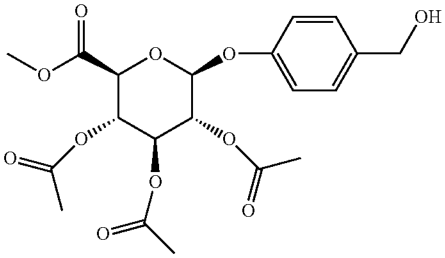
Aceto-b-glucuronic acid methyl ester para-hydroxybenzyl alcohol
35a
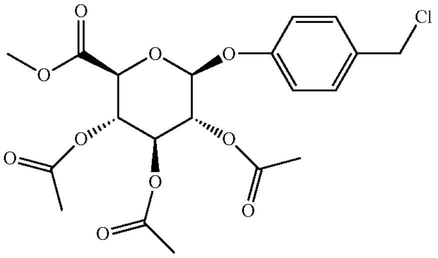
Aceto-b-glucuronic acid methyl ester para-hydroxybenzyl chloride -continued 33b

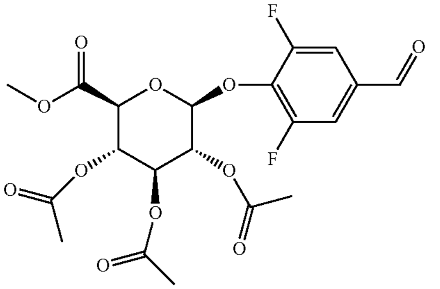

Aceto-b-glucuronic acid methyl ester
3,5-difluoro-para-hydroxybenzaldehyde

34b

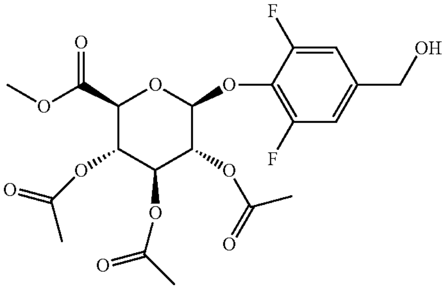

Aceto-b-glucuronic acid methyl ester
3,4-difluoro-para-hydroxybenzyl alcohol

35b

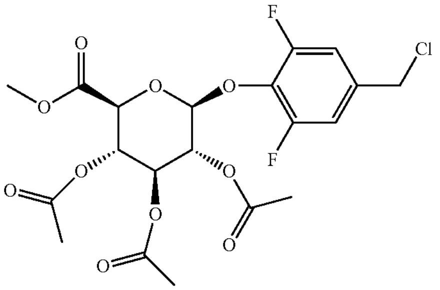

Aceto-b-glucuronic acid methyl ester
3,4-difluoro-para-hydroxybenzyl chloride 32c, d, e and f

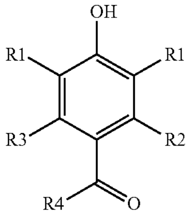

4-Hydroxy
benzaldehyde 33c, d, e and f

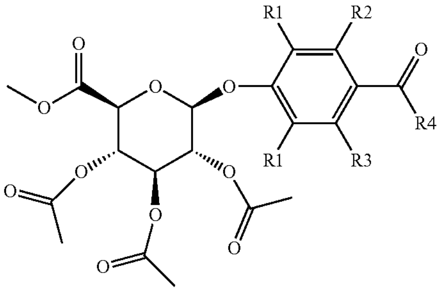

Aceto-b-glucuronic acid methyl ester
para-hydroxybenzaldehyde 34c, d, e and f

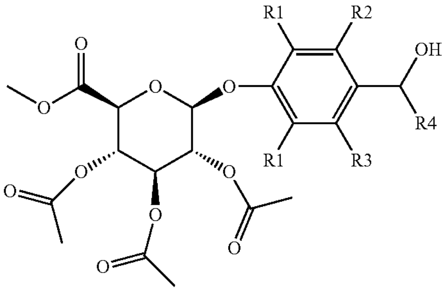

Aceto-b-glucuronic acid methyl
ester para-hydroxybenzyl alcohol 35c, d, e and f

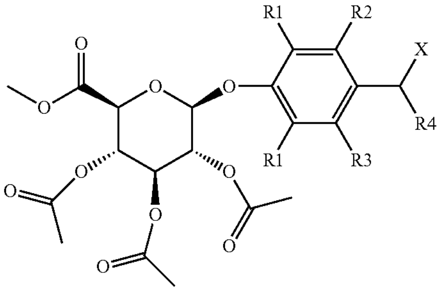

Aceto-b-glucuronic acid methyl
ester para-hydroxybenzyl chloride c: $R_{1,2,3}$ = F, $R_4$ = H, X = Cl
d: $R_{1,2,4}$ = H, $R_3$ = OMe, X = Br
e: $R_{1,2,3}$ = H, $R_4$ = Me, X = Br
f: $R_{1,4}$ = H, $R_{2,3}$ = OMe, X = Br -continued 36a

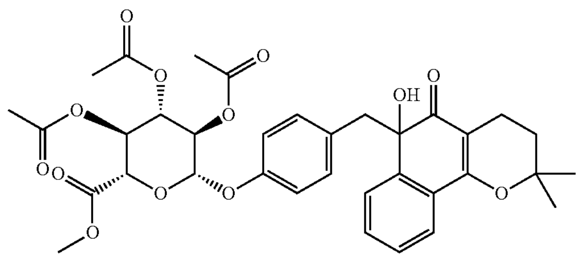

Aceto-b-glucuronic acid methyl ester
para-hydroxybenzyl β-lapa-ketol

36b

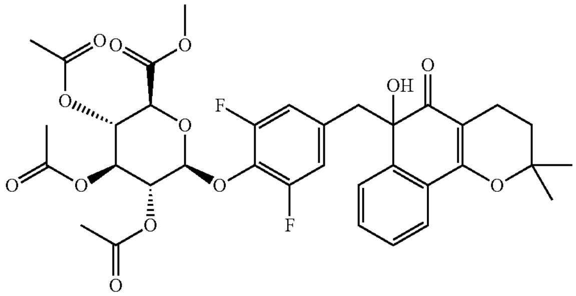

Aceto-b-glucuronic acid methyl ester 3,5-
difluoro-para-hydroxybenzyl β-lapa-ketol 37a

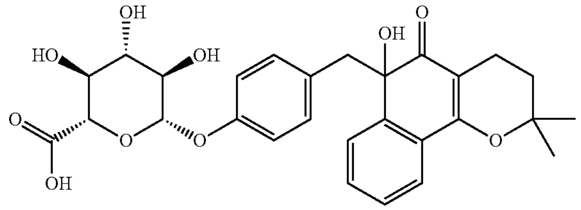

Beta-glucuronide-para-hydroxybenzyl β-lapa-ketol

37b

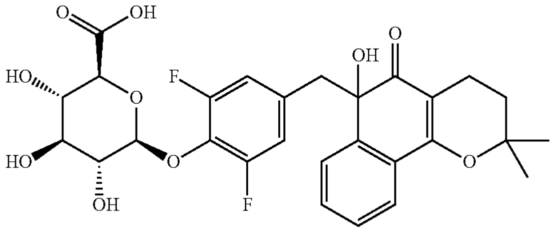

Beta-glucuronide-3,5-difluoro-para-hydroxybenzyl
β-lapa-ketol

38a

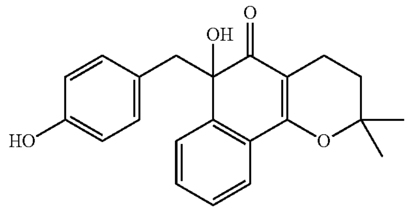

para-hydroxybenzyl β-lapa-ketol

38b

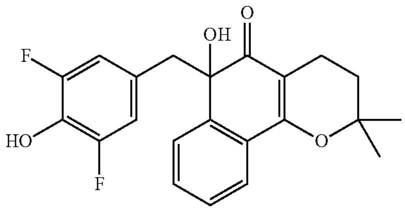

3,5-difluoro-para-hydroxybenzyl β-lapa-ketol 36c, d, e and f

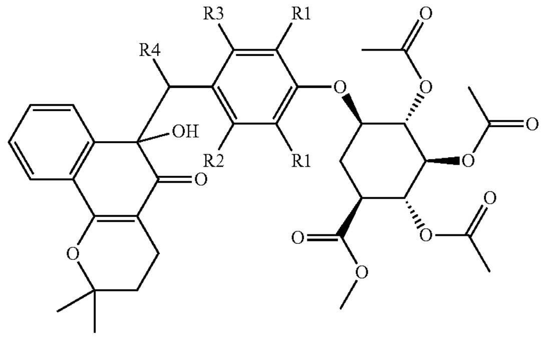

Aceto-b-glucuronic acid methyl ester
para-hydroxybenzyl 37c, d, e and f

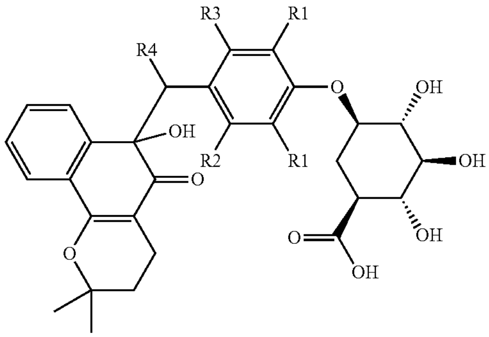

Beta-glucuronide-para-hydroxybenzyl

-continued 38c, d, e and f

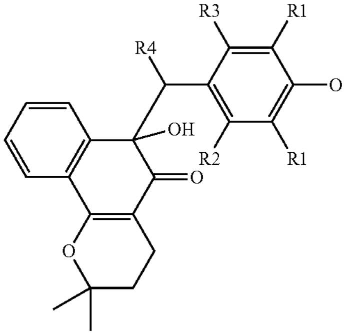

para-hydroxybenzyl c: $R_{1,2,3}$ = F, $R_4$ = H
d: $R_{1,2,4}$ = H, $R_3$ = OMe
e: $R_{1,2,3}$ = H, $R_4$ = Me
f: $R_{1,4}$ = H, $R_{2,3}$ = OMe

Materials and Methods $^1$H NMR Kinetic Analysis of Elimination of PAB-PhQ

Kinetics of the release of PhQ 4, from PAB-PhQ 7 were monitored by $^1$H NMR at 25° C. Analysis was performed in MeOD due to poor solubility of the compound in $H_2O$. To form the active eliminating species, Boc-PAB-PhQ 6 was dissolved in dichloromethane/trifluoroacetic acid 4:1 at 0° C. and stirred for 30 min, upon which the reaction appeared complete by thin-layer chromatography. Product 7 was dried in vacuo before being dissolved in MeOD. Basicity of the solution was altered by addition of triethylamine (drops). pH was estimated using pH paper. pH values are indicative only as analysis is performed in MeOD. Elimination rates were determined from the aromatic region. Kinetics were measured by monitoring the integral of one peak, normalised to number of protons present (i.e. integral of 1H), divided by the total integral of the aromatic region (δ=6.2-8.6 ppm, i.e. integral of 12H). Analysis was performed using Mestrenova 8.0 processing software and rate constants were calculated using GraphPad Prism v8.0 software.

Penicillin-G Amidase Mediated Kinetic Analysis of Elimination at Physiological pH.

Stocks of 2-phenylacetyl-para-aminobenzyl ketol were made up in DMF at a concentration of 10 mM. For a reaction, 17.5 L of ketol stock was added to 17.5 μL of a 10 mM stock of internal standard in DMF and 310 μL of PBS at pH 7.4. To initiate a reaction, 5 μL of a suspension of Penicillin-G amidase (PenG, Sigma Aldrich enzyme 76427, 5-10 U/mg) was added. In control samples 5 μL of PBS was added in place of the enzyme. Test and control samples were then incubated at 37° C. with shaking. At the recorded time points, 20 μL aliquots of the reactions were analysed by HPLC (254 nm, ThermoFisher U3000). HPLC column: Phenomenex Kinetex C18, 5 μm, 50×4.6 mm, 100 Å; flow=1 mL/min. Gradient and solvent system for assay with 2-phenylacetyl-PAB-PhQ 21: A=$H_2O$, B=acetonitrile, t=0-1 min 0% B, t=1-10 min 0-100% B, t=$10^{-11}$ min 0% B. Gradient and solvent system for assay with 2-phenylacetyl-PAB-BL 22 and 2-phenylacetyl-PAB-DN 23: A=$H_2O$+0.1% formic acid, B=acetonitrile+0.1% formic acid, t=0-1 min 0% B, t=1-10 min 0-40% B, t=10-16 min 40-50% B, t=16.1 min 100% B, t=16.1-18 min 100% B, t=18-20 min 0% B. Peaks were identified by LCMS analysis and comparison with pure compounds. Values described represent peak area (mAU*min) divided by peak area of internal standard. Recorded values are averages of three independent reactions and error bars display standard error of the mean. Fitting was performed using GraphPad Prism 8 software. Rate and half-life measurements were calculated by consumption of intermediate para-aminobenzyl ketol and formation of product quinone.

pH-Rate Aqueous Kinetic Analysis of Fragmentation pH-rate analysis was performed by adaption of the PenG assay. To obtain deprotected para-aminobenzyl ketol species, 2-phenylacetyl protected ketol was dissolved in PBS with 33% DMF to a concentration of 3.3 mM. 20 μL of a stock solution of PenG was added to 600 μL of this stock and incubated for 20 min at 37° C. 20 μL of a 100 mM stock of internal standard in DMSO was added. Reactions were then set up immediately. For a reaction, 10 μL of the aminobenzyl ketol/standard stock was added to 190 μL of citrate-phosphate buffer at the specified pH to obtain an aqueous solution containing 1.8% DMSO. Test samples were incubated at 37° C. with shaking. At the recorded time points, 20 μL aliquots of the reactions were analysed by HPLC (254 nm, ThermoFisher U3000). HPLC conditions: column Phenomenex Kinetex C18 5 μm, 50×4.6 mm, 100 Å; solvent system A=$H_2O$, B=acetonitrile; flow=1 mL/min. Gradient and solvent system for assay with PAB-PhQ 7: A=$H_2O$, B=acetonitrile, t=0-1 min 0% B, t=1-10 min 0-100% B, t=$10^{-11}$ min 0% B. Gradient and solvent system for assay with PAB-BL 10 and PAB-DN 18: A=$H_2O$+0.1% formic acid, B=acetonitrile+0.1% formic acid, t=0-1 min 0% B, t=1-10 min 0-40% B, t=10-16 min 40-50% B, t=16.1 min 100% B, t=16.1-18 min 100% B, t=18-20 min 0% B. Values described represent peak area (mAU*min) divided by peak area of internal standard. Where necessary, peaks were deconvoluted using Origin fitting software. Recorded values are averages of three independent reactions and error bars display standard error of the mean. Values were fitted using GraphPad Prism software. Rate and half-life measurements were calculated based on disappearance of the para-aminobenzyl ketol species.

In Vitro Redox-Cycling Ability Analysis

In vitro redox cycling capability of compounds was assessed by phenol red/horseradish peroxidase (HRP) assay by adaption of a previously described protocol (Assay Drug Dev. Technol., 2008, 6, 505-518). Briefly, stocks were prepared as follows: (1) DTT to a concentration of 2.4 μM in PBS pH 7.4 buffer; (2) compound stocks in PBS pH 7.4 buffer to 3× the desired concentration by 1000× dilution of DMSO stocks; (3) a stock of phenol-red-HRP detection reagent containing 300 μg/mL phenol red and 180 μg/mL HRP enzyme in PBS pH 7.4 buffer; (4) a stock of 1 M NaOH in water; (5) a stock of 100 μM $H_2O_2$ in PBS prepared by addition of a 30% solution of $H_2O_2$ in water into 1000 μL of PBS. Into each well of a 96 well clear flat-bottomed plate was then added 40 L of compound stock in PBS followed by 40 μL of DTT stock, followed immediately by 40 μL of phenol-red-HRP reagent. A positive control with 100 μM $H_2O_2$ added in place of compound was included. The plate was incubated in the dark at room temperature for 15 min. Following this 20 μL of 1 M NaOH was added to each well to terminate the reaction. Absorbance was immediately measured at 610 nm (MiniMax i3× Imager, Molecular Devices). Absorbance of treated wells was normalised to control wells treated with PBS only (zero redox cycling). All readings were performed in triplicate and error bars display standard error of the mean.

Cellular ROS Detection

To determine ROS generation by compounds in leukaemia cells, HL-60 cells were washed with PBS, then incubated in serum free media (10 mL of $1.6\times10^6$/mL cell concentration) with 2,7-dichlorofluorescin diacetate (DCFH-DA) at 20 μM for 30 min at 37° C. Following this, the cells were washed with PBS and resuspended in Fluorbrite-DMEM media (ThermoFisher) (10 mL). 450 μL of the cell mixture was seeded into wells of a clear flat bottomed 12 well plate, to which 50 μL of a 10× stock of the compounds in media had been already added, to achieve a final compound concentration of 50 μM. The 10× media stocks were made by 100-fold dilution of DMSO compound stocks, to ensure a final in-plate DMSO concentration of 0.1%. DMSO 0.1% only was used as a negative control. $H_2O_2$ was used as a positive control, for which 10 μL of a 30% aqueous solution was dissolved into 1 mL DMSO, then diluted 100-fold into media for plating, to give a final $H_2O_2$ concentration of 1 μM. After plating the cells were immediately incubated at 37° C. in the dark for 15 min before the fluorescence of the wells (excitation 485 nm, emission 535 nm) was recorded (MiniMax i3× Imager, Molecular Devices). Values recorded are the mean of three repeat wells, with error bars representing the standard error of the mean.

Methaemoglobin Analysis

Defibrinated Oxoid™ sheep's blood (ThermoScientific) was diluted to a 5% v/v suspension in PBS pH 7.4. In a 96 well microtiter plate, 150 μL of blood suspension was added to 50 μL of serially diluted compound in PBS containing a 4× stock of each compound of interest. Serial dilution of compounds from DMSO stocks into PBS was performed to achieve an in-plate DMSO concentration of 0.1%. PBS buffer alone was used as a negative control. Three replicates were performed for each compound concentration analysed. The plate was incubated for the specified time at 37° C. The plate was then centrifuged at 3,500 rpm for 5 min. The supernatant was removed and cells lysed by resuspension in 100 μL of a solution of Triton —X-100 (1%) in PBS. Following this 80 μL of lysed cell contents were transferred to a second microtiter plate for UV measurement. To determine methaemoglobin increase, UV absorbance was measured immediately at 630 nm (MiniMax i3× Imager, Molecular Devices). Methaemoglobin increase was determined by (A630-A0 630)/(A0 630)×100, where A630 is the absorbance of the test well at 630 nm, and A0 630 is the absorbance of the negative control at 630 nm. Mean values and standard error of the mean of three independent replicates are plotted.

In vitro Cleavage of Peptide-Lapachone Prodrugs by Cathepsin B

Cathepsin B cleavage of Cbz-dipeptide protected prodrugs was tested in vitro as follows: cathepsin B (Abcam ab151914) was preactivated by dilution of enzyme stock (20 μL, 0.44 mg/mL, 37 kDa, 12 μM) into activation buffer (45 μL, MES 25 mM pH 5+10 mM DTT). The reaction was incubated at 37° C. for 20 min. Reactions were made up containing the prodrug of interest (15 μL of a 5 mM stock in DMSO) and internal standard acetophenone (0.75 μL of a 100 mM stock in DMF) in MES 20 mM pH 5 buffer (114.25 μL) resulting in a total reaction volume of 150 μL at pH 5 with 10.5% DMSO, 500 μM prodrug and 0.5 M of cathepsin B (1,000 equiv. of substrate compared to enzyme). A 20 μL sample of each reaction was removed immediately at t=0. Following pre-activation, activated cathepsin stock (20 μL) was added to test reactions. Cathepsin activation buffer only (MES 25 mM pH 5+10 mM DTT, 20 μL) was added to negative control samples. Samples were then incubated with shaking (500 rpm) at 37° C. Subsequent 20 μL samples were removed at specified timepoints and analysed by HPLC (254 nm and 430 nm; instrument: ThermoFisher U3000; column: Phenomenex Kinetex C18, 5 μm, 50×4.6 mm, 100 Å; solvent system A=$H_2O$, B=acetonitrile; flow=1 mL/min; gradient: t=0-1.0 min 0% B, t=1.0-5.0 min 0-40% B, t=5.0-12.0 min 40% B, t=12.1-14.0 min 100% B, t=14.1-15.0 min 0% B). Spectra at 254 nm were normalised to the height of the internal standard. Spectra at 430 nm were un-normalised.

Prospective Antibody-Linker Conjugation Reaction

A general approach to preparing an antibody for conjugation is described below. This approach may be adapted as needed for changes in the antibody and the linker.

Antibodies provided in PBS pH 7.2+1 mM EDTA buffer may be refolded prior to reaction. A refolding procedure may be performed as follows. First antibodies may be reduced with tris (2-carboxyethyl) phosphine hydrochloride (20 equiv., to a final concentration of 10% DMF) for 30 min at 37° C. The antibodies may then be desalted with Zeba™ spin desalting columns (0.5 mL, 7 kDa MWCO, size exclusion columns, ThermoFisher) into PBS pH 7.2+1 mM EDTA. (L)-Dehydroascorbic acid (20 equiv., to a final concentration of 10% DMF) may then be added, and the antibodies be incubated for a time from 30 mins to 16 h at 25° C. Antibodies may be desalted with Zeba™ spin desalting columns into NaPi 20 mM pH 8.

Refolding and reactivity may be assessed by reaction of a sample of each antibody (10 μL containing 10 μM antibody) in NaPi 20 mM pH 8 with N-ethyl benzoylacrylic acid (5 equiv./cysteine, +1 μL of a stock in DMF) for 30 min at 37° C., according to a published protocol.[7]

Antibody-drug linker conjugations may be performed by incubation (with shaking) of refolded antibody stock with the specified equiv. of a linker (such as compound 30) for a specified time period in a buffer of NaPi 20 mM pH 8 and final concentration of DMF of 10%. After completion of the reaction, antibodies may be desalted with Zeba™ Spin desalting columns (ThermoScientific) into PBS pH 7.4. Following reaction, a sample of conjugate may be subjected to reduced LCMS analysis to assess conversion. The concentration of the conjugates may be determined by UV absorbance at 280 nm (A280), as measured using a SpectraDrop reader (MiniMax i3× Imager, Molecular Devices).

UV absorbances may be corrected by the following equation A280-(1.929×A330) to account for light scattering.

Prospective Antibody-Conjugate Integrity Analysis

The stability of an antibody conjugate to deconjugation of the payload at physiological temperature may be measured by incubation of the conjugate (10 μL of 20 μM stock) in PBS pH 7.4 buffer at 37° C. with shaking. After 48 h, 10 μL aliquots may be taken and analysed for % conjugated to unconjugated antibody by reduced LCMS analysis. Conjugate stability to storage at 4° C. in PBS pH 7.4 buffer over an extended period (3-4 weeks) may be assessed. Stability of conjugate to deconjugation of payload in human serum may be assessed by incubation of conjugate (10 μL of 20 μM stock) with 1 μL of human serum in PBS pH 7.4 buffer at 37° C. After 48 h, 10 μL aliquots may be taken and analysed for % conjugated to unconjugated antibody by reduced LCMS analysis.

General Cell Culture Conditions

Cells were incubated in a humidified 10% $CO_2$-90% air atmosphere at 37° C. HL-60 cells were cultured in RPMI medium (Gibco™) with 10% heat inactivated fetal bovine serum. HEL cells were grown in RPMI media with 20% heat inactivated fetal bovine serum. Leukaemia cells were maintained at a density of $1\times10^6$ cells/mL. Cells were split every second day to keep them in the exponential growth phase. SKBR-3 and HCT-116 cells were grown in McCoy's 5A Modified Medium (Gibco™) with 10% heat inactivated fetal bovine serum. MCF-7 cells were grown in Dulbecco's Modified Eagle Medium (Gibco™) with 10% heat inactivated fetal bovine serum. Adherent cell lines were passaged by addition of Trypsin-EDTA (0.25%) (Gibco™).

Viability Assays with Small Molecule Lapachone Models and Prodrugs

Assays assessing cytotoxicity of β-lapachone and derivatives were performed by CellTiter-Blue assay (Promega) according to the manufacturer's instructions. Briefly, adherent cancer-cell lines were plated at 20,000 cells/well in 96 well plates or suspension cell lines were plated at a concentration of $2\times10^5$ cells/mL in 24 well plates. Compound stocks in media were made by dilution of DMSO stocks containing the compound of interest to obtain a final in-plate DMSO concentration of only 0.1%. Incubation was performed for 48 h. Following incubation, media was replaced with media containing CellTiter-Blue (Promega) in 1:10 dilution and the plates were incubated for 1.5-4 h. The fluorescence of the plates was recorded (excitation 555 nm, emission 585 nm, MiniMax i3× Reader, Molecular Devices). Cell viability was calculated by division of the fluorescence intensity of treated wells by that of the calculated average fluorescence intensity of replicate negative control wells containing cells with 0.1% DMSO only. Values and reported error bars represent the mean and standard error of the mean of three triplicate repeats for each concentration tested. $IC_{50}$ values were calculated using GraphPad Prism 8 software.

N-acetyl Cysteine Assay

For assays involving cytotoxicity of β-lapachone derivatives with and without antioxidant N-acetyl cysteine, HL-60 cells were plated into 24 well plates at a concentration of $2.5\times10^5$ cells/mL in 450 μL. To each well was then added 25 μL of drug diluted in PBS to obtain the correct in-plate drug concentration, and 25 μL of PBS or a stock of N-acetyl cysteine at 12 mM in PBS. DMSO was maintained at an in-plate concentration of 0.1%. After 96 h incubation, toxicity was assessed by counting of live cells using the Trypan Blue exclusion method with a Countess II Automated Cell Counter (ThermoFisher Scientific) according to the manufacturer's instructions. Cell viability was determined by division of average live cell number of treated wells by average live cell number for control wells treated with 0.1% DMSO. Viability for wells treated with N-acetyl cysteine was assessed by comparison with control wells treated with N-acetyl cysteine and 0.1% DMSO. Values recorded are the mean of three repeat wells, with error bars representing the standard error of the mean for each concentration tested. $IC_{50}$ values were calculated using GraphPad Prism 8 software.

Viability Assays with Small Molecule Prodrugs Using Trypan Blue Exclusion Method For assays assessing cytotoxicity of β-lapachone versus small molecule dipeptide prodrugs, suspension cells were plated into 24 well plates at a density of $2.5\times10^5$ cells/mL in 240 μL. Serial dilutions of compound were made up in PBS. 60 μL of each stock of either PBS, or compound in PBS was added to the cells to achieve the desired final concentration. After the specified incubation time, toxicity was assessed by counting of live cells using the Trypan Blue exclusion method with a Countess II Automated Cell Counter (ThermoFisher Scientific) according to the manufacturer's instructions. Cell viability was determined by division of average live cell number of treated wells by average live cell number for control wells treated with PBS only. Values recorded are the mean of three repeat wells, with error bars representing the standard error of the mean for each concentration tested. $IC_{50}$ values were calculated using GraphPad Prism software.

Lysosomal Inhibition Assay with Small Molecule Prodrugs

Assays to assess the effect of lysosomal activity on prodrugs were performed as follows: HL-60 cells were plated into 96 well plates at a concentration of $2.5\times10^5$ cells/mL in 180 μL media. Cells were treated with 10 μL of a stock of $NH_4Cl$ in PBS (to obtain an in-plate concentration of 3 or 30 mM), 10 μL of a dilution of a DMSO stock of E64d in PBS (to obtain an in-plate concentration of 30 μM), PBS only, or a dilution of DMSO in PBS. Cells were incubated for 30 min. Following this, 10 μL of a stock of test compound made by dilution of a DMSO stock into media was added. DMSO was present in-plate at a maximum of 0.2%.

Cells were incubated overnight for 16 h. Following incubation, media was replaced with media containing CellTiter-Blue (Promega) in 1:4 dilution and the plates were incubated for 6 h. The fluorescence of the plates was recorded (excitation 555 nm, emission 585 nm, MiniMax i3× Reader, Molecular Devices). Cell viability was calculated by division of the fluorescence intensity of treated wells by that of the calculated average fluorescence intensity of the relevant negative control wells. Values and reported error bars represent the mean and standard error of the mean of three triplicate repeats for each concentration tested.

Glucuronide Kinetics Assay Method

Glucuronide prodrug (37a, b, c, d) was dissolved in DMSO to a concentration of 10 mM. A 100 mM stock solution of warfarin in DMSO was also prepared. To obtain deprotected para-hydroxybenzyl ketol species, the glucuronide stock solution was dissolved in PBS with 16.7% DMF to a concentration of 1.7 mM. 15 μL of a stock solution of β-glucuronidase from *E. coli* K-12 (Roche #03707580001, 140 U/mL) was added to 900 μL of this stock and incubated for 20 min at 37° C. 15 μL of a 100 mM stock of warfarin internal standard in DMSO was added. Reactions were then set up immediately. For a reaction, 30 μL of the amino-benzyl ketol/standard stock was added to 195 μL of citrate-phosphate buffer at the specified pH. Test samples were incubated at 37° C. with shaking. At the recorded time points, 20 μL aliquots of the reactions were analysed by HPLC (254 nm, Agilent 1260 Infinity). HPLC conditions: column Agilent InfinityLab Poroshell 120 SB-C18 2.7 μm, 50 ×4.6 mm; solvent system A=$H_2O$+0.1% TFA, B=acetonitrile+0.1% TFA; flow=1 mL/min. Gradient: t=0-1 min 0% B, t=1-2 min 0-30% B, t=2-17 min 30-40% B, t=17-17.1 min 40-100% B, t=17.1-18 min 100% B, t=18-23 min 0% B. Relative peak area represents raw peak area (mAU*s) normalized to raw peak area of the warfarin internal standard. Values recorded are averages of three independent reactions and error bars display standard error of the mean. Values were fitted to first-order kinetics using GraphPad Prism 9 software. A positive control experiment was performed under identical conditions with known substrate 4-nitrophenyl-B-D-glucuronide (Sigma Aldrich) to confirm enzyme activity.

Additional Materials and Methods

CellTiter Glo Viability Assay for Pancreatic Cell Lines

For CellTiter Glo viability assays, 10,000 cells per well were plated on Day 1 and were allowed to adhere to the plate surface for 24 hours. Optimized concentration ranges of prodrugs were determined and made via serial dilution. On Day 2, 1 μL of β-glucorinidase enzyme (pobtained from Roche) was added to each well and the cells were treated with compound for a final in-plate DMSO concentration of less than 0.1%. Cells were incubated with compound for 48 hours and viability was assessed on Day 4 using the CellTiter Glo Viability assay which measures metabolically active cells by quantifying the amount of ATP present.

mRNA Expression Assay for Pancreatic Cell Lines

Figure 8:
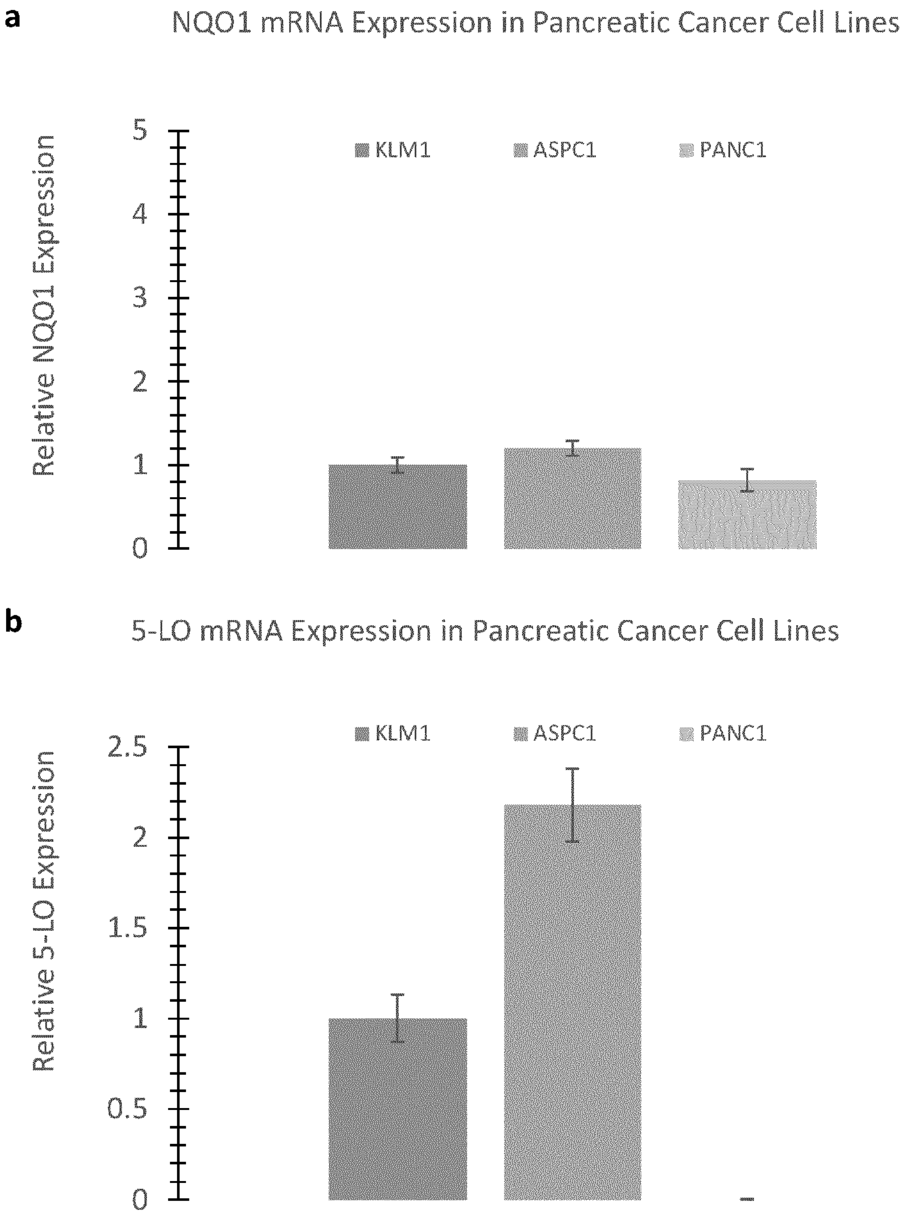
FIG. 8 shows the mRNA expression of β-Lapachone targets in pancreatic cancer cell lines. a displays relative mRNA expression of the NQO1 β-lapachone target in three pancreatic cancer cell lines: Aspc-1, KLM-1, and Panc-1. Aspc-1 and KLM-1 show similar levels of NQO1 expression, while Panc-1 shows the least expression. b shows relative mRNA of the alternative β-lapachone target, 5-LO in the same cell lines. Aspc-1 has the highest expression of 5-LO, KLM-1 shows mid-levels of 5-LO mRNA expression, and Panc-1 shows the lowest recorded expression of 5-LO mRNA.

To measure mRNA levels of the two β-lapachone targets of interest (NQO1 and 5-LO), primers for the two proteins based on a BLAST search for the sequences were ordered from Integrated DNA Technologies (IDT). Primers were ordered such that they covered all the human variants of both NQO1 and 5-LO. mRNA was then extracted from three pancreatic cancer cell lines (PANC-1, ASPC-1, and KLM-1) using the RNeasy Mini Kit and cDNA was created using the iScript cDNA Synthesis Kit. To confirm the validity of the primers, an end-PCR reaction with the cDNA and primers was run and the expected bands on a protein gel were visualized. Finally, a qPCR reaction was run with the acquired cDNA from all three cell lines and the verified NQO1 and 5-LO primers to measure relative mRNA expression. The HPRT gene was used as a housekeeping gene. The graphs shown in FIG. 8 are the most representative across 4 biological replicates.

Pancreatic Cell Culture Conditions

Panc-1 cells were obtained from Tony Kouzarides' lab in the Gurdon Institute at the University of Cambridge and put into culture at passage 10 containing DMEM media (Gibco) supplemented with 1% Pen-Strep antibiotic (Gibco), 1% L-glutamine, and 10% fetal bovine serum (FBS, sterile-filtered). Aspc-1 cells were bought commercially from the American Type Culture Collection (ATCC) and put into culture containing RPMI 1640 media (Gibco) supplemented with 1% Pen-Strep antibiotic (Gibco), 1% L-glutamine, and 20% fetal bovine serum (FBS, sterile-filtered). All cell lines were started at passage 10 and passaged every 3 days by centrifuging at 1000 rpm for 4 minutes.

Synthetic Procedures

Solvents, Reagents and Materials

All non-aqueous reactions were performed in oven-dried glassware under a positive pressure of nitrogen, unless otherwise stated. All reagents, unless otherwise stated, were purchased from commercial suppliers, and used as received without further purification. Anhydrous solvents were used for non-aqueous reactions, unless otherwise stated. Anhydrous DCM and $Et_2O$ were freshly distilled over $CaH_2$ under an atmosphere of argon. Anhydrous DMF was obtained from commercial sources and used directly. Water used experimentally was deionised and prepared on site. Merck Silica gel 60 was used for flash column chromatography. Analysis of reactions was performed using TLC silica gel 60 F254 plates. Analytical TLC plates were visualised by UV at 254 nm or by staining with known indicator solutions.

Characterisation of Synthesised Compounds

NMR spectra were recorded on Bruker 400-AVIII, DPX-400, 500-AVIII HD Smart Probe or Avance-600 BBI as appropriate. NMR spectra were recorded at 25° C. and 400, 500 or 600 MHz for $^1H$ and 100, 126 or 150 MHz for $^{13}C$. The solvent is specified for each spectrum. The residual solvent peaks were used as an internal reference for chemical shift ($^1H$ NMR $CDCl_3$ δ 7.26 ppm, DMSO δ 2.50 ppm, MeOD δ 3.31 ppm; $^{13}C$ NMR $CDCl_3$ δ 77.0 ppm, MeOD δ 49.0 ppm, DMSO δ 39.5 ppm). Splitting patterns are presented as follows: chemical shift (ppm), multiplicity (s, singlet; d, doublet; t, triplet; q, quartet; qu, quintet; sextet; hept, heptet; m, multiplet (denotes complex pattern); br, broad; dd, doublet of doublets; dt, doublet of triplets; td, triplet of doublets), coupling constant (J) and relative integration value. Chemical shifts are given in ppm (o-scale) relative to the resonance of their respective residual solvent peaks, with coupling constants (J) in Hz. Structural assignments are made with the aid of COSY, HSQC and HMBC experiments. H1/H2 denotes a signal which may correspond to H1 or to H2. For signal processing, MestReNova software version 8.0.0 was used. Absorbance and fluorescence spectra of small molecules were recorded on a MiniMax i3x imager in 96 well clear plates or clear bottom black plates. High resolution mass spectra of small molecules were obtained with a Thermo Fisher Orbitrap or Waters Xevo LC-MS and ionized by electrospray (ESI).

β-lapachone 1 was synthesised by the following synthetic route, from lawsone, via lapachol. This route was inspired by two known procedures (ChemMedChem, 2015, 10, 1413-1423 and *Tet. Lett.*, 2014, 55, 1475-1478).

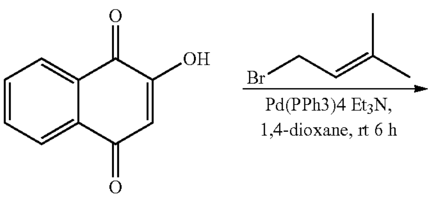

Lawsone

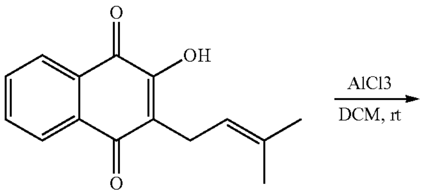

Lapachol

-continued

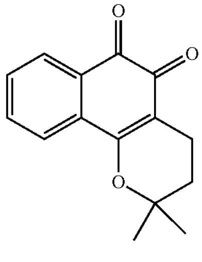

1

A fast synthesis of β-lapachone 1 was also developed, avoiding purification of lapachol.

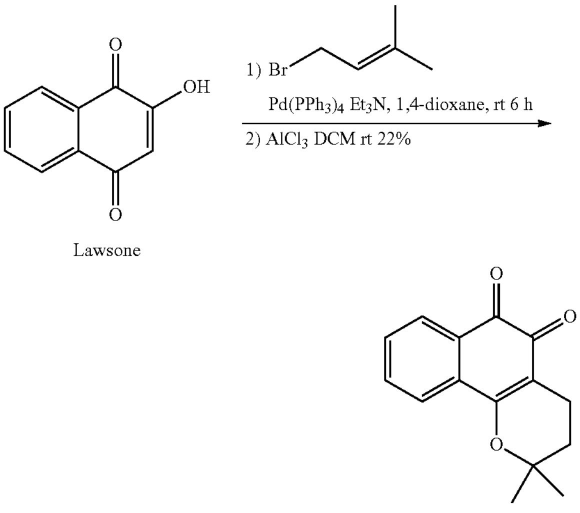

Lawsone

1

Lapachol

To a mixture of lawsone (2.00 g, 11.4 mmol), tetrakis (triphenylphosphine) palladium (0) (26 mg, 0.02 mmol) in dioxane (50 mL), 1-bromo-3-methyl-2-butene (1.60 mL, 13.8 mmol) and triethylamine (1.92 mL, 13.8 mmol) were added. The reaction was stirred at room temperature for 6 hours. Then, water (40 mL) was added, and the crude was extracted into dichloromethane. Organic layers reunited were dried over $MgSO_4$ and filtered. The organic solvent was removed in vacuo and the resulting crude was purified by silica column (diethyl ether/hexane 1:8) affording lapachol (647.8 mg, 2.67 mmol, 23%) as a yellow powder.

$^1$H NMR (400 MHz, $CDCl_3$) δ 8.12 (d, J=7.7 Hz, 1H), 8.07 (d, J=7.6 Hz, 1H), 7.75 (t, J=7.6 Hz, 1H), 7.67 (t, J=7.5 Hz, 1H), 7.30 (s, 1H), 5.21 (t, J=7.5 Hz, 1H), 3.31 (d, J=7.4 Hz, 2H), 1.79 (s, 3H), 1.68 (s, 3H).

β-Lapachone 1

Synthesis from lapachol: To a solution of lapachol (638.8 mg, 2.63 mmol) in anhydrous dichloromethane (13 mL), under inert atmosphere, $AlCl_3$ (1.78 g, 13.3 mmol) was added. The reaction was stirred at room temperature for 1 h. Then the mixture was cooled at 0° C. and water (20 mL) was added dropwise. The crude was extracted into dichloromethane and organic layers reunited were dried over $MgSO_4$ and filtered. The organic solvent was removed in vacuo and the crude was purified by flash chromatography (Petroleum ether/ethyl acetate 4:1) to afford 1 (574.3 mg, 2.37 mmol, 90%) as a red solid.

Synthetic method avoiding purification of intermediate lapachol: To a solution of lawsone (1.00 g, 5.75 mmol) dissolved in 1,4-dioxane (25 mL) was added tetrakis (triphenylphosphine) palladium (0) (0.2 mol %, 13 mg), triethylamine (960 μL, 6.90 mmol) and 1-bromo-3-methyl-2-butene (800 μL, 6.90 mmol). The reaction mixture was stirred under a nitrogen atmosphere for 4 h. Following this, water (10 mL) was added and the reaction was extracted into dichloromethane (3×10 mL), dried (anhydrous magnesium sulphate), filtered, and solvent was removed in vacuo. The crude product was then redissolved in anhydrous dichloromethane (30 mL) and anhydrous aluminium trichloride (3.80 g, 28.5 mmol) was added. The reaction was stirred for 6 h at room temperature before being quenched by addition of water (30 mL). The crude product was isolated by extraction into dichloromethane (3×30 mL). The organic phase was dried (anhydrous magnesium sulphate), filtered and solvent was removed in vacuo. Flash column chromatography (4:1 petroleum ether/ethyl acetate) afforded β-lapachone 1 as a red solid (300 mg, 1.24 mmol, 22%). $R_f$ 0.25 (4:1 petroleum ether/ethyl acetate, UV).

$^1$H NMR (400 MHz, $CDCl_3$): δ 8.03 (d, J=7.7 Hz, 1H, H7), 7.79 (d, J=7.8 Hz, 1H, H10), 7.62 (t, J=7.6 Hz, 1H, H9), 7.48 (t, J=7.6 Hz, 1H, H8), 2.55 (t, J=6.6 Hz, 2H, H4), 1.84 (t, J=6.7 Hz, 2H, H3), 1.45 (s, 6H, H1). $^{13}$C NMR (101 MHz, $CDCl_3$) δ 179.9 (C6), 178.6 (C5), 162.1 (C10b), 134.9 (C9), 132.7 (C10a), 130.7 (C8), 130.2 (C6a), 128.6 (C7), 124.2 (C10), 112.8 (C4a), 79.4 (C2), 31.7 (C3), 26.8 (C1), 16.3 (C4). HRMS (m/z): [M+H]+ calcd. for $C_{15}H_{14}O_3$ 243.1016, found 243.1008.

Synthesis of Dunnione 12

The synthesis of Dunnione was carried out inspired by a previously described methodology (Ough, Cancer Biol. Ther., 2005, 4, 95-102). A solution of Lawsone (2.00 g, 11.50 mmol) in DMF (15 mL) was added to a suspension of $K_2CO_3$ (1.60 g, 11.50 mmol) in DMF (55 mL). The mixture was stirred for 15 min. Then, a solution of 1-bromo-3-methyl-2-butene (3.30 mL, 28.70 mmol) in DMF (5 mL) was added dropwise at room temperature over 30 minutes and then, the reaction was refluxed for 8 hours. Following this, the reaction was cooled, filtered and poured into dichloromethane (30 mL). The crude was washed with water (5×25 mL), and the organic layer was dried over $MgSO_4$, filtered and the solvent was removed in vacuo. Flash column chromatography (Petroleum Ether/Ethyl Acetate 10:1à8:1) afforded (±) Dunnione, 12 (524 mg, 2.16 mmol, 19%) as a red solid.

$^1$H NMR (400 MHz, $CDCl_3$) δ 8.05 (d, J=7.6 Hz, 1H), 7.66-7.61 (m, 2H), 7.59-7.50 (m, 1H), 4.67 (q, J=6.6 Hz, 1H), 1.47 (d, J=6.6 Hz, 3H), 1.45 (s, 3H), 1.26 (s, 3H). $^{13}$C NMR (101 MHz, $CDCl_3$) δ 181.6, 175.5, 168.3, 134.6, 131.7, 130.9, 129.3, 128.0, 124.6, 123.4, 93.0, 44.2, 25.9, 20.5, 14.7. HRMS (m/z): [M+H]+ calcd, for $C_{15}H_{14}O_3$ 243.1016, found 243.1026. NMR are in accordance with previously reported literature (Pink).

3-Hydroxy β-Lapachone 11

To a solution of lapachol (110 mg, 0.45 mmol) in anhydrous dichloromethane (20 mL) was added 3-chloroperoxybenzoic acid (145 mg, 77% (w/w), 0.65 mmol) and the mixture was stirred at room temperature for 24 hr. The reaction was quenched by addition of sodium hydrogen carbonate (20 mL), washed (water, 2×10 mL), dried (magnesium sulfate) and solvent was removed in vacuo. The crude reaction mixture was purified by flash column chromatography (1:1 dichloromethane/ethyl acetate) to obtain 3-hydroxy β-lapachone 11 as a red solid (74 mg, 0.29 mmol, 64%). $^1$H NMR (400 MHz, $CDCl_3$) δ 8.04 (dd, J=7.6, 1.4 Hz, 1H), 7.83 (dd, J=7.9, 1.2 Hz, 1H), 7.64 (ddd, J=7.7, 1.4 Hz, 1H), 7.50 (ddd, J=7.6, 1.2 Hz, 1H), 3.93 (t, J=5.2 Hz, 1H), 2.80 (dd, J=17.7, 4.9 Hz, 1H), 2.61 (dd, J=17.7, 5.4 Hz, 1H), 2.29 (s, 1H), 1.74 (s, 1H), 1.51 (s, 3H), 1.45 (s, 3H). $^{13}$C NMR (101 MHz, $CDCl_3$) δ 179.7, 178.9, 161.7, 135.0, 132.2, 131.1, 130.2, 128.9, 124.5, 110.6, 81.7, 68.4, 25.5, 25.2, 22.2. HRMS (m/z): [M+H]+ calcd. for $C_{15}$H1604, 259.0965 found 259.0960.

9,10-Phenanthrenequinone 4

This compound was obtained commercially.

9,10-Phenanthrenediol 8

9,10-Phenanthrenequinone 4 (1.00 g, 4.81 mmol) was dissolved in water/ether 1:1 (50 mL) and sodium dithionite (2.10 g, 85%, 10.25 mmol) was added to the solution. The reaction was stirred while being degassed with nitrogen for 1 h. Water (50 mL) was added to the reaction and the product was extracted with ethyl acetate (3×30 mL), dried (magnesium sulfate), filtered, and solvents were removed in vacuo to yield phenanthrene-9,10-diol, 8, (860 mg, 4.10 mmol, 85%) as a brown-white solid.

$^1$H NMR (400 MHz, DMSO-$d_6$) δ 8.72 (s, 2H, OH), 8.35 (d, J=8.3 Hz, 2H, H6), 7.90 (d, J=8.2 Hz, 2H, H3), 7.30 (dd, J=7.6 Hz, 2H, H5), 7.20 (dd, J=7.6 Hz, 2H, H4). $^{13}$C NMR (100 MHz, DMSO-$d_6$) δ 134.6, 127.7, 126.6, 126.2, 124.4, 122.9, 121.5, 39.5. HRMS (m/z): [M−H]− calcd, for $C_{14}$H1002 209.0603, found 209.0610.

Linker tert-butyl (4-(bromomethyl)phenyl) carbamate 5 was synthesised from 4-aminobenzyl alcohol S1 by the following synthetic route.

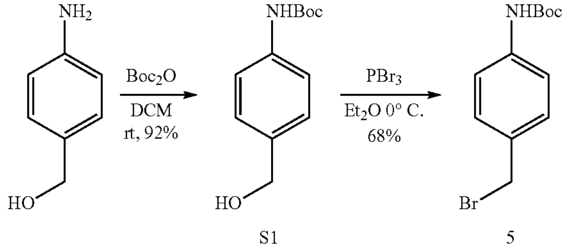

S1 5

Tert-butyl (4-(hydroxymethyl)phenyl) carbamate S1

To a solution of para-aminobenzyl alcohol (1.00 g, 8.13 mg) in anhydrous dichloromethane (30 mL) under nitrogen was added di-tert-butyl dicarbonate (1.95 g, 8.94 mmol) dissolved in anhydrous dichloromethane (10 mL) and the solution was stirred at room temperature for 16 h. Following this, methanol (10 mL) was added and the reaction stirred for 10 min. Solvent was removed in vacuo to give the crude product. The crude product was purified by flash column chromatography (40-60 petroleum ether/ethyl acetate 1:1) to yield tert-butyl (4-(hydroxymethyl)phenyl) carbamate S1 as a yellow solid (1.67 g, 7.52 mmol, 92%).

$^1$H NMR (400 MHz, $CDCl_3$): δ 7.32 (d, J=8.3 Hz, 2H), 7.25 (d, J=8.6 Hz, 2H), 7.08 (s, 1H), 6.64 (s, 1H), 4.59 (s, 2H), 1.51 (s, 9H). $^{13}$C NMR (100 MHz, $CDCl_3$): δ 152.9, 137.9, 136.0, 128.0, 118.8, 80.7, 77.5, 77.2, 76.8, 65.0, 28.5.

Tert-butyl (4-(bromomethyl)phenyl)carbamate 5

A solution of tert-butyl (4-(hydroxymethyl)phenyl) carbamate S1 (1.04 g, 4.65 mmol) dissolved in anhydrous ether (20 mL) was cooled to 0° C. before addition of phosphorous tribromide (1.0 M in dichloromethane, 1.86 mmol, 1.86 mL) dropwise over 30 seconds. The reaction was stirred at 0° C. for 30 min, when thin-layer chromatography indicated completion of the reaction. The solution was poured onto ice cold water (10 mL) and extracted with ether (3×20 mL). The organic phase was dried (sodium sulphate), filtered, and solvent was removed in vacuo to yield the crude product tert-butyl (4-(bromomethyl)phenyl) carbamate 5 as an off-white solid (900 mg, 3.15 mmol, 68%). The product was used without further purification.

$^1$H NMR (400 MHz, $CDCl_3$): δ 7.35-7.28 (m, 4H, H2 & H3), 6.58 (s, 1H, NH), 4.47 (s, 2H, H5), 1.52 (s, 9H, H8). $^{13}$C NMR (100 MHz, $CDCl_3$): δ 152.7, 138.7, 132.3, 130.0, 129.6, 118.7, 80.9, 33.8, 28.4. HRMS (m/z): [M−Br] calcd, for $C_{12}H_{16}NO_2$ 206.1181, found 206.1176.

Boc-para-aminobenzyl phenanthrene-ketol 6 tert-butyl (4-((9-hydroxy-10-oxo-9,10-dihydrophenanthren-9-yl)methyl)phenyl) carbamate

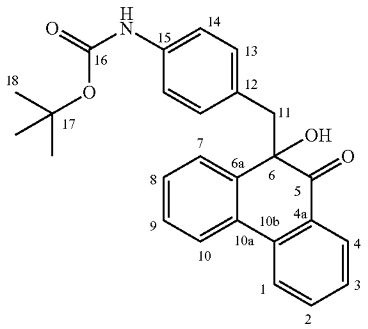 [SMILES: CC(C)(C)OC(=O)Nc1ccc(CC2(O)C(=O)c3ccccc3-c3ccccc32)cc1]

9,10-Phenanthrenequinone 4 (500 mg, 2.40 mmol), sodium dithionite (2.50 g, 85%, 12.2 mmol) and tetrabutylammonium bromide (1.80 g, 5.6 mmol) were dissolved in a solution of tetrahydrofuran/water 1:1 (36 mL). Potassium hydroxide (2.70 g, 48 mmol, 20 equiv.) in water (2 mL) was then added, followed immediately by Boc-para-aminobenzyl bromide 5 (1.40 g, 4.90 mmol) in tetrahydrofuran (2 mL). The reaction was then refluxed for 3.5 h. Water (60 mL) was added, and then the product was extracted into ethyl acetate (3×30 mL), washed (water, 1×30 mL), dried (magnesium sulfate), and solvent was removed in vacuo. The crude product was purified by flash column chromatography (petroleum ether/ethyl acetate 4:1) to yield Boc-para-aminobenzyl phenanthrene-ketol 6 (610 mg, 1.46 mmol, 61%) as a yellow solid.

$^1$H NMR (600 MHz, $CDCl_3$) δ 7.94 (d, J=8.0 Hz, 1H, H1), 7.88 (dd, J=7.6, 1.4 Hz, 1H, H4), 7.85 (dd, J=7.8, 1.6 Hz, 1H, H10), 7.70 (td, J=7.5, 1.5 Hz, 1H, H2), 7.61 (dd, J=7.6, 1.6 Hz, 1H, H7), 7.44 (td, J=7.4, 1.0 Hz, 1H, H3), 7.40 (td, J=7.4, 1.6 Hz, 1H, H8), 7.36 (td, J=7.5, 1.4 Hz, 1H, H9), 7.17 (d, J=8.2 Hz, 2H, H14), 6.77 (d, J=8.4 Hz, 2H, H13), 6.50 (s, 1H, NH), 4.01 (s, 1H, OH), 3.00 (d, J=13.7 Hz, 1H, H11), 2.93 (d, J=13.7 Hz, 1H, H11), 1.51 (s, 9H, H18). $^{13}C$ NMR (151 MHz, $CDCl_3$) δ 202.7 (C5), 152.8 (C16), 140.2 (C4a/C6a/C10a/C10b), 137.7 (C4a/C6a/C10a/C10b), 137.4, (C12), 135.2, (C2), 130.9 (C13), 129.3, (C9), 129.3, (C15), 129.2 (C4a/C6a/C10a/C10b), 128.8 (C8), 128.6 (C4a/C6a/C10a/C10b), 128.3, (C3), 127.49 (C4), 126.4 (C7), 124.1 (C10), 123.4 (C1), 117.8 (C14), 80.5 (C17), 79.4 (C6), 50.6 (C11), 28.5 (C18). HRMS (m/z): [M−H]− calcd. for $C_{26}H_{25}NO4$ 414.1705, found 414.1706.

Boc-para-aminobenzyl β-lapa-ketol 9 tert-butyl (4-((6-hydroxy-2,2-dimethyl-5-oxo-3,4,5,6-tetrahydro-2H-benzo[h]chromen-6-yl)methyl)phenyl)carbamate

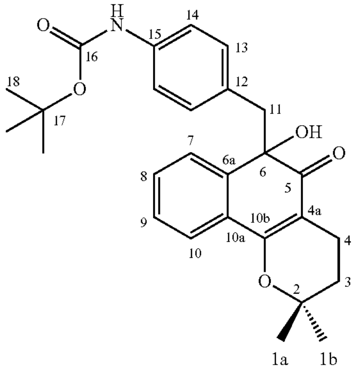

β-lapachone 1 (200 mg, 0.83 mmol), sodium dithionite (85%, 830 mg, 3.52 mmol) and tetrabutylammonium bromide (1350 mg, 4.04 mmol) were dissolved in a solution of tetrahydrofuran/water 1:1 (16 mL). The solution was heated to 80° C. over 10 min. Potassium hydroxide (900 mg, 16.0 mmol, 20 equiv.) in water (2 mL) was then added, followed immediately by Boc-para-aminobenzyl bromide 5 (1300 mg, 4.56 mmol) in tetrahydrofuran (2 mL). The reaction was then refluxed for 4.5 h. Water (30 mL) was added, then the product was extracted into ethyl acetate (3×30 mL), washed (water, 1×30 mL), dried (magnesium sulfate), and solvent was removed in vacuo. The crude product was purified by flash column chromatography (petroleum ether/ethyl acetate 4:1) to yield Boc-para-aminobenzyl β-lapa-ketol 9 (270 mg, 0.60 mmol, 72%) as a yellow solid.

$^1H$ NMR (400 MHz, $CDCl_3$): δ 7.65 (d, J=7.8, 1H, H10), 7.59 (d, J=7.8, 1H, H7), 7.43 (t, J=7.6, 1H, H8), 7.32 (t, J=7.6, 1H, H9), 7.06 (d, J=8.1 Hz, 2H, H14), 6.51 (d, J=8.5 Hz, 2H, H13), 6.38 (s, 1H, NH), 3.96 (s, 1H, OH), 3.01 (s, 2H, H11), 2.53 (dt, J=17.3, 5.6 Hz, 1H, H4), 2.15 (ddd, J=17.3, 8.6, 6.7 Hz, 1H, H4), 1.71-1.60 (m, 2H, H3), 1.49 (s, 9H, H18), 1.35 (s, 3H, H1a/H1b), 1.12 (s, 3H, H1a/H1b). $^{13}C$ NMR (100 MHz, $CDCl_3$): δ 200.6 (C5), 162.3 (C10b), 152.7 (C16), 141.6 (C6a), 137.2 (C12), 130.2 (C8), 130.1 (C13), 129.7 (C10a), 127.6 (C15), 127.5 (C9), 125.8 (C7), 123.1 (C10), 117.7 (C14), 106.9 (C4a), 80.5 (C17), 78.3 (C6), 78.1 (C2), 53.9 (C11), 31.8, (C3), 28.4 (C18), 27.7 (C1a/C1b), 25.7 (C1a/C1b), 15.7. (C4). HRMS (m/z): [M+H]+ calcd, for $C_{27}H31NO5$ 450.2275 found 450.2275.

Boc-para-aminobenzyl dunni-ketol 15

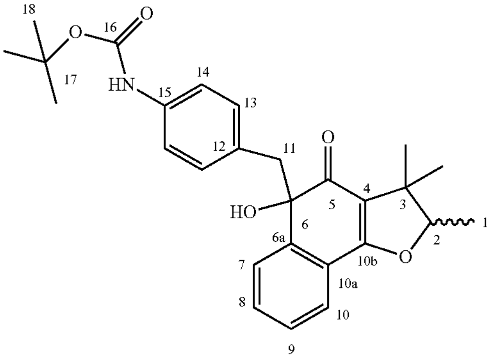 [SMILES: CC1OC2=C(C(=O)C(O)(Cc3ccc(NC(=O)OC(C)(C)C)cc3)c3ccccc32)C1(C)C]

(±)-Dunnione 12 (75 mg, 0.31 mmol), sodium dithionite (85%, 258 mg, 1.26 mmol), and tetrabutylammonium bromide (417 mg, 1.50 mmol) were dissolved in a solution of THF/water 1:1 (5 mL). The solution was heated to 80° C. over 10 min. Potassium hydroxide (337 mg, 6.00 mmol) in water (2.50 mL) was then added, followed immediately by Boc-para-aminobenzyl bromide (5) (479 mg, 1.68 mmol) in THF (2.50 mL). The reaction was then refluxed for 1.5 h. Water (15 mL) was added, then the product was extracted into ethyl acetate, washed with water, dried over $MgSO_4$, filtered and the solvent was removed in vacuo. The crude product was purified by flash column chromatography (Petroleum Ether/Ethyl acetate 6:1) to yield Boc-para-aminobenzyl dunni-ketol 15 (91.60 mg, 0.20 mmol, 64%) as a yellow foam.

$^1H$ NMR (500 MHz, $CDCl_3$, mixture of diastereoisomer 2:1) δ 7.59 & 7.57 (2 ddd, J=7.8, 1.3, 0.5 Hz, 1H, H10/7), 7.53 (ddd, J=7.7, 1.4, 0.5 Hz, 1H, H10/7), 7.48 & 7.46 (2 td, J=7.6, 1.4 Hz, 1H, H8/9), 7.38 & 7.34 (2 td, J=7.5, 1.3 Hz, 2H, H8/9), 7.09 & 7.07 (2 d, J=8.1 Hz, 2H, H14), 6.68-6.59 & 6.59-6.52 (2 m, 2H, H13), 6.41 & 6.38 (2 s, 1H, NH), 4.52 & 4.35 (2 q, J=6.6 Hz, 1H, H2), 3.04 & 3.02 (2 d, J=12.8 Hz, 1H, H11a), 3.01 & 2.98 (2 d, J=12.8 Hz, 1H, H11b), 1.50 & 1.49 (2 s, 9H, H18), 1.38 & 1.16 (2 d, J=6.6 Hz, 3H, H1), 1.35 & 1.30 (2 s, 3H, $CH_3$), 1.22 & 1.10 (s, 3H, $CH_3$). $^{13}C$ NMR (126 MHz, $CDCl_3$, mixture of diastereoisomers) δ 197.6 & 197.1 (C5), 169.0 & 168.5 (C10b), 152.7 (C16), 145.0 & 144.9 (C6a), 137.2 (C12), 131.04 & 131.00 (CHAr), 130.9 & 130.7 (C13), 129.5 & 129.4 (CAr), 127.7 & 127.6 (CAr), 126.7 & 126.6 (CHAr), 123.70 & 123.4 (CHAr), 123.69 & 123.60 (CHAr), 117.9 & 116.9 (C4), 117.6 (C14), 92.6 & 91.9 (C2), 80.6 $(C17)_{79.8}$ & 79.4 (C6), 53.21 & 53.12 (C11), 44.0 & 43.8 (C3), 28.46 & 28.46 (C18), 28.1 & 24.2 ($CH_3$), 27.7 & 19.9 ($CH_3$), 15.9 & 13.7 (C1). HRMS (m/z): [M+H]+ calcd, for $C_{27}H_{32}NO_5$ 450.2275, found 450.2285.

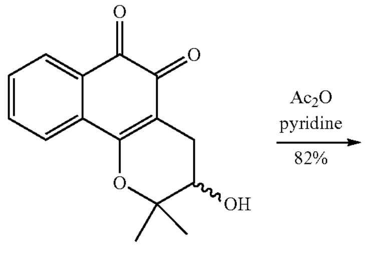

11

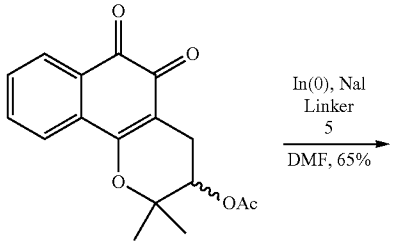

S2

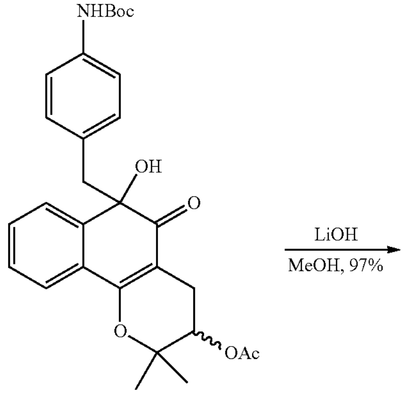

S3

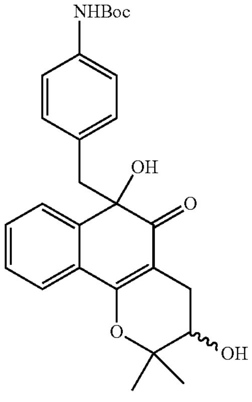

14

(+/−)O-Acetyl-3-hydroxy-β-Lapachone (S2)

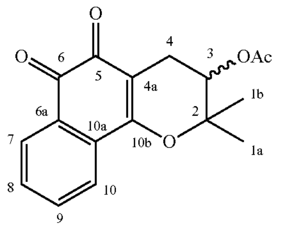 [SMILES: CC(=O)OC1CC2=C(OC1(C)C)c1ccccc1C(=O)C2=O]

To a solution of hydroxy-β-lapachone 11 (85 mg, 0.33 mmol) in anhydrous pyridine (1.00 mL) acetic acid (0.50 mL) was added at 0° C. The mixture was stirred at room temperature for 5 h. Then the pyridine was removed in vacuo and the resulting crude was purified by silica column (Petroleum ether/ethyl acetate 1:6) to afford S2 (79.90 mg, 0.27 mmol, 82%).

$^{1}$H NMR (400 MHz, $CDCl_3$) δ 8.08 (d, J=7.6 Hz, 1H, H7), 7.84 (d, J=7.8 Hz, 1H, H10), 7.67 (td, J=7.7, 1.4 Hz, 1H, H8), 7.53 (td, J=7.6, 1.3 Hz, 1H, H9), 5.13 (t, J=4.6 Hz, 1H, H3), 2.89-2.75 (dd, J=18.2, 4.9 Hz, 1H, H4), 2.75-2.61 (dd, J=18.2, 4.2 Hz, 1H, H4), 2.07 (s, 3H, $CH_3$ Ac), 1.48 (s, 3H, H1), 1.43 (s, 3H, H1). $^{13}$C NMR (101 MHz, $CDCl_3$) δ 179.5 (C6), 178.7 (C5), 170.2 (COOCH3), 161.3 (C10b), 135.0 (C8), 132.1 (C6a), 131.1 (C9), 130.2 (C10b), 129.0 (C7), 124.4 (C10), 110.2 (C4a), 79.8 (C2), 69.2 (C3), 25.0 (C1), 23.3 (C1), 22.8 (C4), 21.1 (COOCH3). HRMS (m/z): [M+H]+ calcd, for $C_{17}$H1605 301.1021, found 301.1101.

(+/−) Boc-para-aminobenzyl-O-acetyl-β-lapa-ketol (S3)

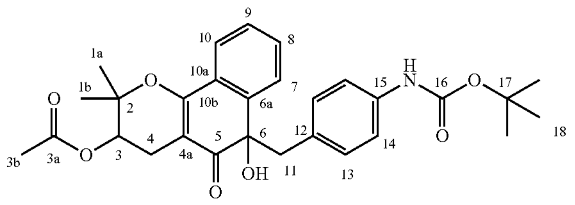 [SMILES: CC(=O)OC1CC2=C(OC1(C)C)c1ccccc1C(O)(Cc1ccc(NC(=O)OC(C)(C)C)cc1)C2=O]

Boc-para-aminobenzyl bromide 5 (0.140 g, 0.49 mmol, 2.9 eq), NaI (0.210 g, 1.4 mmol, 8.5 eq), S2 (0.050 g, 0.16 mmol, 1 eq) and indium (0) powder (0.043 g, 0.38 mmol, 2.3 eq) were added to anhydrous dimethylformamide (4 mL). The solution was heated to 40° C. and sonicated for 3 hr, while monitoring by thin-layer chromatography (1:1 ethyl acetate: petroleum ether). Water (10 mL) and 7 drops 1M HCl were added to quench the reaction and it was extracted with ethyl acetate (3×150 mL). The organic layers were combined and washed with brine (10 mL), dried (sodium sulfate), and the solvent removed in vacuo. The product was purified by flash column chromatography on silica gel 60 (20-30% ethyl acetate: petroleum ether) to give (+/−) Boc-para-aminobenzyl-O-acetyl-β-lapa-ketol S3 as an orange solid (0.054 g, 0.1 mmol, 65%).

$^{1}$H NMR (500 MHz, $CDCl_3$, mixture of diastereoisomers A:B 1:2) δ 7.70 (dd, J=7.9, 1.3 Hz, 1H, AH7), 7.67 (dd, J=6.4, 1.4 Hz, 1H, BH7), 7.66 (dd, J=6.2, 1.4 Hz, 1H, BH10), 7.58 (dd, J=7.7, 1.3 Hz, 1H, AH10), 7.48 (td, J=7.6, 1.3 Hz, 1H, BH8), 7.45 (td, J=7.6, 1.4 Hz, 1H, AH8), 7.35 (tdd, J=7.6, 5.0, 1.3 Hz, 1H, AH9/BH9), 7.10 (d, J=8.1 Hz, 2H, AH14), 7.05 (d, J=8.1 Hz, 2H, BH14), 6.57 (d, J=8.5 Hz, 2H, AH13), 6.46 (brs, 1H, A/B NH), 6.45 (d, J=8.5 Hz, 2H, BH13), 4.96 (dd, J=6.7, 5.4 Hz, 1H, AH3), 4.92 (dd, J=4.8, 3.4 Hz, 1H, BH3), 3.03 (d, J=2.1 Hz, 2H, BH11), 3.01 (s, 2H, AH11), 2.87 (dd, J=17.3, 5.4 Hz, 1H, AH4), 2.61 (dd, J=18.0, 3.4 Hz, 1H, BH4), 2.36 (dd, J=17.9, 4.8 Hz, 1H, BH4), 2.19 (dd, J=16.7, 6.1 Hz, 1H, AH4), 2.08 (s, 3H, AH3b), 1.99 (s, 3H, BH3b), 1.49 (s, 9H, AH18), 1.48 (s, 9H, BH18), 1.35 (s, 3H, AH1a/1b), 1.33 (s, 3H, BH1a/1b), 1.16 (s, 3H, AH1a/1b), 1.01 (s, 3H, BH1a/1b). $^{13}C$ NMR (126 MHz, $CDCl_3$, mixture of diastereoisomers A: B 1:2) δ 200.6 (BC5), 200.4 (AC5), 170.3 (BC3a), 170.0 (AC3a), 161.5 (BC10b), 161.1 (AC10b), 152.6 (A/B $C_{16}$), 141.9 (AC6a), 141.5 (BC6a), 137.3 (A/B $C_{12}$), 130.5 (BC8), 130.4 (AC8), 130.3 (AC13), 130.0 (BC13), 129.4 (BC15), 129.4 (AC15), 127.6 (BC9), 127.6 (AC9), 127.1 (BC10a), 126.6 (AC10a), 125.9 (BC10), 125.9 (AC10), 123.4 (AC7), 123.1 (BC7), 117.8 (A/B $C_{14}$), 104.6 (AC4a), 104.4 (BC4a), 80.5 (A/B $C_{17}$), 78.6 (A/B $C_2$), 78.4 (BC6), 78.3 (AC6), 70.2 (AC3), 69.2 (BC3), 54.0 (BC11), 53.5 (AC11), 28.4 (A/B $C_{18}$), 25.3 (AC1a/b), 24.2 (BC1a/b), 23.5 (BC1a/b), 22.2 (AC4), 22.0 (BC4), 21.5 (AC1a/b), 21.0 (A/B $C_3$b). HRMS (m/z): [M+H]+ calcd, for $C_{29}H_{34}NO_7$ 508.2330, found 508.2324.

Boc para-aminobenzyl 3-hydroxy-β-lapa-ketol (14)

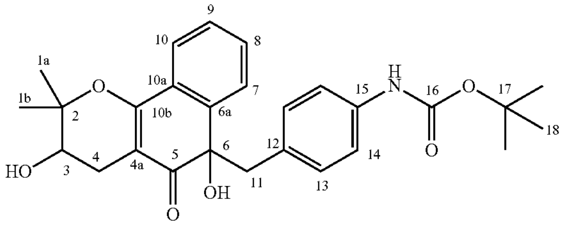 [SMILES: CC(C)(C)OC(=O)Nc1ccc(CC2(O)C(=O)C3=C(OC(C)(C)C(O)C3)c3ccccc32)cc1]

S3 (0.054 g, 0.11 mmol, 1 eq) was dissolved in tetrahydrofuran (2 mL) and methanol (2 mL) and stirred at 0° C. A separate solution of lithium hydroxide monohydrate (9 mg, 0.21 mmol, 2 eq) in water (2 mL) was prepared and added dropwise to the solution over 5 min. The mixture was stirred at 0° C. for 1.5 hr until completion and then acetic acid (12.3 μL, 0.21 mmol, 2 eq) was added to quench the reaction. The solvent was removed in vacuo, and the residue was redissolved in ethyl acetate (25 mL). The organic layer was washed with water (10 mL), brine (10 mL), dried ($Na_2SO_4$), and the solvent removed in vacuo to give 14 as a pink solid (0.048 g, 0.104 mmol, 97%).

$^1H$ NMR (500 MHz, $CDCl_3$, mixture of diastereoisomers A: B 1:2) o 7.65 (dd, J=4.3, 1.5 Hz, 1H, A/B H7), 7.64 (dd, J=4.3, 1.3 Hz, 1H, A/B H10), 7.46 (qd, J=7.4, 1.3 Hz, 1H, A/B H8), 7.33 (qd, J=7.3, 1.3 Hz, 1H, A/B H9), 7.03 (dd, J=13.5, 7.8 Hz, 2H, A/B H14), 6.60 (brs, 1H, A/B NH), 6.46 (d, J=8.5 Hz, 2H, AH13), 6.43 (d, J=8.5 Hz, 2H, BH13), 3.64-3.59 (m, 1H, A/B H3), 3.02 (s, 2H, A/B H11), 2.72 (dd, J=17.1, 5.3 Hz, 1H, AH4), 2.53 (dd, J=17.4, 4.6 Hz, 1H, BH4), 2.34 (dd, J=17.4, 4.7 Hz, 1H, BH4), 2.10 (dd, J=16.9, 6.8 Hz, 1H, AH4), 1.47 (s, 9H, A/B H18), 1.36 (s, 3H, BH1a/1b), 1.32 (s, 3H, AH1a/1b), 1.09 (s, 3H, AH1a/1b), 1.01 (s, 3H, BH1a/1b). $^{13}C$ NMR (126 MHz, $CDCl_3$, mixture of diastereoisomers A: B 1:2) δ 201.1 (BC5), 200.9 (AC5), 161.9 (BC10b), 161.8 (AC10b), 152.9 (A/B $C_{16}$), 141.7 (AC6a), 141.6 (BC6a), 137.3 (AC12), 137.2 (BC12), 130.5 (AC8), 130.5 (BC8), 130.0 (AC13), 129.9 (BC13), 129.6 (BC15), 129.4 (AC15), 127.7 (AC9), 127.6 (BC9), 127.1 (BC10a), 126.9 (AC10a), 125.9 (AC10), 125.9 (BC10), 123.3 (AC7), 123.2 (BC7), 118.0 (A/B $C_{14}$), 105.2 (AC4a), 104.9 (BC4a), 80.5 (A/B $C_{17}$), 80.3 (A/B $C_2$), 78.4 (BC6), 78.3 (AC6), 69.0 (AC3), 68.1 (BC3), 53.9 (BC11), 53.8 (AC11), 28.4 (A/B $C_{18}$), 25.3 (AC1a/1b), 24.8 (AC4), 24.7 (BC4), 24.5 (BC1a/1b), 22.6 (BC1a/1b), 20.7 (AC1a/1b). HRMS (m/z): [M+H]+ calcd. for $C_{27}$H32NO6 466.2224, found 466.2217.

Boc-para-aminobenzyl cryptotanshi-ketol 16

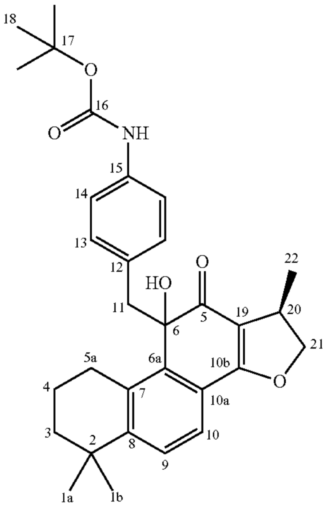 [SMILES: C[C@H]1COC2=C1C(=O)C(O)(Cc1ccc(NC(=O)OC(C)(C)C)cc1)c1c2ccc2c1CCCC2(C)C]

Cryptotanshinone 13 (152.6 mg, 0.51 mmol), sodium dithionite (85%, 439 mg, 2.14 mmol), and tetrabutylammonium bromide (708 mg, 2.55 mmol) were dissolved in a solution of THF/water 1:1 (5 mL). The solution was heated to 80° C. over 10 min. Potassium hydroxide (572.3 mg, 10.2 mmol) in water (3.00 mL) was then added, followed immediately by Boc-para-aminobenzyl bromide 5 (807 mg, 2.83 mmol) in THF (3.00 mL). The reaction was then refluxed for one hour. Water (15 mL) was added, then the product was extracted into ethyl acetate, washed with water, dried over $MgSO_4$, filtered and the solvent was removed in vacuo. The crude product was purified by flash column chromatography (Petroleum Ether/Ethyl acetate 8:1) to yield Boc-para-aminobenzyl cryptotanshi-ketol 16 (206.9 mg, 0.41 mmol, 80%) as a yellow foam.

$^1H$ NMR (500 MHz, $CDCl_3$, mixture of diastereoisomers A:B 1:2) δ 7.41-7.35 (m, 2H, A/B H9/10), 7.10 (d, J=8.2 Hz, 2H, AH14), 7.07 (d, J=8.2 Hz, 2H, BH14), 6.67 (d, J=8.5 Hz, 2H, AH13), 6.58 (d, J=8.5 Hz, 2H, BH13), 6.43 (s, 1H, ANH), 6.40 (s, 1H, BNH), 4.78 (dd, J=10.0, 9.0 Hz, 1H, AH21), 4.52 (dd, J=9.0, 9.0 Hz, 1H, BH21), 4.20 (dd, J=9.0, 4.2 Hz, 1H, AH21), 4.09 (dd, J=12.0, 9.2 Hz, 1H, BH21), 3.52-3.43 (m, 1H, AH20), 3.39-3.25 (m, 2H, A/B H5a, BH20), 3.23-3.13 (m, 2H, A/B H5a, A/B H11), 3.10 (d, J=13.1 Hz, 1H, AH11), 3.02 (d, J=12.9 Hz, 1H, BH11), 1.90-1.82 (m, 1H, A/B H4), 1.78-1.61 (m, 3H, A/B H4, A/B H3), 1.50 (d, J=1.2 Hz, 9H, A/B H18), 1.37 (s, 3H, A/B H1a, 1b), 1.30 (s, 3H, A/B H1a, 1b), 1.29 (d, J=6.8 Hz, 3H, AH22), 1.23 (d, J=6.8 Hz, 3H, AH22). $^{13}C$ NMR (126 MHz, $CDCl_3$, mixture of diastereoisomers A:B 1:2) δ 197.1 (A/B $C_5$), 171.9 (AC10b), 171.5 (BC10b), 152.8 (AC16), 152.7 (BC16), 151.3 (AC8), 151.2 (BC8), 141.6 (AC6a), 141.2 (BC6a), 137.4 (A/B $C_7$), 137.1 (AC15), 137.0 (BC15), 130.9 (AC13), 130.4 (BC13), 129.9 (BC12), 129.5 (AC12), 127.0 (AC10), 126.9 (BC10), 121.8 (AC9), 121.6 (BC9), 121.4 (BC10a), 121.1 (AC10a), 117.5 (A/B $C_{14}$), 112.9 (BC19), 112.5 (AC19), 82.4 (BC6), 81.8 (AC6), 81.0 (BC21), 80.8 (AC21), 80.5 (A/B $C_{17}$), 49.9 (BC11), 49.1 (AC11), 38.8 (A/B $C_3$), 35.4 (AC2), 35.3 (BC2), 34.6 (BC20), 34.4 (AC20), 32.6 (AC1a, 1b), 32.6 (BC1a, 1b), 29.4 (BC5a), 29.3 (AC5a), 28.4 (A/B $C_{18}$), 20.0 (A/B $C_4$), 19.4 (BC22), 18.0 (AC22). HRMS (m/z): [M+H]+ calcd. For $C_{31}$H38NO5 504.2744, found 504.2705.

Para-Aminobenzyl phenanthrene-ketol 7

10-(4-aminobenzyl)-10-hydroxyphenanthren-9 (10H)-one

Boc-para-aminobenzyl phenanthrene-ketol 6 was dissolved in 4:1 dichloromethane/trifluoroacetic acid at 0° C. The deprotection was followed by thin-layer chromatography until completion (30 min to 1 h). The residue was dried to offer para-aminobenzyl phenanthrene-ketol 7.

$^1$H NMR (600 MHz, MeOD) δ 8.01 (d, J=8.0 Hz, 1H), 7.96 (d, J=7.8 Hz, 1H), 7.86 (dd, J=7.7, 1.4 Hz, 1H), 7.72 (td, J=7.7, 1.5 Hz, 1H), 7.50-7.44 (m, 2H), 7.42 (td, J=7.6, 1.4 Hz, 1H), 7.31 (t, J=7.5 Hz, 1H), 7.09 (d, J=8.4 Hz, 2H), 6.90 (d, J=8.4 Hz, 2H), 3.10 (d, J=13.3 Hz, 1H), 3.02 (d, J=13.3 Hz, 1H).

Para-Aminobenzyl β-lapa-ketol 10

6-(4-aminobenzyl)-6-hydroxy-2,2-dimethyl-2,3,4,6-tetrahydro-5H-benzo[h]chromen-5-one Boc-para-aminobenzyl β-lapa-ketol 9 was dissolved in 4:1 dichloromethane/trifluoroacetic acid at 0° C. The deprotection was followed by thin-layer chromatography until completion (30 min to 1 hour). The residue was dried to offer para-aminobenzyl β-lapa-ketol 10.

$^1$H NMR (600 MHz, MeOD) δ 7.66 (d, J=7.7 Hz, 1H), 7.62 (d, J=7.9 Hz, 1H), 7.50 (t, J=6.9 Hz, 1H), 7.37 (t, J=7.7 Hz, 1H), 7.07 (d, J=8.4 Hz, 2H), 6.70 (d, J=8.4 Hz, 2H), 3.21 (d, J=12.3 Hz, 1H), 3.10 (d, J=12.4 Hz, 1H), 2.46 (dt, J=17.3, 5.9 Hz, 1H), 2.16 (ddd, J=17.3, 8.2, 6.4 Hz, 1H), 1.70-1.64 (m, 2H), 1.36 (s, 3H), 1.12 (s, 3H).

Para-Aminobenzyl 3-hydroxy-β-lapa-ketol 17

Boc-para-aminobenzyl 3-hydroxy-β-lapa-ketol 14 was dissolved in 4:1 dichloromethane/trifluoroacetic acid at 0° C. The deprotection was followed by thin-layer chromatography until completion (30 min to 1 hour). The residue was dried to offer para-aminobenzyl β-lapa-ketol 17.

$^1$H NMR (500 MHz, MeOD, mixture of diastereoisomers) δ 7.66 (td, J=7.8, 1.3 Hz, 1H), 7.59 (dd, J=7.8, 1.3 Hz, 1H), 7.49 (dtd, J=16.6, 7.6, 1.4 Hz, 1H), 7.38 (tdd, J=7.6, 3.2, 1.3 Hz, 1H), 7.07 (dd, J=8.5, 7.2 Hz, 2H), 6.76 (d, J=8.4 Hz, 1H), 6.71 (d, J=8.5 Hz, 1H), 3.68 (dd, J=8.0, 5.5 Hz, 1H), 3.63 (t, J=4.9 Hz, 1H), 3.21 (d, J=12.3 Hz, 2H), 3.10 (dd, J=12.4, 3.0 Hz, 2H), 2.73 (dd, J=17.0, 5.5 Hz, 1H), 2.63 (s, 1H), 2.43 (qd, J=17.4, 4.9 Hz, 2H), 2.18 (s, 1H), 2.07 (dd, J=17.0, 8.1 Hz, 1H), 1.36 (s, 3H), 1.25 (s, 3H), 1.08 (s, 3H), 1.04 (s, 3H).

Para-Aminobenzyl dunni-ketol 18

Boc-para-aminobenzyl dunni-ketol 15 was dissolved in 4:1 dichloromethane/trifluoroacetic acid at 0° C. The deprotection was followed by thin-layer chromatography until completion (30 min to 1 hour). The residue was dried to offer para-aminobenzyl β-lapa-ketol 18. 1H NMR (400 MHz, MeOD, mixture of diastereoisomers) δ 7.76-7.64 (m, 1H), 7.61-7.46 (m, 1H), 7.44-7.36 (m, 3H), 7.08 (m, 2H), 6.83-6.70 (m, 2H), 4.28 & 3.61 (2q, J=6.7 Hz, 1H), 3.28-3.20 (m, 1H), 3.13 (m, 1H), 1.37 (d, J=6.6 Hz, 3H), 1.31 (s, 3H), 1.19-1.08 (m, 3H).

Para-Aminobenzyl cryptotanshi-ketol 19

Boc-para-aminobenzyl cryptotanshi-ketol 16 was dissolved in 4:1 dichloromethane/trifluoroacetic acid at 0° C. The deprotection was followed by thin-layer chromatography until completion (30 min to 1 hour). The residue was dried to offer para-aminobenzyl cryptotanshi-ketol 19.

$^1$H NMR (500 MHz, MeOD, mixture of diastereoisomers) δ 7.51 (m, 1H), 7.43-7.38 (m, 1H), 7.15-7.02 (m, 2H), 6.86-6.71 (m, 2H), 4.83-4.80 & 4.54-4.47 (2m, 1H), 4.25 (dd, J=9.2, 4.7 Hz, 1H), 4.10-4.06 (m, 1H), 3.58-3.42 (m, 2H), 3.30-3.13 (m, 3H), 1.92-1.66 (m, 4H), 1.42 (m, 3H), 1.34 (m, 3H), 1.23 (2d, 6.8 Hz, 3H).

Acetyl-β-lapa-hydroquinone 29

2,2-dimethyl-3,4-dihydro-2H-benzo[h]chromene-5, 6-diyl diacetate

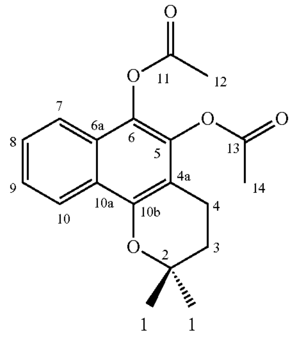

β-lapachone 1 (116 mg, 0.48 mmol), zinc (157 mg, 2.42 mmol) and sodium acetate (19.7 mg, 0.24 mmol) were refluxed in acetic anhydride (15 mL) for 2.5 hr. The reaction mixture was filtered free of solids, water was added (10 mL), and the product was extracted into ethyl acetate (3×10 mL), dried (anhydrous magnesium sulphate) and solvent was removed in vacuo. The crude product was purified by flash column chromatography (5:1 petroleum ether/ethyl acetate) to deliver acetyl-β-lapa-hydroquinone 29 as a white crystalline solid (131.8 mg, 0.402 mmol, 84%). To note, the flash chromatography was performed quickly as the compound is unstable to silica.

$^1$H NMR (400 MHz, $CDCl_3$): δ 8.21 (d, J=7.3 Hz, 1H, H7), 7.68 (d, J=7.5 Hz, 1H, H10), 7.45 (m, 2H, H8 & H9), 2.69 (t, J=6.7 Hz, 2H, H4), 2.43 (s, 3H), 2.36 (s, 3H), 1.88 (t, J=6.7 Hz, 2H, H3), 1.43 (s, 6H, H1). $^{13}$C NMR (101 MHz, $CDCl_3$) δ 169.0 (C11/C13), 168.3 (C11/C13), 148.1 (C6), 138.6 (C5/C10b), 130.1 (C10a), 126.9 (C8/C9), 126.4 (C5/C10b), 125.3 (C8/C9), 124.4 (C6a), 122.3 (C7), 120.8 (C10), 109.5 (C4a), 75.0 (C2), 32.0 (C3), 26.8 (C1), 20.6 (C12/C14), 20.6 (C12/C14), 18.1 (C4). HRMS (m/z): [M+Na]+ calcd. for $C_{19}H_{20}O_5$ 351.1203, found 351.1193.

β-Lapa-hydroquinone 1,4-dioxine 25

7,7-dimethyl-2,3,5,6-tetrahydro-1,4,8-trioxatriphenylene

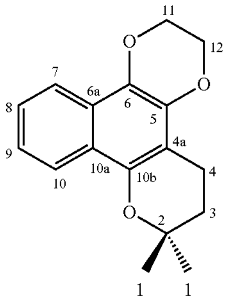

To β-lapachone 1 (70 mg, 0.28 mmol) dissolved in a solution of 1:1 water/tetrahydrofuran (10 mL) was added sodium dithionite (150 mg, 0.86 mmol) and tetrabutylammonium bromide (31 mg, 0.10 mmol). The reaction was stirred for 5 min at room temperature before addition of potassium hydroxide (130 mg, 2.32 mmol) dissolved in water (0.5 mL), followed immediately by 1,2-dibromoethane (176 μL, 2.04 mmol). The reaction was then refluxed at 100° C. Further potassium hydroxide (95 mg, 1.70 mmol) was added after 10 min of reflux. The reflux was continued for 4.5 h after which the solution was cooled to room temperature. Water (30 mL) was added and the crude product was extracted into ethyl acetate (3×10 mL), dried (anhydrous magnesium sulphate), filtered and solvent was removed in vacuo.

The crude product was purified by flash column chromatography (4:1 petroleum ether/ethyl acetate) to obtain 7,7-dimethyl-2,3,5,6-tetrahydro-1,4,8-trioxatriphenylene 25 as a white solid (34 mg, 0.13 mmol, 44%).

$^1$H NMR (400 MHz, $CDCl_3$): δ 8.12 (d, J=8.4 Hz, 1H, H10), 7.96 (d, J=8.4 Hz, 1H, H7), 7.42 (dd, J=8.3, 6.8 Hz, 1H, H8), 7.32 (dd, J=8.3, 6.8 Hz, 1H, H9), 4.38 (m, 4H, H11 and H12), 2.75 (t, J=6.8 Hz, 2H, H4), 1.87 (t, J=6.8 Hz, 2H, H3), 1.40 (s, 6H, H1). $^{13}$C NMR (101 MHz, $CDCl_3$): δ 143.2 (C10b), 137.4 (C5), 129.7 (C6), 125.5 (C8), 124.6 (C10a), 123.2 (C9), 121.5 (C10), 121.1 (C6a), 119.7 (C7), 107.4 (C4a), 74.0 (C2), 65.1 (C11/C12), 64.3 (C11/C12), 32.4 (C3), 26.8 (C1), 17.5 (C4). HRMS (m/z): [M]+ calcd, for $C_{17}H_{18}O3$ 270.1251, found 270.1249.

Benzyl β-lapa-ketol 24

6-benzyl-6-hydroxy-2,2-dimethyl-2,3,4,6-tetrahydro-5H-benzo[h]chromen-5-one

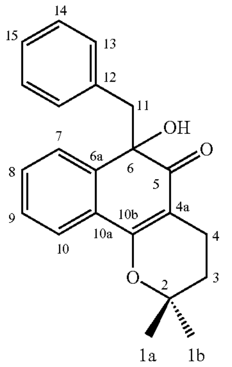

To β-lapachone 1 (30 mg, 0.12 mmol) dissolved in a solution of tetrahydrofuran (4 mL) was added sodium dithionite (107 mg, 0.61 mmol) and tetrabutylammonium bromide (198 mg, 0.61 mmol). The reaction was heated to 80° C. before the addition of potassium hydroxide (138 mg, 2.46 mmol) dissolved in water (6 mL), followed immediately by benzyl bromide (300 μL). The reaction was then refluxed at 100° C. for 4.5 h after which the solution was cooled to room temperature. Water (30 mL) was added, and the crude product was extracted into ethyl acetate (3×10 mL), dried (anhydrous magnesium sulphate), filtered, and solvent was removed in vacuo. The crude product was purified by flash column chromatography (4:1 petroleum ether/ethyl acetate) to obtain benzyl β-lapa-ketol 24 as a pale brown oil (16.8 mg, 0.05 mmol, 41%).

$^1$H NMR (400 MHz, $CDCl_3$): δ 7.65 (d, J=7.8 Hz, 1H, H10), 7.62 (d, J=7.8 Hz, 1H, H7), 7.45 (t, J=7.6 Hz, 1H, H8), 7.34 (t, J=7.6 Hz, 1H, H9), 7.08 (m, 3H, H14 & H15), 6.60 (d, J=6.6 Hz, 2H, H13), 3.96 (s, 1H, OH), 3.07 (s, 2H, H11), 2.54 (dt, J=17.3, 5.8 Hz, 1H, H4), 2.15 (dt, J=17.3, 7.4 Hz, 1H, H4), 1.63 (dd, J=7.4, 5.8 Hz, 2H, H3), 1.35 (s, 3H, H1a/H1b), 1.09 (s, 3H, H1a/H1b). $^{13}$C NMR (101 MHz, $CDCl_3$): δ 200.6 (C5), 162.2 (C10b), 141.6 (C6a), 135.2 (C12), 130.1 (C8), 129.8 (C13), 127.7 (C15), 127.6 (C10a), 127.6 (C9), 126.8 (C14), 125.8 (C7), 123.0 (C10), 106.9 (C4a), 78.2 (C6), 78.0 (C2), 54.5 (C11), 31.7 (C3), 27.6 (C1a/C1b), 25.9 (C1a/C1b), 15.7 (C4). HRMS (m/z): [M+Na]+m/z calcd. For $C_{22}H_{22}O_3$ 335.1642, found. 335.1636.

2-Phenyl-acetyl-para-aminobenzyl phenanthrene-ketol 21

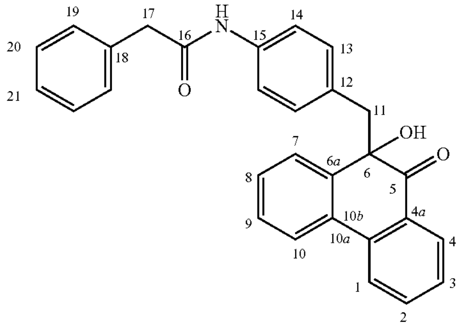 [SMILES: O=C(Cc1ccccc1)Nc1ccc(CC2(O)C(=O)c3ccccc3-c3ccccc32)cc1]

Boc-para-aminobenzyl phenanthrene-ketol 6 (70 mg, 0.169 mmol) was dissolved in dichloromethane/trifluoro-acetic acid 4:1 (2 mL) at 0° C. The deprotection was followed by thin-layer chromatography until completion (30 min to 1 h). The residue was dried to offer para-aminobenzyl phenanthrene-ketol 7, which was subsequently dissolved in anhydrous dichloromethane (5 mL). Phenyl acetic acid (114 mg, 0.838 mmol) was added followed by HATU (318 mg, 0.838 mmol) and triethylamine (1 mL) to achieve a reaction pH of 10. The reaction was stirred for 30 min. Following this, water was added (30 mL) and the product was extracted into ethyl acetate (3×10 mL), dried, and solvents were removed in vacuo. The crude product was purified by flash column chromatography (dichloromethane/methanol 9:1) to obtain product 2-phenyl-acetyl para-aminobenzyl phenanthrene-ketol 21 (23.9 mg, 0.055 mmol, 33%).

$^1$H NMR (400 MHz, $CDCl_3$) δ 7.94 (dd, J=8.1, 1.0 Hz, 1H, ArH), 7.86 (ddd, J=7.8, 3.8, 1.5 Hz, 2H, ArH), 7.71 (td, J=7.7, 1.5 Hz, 1H, ArH), 7.58 (dd, J=7.6, 1.5 Hz, 1H, ArH), 7.48-7.30 (m, 8H, ArH), 7.23 (d, J=8.5 Hz, 2H, H13), 6.96 (s, 1H, NH), 6.78 (d, J=8.4 Hz, 2H, H14), 3.95 (s, 1H, OH), 3.73 (s, 2H, H11), 2.99 (d, J=13.6 Hz, 1H, H17), 2.92 (d, J=13.6 Hz, 1H, H17). $^{13}$C NMR (101 MHz, $CDCl_3$) § 202.7, 169.0, 140.1, 137.7, 136.7, 135.2, 134.5, 131.0, 130.9, 129.7, 129.5, 129.34, 129.2, 128.7, 128.7, 128.4, 127.9, 127.5, 126.4, 124.2, 123.42, 119.1, 50.6, 45.1. HRMS (m/z): [M+H]+m/z calcd, for $C_{29}H_{23}NO_3$ 434.1756, found. 434.1757.

2-Phenyl-acetyl-para-aminobenzyl β-lapa-ketol 22

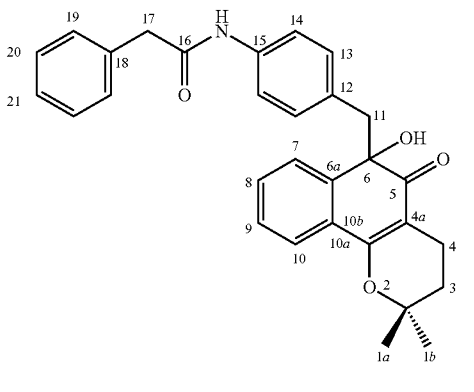

Boc-para-aminobenzyl β-lapa-ketol 9 (25 mg, 0.050 mmol) was dissolved in dichloromethane/trifluoroacetic acid 4:1 (2 mL) at 0° C. The deprotection was followed by thin-layer chromatography until completion (30 min to 1 h). The residue was dried to offer para-aminobenzyl β-lapa-ketol 10, which was subsequently dissolved in anhydrous dichloromethane (5 mL). Phenyl acetic acid (38 mg, 0.279 mmol) was added followed by HATU (105 mg, 0.276 mmol) and triethylamine (1 mL) to achieve a reaction pH of 10. The reaction was stirred for 30 min. Following this, water was added (30 mL) and the product was extracted into ethyl acetate (3×10 mL), dried, and solvents were removed in vacuo. The crude product was purified by flash column chromatography (dichloromethane/methanol 9:1) to obtain product 2-phenyl-acetyl para-aminobenzyl β-lapa-ketol 22 (4.1 mg, 0.009 mmol, 18%).

$^1$H NMR (500 MHz, MeOD) δ 7.74 (dd, J=7.8, 1.3 Hz, 1H, H10), 7.59 (dd, J=7.8, 1.3 Hz, 1H, H7), 7.52 (td, J=7.6, 1.4 Hz, 1H, H8), 7.37 (td, J=7.6, 1.3 Hz, 1H, H9), 7.32-7.30 (m, 4H, ArH), 7.27-7.22 (m, 1H, ArH), 7.20 (d, J=8.5 Hz, 2H, H14), 6.36 (d, J=8.5 Hz, 2H, H13), 4.59 (s, 1H, OH), 3.60 (s, 2H, H17), 3.13 (d, J=12.0 Hz, 1H, H11), 3.02 (d, J=12.0 Hz, 1H, H11), 2.40 (dt, J=17.2, 5.6 Hz, 1H, H4), 2.06-1.96 (m, 1H, H4), 1.60-1.55 (m, 2H, H3), 1.30 (s, 3H, H1a/H1b), 0.85 (s, 3H, H1a/H1b). $^{13}$C NMR (126 MHz, MeOD) δ 202.1, 172.0, 163.5, 143.7, 138.9, 136.9, 131.9, 131.2, 130.6, 130.0, 129.6, 129.6, 128.7, 127.9, 127.3, 123.7, 120.0, 109.3, 79.1, 78.9, 53.9, 44.8, 32.4, 27.8, 25.7, 16.6. HRMS (m/z): [M+H]+m/z calcd, for $C_{30}H_{29}NO_4$ 468.2175, found. 468.2178.

2-phenyl-acetyl-para-aminobenzyl dunni-ketol 23

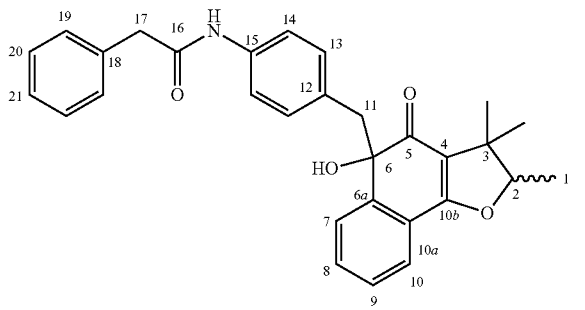 [SMILES: CC1OC2=C(C(=O)C(O)(Cc3ccc(NC(=O)Cc4ccccc4)cc3)c3ccccc32)C1(C)C]

Boc-para-aminobenzyl dunni-ketol 15 (40 mg, 0.09 mmol) was dissolved in dichloromethane/trifluoroacetic acid 5:1 (1 mL) at r.t. The reaction was followed by thin-layer chromatography until completion (1 hour). The residue was dried to afford para-aminobenzyl dunni-ketol 18 which was subsequently dissolved in anhydrous dichloromethane (2.00 mL). Phenyl acetic chloride (13.20 mL, 0.10 mmol) and triethylamine (34 mL, 0.24 mmol) were added at 0° C. The reaction was stirred at room temperature overnight and then washed with mL of 1M aqueous HCl. The organic layer was dried over $MgSO_4$, filtered, and the solvent was removed in vacuo. The crude was purified by flash chromatography (Petroleum ether/Ethyl acetate 4:1 to 2:1) to obtain product 23 (23.40 mg, 0.05 mmol, 56%) as a yellow 10 foam. In order to facilitate the kinetics studies, a portion of the mixture was purified by HPLC to provide the major isomer (racemic mixture of S,S and R,R) as white solid. HPLC purification conditions: YMC-triart $C_{18}$ $_5$ mm 10×250 mm; solvents A=$H_2O$ B=Acetonitrile; flow rate=3 mL/min; gradient t=0.0-5.0 min B=50-100%, t=5.0-10.0 min B=100%, t=10.0-11.0 min B=50%, t=10.0-13.3 min B=50%. Product 23: t=6.36 min.

$^1H$ NMR (500 MHz, $CDCl_3$) δ 7.55 (dd, J=7.8, 1.4 Hz, 1H, H10), 7.52 (dd, J=7.7, 1.4 Hz, 1H, H7), 7.45 (td, J=7.6, 1.4 Hz, 1H, H8), 7.40 (t, J=7.2 Hz, 2H, ArH), 7.36-7.30 (m, 4H, ArH), 7.16 (d, J=8.5 Hz, 2H, H14), 6.96 (s, 1H, NH), 6.65 (d, J=8.5 Hz, 2H, H13), 4.36 (q, J=6.7 Hz, 1H, H2), 3.72 (s, 2H, H17), 3.02 (d, J=13.0 Hz, 1H, H11), 2.97 (d, J=12.9 Hz, 1H, H11), 1.38 (d, J=6.7 Hz, 3H, H1), 1.34 (s, 3H, $CH_3$), 1.09 (s, 3H, $CH_3$). $^{13}C$ NMR (126 MHz, $CDCl_3$) δ 197.5 (C5), 169.01 (C16 or C10b), 168.99 (C16 or C10b), 144.9 (C6a), 136.5 (CAr), 134.5 (CAr), 131.0 (CHAr), 130.8 (CHAr), 129.7 (CHAr), 129.4 (CHAr), 129.2 (CHAr), 128.4 (CHAr), 127.8 (CHAr), 127.6 (CHAr), 126.5 (CHAr), 125.4 (CAr), 123.6 (CHAr), 123.3 (CAr), 118.9 (CHAr), 117.9 (C4), 91.9 (C2), 79.7 (C6), 53.0 (C11), 45.0 (C17), 44.0 (C3), 24.2 ($CH_3$), 20.7 ($CH_3$), 13.7 (C1). HRMS (m/z): [M+H]+ calcd, for $C_{30}H_{30}NO_4$ 468.2169, found, 468.2180.

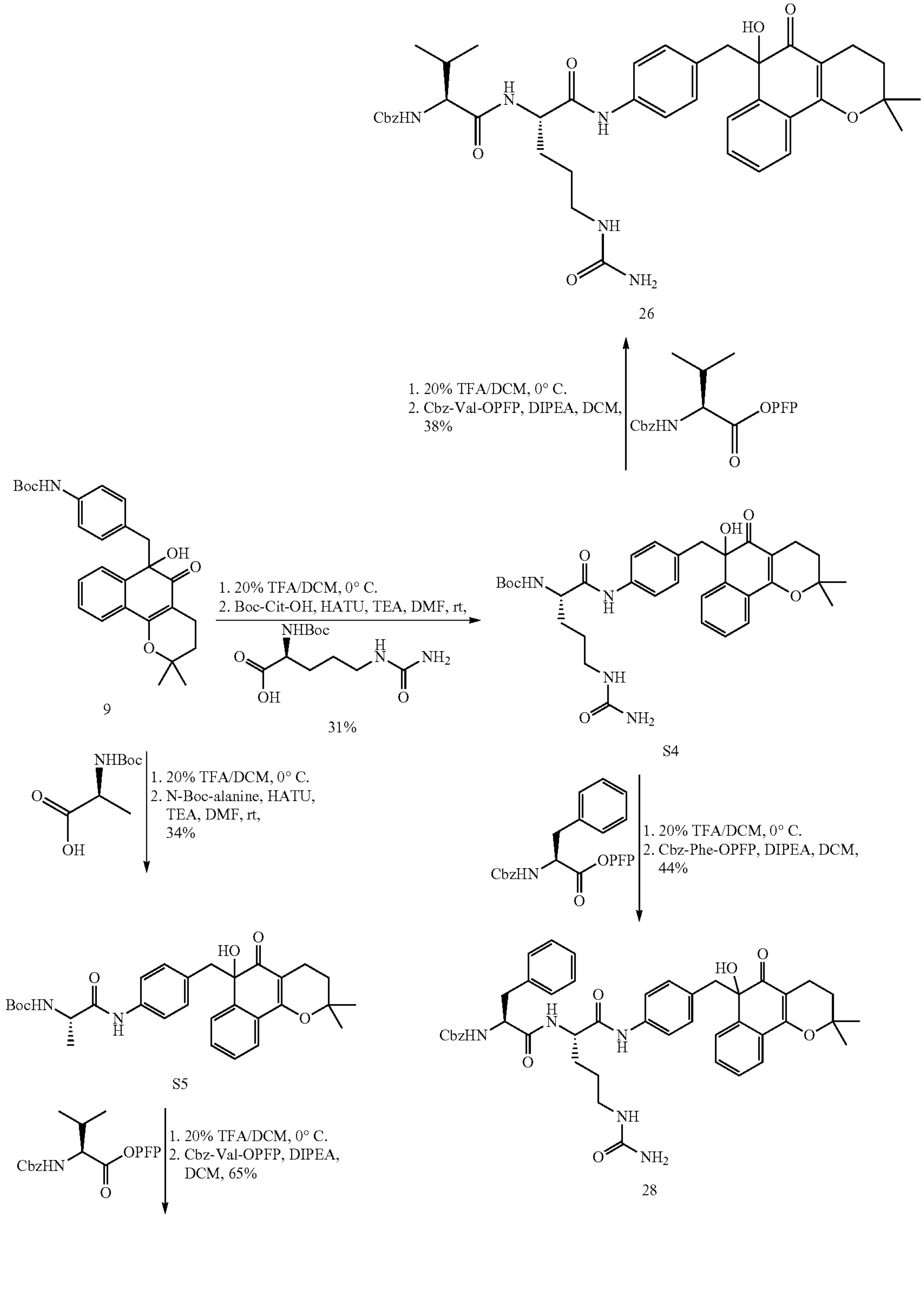

26

9

S4

S5

28

-continued

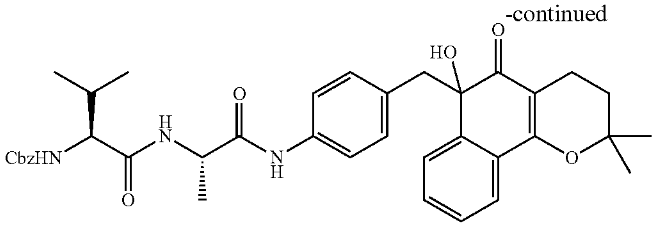

27

Boc-L-Cit-OH

L-citrulline (1.00 g, 5.71 mmol) was dissolved in a solution of 2:1 acetonitrile/water (27 mL). Sodium hydrogen carbonate (720 mg, 18.9 mmol) and di-tert-butyl dicarbonate (1.87 g, 8.14 mmol) were added. The reaction was stirred for 48 h. The reaction was then washed with ether (1×10 mL) to remove excess di-tert-butyl dicarbonate then acidified to pH 3-4 with 1 M citric acid. The product was extracted with a chloroform-isopropanol/water system to yield the product Boc-L-Citrulline (426 mg, 1.55 mmol, 27%).

$^1$H NMR (400 MHz, DMSO-$d_6$): δ 1.38 (s, 11H), 1.51 (m, 1H), 1.64 (m, 1H), 2.92 (d, J=6.3 Hz, 2H), 3.81 (m, 1H), 5.37 (s, 2H), 5.96 (s, 1H), 6.98 (d, J=7.9 Hz, 1H). $^{13}$C NMR (100 MHz, DMSO-$d_6$): δ 26.8, 28.2, 28.4, 39.7, 53.4, 77.9, 155.5, 158.7, 174.2. HRMS (m/z): [M+Na]+ calcd, for $C_{11}H_{21}N_3O_5$ 298.1379 found 298.1372.

Perfluorophenyl ((benzyloxy)carbonyl)-L-valinate

Cbz-L-valine (700 mg, 2.79 mmol) was dissolved in anhydrous dichloromethane (10 mL). The solution was cooled to 0° C. N,N-diisopropylethylamine (1.40 mL, 8.04 mmol) was added, followed by pentafluorophenyl trifluoroacetate (575 μL, 3.35 mmol) and the solution was stirred for 1 h at room temperature. Following this, solvent was removed in vacuo and the crude product purified by flash column chromatography (dichloromethane/methanol 9:1) to yield perfluorophenyl ((benzyloxy)carbonyl)-L-valinate (1.206 g, 2.60 mmol, 93%).

$^1$H NMR (400 MHz, $CDCl_3$) δ 7.42-7.27 (m, 5H), 5.61 (d, J=8.9 Hz, 1H), 5.17 (s, 1H), 4.71 (dd, J=8.9, 4.7 Hz, 1H), 2.40 (dq, J=13.1, 6.6 Hz, 1H), 1.11 (d, J=6.8 Hz, 3H), 1.05 (d, J=6.9 Hz, 2H). $^{13}$C NMR (100 MHz, $CDCl_3$) δ 168.5, 156.4, 136.0, 128.6, 128.3, 128.2, 67.5, 59.2, 31.2, 18.8, 17.2. HRMS (m/z): [M+H]+ calcd, for $C_{19}H_{16}NO_4F_5$ 418.1078 found 418.1068.

Perfluorophenyl ((benzyloxy)carbonyl)-L-phenylalaninate

Cbz-L-phenylalanine (700 mg, 2.34 mmol) was dissolved in anhydrous dichloromethane (10 mL). N,N-diisopropylethylamine (1.22 mL, 7.00 mmol) was added, followed by pentafluorophenyl trifluoroacetate (482 μL, 2.81 mmol) and the solution was stirred for 1 h at room temperature. Following this, solvent was removed in vacuo and the crude product purified by flash column chromatography (dichloromethane/methanol 9:1) to yield perfluorophenyl ((benzyloxy)carbonyl)-L-phenylalaninate (928 mg, 2.00 mmol, 85%). $^1$H NMR (400 MHz, $CDCl_3$) o 7.33 (td, J=9.8, 9.2, 6.0 Hz, 8H), 7.22 (d, J=6.5 Hz, 2H), 5.27 (d, J=8.2 Hz, 1H), 5.13 (s, 2H), 5.03 (d, J=7.8 Hz, 1H), 3.43-3.20 (m, 2H). $^{13}$C NMR (100 MHz, $CDCl_3$) δ 168.2, 155.7, 136.0, 134.7, 129.4, 129.0, 128.7, 128.5, 128.3, 127.7, 67.5, 54.8, 37.9. HRMS (m/z): [M+H]+ calcd, for $C_{23}H_{16}NO_4F_5$ 466.1078 found 466.1075.

Perfluorophenyl (((9H-fluoren-9-yl)methoxy)carbonyl)-L-valinate

Fmoc-L-valine (600 mg, 1.77 mmol) was dissolved in anhydrous dichloromethane (20 mL). The solution was cooled to 0° C. N,N-diisopropylethylamine (920 μL, 5.28 mmol) was added, followed by pentafluorophenyl trifluoroacetate (364 μL, 2.12 mmol) and the solution was stirred for 1 h at room temperature. Following this, solvent was removed in vacuo and the crude product purified by flash column chromatography (dichloromethane/methanol 9:1) to yield perfluorophenyl (((9H-fluoren-9-yl)methoxy)carbonyl)-L-valinate (853 mg, 1.69 mmol, 95%).

$^1$H NMR (600 MHz, $CDCl_3$) o 7.77 (d, J=7.5 Hz, 2H), 7.61 (dd, J=7.6, 3.5 Hz, 2H), 7.41 (t, J=7.5 Hz, 2H), 7.32 (t, J=7.6 Hz, 2H), 5.29 (d, J=9.4 Hz, 1H), 4.69 (dd, J=9.2, 4.8 Hz, 1H), 4.48 (d, J=7.0 Hz, 2H), 4.26 (t, J=6.9 Hz, 1H), 1.10 (d, J=6.8 Hz, 3H), 1.05 (d, J=6.9 Hz, 3H). $^{13}$C NMR (151 MHz, $CDCl_3$) δ 141.5, 127.9, 127.2, 125.1, 120.2, 120.2, 67.4, 59.1, 47.3, 31.4, 17.5. [M+H]+ calcd, for $C_{26}H_{20}NO_4F_5$ 506.1385 found 506.1387.

Perfluorophenyl (E)-4-oxo-4-phenylbut-2-enoate (E)-4-Oxo-4-phenylbut-2-enoic acid (300 mg, 1.70 mmol) was dissolved in anhydrous dichloromethane (20 mL). N,N-diisopropylethylamine (900 μL, 5.1 mmol) was added, followed by pentafluorophenyl trifluoroacetate (357 μL, 2.00 mmol) and the solution was stirred for 2 h at room temperature. Solvent was removed in vacuo and the crude product purified by flash column chromatography (dichloromethane/methanol 9:1) to yield perfluorophenyl (E)-4-oxo-4-phenylbut-2-enoate as a yellow solid (460 mg, 1.30 mmol, 76%).

$^1$H NMR (600 MHz, $CDCl_3$): δ 8.17 (d, J=15.6 Hz, 1H), 8.04 (d, J=7.2 Hz, 2H), 7.67 (t, J=7.4 Hz, 1H), 7.56 (t, J=7.8 Hz, 2H), 7.11 (d, J=15.6 Hz, 1H). $^{13}$C NMR (151 MHz, $CDCl_3$) 150.9, 102.7, 98.6, 96.9, 91.6, 91.5, 91.1. HRMS (m/z): [M+H]+ calcd, for $C_{16}H_7O_3F_5$ 343.0394, found 343.0380.

Boc-L-Cit-para-aminobenzyl β-lapa-ketol (S4)

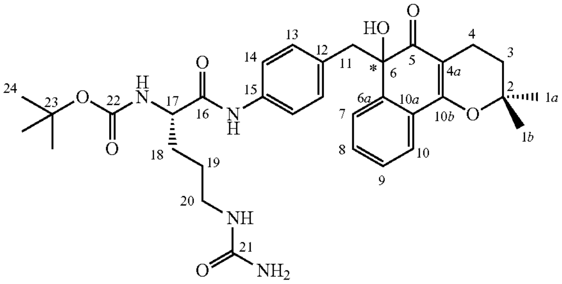

Boc-para-aminobenzyl β-lapa-ketol 9 (200 mg, 0.445 mmol) was deprotected by addition of 20% trifluoroacetic acid in dichloromethane (5 mL) at 0° C. for 30 min. The deprotected residue was dried in vacuo. Meanwhile, Boc -L-citrulline (610 mg, 2.22 mmol) and HATU (200 mg, 0.526 mmol) were dissolved in anhydrous dimethylformamide (8 mL) and stirred for 20 min. The crude amine salt was dissolved in anhydrous dimethylformamide (2 mL) and was then added to the mixture, immediately followed by triethylamine (1.2 mL). The pH of the reaction was 9-10 as estimated by indicator paper. The solution was stirred for 30 min. Following this, water was added (30 mL) and the product was extracted into ethyl acetate (3×10 mL), dried, and solvents were removed in vacuo. The crude product was purified by flash column chromatography (9:1 dichloromethane/methanol) to obtain Boc-L-Cit-para-aminobenzyl β-lapa-ketol S4 (82.7 mg, 0.136 mmol, 31%).

$^1$H NMR (500 MHz, DMSO-$d_6$) δ 9.75 (d, J=6.9 Hz, 1H, NH), 7.61 (dt, J=7.9, 1.4 Hz, 1H, H10), 7.53-7.45 (m, 2H, H7, H8), 7.39-7.31 (m, 1H, H9), 7.26-7.20 (m, 2H, H14), 6.93 (dd, J=8.1, 3.3 Hz, 1H, NH), 6.31 (d, J=8.3 Hz, 2H, H13), 5.77 (s, 1H, NH), 5.39 (d, J=8.4 Hz, 2H, NH2), 4.04-3.95 (m, 1H, H17), 3.01 (d, J=12.1 Hz, 1H, H11), 3.00-2.88 (m, 2H, H20), 2.86 (d, J=12.2 Hz, 1H, H11), 2.31 (dt, J=17.2, 5.6 Hz, 1H, H4), 2.03-1.90 (m, 1H, H4), 1.65-1.43 (m, 4H, H3, H18), 1.36 (s, 9H, H24), 1.27 (d, J=3.2 Hz, 5H, H1a/H1b, H19), 0.90 (s, 3H, H1a/H1b). $^{13}$C NMR (126 MHz, DMSO-$d_6$) δ199.8 (C5), 199.8 (C5'), 171.6 (C16), 171.5 (C16'), 160.4 (C10b), 160.4 (C10b'), 159.4 (C21), 159.3 (C21'), 155.9 (C22), 155.9 (C22'), 143.0 (C6a), 138.0 (C12), 130.0 (C10a), 130.0 (C7/C8), 129.7 (C13), 128.1 (C15), 127.7 (C9), 126.8 (C10), 126.8 (C10'), 122.4 (C7/C8), 118.3 (C14), 108.2 (C4a), 108.2 (C4a), 78.5 (C23), 77.7 (C2/C6), 77.7 (C2'/C6'), 77.6 (C2/C6), 77.6 (C2'/C6'), 55.0 (C17), 55.0 (C17'), 52.8 (C11), 39.1 (C20), 31.4 (C3), 29.7 (C18), 29.7 (C18), 28.7 (C24), 27.7 (C1a/C1b), 27.7 (C1a'/C1b'), 27.2 (C19), 25.4 (C1a/C1b), 25.3 (C1a'/C1b'), 15.8 (C4). HRMS (m/z): [M+H]+ calcd, for $C_{33}H_{42}N_4O_7$ 607.3125, found 607.3123.

Boc-L-Ala-para-aminobenzyl β-lapa-ketol (S5)

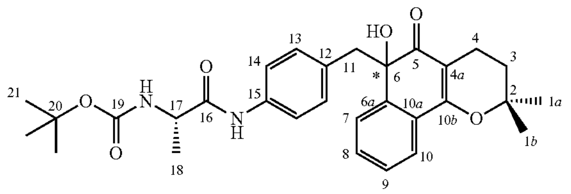

Boc-para-aminobenzyl β-lapa-ketol 9 (120 mg, 0.260 mmol) was deprotected by addition of 20% trifluoroacetic acid in dichloromethane (5 mL) at 0° C. for 30 min. The deprotected residue was dried in vacuo. Meanwhile, Boc -L-alanine (100 mg, 0.529 mmol) and HATU (121 mg, 0.318 mmol) were dissolved in anhydrous dimethylformamide (8 mL) and stirred for 20 min. The crude amine-TFA salt was dissolved in anhydrous dimethylformamide (2 mL) then added to the mixture, immediately followed by triethylamine (1.2 mL). The pH of the reaction was 9-10 as estimated by indicator paper. The solution was stirred for 30 min. Following this, water was added (30 mL) and the product was extracted into ethyl acetate (3×10 mL), dried, and solvents were removed in vacuo. The crude product was purified by flash column chromatography (2:1 40-60 petroleum ether/ethyl acetate) to obtain Boc-L-Ala-para-aminobenzyl β-lapa-ketol S5 (44.5 mg, 0.086 mmol, 34%).

$^1$H NMR (400 MHz, MeOD) o 7.73 (d, J=7.8 Hz, 1H, H10), 7.60 (dt, J=7.9, 1.6 Hz, 1H, H7), 7.52 (td, J=7.6, 1.4 Hz, 1H, H8), 7.37 (td, J=7.6, 1.3 Hz, 1H, H9), 7.21 (dd, J=8.5, 1.2 Hz, 2H, H14), 6.38 (d, J=8.1 Hz, 2H, H13), 4.13 (d, J=7.0 Hz, 1H, H17), 3.14 (d, J=12.0 Hz, 1H, H11), 3.02 (d, J=12.1 Hz, 1H, H11), 2.81 (s, 1H), 2.42 (dt, J=17.3, 5.6 Hz, 1H, H4), 2.11-1.98 (m, 1H, H4), 1.61 (dd, J=7.8, 3.6 Hz, 2H, H3), 1.44 (s, 9H, H21), 1.39-1.29 (m, 6H, H18 and H1a/H1b), 0.96 (s, 3H, H1a/H1b). $^{13}$C NMR (100 MHz, MeOD) δ 202.1 (C5), 163.5 (C10b), 143.7 (C6a), 138.6 (C16/C19), 131.9 (C16/C19), 131.2 (C9), 130.7 (C13), 129.6 (C10a), 128.7 (C9), 127.3 (C10), 123.7 (C7), 120.1 (C14), 120.1 (C14'), 109.3 (C4a), 109.3 (C4a), 80.6 (C20), 79.1 (C2), 78.9 (C6), 53.9 (C11), 52.1 (C17), 32.5 (C3), 28.7 (C21), 27.8 (C18/C1a/C1b), 27.8 (C18'/C1a'/C1b'), 25.9 (C1a/C1b), 18.4 (C18/C1a/C1b), 16.6 (C4). HRMS (m/z): [M+H]+ calcd, for $C_{30}H_{36}N_2O_6$ 521.2652 found 521.2653.

Cbz-Val-Cit-para-aminobenzyl β-lapa-ketol 26

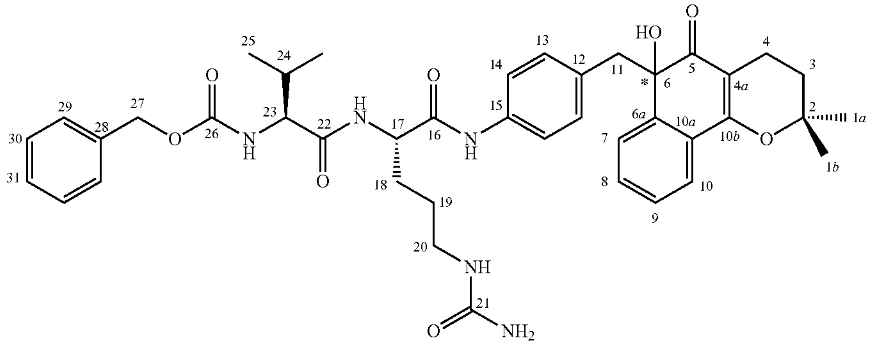

Boc-L-Cit-para-aminobenzyl β-lapa-ketol S4 (30 mg, 0.0495 mmol) was deprotected by addition of 20% trifluoroacetic acid in dichloromethane (2 mL) at 0° C. The deprotection was followed by thin layer chromatography and upon completion (30 min) the amine salt was dried in vacuo. Perfluorophenyl ((benzyloxy)carbonyl)-L-valinate (48 mg, 0.140 mmol) was dissolved in anhydrous dichloromethane (15 mL) at 0° C., to which was added N,N-diisopropylethylamine (100 μL). The deprotected amine dissolved in dichloromethane (5 mL) was added to the reaction dropwise. The pH of the reaction was 9, as measured by universal indicator paper. The temperature of the reaction was slowly raised to room temperature and the reaction was stirred for 6 h. Solvent was removed in vacuo to obtain the crude product, which was purified by flash column chromatography (dichloromethane/methanol 9:1). The product was further purified by semi-preparative HPLC to obtain pure Cbz-Val-Cit-para-aminobenzyl β-lapa-ketol 26 (13.7 mg, 0.019 mmol, 38%). HPLC purification conditions: column: Agilent Zorbax SB-C18 80 Å 5 μm 9.4×250 mm; solvents: A=$H_2O$+0.1% formic acid, B=acetonitrile+0.1% formic acid; flow rate=5 mL/min; gradient t=0.0-1.0 min B=0%, t=1.0-10.0 min B=0-90%, t=10.0-15.0 min B=90-100%, t=15.0-18.0 min B=100%, t=18.0-20.0 min B=0%. Product 26: t =11.9 min.

$^1$H NMR (400 MHz, MeOD) δ 7.73 (dt, J=7.7, 1.6 Hz, 1H, ArH), 7.64-7.55 (m, 1H, ArH), 7.51 (ddd, J=8.4, 7.4, 1.3 Hz, 1H, ArH), 7.33 (tdd, J=10.1, 6.3, 2.9 Hz, 6H, ArH), 7.22 (d, J=8.1 Hz, 2H, H14), 6.37 (dd, J=8.4, 1.5 Hz, 2H, H13), 5.08 (s, 2H, H27), 4.44 (t, J=7.1 Hz, 1H, H17), 3.94 (d, J=6.8 Hz, 1H, H23), 3.13 (d, J=12.0 Hz, 1H, H11), 3.07 (m, 2H, H20), 3.01 (d, J=12.1 Hz, 1H, H11, H11), 2.46-2.35 (m, 1H, H4), 2.04 (hept, J=7.3 Hz, 2H, H4, H24), 1.86-1.76 (m, 1H, H18), 1.73-1.65 (m, 1H, H18), 1.63-1.49 (m, 4H, H3, H19), 1.31 (d, J=1.5 Hz, 3H, H1a/H1b), 0.99-0.90 (m, 9H, H1a/H1b and H25). $^{13}$C NMR (101 MHz, MeOD) δ 202.1, 174.3, 171.9, 163.5, 162.3, 162.3, 158.8, 143.7, 138.5, 138.2 133.6, 132.4, 132.0, 132.0, 131.2, 130.7, 129.9, 129.6, 129.5, 129.0, 128.9, 128.7, 127.3, 123.7, 120.2, 120.1, 109.4, 109.3, 79.2, 78.9, 69.1, 67.8, 62.3, 62.3, 54.9, 53.8, 40.2, 32.5, 31.9, 31.6, 30.5, 30.1, 27.8, 25.9, 25.8, 25.0, 24.0, 19.8, 18.7, 16.6, 14.4, 11.4. HRMS (m/z): [M+H]+ calcd, for $C_{41}H_{49}N_5O_8$ 740.3659 found 740.3687.

Cbz-Val-Ala-para-aminobenzyl β-lapa ketol 27

Boc-L-Ala-para-aminobenzyl β-lapa-ketol S5 (10.5 mg, 0.020 mmol) was deprotected by addition of 20% trifluoroacetic acid in dichloromethane (2 mL) at 0° C. The deprotection was followed by thin layer chromatography and upon completion (30 min) the amine salt was dried in vacuo. Perfluorophenyl ((benzyloxy)carbonyl)-L-valinate (25 mg, 0.060 mmol) was dissolved in anhydrous dichloromethane (15 mL) at 0° C., to which was added N,N-diisopropylethylamine (100 μL). The deprotected amine dissolved in dichloromethane (5 mL) was added to the reaction dropwise. The pH of the reaction was 9, as measured by universal indicator paper. The temperature of the reaction was slowly raised to room temperature and the reaction was stirred for 6 h. Solvent was removed in vacuo to obtain the crude product, which was purified by flash column chromatography (dichloromethane/methanol 9:1). The product was further purified by semi-preparative HPLC to obtain pure Cbz-Val-Ala-para-aminobenzyl β-lapa-ketol 27 (8.8 mg, 0.013 mmol, 65%). HPLC purification conditions: column: Agilent Zorbax SB-C18 80 Å 5 μm 9.4×250 mm; solvents: A=$H_2O$+0.1% formic acid, B=acetonitrile+0.1% formic acid; flow rate=5 mL/min; gradient t=0.0-1.0 min B=0%, t=1.0-10.0 min B=0-80%, t=10.0-25.0 min B=80-95%, t=25.0-25.1 min B=95-100%, t=25.1-28.0 B=100%, t=28.0-30.0 min B=0%. Product 27: t=14.5 min.

$^1$H NMR (600 MHz, MeOD) δ 7.73 (ddd, J=7.8, 2.6, 1.3 Hz, 1H, H10), 7.59 (ddd, J=9.9, 7.9, 1.3 Hz, 1H, H7), 7.52 (td, J=7.6, 1.4 Hz, 1H, H8), 7.39-7.26 (m, 6H, H9), 7.23 (d, J=8.1 Hz, 2H, H14), 6.38 (dd, J=8.6, 1.8 Hz, 2H, H13), 5.09 (s, 2H, H24), 4.59 (s, 1H, NH), 4.42 (q, J=7.2 Hz, 1H, H17), 3.94 (dd, J=6.7, 3.9 Hz, 1H, H20), 3.14 (dd, J=12.2, 1.4 Hz, 1H, H11), 3.02 (dd, J=12.2, 1.3 Hz, 1H, H11), 2.41 (dt, J=17.2, 5.6 Hz, 1H, H4), 2.12-1.99 (m, 2H, H4 and H21), 1.64-1.52 (m, 2H, H3), 1.38 (d, J=7.2 Hz, 3H, H18), 1.32 (s, 3H, H1a/H1b), 1.01-0.91 (m, 9H, H1a/H1b and H22). $^{13}$C NMR (126 MHz, MeOD) δ 202.1, 174.0, 172.7, 163.6, 163.6, 158.8, 143.7, 138.5, 138.5, 138.2, 132.0, 131.9, 131.2, 130.7, 129.6, 129.5, 129.5, 129.0, 128.9, 128.7, 128.7, 127.3, 127.3, 123.7, 123.7, 120.2, 120.1, 109.4, 109.3, 79.2, 79.2, 78.9, 67.8, 62.2, 62.2, 53.9, 53.8, 51.0, 32.5, 31.9, 27.8, 25.9, 25.8, 19.7, 19.7, 18.5, 18.1, 18.1, 16.6. HRMS (m/z): [M+H]+ calcd, for $C_{38}H_{43}N_3O_7$ 654.3179 found 654.3198.

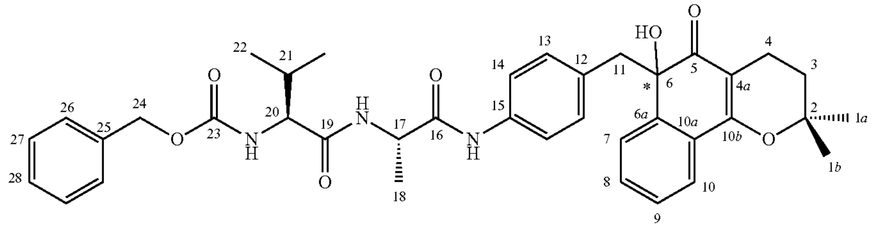

Cbz-Phe-Cit-para-aminobenzyl β-lapa-ketol 28

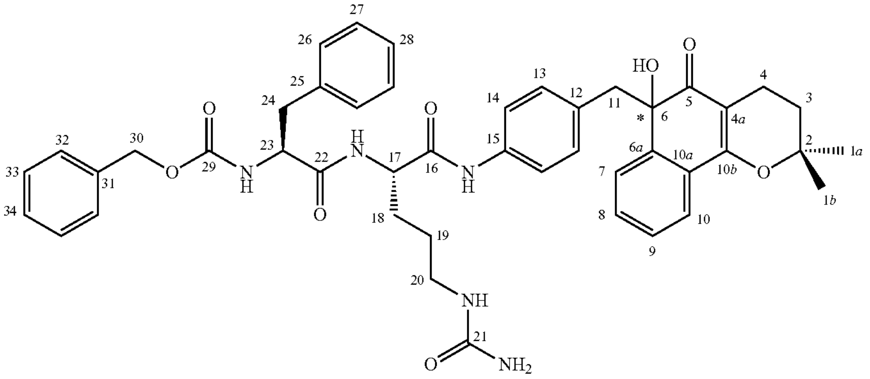

Boc-L-Cit-para-aminobenzyl β-lapa-ketol S4 (15 mg, 0.025 mmol) was deprotected by addition of 20% trifluoroacetic acid in dichloromethane (2 mL) at 0° C. The deprotection was followed by thin layer chromatography and upon completion (30 min) the amine salt was dried in vacuo. Perfluorophenyl ((benzyloxy)carbonyl)-L-phenylalaninate (23 mg, 0.049 mmol) was dissolved in anhydrous dichloromethane (15 mL) at 0° C., to which was added N,N-diisopropylethylamine (100 μL). The deprotected amine dissolved in dichloromethane (5 mL) was then added to the reaction dropwise. The pH of the reaction was 9, as measured by universal indicator paper. The temperature of the reaction was slowly raised to room temperature and the reaction was stirred for 6 h. Solvent was removed in vacuo to obtain the crude product, which was purified by flash column chromatography (dichloromethane/methanol 9:1). The product was further purified by semi-preparative HPLC to obtain pure Cbz-Phe-Cit-para-aminobenzyl β-lapa-ketol 28 (7 mg, 0.011 mmol, 44%). HPLC purification conditions: column: Agilent Zorbax SB-C18 80 Å 5 μm 9.4×250 mm; solvents: A=$H_2O$+0.1% formic acid, B=acetonitrile+0.1% formic acid; flow rate=5 mL/min; gradient t=0-1 min B=0%, t=1-10 min B=0-90%, t=$10^{-15}$ min B=90-100%, t=15.0-18.0 min B=100 t=18.0-20.0 min B=0%. Product 28: t=12.5 min.

$^1$H NMR (400 MHz, MeOD) δ 7.76-7.71 (m, 1H, H10), 7.62-7.56 (m, 1H, H7), 7.55-7.48 (m, 1H, H8), 7.39-7.32 (m, 1H, H9), 7.32-7.11 (m, 7H, ArH), 6.39 (d, J=8.4 Hz, 2H, H13), 5.01 (d, J=2.3 Hz, 2H, H30), 4.59 (s, 2H, NH2), 4.40 (td, J=9.0, 4.5 Hz, 2H, H17 and H23), 3.14 (dd, J=12.0, 2.3 Hz, 1H, H11), 3.11-3.05 (m, 3H, H24 and H20), 3.02 (d, J=11.9 Hz, 1H, H11), 2.91-2.82 (m, 1H, H24), 2.41 (dd, J=17.4, 3.5 Hz, 1H, H4), 2.11-1.97 (m, 1H, H4), 1.80 (d, J=5.2 Hz, 1H, H18), 1.72-1.54 (m, 3H, H3 and H18), 1.48 (q, J=7.1 Hz, 2H, H19), 1.31 (s, 3H, H1a/H1b), 0.94 (d, J=5.8 Hz, 3H, H1a/H1b). $^{13}$C NMR (101 MHz, MeOD) δ 202.2, 174.2, 171.9, 171.9, 163.6, 162.4, 158.4, 143.8, 138.4, 138.2, 132.1, 131.3, 130.7, 130.4, 129.6, 129.5, 129.0, 128.8, 128.8, 128.7, 127.8, 127.4, 123.8, 120.3, 109.4, 79.7, 79.3, 79.0, 78.9, 78.9, 67.7, 58.0, 54.9, 53.9, 40.3, 39.0, 32.5, 30.6, 27.9, 27.7 25.9, 16.7. HRMS (m/z): [M+H]+ calcd, for $C_{45}H_{49}N_5O_8$ 788.3659 found 788.3694.

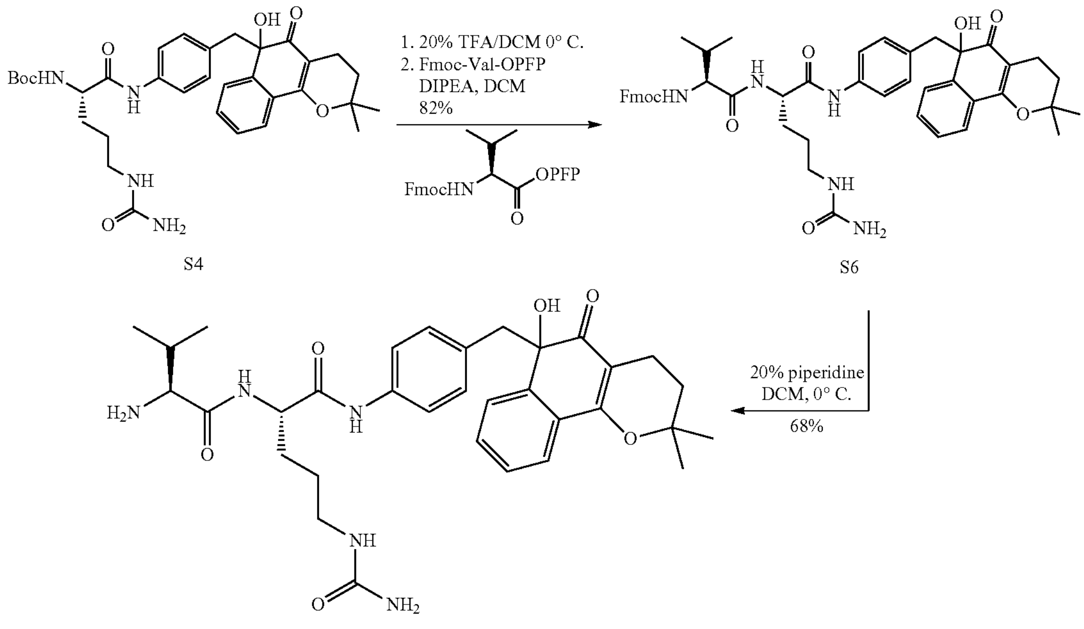

S4 S6 S7

-continued

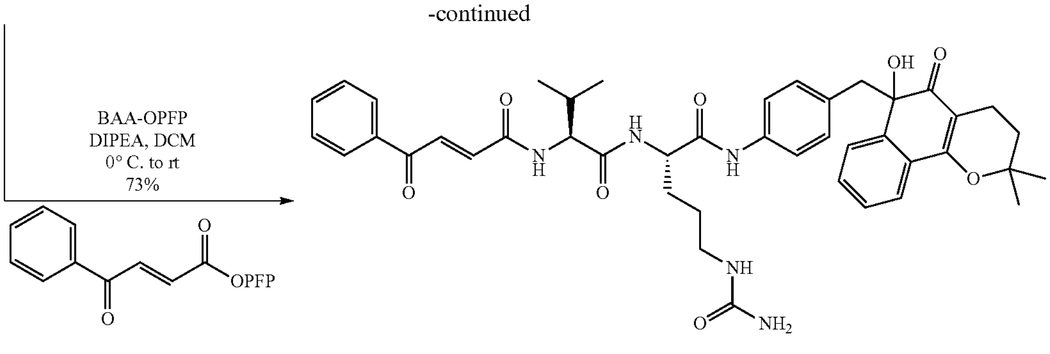

30

Fmoc-Val-Cit-para-aminobenzyl β-lapa-ketol S6

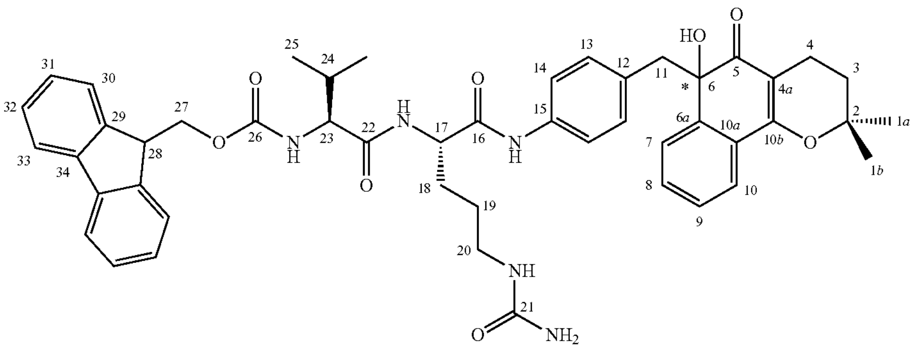

Boc-L-Cit-para-aminobenzyl β-lapa-ketol S4 (75 mg, 0.124 mmol) was deprotected by addition of 20% trifluoroacetic acid in dichloromethane (2 mL) at 0° C. The deprotection was followed by thin layer chromatography and upon completion (30 min) the amine salt was dried in vacuo. Perfluorophenyl (((9H-fluoren-9-yl)methoxy)carbonyl)-L-valinate (125 mg, 0.248 mmol) was dissolved in anhydrous dichloromethane (15 mL) at 0° C., and to this 10 solution N,N-diisopropylethylamine (50 μL) was added. The deprotected amine in dichloromethane (5 mL) was then added to the reaction dropwise. Further N,N-diisopropylethylamine (50 μL) was added to the reaction following amine addition to obtain a reaction pH of 9, as measured by universal indicator paper. The temperature of the reaction was slowly raised to room temperature and the reaction was stirred for 6 h. Solvent was removed in vacuo to obtain the crude product, which was purified by flash column chromatography (dichloromethane/methanol 9:1) to obtain Fmoc-Val-Cit-para-aminobenzyl β-lapa-ketol S6 (84 mg, 0.102 mmol, 82%). $^{1}$H NMR (600 MHz, MeOD) δ 7.80 (d, J=7.6 Hz, 2H, ArH), 7.73 (d, J=7.5 Hz, 1H, ArH), 7.67 (dd, J=11.4, 6.5 Hz, 2H, ArH), 7.58 (t, J=7.3 Hz, 1H, ArH), 7.52 (t, J=7.6 Hz, 1H, ArH), 7.42-7.33 (m, 3H, ArH), 7.31 (td, J=6.9, 3.2 Hz, 2H, ArH), 7.22 (dd, J=8.2, 5.9 Hz, 2H, H14), 6.35 (dd, J=8.5, 2.9 Hz, 2H, H13), 4.45 (dt, J=9.8, 5.3 Hz, 1H, H17), 4.43-4.31 (m, 2H, H27), 4.23 (t, J=6.7 Hz, 1H, H28), 3.94 (d, J=7.0 Hz, 1H, H23), 3.22-3.10 (m, 2H, H11 & H20), 3.07 (dt, J=13.7, 6.7 Hz, 1H, H11), 3.04-2.96 (m, 1H, H20), 2.39 (dt, J=17.1, 5.8 Hz, 1H, H4), 2.11-1.95 (m, 2H, H4 & H24), 1.83 (s, 1H, H18), 1.69 (d, J=9.4 Hz, 1H, H18), 1.64-1.45 (m, 4H, H3 & H19), 1.30 (d, J=8.3 Hz, 3H, H1a/H1b), 0.99-0.92 (m, 6H, H25), 0.91 (d, J=6.7 Hz, 3H, H1a/H1b). $^{13}$C NMR (126 MHz, MeOD) δ 202.1, 174.3, 171.9, 163.5, 162.3, 158.8, 145.3, 145.2, 143.7, 142.6, 138.4, 132.0, 131.2, 130.6, 129.6, 128.8, 128.7, 128.2, 127.3, 126.2, 123.7, 121.0, 120.1, 109.4, 79.2, 78.9, 68.1, 62.3, 54.9, 53.9, 49.9, 40.2, 32.5, 31.8, 30.5, 27.8, 25.8, 19.8, 18.8, 16.6. HRMS (m/z): [M+H]+ calcd. for $C_{48}H_{53}N_5O_8$ 828.3972 found 828.3958.

$NH_2$-Val-Cit-para-aminobenzyl β-lapa-ketol S7

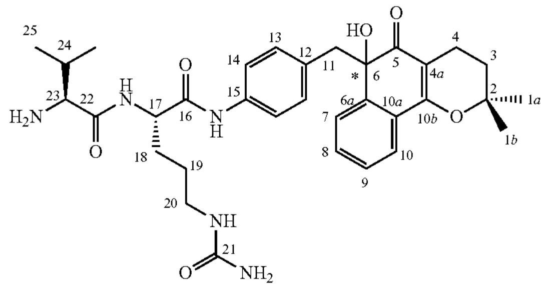

Fmoc-Val-Cit-para-aminobenzyl β-lapa-ketol S6 (18.5 mg, 0.02 mmol) was deprotected with a solution of 20% piperidine in dichloromethane at 0° C. for 30 min. Then, the solvent was removed in vacuo and the mixture was purified by semi-preparative HPLC to yield intermediate $NH_2$-Val-Cit-para-aminobenzyl β-lapa-ketol S7 (8.2 mg, 0.014 mmol, 68%). HPLC purification conditions: column: YMC-Triart-C18 80 Å 5 μm 10.0×250 mm; solvents: A=$H_2O$+0.1% formic acid, B=acetonitrile+0.1% formic acid; flow rate=3 mL/min; gradient t=0.0-5.0 min B=0%, t=5.0-10.0 min B=0-45%, t=10.0-22.0 min B=45-70%, t =22.0-22.1 min B=70-100%, t=22.1-26.0 B=100%, t=26.1-30.0 min B=0%. Product S7: t=13.4 min.

$^{1}$H NMR (600 MHz, MeOD) § 8.36 (s, 2H, NH2), 7.74 (d, J=7.8 Hz, 1H, H10), 7.64-7.56 (m, 1H, H7), 7.53 (td, J=7.6, 1.3 Hz, 1H, H8), 7.38 (t, J=7.6 Hz, 1H, H9), 7.25-7.14 (m, 2H, H14), 6.40 (dd, J=8.5, 1.7 Hz, 2H, H13), 4.52 (dt, J=9.2, 5.1 Hz, 1H, H17), 3.69 (d, J=5.8 Hz, 1H, H23), 3.21-3.07 (m, 3H, H11 and H20), 3.02 (d, J=12.1 Hz, 1H, H11), 2.42 (dt, J=17.2, 5.6 Hz, 1H, H4), 2.24-2.17 (m, 1H, H24), 2.10-1.99 (m, 1H, H4), 1.89-1.86 (m, 1H, H18), 1.77-1.66 (m, 1H, H18), 1.65-1.51 (m, 4H, H3 and H19), 1.33 (d, J=2.0 Hz, 3H, H1a/H1b), 1.05 (ddd, J=16.6, 6.9, 4.1 Hz, 6H, H25), 0.95 (d, J=2.9 Hz, 3H, H1a/H1b). HRMS (m/z): [M+H]+ calcd, for $C_{33}H_{43}N_5O_6$ 605.3292 found. 606.3303.

BAA-Val-Cit-para-aminobenzyl β-lapa ketol 30

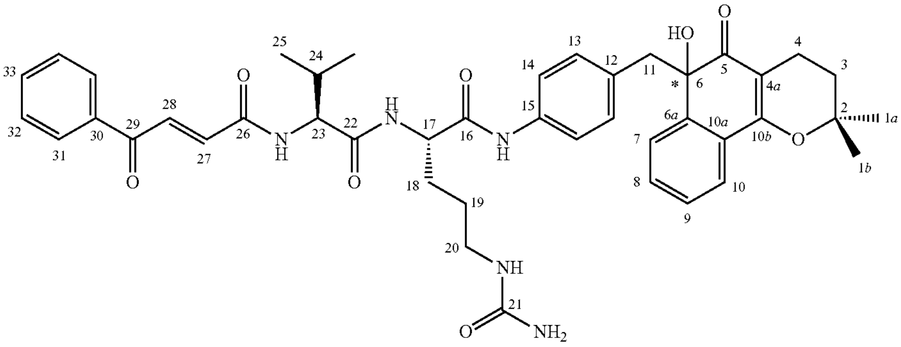

Perfluorophenyl (E)-4-oxo-4-phenylbut-2-enoate (2 mg, 0.0058 mmol) was dissolved in anhydrous dichloromethane (2 mL) under a nitrogen atmosphere at 0° C.

N,N-diisopropylethylamine (300 μL) was added. $NH_2$-Val-Cit-para-aminobenzyl β-lapa-ketol S7 (2.4 mg, 0.0040 mmol) dissolved in anhydrous dichloromethane (2 mL) was added to the solution dropwise. The reaction was stirred for 2 h at 0° C. and followed by thin-layer chromatography. Solvent was removed in vacuo and the crude product was purified by semi-preparative HPLC to yield BAA-Val-Cit-para-aminobenzyl β-lapa-ketol 30 (2.2 mg, 0.0028 mmol, 73%). HPLC purification conditions: column: Agilent Zorbax SB-C18 80 Å, 5 μm, 9.4×250 mm; solvents: A=$H_2O$, B=acetonitrile; flow rate=5 mL/min; gradient t=0.0-10.0 min B=0-60%, t=10.0-20.0 min B=60-65%, t=20.0-25.0 min B=65-100%, t=25.0-27.0 min B=100%, t=27.0-27.1 B=100-0%, t=27.1-30.0 min B=0%. Product 30: t=16.2 min.

$^{1}$H NMR (500 MHz, MeOD) δ 8.55 (s, 2H, NH2), 8.06-7.98 (m, 2H, ArH), 7.87 (d, J=15.3 Hz, 1H, H28), 7.74 (dd, J=7.8, 1.3 Hz, 1H, ArH), 7.70-7.64 (m, 1H, ArH), 7.62-7.48 (m, 4H, ArH), 7.37 (tdd, J=7.6, 4.9, 1.3 Hz, 1H, ArH), 7.24 (dq, J=9.1, 2.6 Hz, 2H, H14), 7.17 (d, J=15.3 Hz, 1H, H27), 6.38 (dd, J=8.5, 1.6 Hz, 2H, H13), 4.59 (s, 4H, NH), 4.46 (ddd, J=8.7, 5.3, 3.3 Hz, 1H, H17), 4.31 (d, J=7.3 Hz, 1H, H23), 3.14 (d, J=12.1 Hz, 1H, H11), 3.09 (m, 2H, H20), 3.02 (d, J=12.1 Hz, 1H, H11), 2.47-2.37 (m, 1H, H4), 2.20-2.09 (m, 1H, H24), 2.04 (dtd, J=16.7, 9.2, 6.8 Hz, 1H, H4), 1.91-1.80 (m, 1H, H18), 1.78-1.67 (m, 1H, H18), 1.64-1.41 (m, 4H, H3 and H19), 1.32 (s, 3H, H1a/H1b), 1.01 (ddd, J=6.6, 3.5, 2.6 Hz, 6H, H25), 0.94 (d, J=3.0 Hz, 3H, H1a/H1b). $^{13}$C NMR (126 MHz, MeOD) δ 200.1, 200.1, 191.6, 173.4, 172.0, 166.9, 163.6, 163.6, 162.3, 143.7, 138.5, 138.5, 138.3, 136.3, 134.9, 134.6, 132.0, 132.0, 131.2, 130.7, 130.1, 129.9, 129.6, 128.7, 127.3, 123.7, 123.7, 120.1, 109.5, 109.5, 79.2, 79.2, 78.9, 68.9, 61.0, 61.0, 55.0, 55.0, 53.9, 53.9, 33.1, 31.8, 30.8, 30.5, 30.4, 27.8, 27.8, 25.9, 25.8, 19.8, 18.9, 18.9, 16.6. HRMS (m/z): [M+H]+ calcd. For $C_{43}H_{49}N_5O_8$ 764.3654, found 764.3641.

Fragmentation of PHB-BL

A glucuronide linker was synthesised (as shown below). With linker 35a, using a Barbier-type reaction with indium, a protected-glucuronide-lapachone conjugate could be obtained, 36a. The protecting groups were then removed to form the desired product glucuronide-PHB-BL 37a. Due to the racemic nature of the reductive benzylation reaction, 37a was a mixture of two diastereoisomers.

An experiment testing the stability of compound 37a to incubation at pH 7.4 at 37° C. was also performed. The compound was completely stable and no β-lapachone was observed even after 6 days incubation.

Compound 37a was incubated with β-glucuronidase. As anticipated, the sugar deprotection reaction was rapid and fragmentation of PHB-BL 38a to release β-lapachone 1 could be observed at pH 7.4, 37° C.

Figure 6:
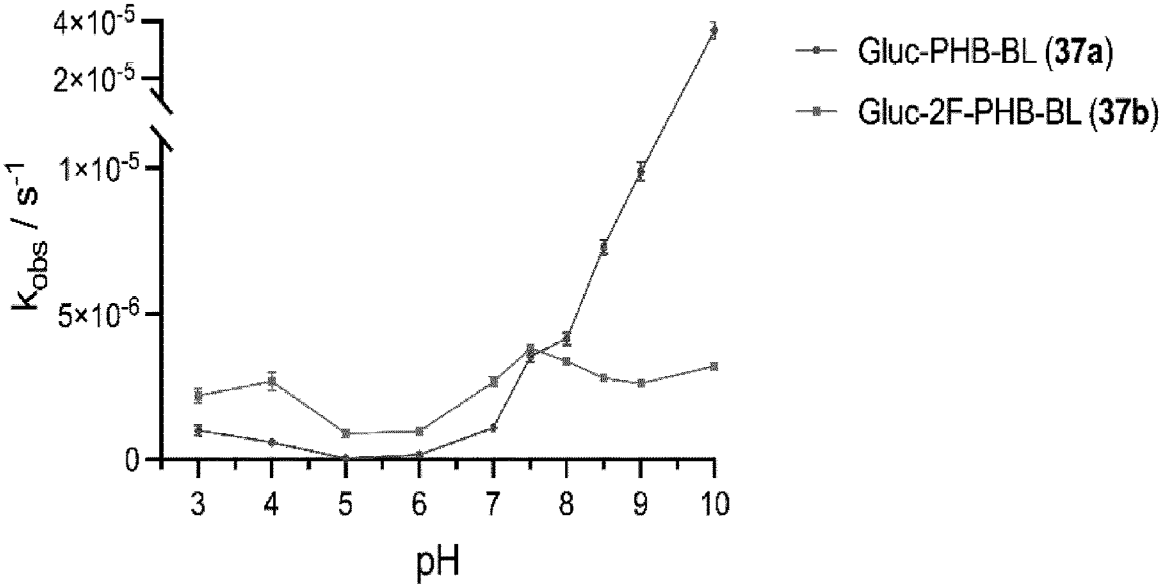
FIG. 6 shows the pH dependent release kinetics of two glucuronide-PHB b-lapachone prodrugs. The pseudo first-order $K_{obs}$ rate constants for PHB-BL (37a, blue) and 2F-PHB-BL (37b, red) were plotted as a function of pH (mean±S.E.M., triplicates). Both PHB prodrugs exhibited faster release rates at basic pHs, while the PAB prodrug favored acidic pHs. The difluoro PHB derivative eliminated faster than the plain PHB linker at pH 3-7, but slower than the plain PHB linker at pH 8-10.

In comparison to the ortho-quinone prodrugs containing a para-aminobenzyl linker moiety (PAB), those developed with a para-hydroxybenzyl linker (PHB) display a basic pH dependence for ortho-quinone release rate rather than acidic dependence. The observed release rate of β-lapachone 1 at pH 7 for the β-glucuronide-PHB-β-lapachone prodrug 37a after β-glucuronide deprotection was found to be $K_{obs}$=1.09×10$^{-6}$ s$^{-1}$, $t_{1/2=176}$ hr, in comparison to that of the PAB derivative at pH 7 ($K_{obs}$=2.4×10$^{-7}$ s$^{-1}$, $t_{1/2=789.7}$ hr). Additional repeats of the experiments revealed that the release kinetics of the PAB derivative at pH 7 may be even slower than initial reported ($K_{obs}$=1.4×10$^{-8}$ s$^{-1, 11/2=13000}$ hr). Since the $pK_a$ of the PHB hydroxy group is much more accessible at physiological conditions than that of the PAB aniline group, modulating the $pK_a$ of the phenol linker by derivatizing the benzene ring should allow the pH dependence of the release rate of the ortho-quinone to be controlled. A difluoro derivative (37b) was synthesized to explore this hypothesis, in which the $pK_a$ of the phenol was lowered by attaching two F's ortho to the phenol. This increased the quinone release rate at pH 7 ($K_{obs}$=2.68×10$^{-6}$ s$^{-1}$, $t_{1/2=71.8}$ hr) in comparison to the plain PHB linker (37a), as well as increasing the rate at pH 3-6 (FIG. 6). Further modification to both the phenol $pK_a$ and the electronics of the linker benzene should yield even faster releasing derivatives with various pH dependence kinetic profiles.

Additional Fragmentation of PHB-BL Experiments

The procedure used to prepare derivative 37a, described above, was also followed with slight modification to further synthesize derivatives 37b, 37c, 37d and linkers 35e and 35f, as shown below.

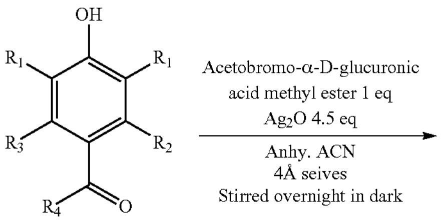

32
1.68 eq
a: $R_{1,2,3,4}$ = H
b: $R_1$ = F, $R_{2,3,4}$ = H
c: $R_{1,2,3}$ = F, $R_4$ = H
d: $R_{1,2,4}$ = H, $R_3$ = OMe
e: $R_{1,2,3}$ = H, $R_4$ = Me
f: $R_{1,4}$ = H, $R_{2,3}$ = OMe

-continued

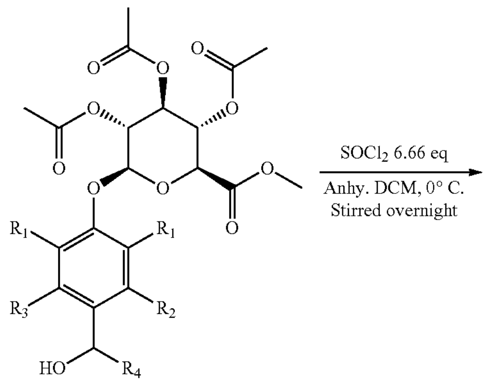

34
a: 92%
b: 80%
c: N/A*
d: 93%
e: Quant.**
f: 90%
**Conditions: $NaBH_4$ 2 eq, THF:MeOH 1:1, Stir 2 hr, 0° C.

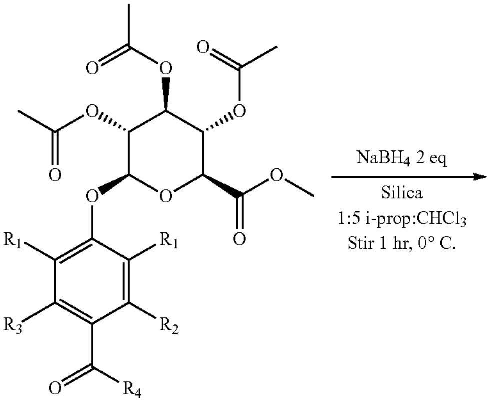

33
a: 49%
b: 63%
c: N/A*
d: 68%
e: 74%
f: 28%
*Synthesis of c began with glycosylation of the benzyl alcohol, yield = Quant.

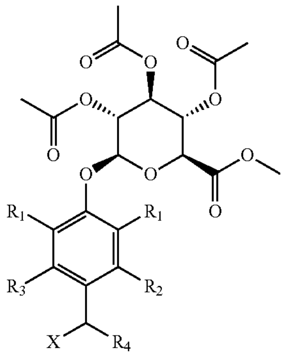

35
1.55 eq
a: X = Cl, 90%
b: X = Cl, 94%
c: X = Cl, Quant.
d: X = Br, 94%***
e: X = Br, Quant.***
f: X = Br, Quant.***
***Conditions: $PBr_3$ 1 eq. Anhy ether, Stir 2-5 hr, 0° C.

-continued

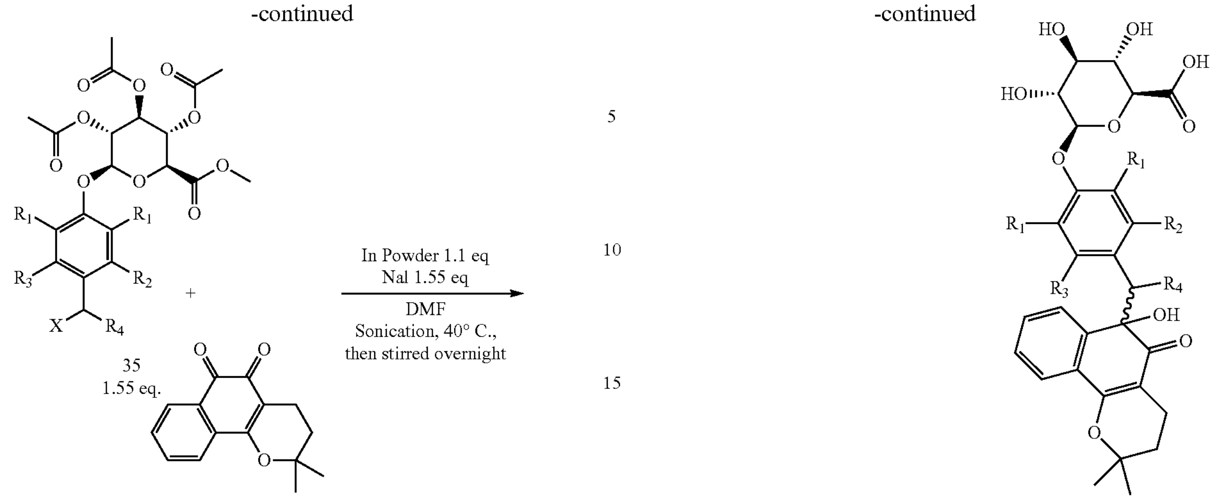

35
1.55 eq.

1
1 eq 37
a: 82%
b: 98%
c: 60%
d: 74%
e: 80%

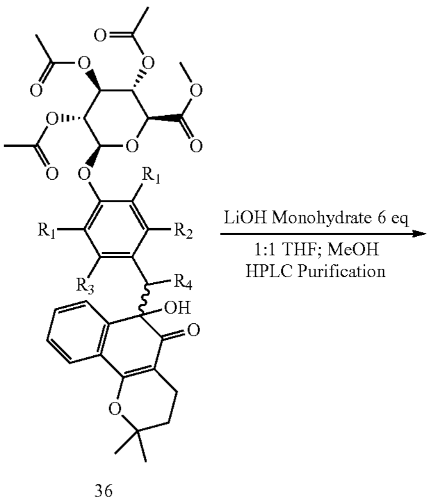

36
a: 37%
b: 70%
c: 75%
d: 47%
e: 4%

Experiments testing the stability of compounds 37b, 37c, and 37d to incubation at pH 7.4 at 37° C. were then performed using the same procedure described above in relation to compound 37a.

The observed release rate for the difluoro derivative 37b was then measured. The quinone release rate for compound 37b was observed to be $K_{obs}$=4.2x10$^{-6}$ s$^{-1}$ and $t_{1/2=45}$ hr at pH7. This observed release rate was increased in comparison to the plain PHB linker (37a).

Figure 7:
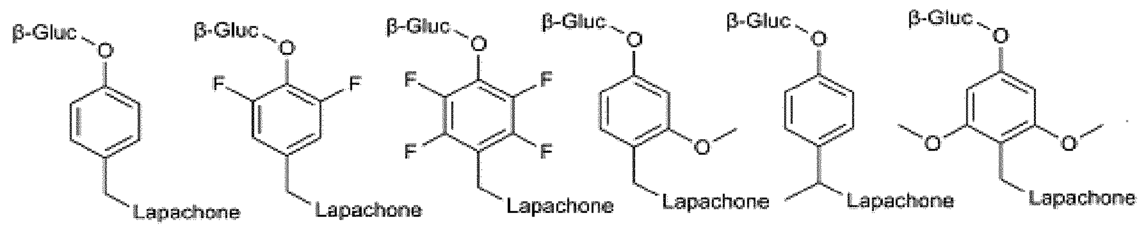
FIG. 7 shows the pH dependent release kinetics of four glucuronide-PHB β-lapachone prodrugs (37a-d) in comparison to a PAB β-lapachone prodrug (10). a, six glucuronide-PHB β-lapachone prodrugs (37a-f) were evaluated. First lowering the phenol pKa was explored with derivatives 37b and 37c, and then stabilizing the transition state was examined with derivatives 37d, 37e and 37f. b, The pseudo first-order $K_{obs}$ rate constants for derivatives 37a-d were plotted as a function of pH (mean±S.E.M., triplicates) in comparison to PAB prodrug 10. Most PHB prodrugs exhibited faster release rates at basic pHs, while the PAB prodrug favored faster release at acidic pHs. The difluoro PHB derivative 37b eliminated faster than the plain PHB linker 37a at pH 3-8.5, but slower than the plain PHB linker at pH 9-10. The methoxy derivative 37d displayed orders of magnitude faster release at pH 6-10, indicating that the impact of transition state stabilization on ortho-quinone release rate is large.
Figure 7:
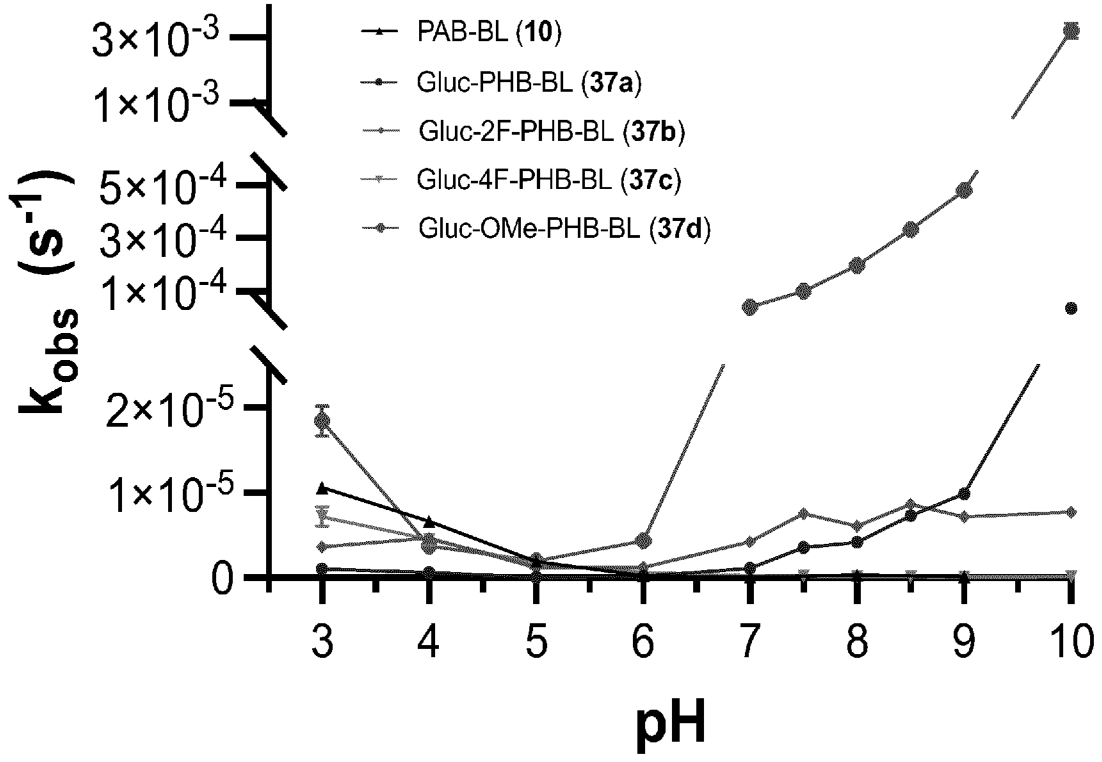

A tetrafluoro derivative (37c) was also explored, and the observed release kinetics were as follows: pH 7 $K_{obs}$=1.9x10$^{-7}$ s$^{-1}$ and $t_{1/2=1011}$ hr. Next, stabilization of the release transition state was explored by addition of methoxy groups meta to the phenol in the PHB linker. The single methoxy derivative, 37d, displayed orders of magnitude faster release (pH 7 $K_{obs}$=3.9x10$^{-5}$ s$^{-1}$, $t_{1/2=4.8}$ hr, FIG. 7).

Glucuronide-β-lapa-ketol Prodrugs

The potential of compound 37a, glucuronide-PHB-BL, as a prodrug was investigated. As discussed above, at physiological pH the compound has a relatively slow-release rate.

Toxicity of Gluc-PHB-BL 37a was tested against a range of cell lines with and without added β-glucuronidase. Addition of the enzyme mimics conditions of the solid tumour environment. In vitro mono-layer cell cultures do not externally express the enzyme, and glucuronide prodrugs typically perform better in in vivo studies where extracellular expression of β-glucuronidase is found in solid tumours.

Toxicity of glucuronide-PHB-BL 37a was not seen even at concentrations up to 100 μM, apart from in HEK-293T cells where a low toxicity is seen. This was in keeping with the low toxicity profile of glucuronide-derivatives, believed to be due to their inability to enter inside cells (Biochem. Pharma., 1996, 52 (3), 445-463). Upon addition of enzyme, however, toxicity of the compound increased. However, the toxicity of β-lapachone was not completely regained upon enzyme incubation, even after 48 h. By comparison of estimated $IC_{50}$ values, toxicity of the compound 37a treated with β-glucuronidase was between 3.5-9.7 times less than the toxicity of β-lapachone 1 to the cell line (Table 1).

TABLE 1

| IC$_{50}$ Values | | | |
|---|---|---|---|
| Cell line | IC$_{50}$ β-lapachone, 1/μM | IC$_{50}$ Gluc-PHB-BL 37a/μM | IC$_{50}$ (37a)/ IC$_{50}$ (1) |
| HeLa | 4.26 | 41.5 | 9.74 |
| SkBr-3 | 2.75 | 24.0 | 8.73 |
| HEK-293T | 2.91 | 20.9 | 7.18 |
| HL-60 | 4.33 | 15.2 | 3.51 |
| MOLM-13 | 12.1 | 78.6 | 6.50 |

Control tests were performed to test whether the toxicity of β-lapachone was affected by β-glucuronidase addition, and it was not significantly affected.

Additional Data Relating to the Glucuronide-β-lapa-ketol Prodrugs

Figure 9:
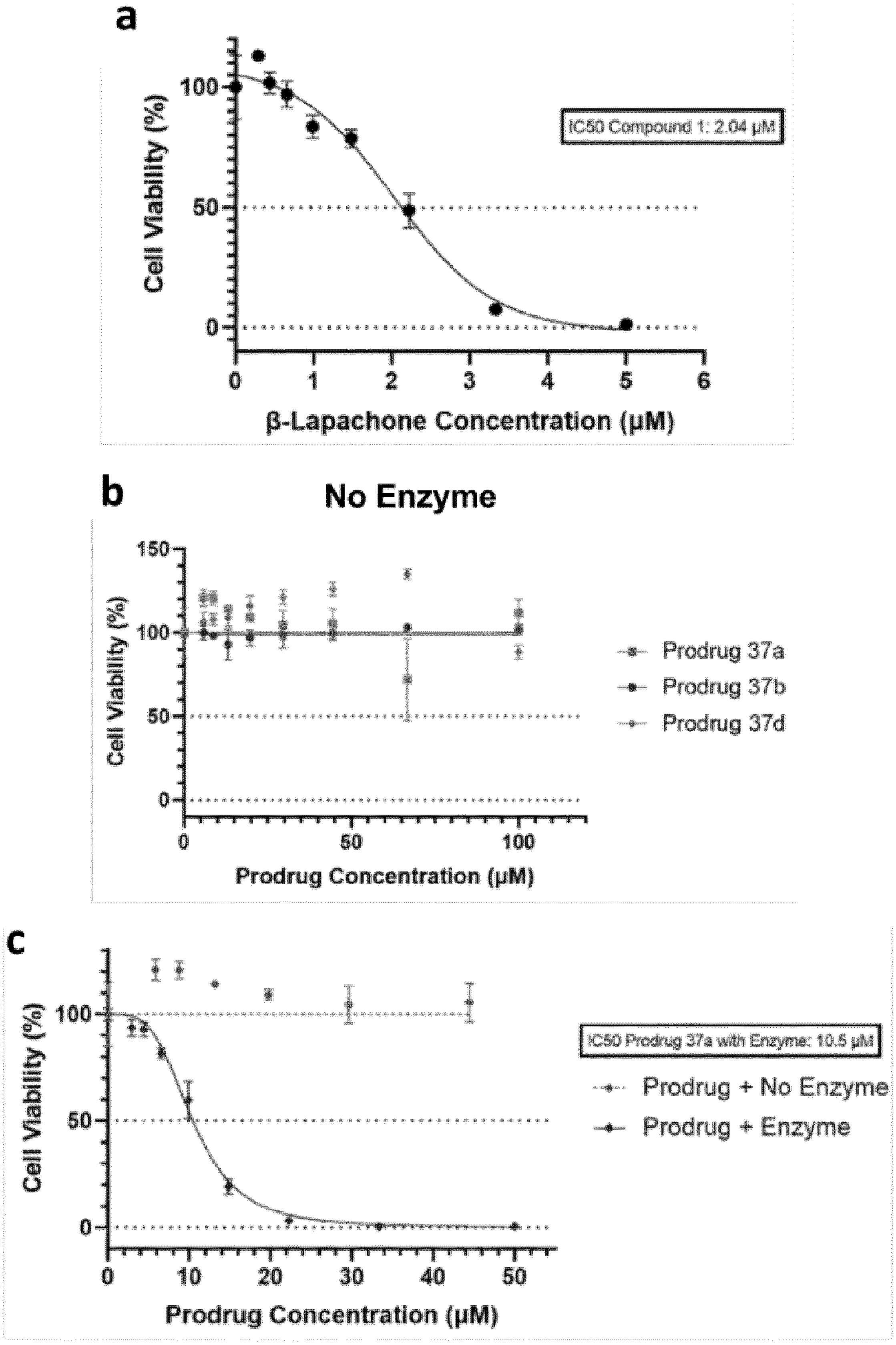
FIG. 9 shows the in vitro viability of glucuronide ortho-quinone prodrugs in pancreatic cancer cells. Panels a-e show viability of the Panc-1 pancreatic cancer cell line while Panels f-j show viability of the Aspc-1 pancreatic cancer cell line against β-lapachone and its prodrug derivatives. For β-lapachone (1), an $IC_{50}$ of 2.04 μM in Panc-1 (a) and 7.66 μM in Aspc-1 (f) is observed. Without the β-glucuronidase enzyme present, all three releasing prodrugs (37a, 37b, 37d) show no toxicity against Panc-1 or Aspc-1 up to 100 M (b and g). With B-glucuronidase present to mimic the tumour microenvironment, prodrug 37a demonstrates an $IC_{50}$ of 10.5 μM in Panc-1 (c) and 17.4 μM in Aspc-1 (h); prodrug 37b demonstrates an $IC_{50}$ of 13.4 μM in Panc-1 (d) and 24.4 μM in Aspc-1 (i); and prodrug 37d demonstrates an $IC_{50}$ of 0.904 μM in Panc-1 (e) and 2.99 μM in Aspc-1 (j). The lower toxicity of 37a and 37b with enzyme added in comparison to 1 can be attributed to incomplete drug release during the time frame of the assay based on the kinetics measured. 37d, which releases completely during the time frame of the assay, displayed toxicity at similar levels as 1 alone. 37c was not tested in this study.
Figure 9:
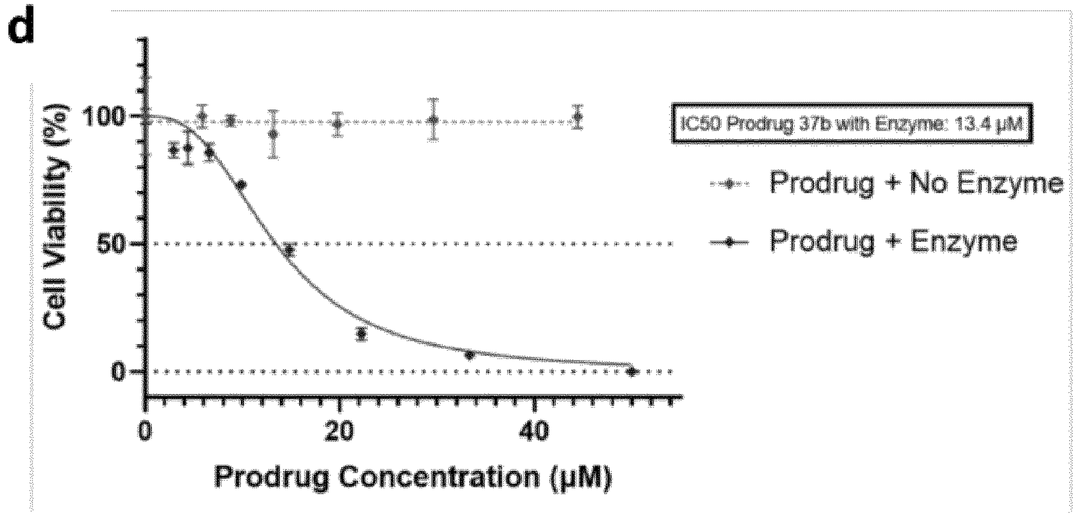
Figure 9:
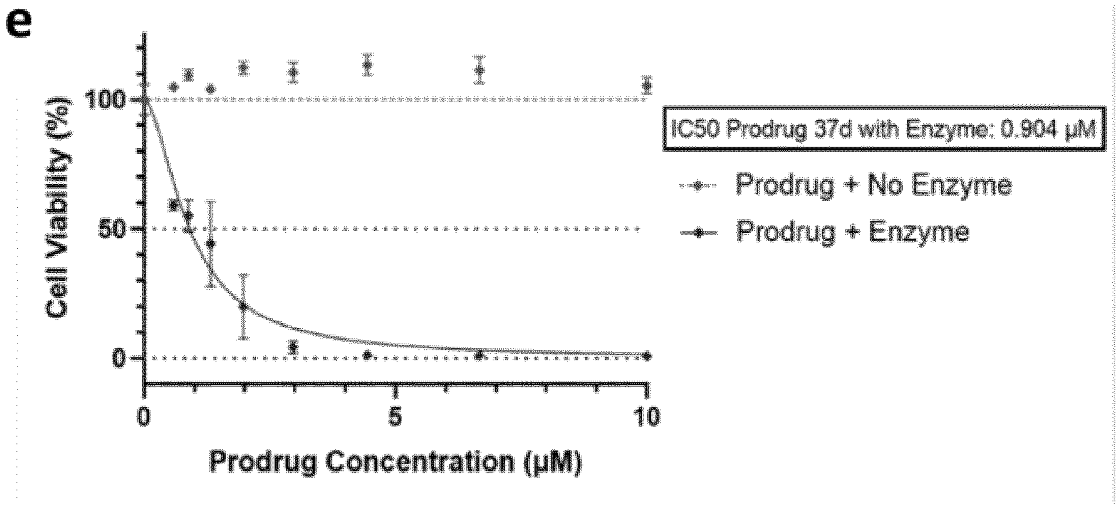

The activity of the glucuronide prodrugs towards pancreatic cancer cell lines was then examined (FIG. 9). Results showed that all releasing prodrug derivatives were effective against both pancreatic cancer cell lines Aspc-1 and Panc-1. The same trend was observed in both cell lines with the methoxy prodrug derivative (37d) being the most effective, followed by the original prodrug (37a), and ending with the di-fluoro prodrug derivative (37b). Prodrug 37d was shown to be more toxic than β-lapachone by itself in both cell lines.

To explore the differential toxicities, the relative mRNA expression levels of the two main β-lapachone protein targets were quantified, NQO1 and 5-LO (FIG. 8). This data suggests that Aspc-1 has the highest mRNA expression of both NQO1 and 5-LO, followed by the KLM-1 cell line and Panc-1 cell line respectively.

Synthesis of Glucuronide-β-lapa-ketol Prodrugs

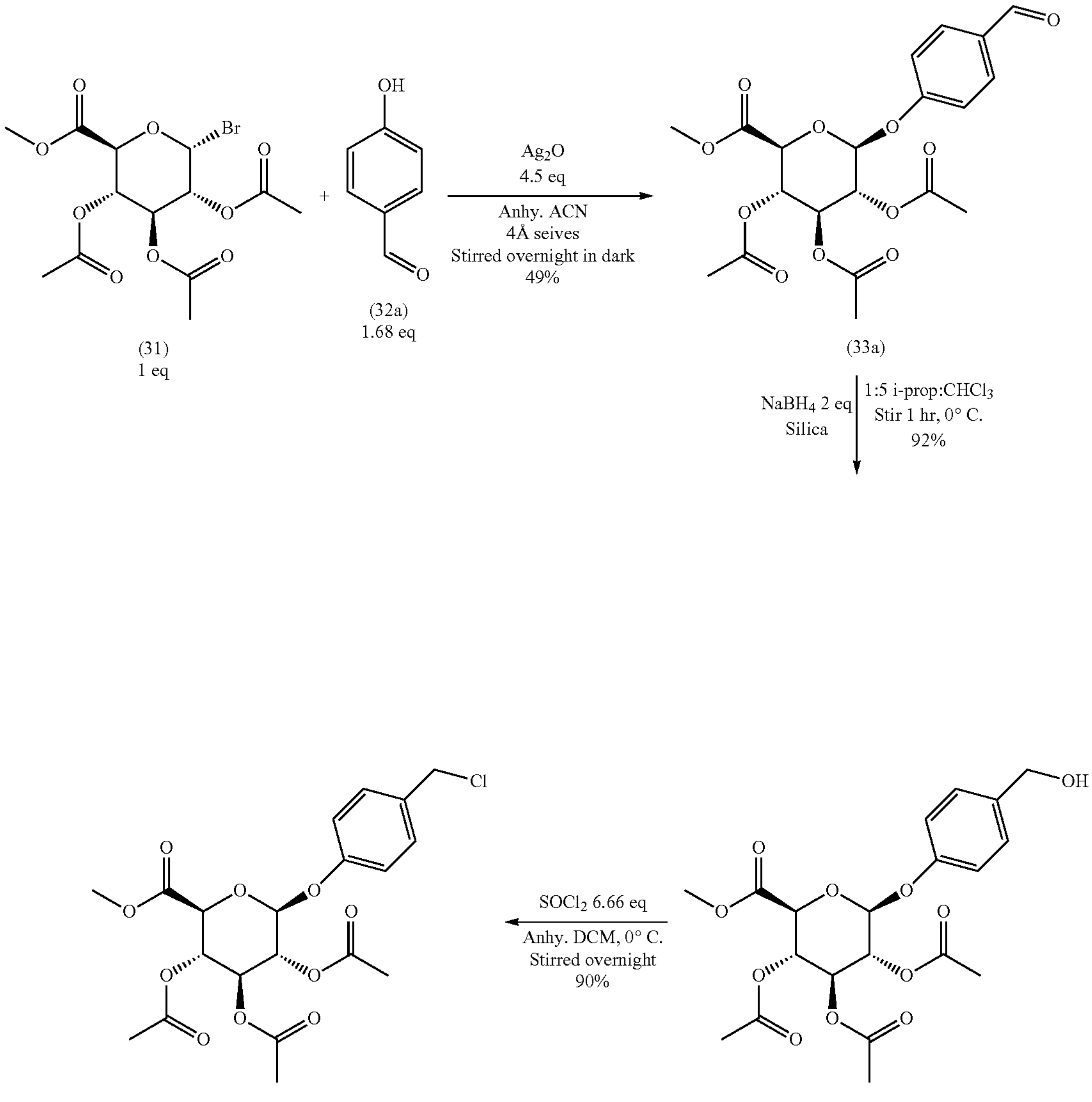

(31)
1 eq (32a)
1.68 eq (33a)

(34a)

(35a)

(2S,3S,4R,5R,6S)-6-(4-formylphenoxy)-5-hydroxy-2-(methoxycarbonyl)tetrahydro-2H-pyran-3,4-diyl diacetate (33a)

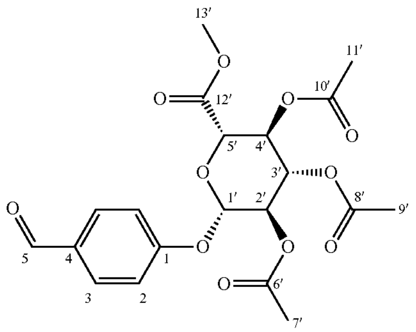 [SMILES: COC(=O)[C@H]1O[C@@H](Oc2ccc(C=O)cc2)[C@H](OC(C)=O)[C@@H](OC(C)=O)[C@@H]1OC(C)=O]

Acetobromo-α-D-glucuronic acid methyl ester (31) (0.504 g, 1.27 mmol, 1 eq) and 4-hydroxybenzaldehyde (32a) (0.261 g, 2.1 mmol, 1.67 eq) were combined in anhydrous acetonitrile (15 mL) under $N_2$ in the dark and stirred for 30 min. $Ag_2O$ (1.294 g, 5.59 mmol, 4.43 eq) and 4 Å activated molecular sieves (1.27 g) were added and the reaction was stirred at room temperature overnight in the dark. Thin-layer chromatography monitored reaction progress (25% ethyl acetate/petroleum ether). The reaction was filtered through celite and the solvent removed in vacuo. The residue was dissolved in ethyl acetate, washed with sat. $NaHCO_3$ (3×10 mL), water (10 mL), and brine (10 mL). It was then dried (magnesium sulfate), and the solvent was removed in vacuo. The product was purified by flash column chromatography on silica gel 60 (25-40% EtOAc/Pet ether) to give (2S,3S,4R,5R,6S)-6-(4-formylphenoxy)-5-hydroxy-2-(methoxycarbonyl)tetrahydro-2H-pyran-3,4-diyl diacetate (33a) as white circular crystals (0.272 g, 0.62 mmol, 49%).

$^1$H NMR (600 MHz, $CDCl_3$) δ 9.17 (s, 1H, H5), 7.10 (d, J=8.7 Hz, 2H, H3), 6.37 (d, J=8.7 Hz, 2H, H2), 4.66-4.53 (m, 4H, H1', H2', H3', H4'), 3.58-3.51 (m, 1H, H5'), 2.96 (s, 3H, H13'), 1.33-1.28 (m, 9H, H11', H9', H7'). $^{13}$C NMR (151 MHz, $CDCl_3$) δ 190.7 (C5), 170.0 (C8'), 169.3 (C10'), 169.2 (C6'), 166.7 (C12'), 162.5 (C1), 161.0 (C4), 131.9 (C3), 131.8 (C3), 116.8 (C2), 98.0 (C1'), 72.7 (C5'), 71.6 (C3'), 70.9 (C2'), 68.9 (C4'), 53.0 (C13'), 20.6 (C7'), 20.6 (C9'), 20.5 (C11'). $R_f$: 0.07 (25% EtOAc/Pet ether). HRMS (ESI$^+$): m/z calcd. for $[C_{20}H_{22}O_{11}+Na]^+$ calcd. 461.1060 found 461.1053.

(2S,3R,4S,5S,6S)-2-(4-(hydroxymethyl) phenoxy)-6-(methoxycarbonyl)tetrahydro-2H-pyran-3,4,5-triyl triacetate (34a)

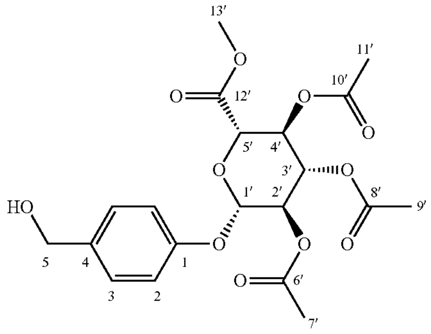 [SMILES: COC(=O)[C@H]1O[C@@H](Oc2ccc(CO)cc2)[C@H](OC(C)=O)[C@@H](OC(C)=O)[C@@H]1OC(C)=O]

(2S,3S,4R,5R,6S)-6-(4-formylphenoxy)-5-hydroxy-2-(methoxycarbonyl)tetrahydro-2H-pyran-3,4-diyl diacetate (33a) (0.272 g, 0.62 mmol, 1 eq) was dissolved in chloroform (5 mL) and isopropanol (1 mL) with silica gel (0.272 g) and stirred at 0° C. under $N_2$ for 15 min. $NaBH_4$ (0.048 g, 1.27 mmol, 2.0 eq) was added and the reaction was stirred for 45 min. It was monitored by thin-layer chromatography (1:1 ethyl acetate:petroleum ether). The reaction was diluted with dichloromethane (10 mL), filtered over celite, and washed with dichloromethane (10 mL). The filtrate was washed with brine (10 mL), dried (magnesium sulfate), and the solvent removed in vacuo to give (2S,3R,4S,5S,6S)-2-(4-(hydroxymethyl) phenoxy)-6-(methoxycarbonyl)tetrahydro-2H-pyran-3,4,5-triyl triacetate (34a) as an off-white solid (0.252 g, 0.57 mmol, 92%).

$^1$H NMR (600 MHz, $CDCl_3$) δ 7.23 (d, J=8.6 Hz, 2H, H3), 6.92 (d, J=8.6 Hz, 2H, H2), 5.31 (t, J=9.3 Hz, 1H, H2'), 5.27-5.20 (m, 2H, H3', H4'), 5.10 (d, J=7.6 Hz, 1H, H1'), 4.54 (s, 2H, H5), 4.18 (d, J=9.6 Hz, 1H, H5'), 3.67 (s, 3H, H13'), 2.89 (s, 1H, OH), 2.05-1.95 (m, 9H, H11', H9', H7'). $^{13}$C NMR (151 MHz, $CDCl_3$) δ 170.1 (C6'), 169.5 (C8'), 169.3 (C10'), 166.9 (C12'), 155.9 (C1), 136.2 (C4), 128.3 (C3), 116.8 (C2), 98.9 (C1'), 72.2 (C5'), 71.7 (C3'), 70.8 (C2'), 69.0 (C4'), 64.2 (C5), 52.9 (C13'), 20.5 (C11'), 20.5 (C9'), 20.4 (C7'). $R_f$: 0.15 (1:1 EtOAc: Pet ether). HRMS (ESI$^+$): m/z calcd for $[C_{20}H_{24}O_{11+}Na]^+$ calcd. 463.1216 found 463.1213.

(2S,3R,4S,5S,6S)-2-(4-(chloromethyl) phenoxy)-6-(methoxycarbonyl)tetrahydro-2H-pyran-3,4,5-triyl triacetate (35a)

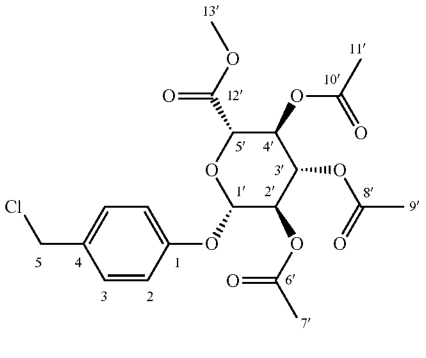 [SMILES: COC(=O)[C@H]1O[C@@H](Oc2ccc(CCl)cc2)[C@H](OC(C)=O)[C@@H](OC(C)=O)[C@@H]1OC(C)=O]

(2S,3R,4S,5S,6S)-2-(4-(hydroxymethyl) phenoxy)-6-(methoxycarbonyl)tetrahydro-2H-pyran-3,4,5-triyl triacetate (34a) (0.179 g, 0.41 mmol, 1 eq) was dissolved in anhydrous dichloromethane (20 mL) at 0° C. under $N_2$. $SOCl_2$ (0.2 mL, 2.74 mmol, 6.7 eq) was added and the reaction was stirred under $N_2$ overnight. Thin-layer chromatography monitored the reaction (1:1 ethyl acetate:petroleum ether) to completion. The reaction was quenched with sat. $NaHCO_3$ (10 mL), washed with brine (10 mL), dried (magnesium sulfate), and the solvent removed in vacuo to give (2S,3R,4S,5S,6S)-2-(4-(chloromethyl) phenoxy)-6-(methoxy carbonyl)tetrahydro-2H-pyran-3,4,5-triyl triacetate (35a) as an off-white solid (0.165 g, 0.36 mmol, 90%). $^1H$ NMR (400 MHz, $CDCl_3$) δ 7.29 (d, J=8.7 Hz, 2H, H3), 6.95 (d, J=8.6 Hz, 2H, H2), 5.34 (q, J=9.3 Hz, 2H, H3', H4'), 5.30-5.21 (m, 1H, H2'), 5.16 (d, J=7.4 Hz, 1H, H1'), 4.52 (s, 2H, H5), 4.23 (d, J=9.0 Hz, 1H, H5'), 3.69 (s, 3H, H13'), 2.02 (s, 9H, H11', H9', H7'). $^{13}C$ NMR (100 MHz, $CDCl_3$) δ 169.9 (C6'), 169.3 (C8'), 169.1 (C10'), 166.8 (C12'), 156.5 (C1), 132.5 (C4), 130.0 (C3), 117.0 (C2), 98.7 (C1'), 72.4 (C5'), 71.7 (C3'), 70.9 (C2'), 69.0 (C4'), 52.9 (C13'), 45.7 (C5), 20.5 (C11'), 20.5 (C9'), 20.4 (C7'). $R_f$: 0 (1:1 EtOAc: Pet ether). HRMS ($ESI^+$): m/z calcd for $[C_{20}H_{23}O_{10}Cl+Na]^+$ calcd. 481.0877 found 481.0876.

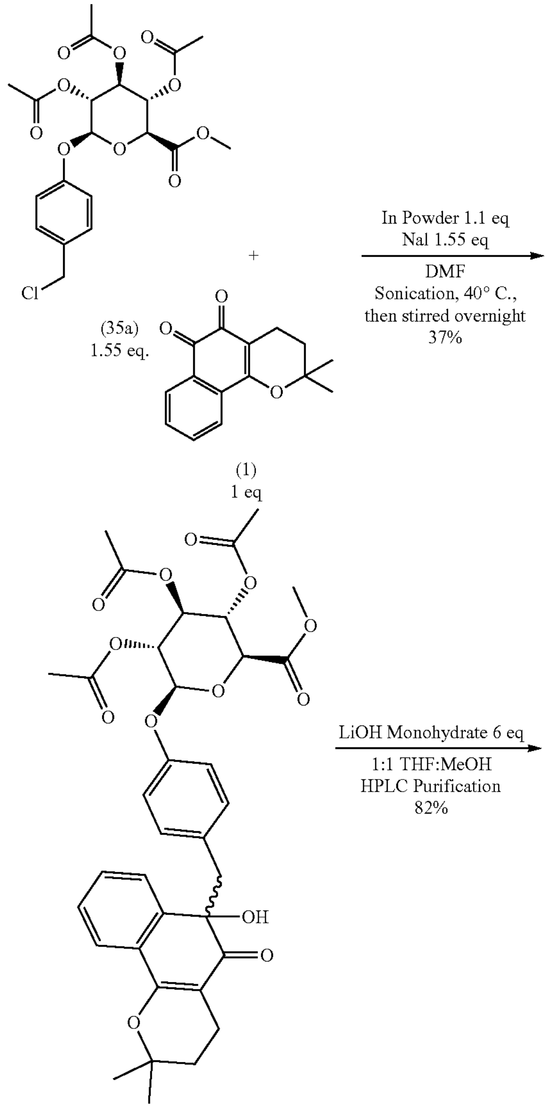

(35a) 1.55 eq.

(1) 1 eq (36a)

-continued

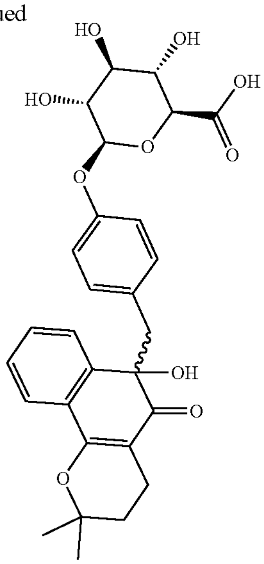

(37a)

Acetyl-glucuronide-para-hydroxybenzyl β-lapa-ketol 36a (2S,3R,4S,5S,6S)-2-(4-((6-hydroxy-2,2-dimethyl-5-oxo-3,4,5,6-tetrahydro-2H-benzo[h]chromen-6-yl) methyl) phenoxy)-6-(methoxycarbonyl)tetrahydro-2H-pyran-3,4,5-triyl triacetate

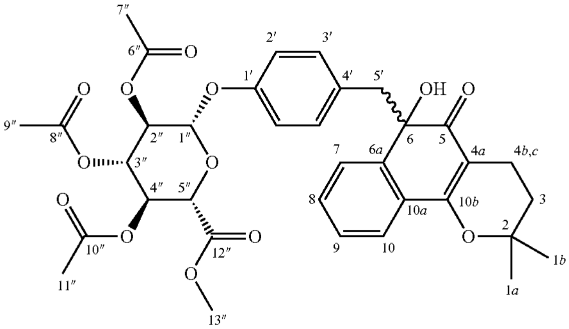 [SMILES: COC(=O)[C@H]1O[C@@H](Oc2ccc(CC3(O)C(=O)C4=C(OC(C)(C)CC4)c4ccccc43)cc2)[C@H](OC(C)=O)[C@@H](OC(C)=O)[C@@H]1OC(C)=O]

(2S,3R,4S,5S,6S)-2-(4-(chloromethyl) phenoxy)-6-(methoxycarbonyl)tetrahydro-2H-pyran-3,4,5-triyl triacetate (35a) (0.231 g, 0.50 mmol, 1.2 eq), NaI (0.255 g, 1.7 mmol, 4.2 eq), β-lapachone (1) (0.098 g, 0.40 mmol, 1 eq) and indium (0) powder (0.058 g, 0.51 mmol, 1.2 eq) were added to anhydrous dimethylformamide (6 mL). The solution was heated to 40° C. and sonicated for 45 min, while monitoring by thin-layer chromatography (2:3 petroleum ether:ethyl acetate). Excess In (0) powder was added and the reaction was left stirring at room temperature overnight. The next day, it was again sonicated at 40° C. for 1.5 hr. Water (10 mL) and 7 drops 1M HCl were added to quench the reaction and it was extracted with ethyl acetate (3×150 mL). The organic layers were combined and washed with brine (10 mL), dried (magnesium sulfate), and the solvent removed in vacuo. The product was purified by flash column chromatography on silica gel 60 (2% methanol:dichloromethane) to give (2S,3R,4S,5S,6S)-2-(4-((6-hydroxy-2,2-dimethyl-5-oxo-3,4,5,6-tetrahydro-2H-benzo[h]chromen-6-yl)methyl) phenoxy)-6-(methoxycarbonyl)tetrahydro-2H-pyran-3,4,5-triyl triacetate (36a) as an off-white solid (0.099 g, 0.15 mmol, 37%).

$^1$H NMR (400 MHz, $CDCl_3$) δ 7.69-7.63 (m, 1H, H10), 7.57 (ddd, J=15.7, 7.7, 1.3 Hz, 1H, H7), 7.43 (tdd, J=7.6, 4.7, 1.4 Hz, 1H, H8), 7.33 (td, J=7.6, 1.3 Hz, 1H, H9), 6.70 (dd, J=8.5, 6.1 Hz, 2H, H2'), 6.54 (t, J=8.6 Hz, 2H, H3'), 5.32-5.26 (m, 2H, H3", H4"), 5.25-5.19 (m, 1H, H2"), 5.02 (t, J=7.0 Hz, 1H, H1"), 4.15-4.10 (m, 1H, H5"), 3.93 (d, J=2.1 Hz, 1H, OH), 3.72 (d, J=4.6 Hz, 3H, H13"), 3.00 (d, J=2.3 Hz, 2H, H5'), 2.54 (dtd, J=17.3, 5.7, 2.5 Hz, 1H, H4b,c), 2.13-2.08 (m, 1H, H4b,c), 2.05-1.96 (m, 9H, H7", H9", H11"), 1.65 (qd, J=8.3, 7.6, 3.8 Hz, 2H, H3), 1.36 (d, J=1.8 Hz, 3H, H1a/H1b), 1.11 (d, J=8.7 Hz, 3H, H1a/H1b). $^{13}$C NMR (100 MHz, $CDCl_3$) δ 200.5 (C5), 200.5 (C5), 170.2 (C8"), 169.4 (C10"), 169.2 (C6"), 169.2 (C6"), 166.9 (C12"), 166.9 (C12"), 162.2 (C10b), 162.2 (C10b), 155.8 (C1'), 155.7 (C1'), 141.5 (C6a), 130.9 (C3'), 130.9 (C3'), 130.3 (C4'), 130.3 (C4'), 130.2 (C8), 130.1 (C8), 127.6 (C9), 127.5 (C10a), 127.4 (C10a), 125.7 (C7), 125.7 (C7), 123.1 (C10), 123.1 (C10), 116.2 (C2'), 116.1 (C2'), 106.7 (C4a), 106.7 (C4a), 99.2 (C1"), 99.0 (C1"), 78.1 (C6), 78.1 (C6), 78.0 (C2), 72.7 (C5"), 72.7 (C5"), 72.0 (C3"), 71.1 (C2"), 71.0 (C2"), 69.2 (C4"), 69.2 (C4"), 53.5 (C5'), 53.4 (C5'), 53.0 (C13"), 53.0 (C13"), 31.7 (C3), 31.7 (C3), 27.6 (C1a, $C_1$b), 27.6 (C1a, $C_1$b), 25.7 (C1a, $C_1$b), 20.7 (C11", $C_9$", $C_7$"), 20.6 (C11", $C_9$", $C_7$"), 15.7 (C4b,c), 15.7 (C4b,c). $R_f$: 0.54 (2% MeOH: DCM). HRMS (ESI$^+$): m/z calcd for $[C_{35}H_{38}O_{13}+H]^+$ calcd. 667.2391 found 667.2403.

Glucuronide-para-hydroxybenzyl β-lapa-ketol 37a (2S,3S,4S,5R,6S)-3,4,5-trihydroxy-6-(4-((6-hydroxy-2,2-dimethyl-5-oxo-3,4,5,6-tetrahydro-2H-benzo[h]chromen-6-yl)methyl) phenoxy)tetrahydro-2H-pyran-2-carboxylic acid

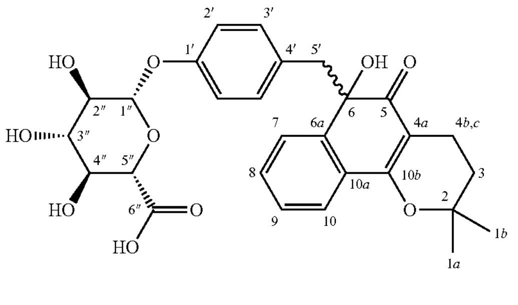

The acyl-protected glucuronide β-lapachone prodrug (36a) (0.066 g, 0.1 mmol, 1 eq) was dissolved in tetrahydrofuran (1 mL) and methanol (1 mL) and stirred at 0° C. A separate solution of LiOH monohydrate (0.025 g, 0.6 mmol, 6 eq) in water (1 mL) was prepared and added to the solution of 36a dropwise. The reaction was stirred for 1.5 hr and product formation was monitored by LCMS. After complete conversion, glacial acetic acid (33.9 μL, 0.6 mmol, 6 eq) was added and the solvent removed in vacuo. Crude product 37a was purified by semi-preparative HPLC to give (2S,3S,4S,5R,6S)-3,4,5-trihydroxy-6-(4-((6-hydroxy-2,2-dimethyl-5-oxo-3,4,5,6-tetrahydro-2H-benzo[h]chromen-6-yl)methyl) phenoxy) tetrahydro-2H-pyran-2-carboxylic acid (37a) as a white solid (0.054 g, 0.10 mmol, 82%). HPLC Purification Method: Column=YMC Pack Pro C18 5 μm 250×10 mm 120 Å; mobile phases: A=$H_2O$+0.1% formic acid, B=ACN+0.1% formic acid; gradient: t=0-1 min 0% B, t=1-10 min 0-100% B, t=$10^{-12}$ min 100% B. Retention time of 37a=8.06 min.

$^1$H NMR (500 MHz, $CD_3CN$) δ 8.03 (s, 1H, COOH), 7.62 (ddt, J=7.4, 2.6, 1.5 Hz, 2H, H10, H7), 7.48 (tdd, J=7.6, 3.2, 1.3 Hz, 1H, H8), 7.38 (tdd, J=7.6, 3.0, 1.4 Hz, 1H, H9), 6.72 (dd, J=8.6, 3.6 Hz, 2H, H2'), 6.50 (dd, J=8.7, 2.8 Hz, 2H, H3'), 4.86 (d, J=7.4 Hz, 0.5H, H1"), 4.83 (d, J=7.4 Hz, 0.5H, H1"), 4.11 (s, 1H, OH), 3.93 (dd, J=9.8, 6.6 Hz, 1H, H3"), 3.54 (ddd, J=9.8, 8.7, 1.0 Hz, 1H, H4"), 3.48-3.33 (m, 2H, H5", H2"), 3.05-2.94 (m, 2H, H5'), 2.44 (dtd, J=17.3, 5.7, 3.3 Hz, 1H, H4b,c), 2.22 (s, 2H, Gluc 2× OH's), 2.11 (dddd, J=17.4, 8.9, 6.5, 4.3 Hz, 2H, Gluc OH, H4b,c), 1.72-1.58 (m, 2H, H3), 1.34 (d, J=4.4 Hz, 3H, H1a, H1b), 1.09 (d, J=3.7 Hz, 3H, H1a, H1b). $^1$H NMR (400 MHz, MeOD) δ 7.72 (ddd, J=7.7, 6.0, 1.3 Hz, 1H, H10), 7.59 (ddd, J=7.8, 5.3, 1.3 Hz, 1H, H7), 7.51 (tt, J=7.6, 1.5 Hz, 1H, H8), 7.36 (td, J=7.6, 1.3 Hz, 1H, H9), 6.71 (dd, J=11.1, 8.6 Hz, 2H, H2'), 6.37 (dd, J=8.6, 5.0 Hz, 2H, H3'), 4.82 (d, J=7.3 Hz, 0.5H, H1"), 4.77 (d, J=7.7 Hz, 0.5H, H1"), 3.85 (dd, J=9.7, 6.6 Hz, 1H, H3"), 3.57 (td, J=9.4, 3.0 Hz, 1H, H4"), 3.50-3.38 (m, 2H, H5", H2"), 3.13 (dd, J=12.1, 3.8 Hz, 1H, H5'), 3.00 (dd, J=12.1, 4.3 Hz, 1H, H5'), 2.47-2.32 (m, 1H, H4b,c), 2.11-2.00 (m, 1H, H4b,c), 1.64-1.54 (m, 2H, H3), 1.37-1.24 (m, 3H, H1a, H1b), 1.00 (d, J=2.2 Hz, 3H, H1a, H1b). $^{13}$C NMR (126 MHz, $CD_3CN$) δ 200.9 (C5), 200.8 (C5), 170.0 (C6"), 170.0 (C6"), 162.2 (C10b), 162.2 (C10b), 157.0 (C1'), 156.9 (C1'), 142.7 (C6a), 142.7 (C6a), 131.5 (C3'), 131.5 (C3'), 130.7 (C8), 130.7 (C8), 130.3 (C4'), 130.3 (C4'), 128.6 (C10a), 128.4 (C9), 128.3 (C9), 126.8 (C7), 126.7 (C7), 123.3 (C10), 123.3 (C10), 116.2 (C2'), 116.2 (C2'), 108.3 (C4a), 108.2 (C4a), 101.3 (C1"), 101.1 (C1"), 78.9 (C6), 78.8 (C6), 78.7 (C2), 78.7 (C2), 76.5 (C5"), 75.2 (C3"), 75.2 (C3"), 73.8 (C2"), 72.2 (C4"), 72.2 (C4"), 53.8 (C5'), 53.7 (C5'), 32.0 (C3), 32.0 (C3), 27.6 (C1a, $C_1$b), 27.5 (C1a, $C_1$b), 25.9 (C1a, $C_1$b), 25.8 (C1a, $C_1$b), 16.3 (C4b,c), 16.3 (C4b,c). HRMS (ESI$^+$): m/z calcd for $[C_{28}H_{30}O_{10}+H]^+$ calcd. 527.1917 found 527.1914.

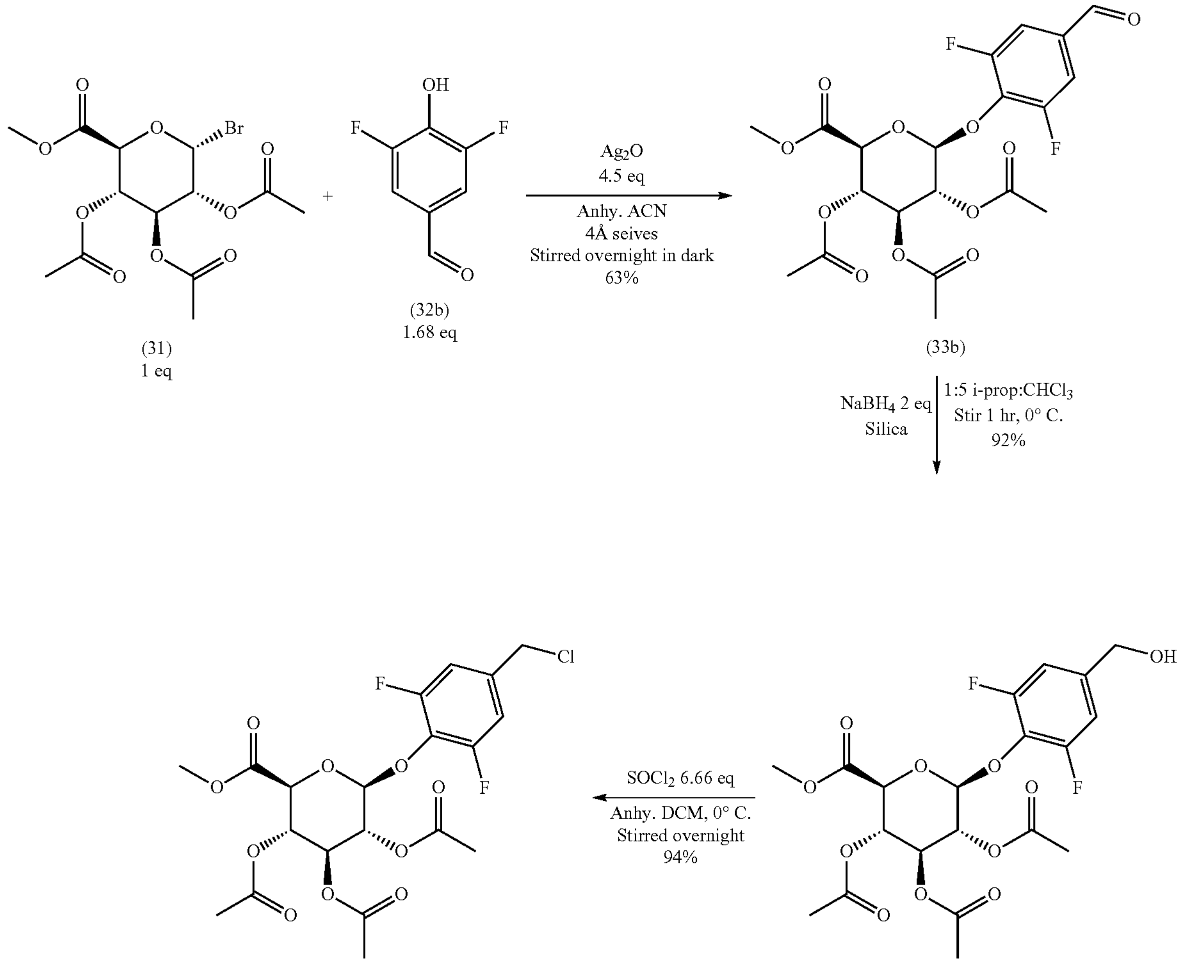

(31)
1 eq (32b)
1.68 eq (33b)

(34b)

(35b)

(2S,3R,4S,5S,6S)-2-(2,6-difluoro-4-formylphenoxy)-6-(methoxycarbonyl)tetrahydro-2H-pyran-3,4,5-triyl triacetate (33b)

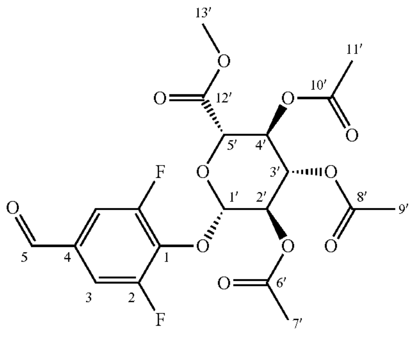

Acetobromo-α-D-glucuronic acid methyl ester (31) (1.009 g, 2.5 mmol, 1 eq) and 3,5-difluoro-4-hydroxybenzaldehyde (32b) (0.669 g, 4.2 mmol, 1.67 eq) were combined in anhydrous acetonitrile (15 mL) under $N_2$ in the dark and stirred for 30 min. $Ag_2O$ (2.07 g, 8.9 mmol, 3.6 eq) and 4 Å activated molecular sieves (2 g) were added and the reaction was stirred at room temperature overnight in the dark. Thin-layer chromatography monitored reaction progress (1:2 ethyl acetate/petroleum ether). The reaction was filtered through celite and the solvent removed in vacuo. The residue was dissolved in ethyl acetate, washed with sat. $Na_2CO_3$ (10 mL), water (10 mL), and brine (10 mL). It was then dried (magnesium sulfate), and the solvent was removed in vacuo. The product was purified by flash column chromatography on silica gel 60 (20-50% EtOAc/Pet ether) to give (2S,3R,4S,5S,6S)-2-(2,6-difluoro-4-formylphenoxy)-6-(methoxycarbonyl)tetrahydro-2H-pyran-3,4,5-triyl triacetate (33b) as an off white solid (0.756 g, 1.6 mmol, 63%).

$^1$H NMR (400 MHz, $CDCl_3$) δ 9.81 (s, 1H, H5), 7.43 (d, J=7.3 Hz, 2H, H3), 5.75-4.65 (m, 4H, H1', H2', H3', H4'), 4.07 (dd, J=10.8, 6.6 Hz, 1H, H5'), 3.66 (s, 3H, H13'), 2.04 (s, 3H, H11'/H9'/H7'), 2.00 (s, 3H, H11'/H9'/H7'), 1.97 (s, 3H, H11'/H9'/H7'). $^{13}$C NMR (101 MHz, $CDCl_3$) δ 188.7 (t, J=2.2 Hz) (C5), 169.9 (C8'), 169.3 (C10'), 169.1 (C6'), 166.5 (C12'), 155.7 (dd, J=254.1, 4.2 Hz) (C2), 137.4 (t, J=14.3 Hz) (C1), 132.7 (t, J=6.6 Hz) (C4), 113.3 (dd, J=17.5, 6.0 Hz) (C3), 101.17 (t, J=2.9 Hz) (C1'), 72.7 (C5'), 71.5 (C3'), 71.1 (C2'), 68.9 (C4'), 52.9 (C13'), 20.5 (C7'), 20.5 (C9'), 20.44 (C11'). $R_f$: 0.21 (2:1 Pet ether: EtOAC). HRMS ($ESI^+$): m/z calcd for $[C_{20}H_{20}O_{11}F_2+Na]^+$ calcd. 497.0866 found 497.0855.

(2S,3R,4S,5S,6S)-2-(2,6-difluoro-4-(hydroxymethyl) phenoxy)-6-(methoxycarbonyl)tetrahydro-2H-pyran-3,4,5-triyl triacetate (34b)

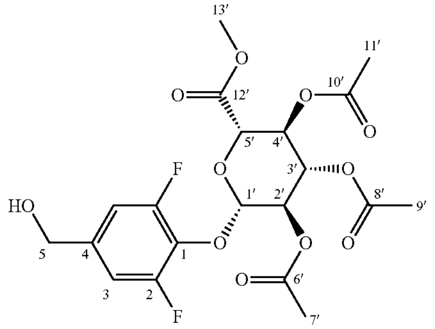

(2S,3R,4S,5S,6S)-2-(2,6-difluoro-4-formylphenoxy)-6-(methoxycarbonyl)tetrahydro-2H-pyran-3,4,5-triyl triacetate (33b) (0.756 g, 1.6 mmol, 1 eq) was dissolved in chloroform (8 mL) and isopropanol (2 mL) with silica gel (0.750 g) and stirred at 0° C. under $N_2$ for 15 min. $NaBH_4$ (0.120 g, 3.2 mmol, 2 eq) was added and the reaction was stirred for 45 min. It was monitored by thin-layer chromatography (1:2 ethyl acetate:petroleum ether). The reaction was diluted with dichloromethane (10 mL), filtered over celite, and washed with dichloromethane (10 mL). The filtrate was washed with brine (10 mL), dried (magnesium sulfate), and the solvent removed in vacuo to give (2S,3R,4S,5S,6S)-2-(2,6-difluoro-4-(hydroxy methyl) phenoxy)-6-(methoxycarbonyl)tetrahydro-2H-pyran-3,4,5-triyl triacetate (34b) as an off-white solid (0.604 g, 1.26 mmol, 80%).

$^1$H NMR (400 MHz, $CDCl_3$) δ 6.86 (d, J=8.5 Hz, 2H, H3), 5.32-5.18 (m, 3H, H2', H3', H4'), 4.98 (d, J=6.8 Hz, 1H, H1'), 4.54 (s, 2H, H5), 4.00 (d, J=9.4 Hz, 1H, H5'), 3.66 (s, 3H, H13'), 3.23 (brs, 1H, OH), 2.02 (s, 3H, H11'/H9'/H7'), 1.97 (s, 3H, H11'/H9'/H7'), 1.95 (s, 3H, H11'/H9'/H7'). $^{13}$C NMR (101 MHz, $CDCl_3$) δ 170.1 (C6'), 169.5 (C8'), 169.4 (C10'), 166.8 (C12'), 155.5 (dd, J=250.4, 4.6 Hz) (C2), 139.6 (t, J=7.8 Hz) (C4), 131.2 (t, J=14.8 Hz) (C1), 110.0 (dd, J=16.7, 5.3 Hz) (C3), 102.0 (C1'), 72.5 (C5'), 71.7 (C3'), 71.1 (C2'), 69.2 (C4'), 63.2 (t, J=1.7 Hz) (C5), 52.9 (C13'), 20.5 (C11'), 20.4 (C9'), 20.4 (C7'). $R_f$: 0.13 (1:2 EtOAc: Pet ether). HRMS (ESI$^-$): m/z calcd for $[C_{20}H_{22}O_{11}F_2]$ calcd. 476.11302 found 476.1136.

(2S,3R,4S,5S,6S)-2-(4-(chloromethyl)-2,6-difluoro-phenoxy)-6-(methoxycarbonyl)tetrahydro-2H-pyran-3,4,5-triyl triacetate (35b)

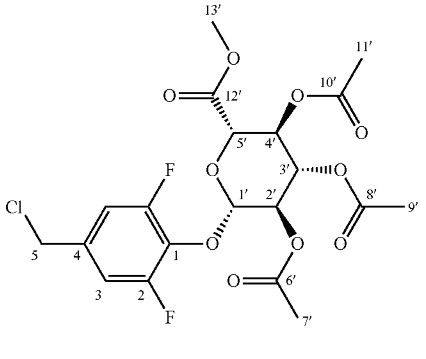

(2S,3R,4S,5S,6S)-2-(2,6-difluoro-4-(hydroxymethyl) phenoxy)-6-(methoxy carbonyl)tetrahydro-2H-pyran-3,4,5-triyl triacetate (34b) (0.604 g, 1.26 mmol, 1 eq) was dissolved in anhydrous dichloromethane (25 mL) at 0° C. under $N_2$. $SOCl_2$ (0.62 mL, 8.5 mmol, 6.7 eq) was added and the reaction was stirred under $N_2$ overnight. Thin-layer chromatography (1:1 ethyl acetate:petroleum ether) and LCMS monitored the reaction to completion. The reaction was quenched with sat. $NaHCO_3$ (10 mL), washed with brine (10 mL), dried (magnesium sulfate), and the solvent removed in vacuo to give (2S,3R,4S,5S,6S)-2-(4-(chloromethyl)-2,6-difluorophenoxy)-6-(methoxycarbonyl)tetrahydro-2H-pyran-3,4,5-triyl triacetate (35b) as an off-white solid (0.588 g, 1.19 mmol, 94%).

$^1$H NMR (400 MHz, $CDCl_3$) o 6.94 (d, J=8.1 Hz, 2H, H3), 5.34-5.22 (m, 3H, H2', H3', H4'), 5.04 (d, J=7.0 Hz, 1H, H1'), 4.45 (s, 2H, H5), 4.07-3.98 (m, 1H, H5'), 3.69 (s, 3H, H13'), 2.05 (s, 3H, H11'/H9'/H7'), 2.00 (s, 3H, H11'/H9'/H7'), 1.98 (s, 3H, H11'/H9'/H7'). $^{13}$C NMR (101 MHz, $CDCl_3$) δ 170.0 (C6'), 169.3 (C8'), 169.3 (C10'), 166.6 (C12'), 155.5 (dd, J=251.5, 4.9 Hz) (C2), 135.19 (t, J=8.6 Hz) (C4), 132.47 (t, J=14.5 Hz) (C1), 112.53 (dd, J=17.5, 6.5 Hz) (C3), 101.9 (t, J=2.2 Hz) (C1'), 72.7 (C5'), 71.7 (C3'), 71.1 (C2'), 69.1 (C4'), 52.9 (C13'), 44.5 (t, J=1.9 Hz) (C5), 20.6 (C11'), 20.5 (C9'), 20.4 (C7'). HRMS (ESI$^+$): m/z calcd for $[C_{20}H_{21}O_{10}ClF_2+Na]^+$ calcd. 517.0684 found 517.0668.

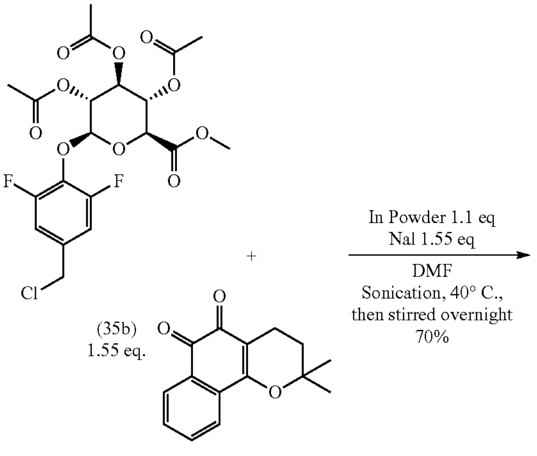

(35b)
1.55 eq.

(1)
1 eq

-continued

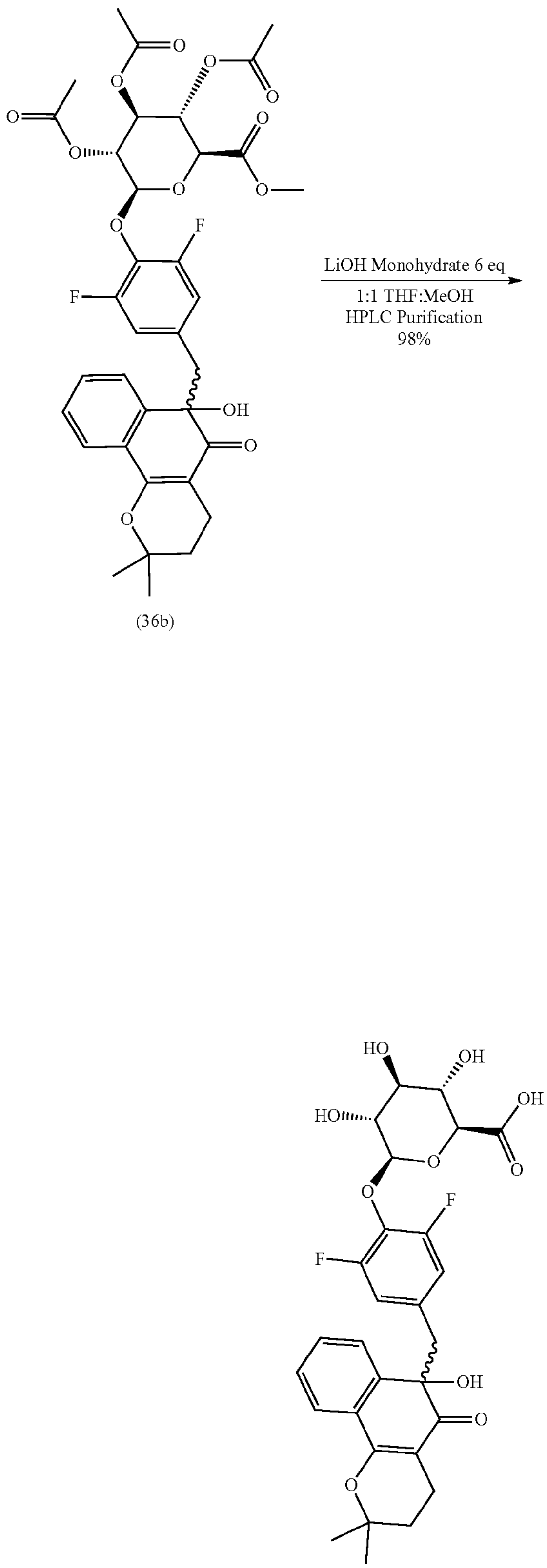

(36b)

(37b)

Acyl-Protected Difluoro Glucuronide β-Lapachone Prodrug (36b)

(2S,3R,4S,5S,6S)-2-(2,6-difluoro-4-((6-hydroxy-2,2-dimethyl-5-oxo-3,4,5,6-tetrahydro-2H-benzo[h]chromen-6-yl)methyl) phenoxy)-6-(methoxycarbonyl)tetrahydro-2H-pyran-3,4,5-triyl triacetate (36b)

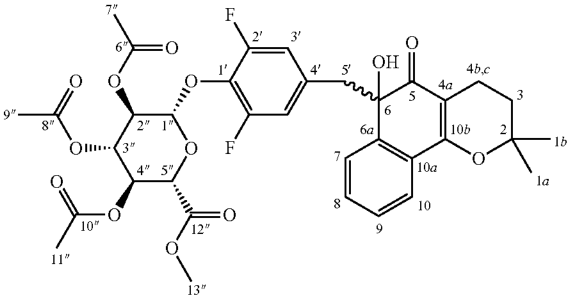 [SMILES: COC(=O)[C@H]1O[C@@H](Oc2c(F)cc(CC3(O)C(=O)C4=C(OC(C)(C)CC4)c4ccccc43)cc2F)[C@H](OC(C)=O)[C@@H](OC(C)=O)[C@@H]1OC(C)=O]

(2S,3R,4S,5S,6S)-2-(4-(chloromethyl)-2,6-difluorophenoxy)-6-(methoxycarbonyl)tetrahydro-2H-pyran-3,4,5-triyl triacetate (35b) (0.588 g, 1.2 mmol, 2.1 eq), NaI (0.503 g, 3.4 mmol, 6 eq), β-lapachone (1) (0.139 g, 0.57 mmol, 1 eq) and indium (0) powder (0.139 g, 1.2 mmol, 2.1 eq) were added to anhydrous dimethylformamide (6 mL). The solution was heated to 40° C. and sonicated for 4 hr, while monitoring by thin-layer chromatography (1:1 petroleum ether:ethyl acetate) and LCMS. The reaction was left stirring at room temperature overnight. Water (10 mL) was added to quench the reaction and it was extracted with ethyl acetate (3×150 mL). The organic layers were combined and washed with brine (10 mL), dried (magnesium sulfate), and the solvent removed in vacuo. The product was purified by flash column chromatography on silica gel 60 (40-60% ethyl acetate/petroleum ether) to give (2S,3R,4S,5S,6S)-2-(2,6-difluoro-4-((6-hydroxy-2,2-dimethyl-5-oxo-3,4,5,6-tetrahydro-2H-benzo[h]chromen-6-yl)methyl) phenoxy)-6-(methoxycarbonyl)tetrahydro-2H-pyran-3,4,5-triyl triacetate (36b) as an off-white solid (0.529 g, 0.75 mmol, 70%).

$^{1}$H NMR (400 MHz, $CDCl_3$) δ 7.67 (td, J=7.5, 1.4 Hz, 1H, H10), 7.47 (ddd, J=12.9, 7.7, 1.4 Hz, 1H, H7), 7.39 (tdd, J=7.5, 5.2, 1.4 Hz, 1H, H8), 7.31 (td, J=7.6, 1.4 Hz, 1H, H9), 6.20 (t, J=8.2 Hz, 2H, H3'), 5.32-5.19 (m, 3H, H2", H3", H4"), 4.93 (dd, J=7.0, 3.1 Hz, 1H, H1"), 4.04 (s, 1H, OH), 3.99 (d, J=9.2 Hz, 1H, H5"), 3.69 (d, J=2.7 Hz, 3H, H13"), 2.91 (d, J=6.0 Hz, 2H, H5'), 2.53 (dt, J=17.4, 5.8 Hz, 1H, H4b,c), 2.26-2.15 (m, 1H, H4b,c), 2.08-1.96 (m, 9H, H7", H9", H11"), 1.77-1.60 (m, 2H, H3), 1.36 (s, 3H, H1a/H1b), 1.19 (d, J=6.8 Hz, 3H, H1a/H1b). $^{13}$C NMR (101 MHz, $CDCl_3$) δ 199.9 (d, J=7.4 Hz) (C5), 170.0 (d, J=1.0 Hz) (C8"), 169.3 (C10"), 169.2 (d, J=4.5 Hz) (C6"), 166.6 (d, J=1.9 Hz) (C12"), 162.2 (d, J=2.0 Hz) (C10b), 154.2 (ddd, J=250.2, 4.9, 2.6 Hz) (C2'), 140.9 (C6a), 133.2 (td, J=8.0, 4.9 Hz) (C4'), 131.4 (t, J=14.5 Hz) (C1'), 130.2 (d, J=4.8 Hz) (C8), 127.8 (d, J=1.4 Hz) (C9), 127.0 (d, J=4.8 Hz) (C10a), 125.6 (d, J=2.7 Hz) (C7), 123.3 (d, J=2.8 Hz) (C10), 113.6 (dd, J=22.3, 5.1 Hz) (C3'), 106.4 (d, J=8.1 Hz) (C4a), 102.1 (C1"), 78.2 (d, J=1.3 Hz) (C6), 77.5 (C2), 72.7 (d, J=1.5 Hz) (C5"), 71.7 (d, J=2.2 Hz) (C3"), 71.1 (d, J=2.5 Hz) (C2"), 69.2 (C4"), 52.9 (C5'), 52.8 (C13"), 31.5 (C3), 27.4 (d, J=2.9 Hz) (C1a/C1b), 25.5 (d, J=7.1 Hz) (C1a/C1b), 20.6 (C11"/

C9"/C7"), 20.5 (C11"/C9"/C7"), 20.4 (C11"/C9"/C7"), 15.7 (d, J=2.4 Hz) (C4b,c). $R_f$: 0.48 (1:1 Pet ether: EtOAc). HRMS (ESI+): m/z calcd for $[C_{35}H_{36}O_{13}F_2+H]^+$ calcd. 703.2197 found 703.2195.

β-Glucuronide-Difluoro-PHB-β-Lapachone Prodrug (37b)

(2S,3S,4S,5R,6S)-6-(2,6-difluoro-4-((6-hydroxy-2,2-dimethyl-5-oxo-3,4,5,6-tetrahydro-2H-benzo[h] chromen-6-yl)methyl) phenoxy)-3,4,5-trihydroxytetrahydro-2H-pyran-2-carboxylic acid (37b)

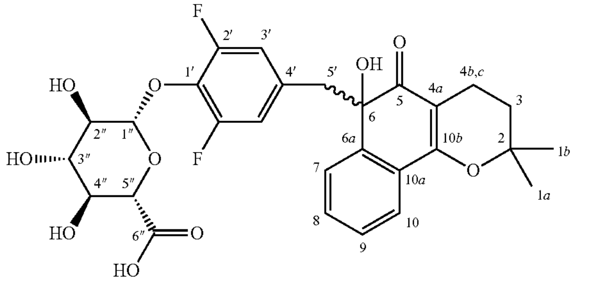 [SMILES: CC1(C)CCC2=C(O1)c1ccccc1C(O)(Cc1cc(F)c(O[C@@H]3O[C@H](C(=O)O)[C@@H](O)[C@H](O)[C@H]3O)c(F)c1)C2=O]

The acyl-protected glucuronide β-lapachone prodrug (36b) (0.529 g, 0.75 mmol, 1 eq) was dissolved in tetrahydrofuran (1 mL) and methanol (1 mL) and stirred at 0° C. A separate solution of LiOH monohydrate (0.189 g, 4.5 mmol, 6 eq) in water (1 mL) was prepared and added to the solution of 36b dropwise. The reaction was stirred for 1.5 hr and product formation was monitored by LCMS. After complete conversion, glacial acetic acid (258.5 μL, 4.5 mmol, 6 eq) was added and the solvent removed in vacuo. Crude product 37b was purified by semi-preparative HPLC to give (2S,3S, 4S,5R,6S)-6-(2,6-difluoro-4-((6-hydroxy-2,2-dimethyl-5-oxo-3,4,5,6-tetrahydro-2H-benzo[h]chromen-6-yl)methyl) phenoxy)-3,4,5-trihydroxy tetrahydro-2H-pyran-2-carboxylic acid (37b) as an off-white solid (0.347 g, 0.616 mmol, 98%). HPLC Purification Method: Column=YMC Pack Pro C18 5 μm 250×10 mm 120 Å; mobile phases: A=$H_2O$+0.1% formic acid, B=ACN+0.1% formic acid; gradient: t=0-1 min 0% B, t=1-10 min 0-100% B, t=$10^{-12}$ min 100% B. Retention time of 37b=8.48 min.

$^1$H NMR (500 MHz, MeOD) o 8.12 (s, 1H, COOH), 7.67 (tdd, J=8.5, 6.8, 1.3 Hz, 2H, H10, H7), 7.52 (tt, J=7.6, 1.5 Hz, 1H, H8), 7.44-7.37 (m, 1H, H9), 6.12 (dd, J=9.2, 6.7 Hz, 2H, H3'), 4.83 (dd, J=7.3, 2.2 Hz, 1H, H1"), 3.70 (dd, J=9.8, 8.1 Hz, 1H, H3"), 3.58 (td, J=9.3, 2.0 Hz, 1H, H4"), 3.50-3.38 (m, 2H, H5", H2"), 3.13-2.96 (m, 2H, H5'), 2.49 (dq, J=17.0, 5.6 Hz, 1H, H4b,c), 2.23-2.11 (m, 1H, H4b,c), 1.71 (tp, J=7.9, 5.5 Hz, 2H, H3), 1.40 (d, J=1.7 Hz, 3H, H1a, H1b), 1.14 (d, J=10.2 Hz, 3H, H1a, H1b). $^{13}$C NMR (126 MHz, MeOD) δ 201.5 (d, J=6.0 Hz, $C_5$), 172.2 (C6"), 163.5 (d, J=8.6 Hz, C10b), 157.1 (dd, J=13.1, 5.5 Hz, $C_2$'), 155.1 (dd, J=12.7, 5.5 Hz, $C_2$'), 143.2 (C6a), 133.7-133.4 (m, $C_4$'), 132.9-132.5 (m, $C_1$'), 131.3 (d, J=2.4 Hz, $C_8$), 129.1 (d, J=3.1 Hz, $C_{10}$a), 128.9 (C9), 127.3 (d, J=7.3 Hz, $C_7$), 123.9 (C10), 114.4-114.0 (m, $C_3$'), 109.1 (d, J=6.3 Hz, $C_4$a), 105.2 (d, J=21.6 Hz, $C_1$"), 79.3 (C2), 78.3 (d, J=2.9 Hz, $C_6$), 77.2 (d, J=4.6 Hz, $C_5$", $C_3$"), 75.0, (C2"), 72.9 (d, J=4.9 Hz, $C_4$"), 52.8 (d, J=10.5 Hz, $C_5$'), 32.4 (d, J=5.8 Hz, $C_3$), 27.6 (d, J=15.0 Hz, $C_1$a, $C_1$b), 25.7 (d, J=40.7 Hz, $C_1$a, $C_1$b), 16.7 (C4b,c). HRMS ($^{ESI}$+): m/z calcd. for $[C_{28}H_{28}O_{10}F_2+H]^+$ calcd. 563.1723 found 563.1723.

Additional Synthetic Procedures for Glucuronide-β-lapa-ketol Prodrugs

Aceto-β-glucuronic acid methyl ester 2,3,5,6-tetrafluoro-para-hydroxybenzyl alcohol (2S,3S,4S,5R,6S)-2-(methoxycarbonyl)-6-(2,3,5,6-tetrafluoro-4-(hydroxymethyl) phenoxy)tetrahydro-2H-pyran-3,4,5-triyl triacetate (34c)

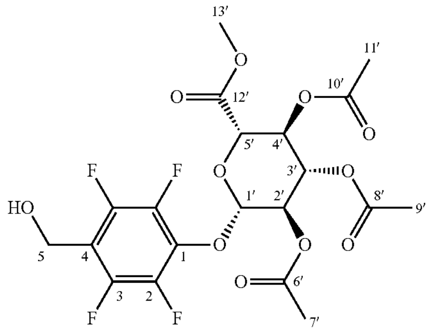

Acetobromo-α-D-glucuronic acid methyl ester (31) (0.127 g, 0.32 mmol, 1 eq) and 2,3,5,6-tetrafluoro-4-(hydroxymethyl) phenol (0.100 g, 0.51 mmol, 1.6 eq) were combined in anhydrous acetonitrile (5 mL) under nitrogen in the dark and stirred for 30 min. $Ag_2O$ (0.340 g, 1.46 mmol, 4.5 eq) was added and the reaction was stirred at room temperature overnight in the dark. Thin-layer chromatography monitored reaction progress (3:1 toluene: methanol). The reaction was vacuum filtered through celite, washed with ethyl acetate (100 mL), and the solvent removed in vacuo. The residue was dissolved in ethyl acetate (40 mL), washed with sat. $Na_2CO_3$ (5×10 mL), and brine (2×10 mL). It was then dried (sodium sulfate), and the solvent was removed in vacuo to give pure (2S,3S,4S,5R,6S)-2-(methoxycarbonyl)-6-(2,3,5,6-tetrafluoro-4-(hydroxymethyl) phenoxy)tetrahydro-2H-pyran-3,4,5-triyl triacetate (34c) as a pink oil (0.165 g, 0.32 mmol, quantitative).

$^1$H NMR (400 MHz, $CD_3CN$) δ 5.40 (t, J=9.0 Hz, 1H, H2'), 5.27 (d, J=8.0 Hz, 2H, H1', H3'), 5.19 (t, J=9.7 Hz, 1H, H4'), 4.63 (s, 2H, H5), 4.21 (d, J=9.9 Hz, 1H, H5'), 3.65 (s, 3H, H13'), 2.05 (s, 3H, H11'/H9'/H7'), 1.99 (d, J=2.5 Hz, 6H, H11'/H9'/H7'). $^{13}$C NMR (101 MHz, $CD_3CN$) δ 170.6 (C6'/C8'/C10'), 170.5 (C6'/C8'/C10'), 170.2 (C6'/C8'/C10'), 167.8 (C12'), 146.2 (d, J=245.7 Hz, $C_3$), 142.0 (dd, J=247.5, 16.2 Hz, $C_2$), 134.8 (t, J=13.0 Hz, $C_1$), 116.5 (t, J=18.6 Hz, $C_4$), 102.7 (C1'), 72.9 (C5'), 72.0 (C2'), 71.6 (C3'), 69.9 (C4'), 53.4 (C13'), 52.1 (C5), 20.7 (C7'/C9'/C11'), 20.7 (C7'/C9'/C11'), 20.6 (C7'/C9'/C11'). $R_f$: 0.47 (3:1 toluene: methanol, $KMnO_4$ stain).

Aceto-β-glucuronic acid methyl ester 2,3,5,6-tetrafluoro-para-hydroxybenzyl chloride (2S,3R,4S,5S,6S)-2-(4-(chloromethyl)-2,3,5,6-tetrafluorophenoxy)-6-(methoxycarbonyl)tetrahydro-2H-pyran-3,4,5-triyl triacetate (35c)

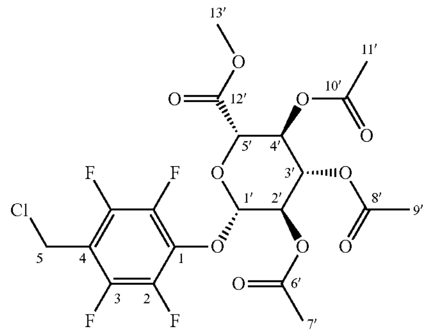

(2S,3S,4S,5R,6S)-2-(methoxycarbonyl)-6-(2,3,5,6-tetrafluoro-4-(hydroxymethyl) phenoxy)tetrahydro-2H-pyran-3,4,5-triyl triacetate (34c) (0.165 g, 0.32 mmol, 1 eq) was dissolved in anhydrous dichloromethane (10 mL) at 0° C. under $N_2$. $SOCl_2$ (0.5 mL, 6.8 mmol, 21.4 eq) was added and the reaction was stirred under $N_2$ overnight. Thin-layer chromatography (3:1 toluene: methanol) showed that some starting material remained, so additional $SOCl_2$ (0.5 mL, 6.8 mmol, 21.4 eq) was added and the reaction stirred for 4 hr. LCMS then showed completion. The reaction was quenched with sat. $NaHCO_3$ (10 mL), washed with brine (10 mL), dried (magnesium sulfate), and the solvent removed in vacuo to give (2S,3R,4S,5S,6S)-2-(4-(chloromethyl)-2,3,5,6-tetrafluorophenoxy)-6-(methoxycarbonyl) tetrahydro-2H-pyran-3,4,5-triyl triacetate (35c) as an off-white solid (0.185 g, 0.32 mmol, quantitative).

$^1$H NMR (400 MHz, $CDCl_3$) δ 5.29 (d, J=8.6 Hz, 3H, H2', H3', H4'), 5.14 (dd, J=14.1, 4.7 Hz, 1H, H1'), 4.78-4.60 (m, 2H, H5), 4.12-4.00 (m, 1H, H5'), 3.71 (s, 3H, H13'), 2.08 (s, 3H, $C_7$'/C9'/C11'), 2.02 (s, 1H, $C_7$'/C9'/C11'), 2.01 (s, 1H, $C_7$'/C9'/C11'). $^{13}$C NMR (101 MHz, $CDCl_3$) δ 170.1 (d, J=2.2 Hz, $C_6$'/C8'/C10'), 169.4 (C6'/C8'/C10'), 169.3 (d, J=4.8 Hz, $C_6$'/C8'/C10'), 166.5 (d, J=3.0 Hz, $C_{12}$'), 145.2 (d, J=245.7 Hz, $C_3$), 141.1 (dd, J=247.5, 16.2 Hz, $C_2$), 134.6 (t, J=13.0 Hz, $C_1$), 113.6 (dt, J=235.4, 18.3 Hz, $C_4$), 101.7 (d, J=14.7 Hz, $C_1$'), 72.8 (C5'), 71.6 (d, J=7.1 Hz, $C_3$'), 71.0 (d, J=2.6 Hz, $C_2$'), 69.0 (d, J=5.5 Hz, $C_4$'), 53.1 (d, J=1.9 Hz, $C_{13}$'), 30.7 (d, J=196.8 Hz, $C_5$), 20.6 (C7'/C9'/C11'), 20.5 (C7'/C9'/C11'), 20.5 (C7'/C9'/C11'). HRMS (ESI$^+$): m/z calcd for $[C_{20}H_{19}O_{10}ClF_4+Na]^+$ calcd. 553.0495 found 553.0487.

Aceto-β-glucuronic acid methyl ester 2,3,5,6-tetrafluoro-para-hydroxybenzyl β-lapa-ketol (2S,3S,4S,5R,6S)-2-(methoxycarbonyl)-6-(2,3,5,6-tetrafluoro-4-((6-hydroxy-2,2-dimethyl-5-oxo-3,4,5,6-tetrahydro-2H-benzo[h]chromen-6-yl)methyl) phenoxy)tetrahydro-2H-pyran-3,4,5-triyl triacetate (36c)

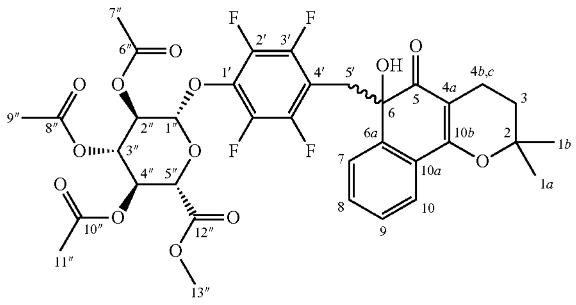 [SMILES: COC(=O)[C@H]1O[C@@H](Oc2c(F)c(F)c(CC3(O)C(=O)C4=C(OC(C)(C)CC4)c4ccccc43)c(F)c2F)[C@H](OC(C)=O)[C@@H](OC(C)=O)[C@@H]1OC(C)=O]

(2S,3R,4S,5S,6S)-2-(4-(chloromethyl)-2,3,5,6-tetrafluorophenoxy)-6-(methoxy carbonyl)tetrahydro-2H-pyran-3,4,5-triyl triacetate (35c) (0.185 g, 0.32 mmol, 1.5 eq), NaI (0.153 g, 1.0 mmol, 5 eq), β-lapachone (1) (0.05 g, 0.21 mmol, 1 eq) and indium (0) powder (0.047 g, 0.41 mmol, 2 eq) were added to anhydrous dimethylformamide (4 mL). The solution was heated to 40° C. and sonicated overnight, while monitoring by thin-layer chromatography (40% ethyl acetate/petroleum ether) and LCMS. Water (10 mL) was added to quench the reaction and it was extracted with ethyl acetate (3×150 mL). The organic layers were combined and washed with brine (10 mL), dried (magnesium sulfate), and the solvent removed in vacuo. The product was purified by flash column chromatography on silica gel 60 (40-50% ethyl acetate/petroleum ether) to give (2S,3S,4S,5R,6S)-2-(methoxycarbonyl)-6-(2,3,5,6-tetrafluoro-4-((6-hydroxy-2,2-dimethyl-5-oxo-3,4,5,6-tetrahydro-2H-benzo[h]chromen-6-yl)methyl) phenoxy)tetrahydro-2H-pyran-3,4,5-triyl triacetate (36c) as an off-white solid (0.117 g, 0.15 mmol, 75%).

$^1$H NMR (700 MHz, $CDCl_3$) δ 7.78-7.74 (m, 1H, H10), 7.58 (dd, J=11.2, 7.8 Hz, 1H, H7), 7.42 (q, J=6.9 Hz, 1H, H8), 7.36 (t, J=7.6 Hz, 1H, H9), 5.36-5.29 (m, 3H, H2", H3", H4"), 5.11 (t, J=7.0 Hz, 1H, H1"), 4.79 (s, 1H, OH), 4.07 (d, J=9.2 Hz, 1H, H5"), 3.78-3.73 (m, 3H, H13"), 3.11 (dd, J=66.6, 13.4 Hz, 2H, H5'), 2.62 (dt, J=17.4, 6.2 Hz, 1H, H4b,c), 2.38 (dq, J=15.3, 7.3 Hz, 1H, H4b,c), 2.05 (s, 3H, H7"/H9"/H11"), 2.04 (s, 3H, H7"/H9"/H11"), 2.03 (s, 3H, H7"/H9"/H11"), 1.89-1.71 (m, 2H, H3), 1.44 (s, 3H, H1a/H1b), 1.40 (d, J=9.0 Hz, 3H, H1a/H1b). $^{13}$C NMR (176 MHz, $CDCl_3$) δ 199.4 (C5), 170.1 (C8"), 169.3 (d, J=23.2 Hz, C10", C6"), 166.5 (d, J=3.9 Hz, C12"), 161.9 (C10b), 141.3 (C6a), 130.3 (d, J=6.1 Hz, C8), 128.0 (C9), 126.7 (C10a), 125.4 (C7), 123.6 (C10), 110.1 (C1'), 106.1 (C4a), 101.9 (d, J=22.1 Hz, C1"), 78.5 (d, J=3.3 Hz, C6, C2), 73.0 (C5"), 71.8 (d, J=3.8 Hz, C3"), 71.2 (d, J=5.5 Hz, C2"), 69.1 (d, J=8.2 Hz, C4"), 53.0 (C13"), 39.5 (C5'), 31.8 (C3), 27.5 (d, J=5.8 Hz, C1a/C1b), 25.8 (d, J=11.6 Hz, C1a/C1b), 20.8-19.9 (m, C11"/C9"/C7"), 16.1 (C4b,c). $R_f$: 0.25 (40% EtOAc/Pet ether). HRMS (ESI$^+$): m/z calcd for $[C_{35}H_{34}O_{13}F_4+H]^+$ calcd. 739.2008 found 739.2029.

β-glucuronide-2,3,5,6-tetrafluoro-para-hydroxybenzyl β-lapa-ketol (2S,3S,4S,5R,6S)-3,4,5-trihydroxy-6-(2,3,5,6-tetrafluoro-4-((6-hydroxy-2,2-dimethyl-5-oxo-3,4,5,6-tetrahydro-2H-benzo[h]chromen-6-yl)methyl) phenoxy)tetrahydro-2H-pyran-2-carboxylic acid (37c)

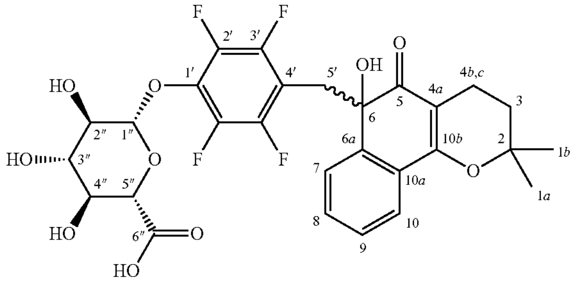 [SMILES: CC1(C)CCC2=C(O1)c1ccccc1C(O)(Cc1c(F)c(F)c(O[C@@H]3O[C@H](C(=O)O)[C@@H](O)[C@H](O)[C@H]3O)c(F)c1F)C2=O]

The acyl-protected glucuronide β-lapachone prodrug (36c) (0.117 g, 0.15 mmol, 1 eq) was dissolved in tetrahydrofuran (1 mL) and methanol (1 mL) and stirred at 0° C. A separate solution of LiOH monohydrate (0.039 g, 0.95 mmol, 6 eq) in water (1 mL) was prepared and added to the solution of 36c dropwise. The reaction was stirred for 1.5 hr and product formation was monitored by LCMS. After complete conversion, glacial acetic acid (54 μL, 0.95 mmol, 6 eq) was added and the solvent removed in vacuo. Crude product 37c was purified by semi-preparative HPLC to give (2S,3S,4S,5R,6S)-3,4,5-trihydroxy-6-(2,3,5,6-tetrafluoro-4-((6-hydroxy-2,2-dimethyl-5-oxo-3,4,5,6-tetrahydro-2H-benzo[h]chromen-6-yl)methyl) phenoxy)tetrahydro-2H-pyran-2-carboxylic acid (37c) as an off-white solid (0.024 g, 0.04 mmol, 27%). HPLC Purification Method: Column=YMC Pack Pro C18 5 μm 250×10 mm 120 Å; mobile phases: A=$H_2O$+0.1% formic acid, B=ACN+0.1% formic acid; gradient: t=0-1 min 0% B, t=1-10 min 0-100% B, t=$10^{-12}$ min 100% B. Retention time of 37c=9.03 min.

$^1$H NMR (700 MHz, MeOD) δ 7.68 (dd, J=15.0, 7.8 Hz, 1H, H10), 7.62 (dd, J=18.8, 7.6 Hz, 1H, H7), 7.44 (tt, J=7.6, 1.4 Hz, 1H, H8), 7.36 (tdd, J=7.6, 3.1, 1.3 Hz, 1H, H9), 4.98 (dd, J=13.5, 7.5 Hz, 1H, H1"), 3.78 (dd, J=12.8, 9.8 Hz, 1H, H3"), 3.61 (t, J=9.3 Hz, 1H, H4"), 3.50 (t, J=7.6 Hz, 1H, H5"), 3.46 (td, J=9.0, 4.5 Hz, 1H, H2"), 3.19 (dd, J=13.5, 4.3 Hz, 1H, H5'), 3.09 (dd, J=13.5, 6.3 Hz, 1H, H5'), 2.55 (dtd, J=17.2, 5.8, 2.8 Hz, 1H, H4b,c), 2.32 (dddd, J=17.2, 8.5, 6.2, 2.0 Hz, 1H, H4b,c), 1.83 (dtd, J=13.6, 6.0, 1.6 Hz, 1H, H3), 1.75 (ddd, J=14.2, 8.7, 6.1 Hz, 1H, H3), 1.43 (d, J=4.8 Hz, 3H, H1a/H1b), 1.32 (d, J=2.8 Hz, 3H, H1a/H1b). $^{13}$C NMR (176 MHz, MeOD) δ 201.1 (d, J=3.4 Hz, $C_5$), 172.0 (C6"), 163.1 (d, J=3.7 Hz, C10b), 147.7 (d, J=243.6 Hz, 3'), 142.9 (d, J=12.0 Hz, $C_6$a), 142.6 (C1'), 138.1 (d, J=1119.5 Hz, $C_2$'), 131.1 (d, J=2.4 Hz, $C_8$), 128.9 (d, J=4.0 Hz, $C_{10}$a), 128.3 (d, J=2.1 Hz, $C_9$), 126.9 (d, J=7.4 Hz, $C_7$), 124.0 (d, J=9.2 Hz, $C_{10}$), 110.5 (d, J=18.8 Hz, $C_4$'), 108.2 (d, J=17.0 Hz, $C_4$a), 105.2 (d, J=21.3 Hz, $C_1$"), 79.5 (d, J=4.9 Hz, $C_2$), 78.5 (C6), 77.2 (d, J=5.5 Hz, $C_5$", $C_3$"), 74.9 (d, J=3.2 Hz, $C_2$"), 72.9 (d, J=7.4 Hz, $C_4$"), 39.7 (d, J=5.6 Hz, $C_5$'), 32.6 (d, J=4.9 Hz, $C_3$), 27.6 (d, J=9.9 Hz, $C_1$a, $C_1$b), 25.9 (d, J=8.4 Hz, $C_1$a, $C_1$b), 17.0 (C4b,c). HRMS ($ESI^+$): m/z calcd for $[C_{28}H_{26}O_{10}F_4+H]^+$ calcd. 599.1535 found 599.1529.

Aceto-β-glucuronic acid methyl ester 2-methoxy-para-hydroxybenzaldehyde (2S,3R,4S,5S,6S)-2-(4-formyl-3-methoxyphenoxy)-6-(methoxycarbonyl)tetrahydro-2H-pyran-3,4,5-triyl triacetate (33d)

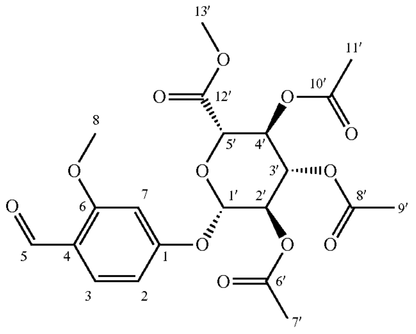

Acetobromo-α-D-glucuronic acid methyl ester (31) (0.503 g, 1.2 mmol, 1 eq) and 2-methoxy-4-hydroxybenzaldehyde (32d) (0.307 g, 2.0 mmol, 1.67 eq) were combined in anhydrous acetonitrile (15 mL) under $N_2$ in the dark and stirred for 30 min. $Ag_2O$ (1.32 g, 5.7 mmol, 4.7 eq) was added and the reaction was stirred at room temperature overnight in the dark. Thin-layer chromatography monitored reaction progress (40% ethyl acetate/petroleum ether). The reaction was filtered through celite and the solvent removed in vacuo. The residue was dissolved in ethyl acetate, washed with sat. $Na_2CO_3$ (10 mL), water (10 mL), and brine (10 mL). It was then dried (magnesium sulfate), and the solvent was removed in vacuo. The product was purified by flash column chromatography on silica gel 60 (25-60% EtOAc/Pet ether) to give (2S,3R,4S,5S,6S)-2-(4-formyl-3-methoxyphenoxy)-6-(methoxycarbonyl)tetrahydro-2H-pyran-3,4,5-triyl triacetate (33d) as a yellow solid (0.403 g, 0.86 mmol, 68%).

$^1$H NMR (400 MHz, $CDCl_3$) o 10.17 (s, 1H, H5), 7.64 (d, J=8.6 Hz, 1H, H3), 6.53 (d, J=8.6 Hz, 1H, H2), 6.50 (d, J=2.1 Hz, 1H, H7), 5.33-5.16 (m, 4H, H1', H2', H3', H4'), 4.27 (d, J=9.3 Hz, 1H, H5'), 3.78 (s, 3H, H8), 3.61 (s, 3H, H13'), 1.97-1.93 (m, 9H, H11', H9', H7'). $^{13}$C NMR (101 MHz, $CDCl_3$) δ 188.1 (C5), 169.8 (C8'), 169.2 (C10'), 169.1 (C6'), 166.6 (C12'), 163.2 (C1), 162.4 (C4), 130.2 (C3), 120.5 (C6), 107.6 (C2), 100.7 (C7), 97.5 (C1'), 72.2 (C5'), 71.5 (C3'), 70.7 (C2'), 68.7 (C4'), 55.6 (C8), 52.8 (C13'), 20.4 (C7'), 20.4 (C9'), 20.3 (C11'). $R_f$: 0.22 (40% Pet ether: EtOAC). HRMS ($ESI^+$): m/z calcd for $[C_{21}H_{24}O_{12}+H]^+$ calcd. 469.1341 found 469.1381.

Aceto-β-glucuronic acid methyl ester 2-methoxy-para-hydroxybenzyl alcohol (2S,3R,4S,5S,6S)-2-(4-(hydroxymethyl)-3-methoxyphenoxy)-6-(methoxycarbonyl)tetrahydro-2H-pyran-3,4,5-triyl triacetate (34d)

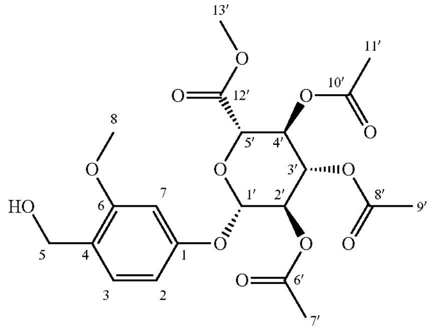

(2S,3R,4S,5S,6S)-2-(4-formyl-3-methoxyphenoxy)-6-(methoxycarbonyl)tetrahydro-2H-pyran-3,4,5-triyl triacetate (33d) (0.403 g, 0.86 mmol, 1 eq) was dissolved in chloroform (5 mL) and isopropanol (1 mL) with silica gel (0.4 g) and stirred at 0° C. under $N_2$ for 15 min. $NaBH_4$ (0.065 g, 1.7 mmol, 2 eq) was added and the reaction was stirred for 45 min. It was monitored by thin-layer chromatography (1:1 ethyl acetate:petroleum ether). The reaction was diluted with dichloromethane (10 mL), filtered over celite, and washed with dichloromethane (10 mL). The filtrate was washed with brine (10 mL), dried (magnesium sulfate), and the solvent removed in vacuo to give (2S,3R,4S,5S,6S)-2-(4-(hydroxymethyl)-3-methoxyphenoxy)-6-(methoxy carbonyl)tetrahydro-2H-pyran-3,4,5-triyl triacetate (34d) as an off-white solid (0.375 g, 0.79 mmol, 93%).

$^1$H NMR (400 MHz, $CDCl_3$) δ 7.11 (d, J=8.5 Hz, 1H, H3), 6.50-6.43 (m, 2H, H2, H7), 5.31-5.13 (m, 3H, H2', H3', H4'), 5.10 (d, J=7.5 Hz, 1H, H1'), 4.49 (s, 2H, H5), 4.16 (d, J=9.2 Hz, 1H, H5'), 3.70 (s, 3H, H8), 3.62 (s, 3H, H13'), 2.73 (brs, 1H, OH), 1.96 (d, J=4.1 Hz, 9H, H11', H9', H7'). $^{13}$C NMR (101 MHz, $CDCl_3$) δ 169.9 (C6'), 169.2 (C8'), 169.1 (C10'), 166.7 (C12'), 157.9 (C1), 157.1 (C4), 128.9 (C3), 124.5 (C6), 107.2 (C2), 100.9 (C7), 98.7 (C1'), 72.2 (C5'), 71.7 (C3'), 70.9 (C2'), 68.9 (C4'), 60.4 (C5), 55.2 (C8), 52.7 (C13'), 20.4 (C11'), 20.4 (C9'), 20.2 (C7'). $R_f$: 0.17 (1:1 EtOAc: Pet ether). HRMS (ESI$^+$): m/z calcd for $[C_{21}H_{26}O_{12}+Na]^+$ calcd. 493.1316 found 493.1332.

Aceto-β-glucuronic acid methyl ester 2-methoxy-para-hydroxybenzyl bromide (2S,3R,4S,5S,6S)-2-(4-(bromomethyl)-3-methoxyphenoxy)-6-(methoxycarbonyl)tetrahydro-2H-pyran-3,4,5-triyl triacetate (35d)

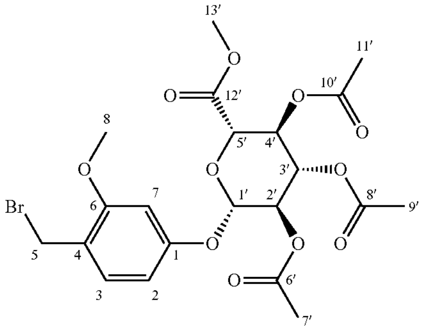

(2S,3R,4S,5S,6S)-2-(4-(hydroxymethyl)-3-methoxyphenoxy)-6-(methoxycarbonyl) tetrahydro-2H-pyran-3,4,5-triyl triacetate (34d) (0.375 g, 0.8 mmol, 1 eq) was dissolved in anhydrous diethyl ether (10 mL) at 0° C. under $N_2$. Neat $PBr_3$ (0.1 mL, 1.0 mmol, 1.3 eq) was added and the reaction was stirred under $N_2$ for 30 min. Thin-layer chromatography (1:1 petroleum ether:ethyl acetate) showed that some starting material remained, so additional $PBr_3$ (0.05 mL, 0.5 mmol, 0.6 eq) was added and the reaction stirred for 15 min. LCMS then showed completion. The reaction was quenched with cold water (10 mL), extracted into ether (3×50 mL) washed with brine (10 mL), dried (magnesium sulfate), and the solvent removed in vacuo to give (2S,3R,4S,5S,6S)-2-(4-(bromomethyl)-3-methoxyphenoxy)-6-(methoxy carbonyl)tetrahydro-2H-pyran-3,4,5-triyl triacetate (35d) as an off-white solid (0.401 g, 0.753 mmol, 94%).

$^1$H NMR (400 MHz, $CDCl_3$) δ 7.17 (d, J=8.2 Hz, 1H, H3), 6.53-6.47 (m, 2H, H2, H7), 5.34-5.18 (m, 3H, H2', H3', H4'), 5.15 (d, J=7.4 Hz, 1H, H1'), 4.45 (d, J=2.8 Hz, 2H, H5), 4.20 (d, J=8.6 Hz, 1H, H5'), 3.78 (s, 3H, H8), 3.66 (s, 3H, H13'), 1.99 (d, J=4.4 Hz, 9H, H11', H9', H7'). $^{13}$C NMR (101 MHz, $CDCl_3$) δ 169.9 (C6'), 169.3 (C8'), 169.2 (C10'), 166.7 (C12'), 158.4 (C1), 158.1 (C4), 131.5 (C3), 121.3 (C6), 107.6 (C2), 101.4 (C7), 98.5 (C1'), 72.4 (C5'), 71.8 (C3'), 70.9 (C2'), 68.9 (C4'), 55.7 (C8), 52.9 (C13'), 28.8 (C5), 20.5 (C11'), 20.5 (C9'), 20.4 (C7'). HRMS could not be obtained due to compound instability.

Aceto-β-glucuronic acid methyl ester 2-methoxy-para-hydroxybenzyl β-lapa-ketol (2S,3R,4S,5S,6S)-2-(4-((6-hydroxy-2,2-dimethyl-5-oxo-3,4,5,6-tetrahydro-2H-benzo[h]chromen-6-yl)methyl)-3-methoxyphenoxy)-6-(methoxycarbonyl)tetrahydro-2H-pyran-3,4,5-triyl triacetate (36d)

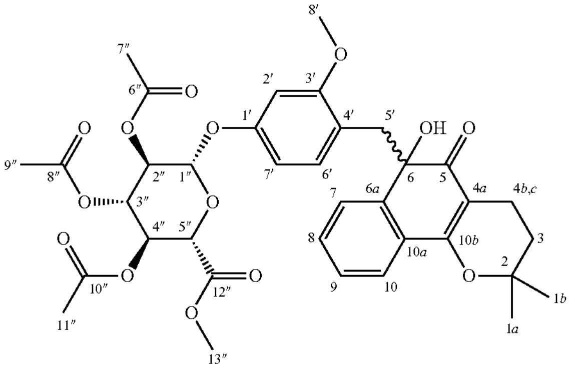 [SMILES: COC(=O)[C@H]1O[C@@H](Oc2ccc(CC3(O)C(=O)C4=C(OC(C)(C)CC4)c4ccccc43)c(OC)c2)[C@H](OC(C)=O)[C@@H](OC(C)=O)[C@@H]1OC(C)=O]

(2S,3R,4S,5S,6S)-2-(4-(bromomethyl)-3-methoxyphenoxy)-6-(methoxycarbonyl)tetrahydro-2H-pyran-3,4,5-triyl triacetate (35d) (0.401 g, 0.753 mmol, 1.2 eq), NaI (0.299 g, 2.0 mmol, 3.1 eq), β-lapachone (1) (0.154 g, 0.63 mmol, 1 eq) and indium (0) powder (0.087 g, 0.75 mmol, 1.2 eq) were added to anhydrous dimethylformamide (3 mL). The solution was heated to 40° C. and sonicated overnight, while monitoring by thin-layer chromatography (50% ethyl acetate/petroleum ether) and LCMS. 1 M HCl (~0.5 mL) was added to quench the reaction and it was extracted with ethyl acetate (3×150 mL). The organic layers were combined and washed with brine (10 mL), dried (magnesium sulfate), and the solvent removed in vacuo. The product was purified by flash column chromatography on silica gel 60 (30-70% ethyl acetate/petroleum ether) to give (2S,3R,4S,5S,6S)-2-(4-((6-hydroxy-2,2-dimethyl-5-oxo-3,4,5,6-tetrahydro-2H-benzo[h]chromen-6-yl)methyl)-3-methoxyphenoxy)-6-(methoxy carbonyl)tetrahydro-2H-pyran-3,4,5-triyl triacetate (36d) as an orange solid (0.209 g, 0.3 mmol, 47%).

$^1$H NMR (400 MHz, MeOD, mixture of diastereomers 1:1) δ 7.59 (q, J=8.2 Hz, 2H, H7, H10), 7.41 (t, J=7.6 Hz, 1H, H8), 7.29 (t, J=7.6 Hz, 1H, H9), 6.47 (d, J=8.0 Hz, 1H, H6'), 6.41-6.25 (m, 2H, H7', H2'), 5.50-5.35 (m, 1H, H3"), 5.31 (t, J=8.4 Hz, 1H, H1"), 5.25-5.11 (m, 2H, H2", H4"), 4.49 (d, J=4.3 Hz, 1H, H5"), 4.46 (d, J=4.2 Hz, 1H, H5"), 3.69 (d, J=4.6 Hz, 3H, H13"), 3.36 (d, J=7.9 Hz, 3H, H8'), 3.13 (dd, J=99.4, 14.3 Hz, 1H, H8'), 2.95 (t, J=13.2 Hz, 1H, H5'), 2.45 (dt, J=17.4, 5.6 Hz, 1H, H4b,c), 2.11 (ddd, J=17.0, 9.0, 6.5 Hz, 1H, H4b,c), 2.02 (dd, J=7.5, 3.5 Hz, 9H, H7", H9", H11"), 1.74-1.55 (m, 2H, H3), 1.34 (d, J=4.1 Hz, 3H, H1a/H1b), 1.10 (d, J=5.9 Hz, 3H, H1a/H1b). $^{13}$C NMR (101 MHz, MeOD, mixture of diastereomers 1:1) δ 202.2 (C5), 202.1 (C5), 171.3 (C6"), 171.0 (C10"), 170.8 (C8"), 168.7 (C12"), 168.7 (C12"), 162.9 (C10b), 159.7 (C3'), 158.1 (C1'), 158.0 (C1'), 143.9 (C6a), 143.8 (C6a), 132.9 (C6'), 132.9 (C6'), 130.6 (C8), 128.9 (C10a), 128.8 (C10a), 128.2 (C9), 127.0 (C7/C10), 123.5 (C7/C10), 123.4 (C7/C10), 119.4 (C4'), 119.2 (C4'), 108.5 (C4a), 108.4 (C4a), 107.8 (C2'/C7'), 107.6 (C2'/C7'), 100.8 (C2'/C7'), 100.6 (C2'/C7'), 99.4 (C1"), 99.1 (C1"), 79.1 (C6), 79.1 (C6), 78.9 (C2), 73.3 (C3"), 73.2 (C3"), 72.9 (C5"), 72.3 (C2"), 72.3 (C2"), 70.5 (C4"), 55.6 (C8'), 53.3 (C13"), 46.9 (C5'), 46.8 (C5'), 32.5 (C3), 27.8 (C1a/C1b), 27.8 (C1a/C1b), 26.0 (C1a/C1b), 25.9 (C1a/C1b), 20.6 (C7"/C9"/C11"), 20.5 (C7"/C9"/C11"), 20.5 (C7"/C9"/C11"), 16.8 (C4b,c). $R_f$: 0.41 (50% EtOAc/Pet ether).

β-glucuronide-2-methoxy-para-hydroxybenzyl β-lapa-ketol (2S,3S,4S,5R,6S)-3,4,5-trihydroxy-6-(4-((6-hydroxy-2,2-dimethyl-5-oxo-3,4,5,6-tetrahydro-2H-benzo[h]chromen-6-yl)methyl)-3-methoxyphenoxy)tetrahydro-2H-pyran-2-carboxylic acid (37d)

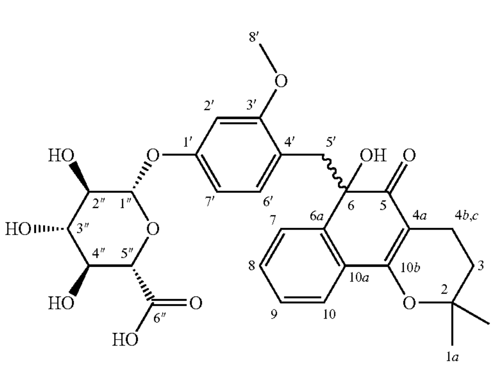

The acyl-protected glucuronide β-lapachone prodrug (36d) (0.209 g, 0.3 mmol, 1 eq) was dissolved in tetrahydrofuran (3 mL) and methanol (3 mL) and stirred at 0° C. A separate solution of LiOH monohydrate (0.075 g, 1.8 mmol, 6 eq) in water (1 mL) was prepared and added to the solution of 36d dropwise. The reaction was stirred for 1.5 hr and product formation was monitored by LCMS. After complete conversion, glacial acetic acid (103 μL, 1.8 mmol, 6 eq) was added and the solvent removed in vacuo. Crude product 37d was purified by semi-preparative HPLC to give (2S,3S,4S,5R,6S)-3,4,5-trihydroxy-6-(4-((6-hydroxy-2,2-dimethyl-5-oxo-3,4,5,6-tetrahydro-2H-benzo[h]chromen-6-yl)methyl)-3-methoxyphenoxy)tetrahydro-2H-pyran-2-carboxylic acid (37d) as an orange solid after lyophilization (0.123 g, 0.22 mmol, 74%). HPLC Purification Method: Column=YMC Pack Pro C18 5 μm 250×10 mm 120 Å; mobile phases: A=$H_2O$+0.1% formic acid, B=ACN+0.1% formic acid; gradient: t=0-1 min 0% B, t=1-10 min 0-100% B, t=$10^{-12}$ min 100% B. Retention time of 37d=8.5 min.

$^1$H NMR (400 MHz, MeOD, mixture of diastereomers 1:1) δ 7.66-7.53 (m, 2H, H7, H10), 7.42 (tdd, J=7.6, 3.4, 1.3 Hz, 1H, H8), 7.29 (td, J=7.6, 1.3 Hz, 1H, H9), 6.49-6.30 (m, 3H, H2', H7', H6'), 4.89 (d, J=7.2 Hz, 1H, H1"), 4.84 (d, J=7.3 Hz, 1H, H1"), 3.95 (d, J=4.5 Hz, 1H, H3"), 3.92 (d, J=4.5 Hz, 1H, H3"), 3.63 (td, J=9.2, 1.9 Hz, 1H, H4"), 3.56-3.43 (m, 2H, H2", H5"), 3.37 (s, 3H, H8'), 3.16 (dd, J=12.3, 2.3 Hz, 1H, H5'), 2.97 (dd, J=12.4, 3.0 Hz, 1H, H5'), 2.44 (dq, J=17.7, 6.0 Hz, 1H, H4b,c), 2.18-2.05 (m, 1H, H4b,c), 1.73-1.53 (m, 2H, H3), 1.33 (d, J=8.3 Hz, 3H, H1a/H1b), 1.11 (d, J=7.8 Hz, 3H, H1a/H1b). $^{13}$C NMR (101 MHz, MeOD, mixture of diastereomers 1:1) o 202.5 (C5), 202.4 (C5), 172.1 (C6"), 172.0 (C6"), 163.2 (C10b), 163.1 (C10b), 159.6 (C3'), 159.6 (C3'), 159.0 (C1'), 158.8 (C1'), 143.9 (C6a), 143.9 (C6a), 132.7 (C6'), 132.6 (C6'), 130.6 (C8), 128.9 (C10a), 128.9 (C10a), 128.2 (C9), 127.0 (C10/C7), 127.0 (C10/C7), 123.4 (C10/C7), 123.4 (C10/C7), 118.7 (C4'), 118.4 (C4'), 108.6 (C4a), 108.6 (C4a), 108.4 (C2'/C7'), 107.9 (C2'/C7'), 102.6 (C1"), 102.0 (C1"), 101.1 (C2'/C7'), 100.6 (C2'/C7'), 79.2 (C6), 79.2 (C6), 79.0 (C2), 78.9 (C2), 77.1 (C2"/C5"), 76.4 (C3"), 74.4 (C2"/C5"), 74.4 (C2"/C5"), 72.8 (C4"), 72.8 (C4"), 55.5 (C8'), 55.5 (C8'), 47.0 (C5'), 46.8 (C5'), 32.5 (C3), 32.4 (C3), 27.7 (C1a/C1b), 27.6 (C1a/C1b), 26.1 (C1a/C1b), 25.9 (C1a/C1b), 16.8 (C4b,c). HRMS (ESI$^+$): m/z calcd for $[C_{29}H_{32}O_{11}+Na]^+$ calcd. 579.1837 found 579.1860.

Aceto-β-glucuronic Acid Methyl Ester Para-Hydroxybenzyl Ketone (2S,3R,4S,5S,6S)-2-(4-acetylphenoxy)-6-(methoxy-carbonyl)tetrahydro-2H-pyran-3,4,5-triyl triacetate (33e)

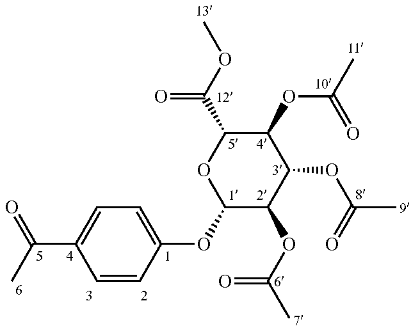 [SMILES: COC(=O)[C@H]1O[C@@H](Oc2ccc(C(C)=O)cc2)[C@H](OC(C)=O)[C@@H](OC(C)=O)[C@@H]1OC(C)=O]

Acetobromo-α-D-glucuronic acid methyl ester (31) (0.501 g, 1.2 mmol, 1 eq) and 4-hydroxyacetophenone (32e) (0.289 g, 2.1 mmol, 1.7 eq) were combined in anhydrous acetonitrile (12 mL) under $N_2$ in the dark and stirred for 30 min. $Ag_2O$ (0.609 g, 2.6 mmol, 2.2 eq) was added and the reaction was stirred at room temperature overnight in the dark. Thin-layer chromatography monitored reaction progress (40% ethyl acetate/petroleum ether). The reaction was filtered through celite and the solvent removed in vacuo. The residue was dissolved in ethyl acetate, washed with sat. $Na_2CO_3$ (10 mL), water (10 mL), and brine (10 mL). It was then dried (sodium sulfate), and the solvent was removed in vacuo. The product was purified by flash column chromatography on silica gel 60 (30-40% EtOAc/Pet ether) to give (2S,3R,4S,5S,6S)-2-(4-acetylphenoxy)-6-(methoxycarbonyl)tetrahydro-2H-pyran-3,4,5-triyl triacetate (33e) as a yellow solid (0.392 g, 0.86 mmol, 74%).

$^1$H NMR (400 MHz, $CDCl_3$) δ 7.80 (d, J=8.9 Hz, 2H, H2), 6.94 (d, J=8.9 Hz, 2H, H3), 5.36-5.09 (m, 4H, H1', H2', H3', H4'), 4.27 (d, J=9.4 Hz, 1H, H5'), 3.60 (s, 3H, H13'), 2.43 (s, 3H, H6), 1.94 (m, 9H, H11', H9', H7'). $^{13}$C NMR (101 MHz, $CDCl_3$) δ 196.4 (C5), 169.7 (C8'), 169.2 (C10'), 169.0 (C6'), 166.7 (C12'), 159.9 (C1), 132.2 (C4), 130.3 (C3), 116.1 (C2), 97.7 (C1'), 72.2 (C5'), 71.5 (C3'), 70.7 (C2'), 68.8 (C4'), 52.7 (C13'), 26.2 (C6), 20.3 (C7'), 20.3 (C9'), 20.2 (C11'). $R_f$: 0.16 (40% Pet ether: EtOAC). HRMS (ESI$^+$): m/z calcd for $[C_{21}H_{24}O_{11}+Na]^+$ calcd. 475.1216 found 475.1219.

Aceto-β-glucuronic Acid Methyl Ester Para-Hydroxybenzyl Methyl Alcohol (2S,3R,4S,5S,6S)-2-(4-(1-hydroxyethyl) phenoxy)-6-(methoxycarbonyl)tetrahydro-2H-pyran-3,4,5-triyl triacetate (34e)

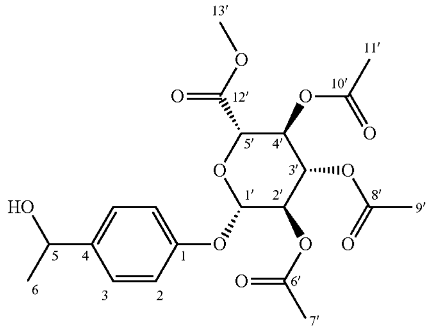 [SMILES: COC(=O)[C@H]1O[C@@H](Oc2ccc(C(C)O)cc2)[C@H](OC(C)=O)[C@@H](OC(C)=O)[C@@H]1OC(C)=O]

(2S,3R,4S,5S,6S)-2-(4-acetylphenoxy)-6-(methoxycarbonyl)tetrahydro-2H-pyran-3,4,5-triyl triacetate (33e) (0.1 g, 0.2 mmol, 1 eq) was dissolved in methanol (3 mL) and tetrahydrofuran (3 mL) and stirred at 0° C. under $N_2$ for 15 min. $NaBH_4$ (0.017 g, 0.4 mmol, 2 eq) was added and the reaction was stirred for 2 hr. It was monitored by LCMS until no starting material was detected. The reaction was quenched with sat. $NH_4Cl$ (5 mL) and extracted with dichloromethane (3×20 mL). The organic layers were combined and washed with brine (10 mL), dried (sodium sulfate), and the solvent removed in vacuo to give (2S,3R,4S,5S,6S)-2-(4-(1-hydroxyethyl) phenoxy)-6-(methoxycarbonyl)tetrahydro-2H-pyran-3,4,5-triyl triacetate (34e) as an off-white solid (0.104 g, 0.2 mmol, quantitative).

$^1$H NMR (400 MHz, $CDCl_3$, mixture of diastereomers 1:1) δ 7.21 (d, J=8.3 Hz, 2H, H3), 6.89 (d, J=8.6 Hz, 2H, H2), 5.32-5.14 (m, 3H, H2', H3', H4'), 5.08 (dd, J=7.5, 3.0 Hz, 1H, H1'), 4.75 (qd, J=6.4, 1.9 Hz, 1H, H5), 4.16 (d, J=9.2 Hz, 1H, H5'), 3.64 (s, 3H, H13'), 2.70 (brs, 1H, OH), 1.99-1.92 (m, 9H, H11', H9', H7'), 1.35 (d, J=6.5 Hz, 3H, H6). $^{13}$C NMR (101 MHz, $CDCl_3$) δ 170.0 (C6'), 169.3 (C8'), 169.2 (C10'), 166.8 (C12'), 155.7 (C1), 141.2 (C4), 126.6 (C3), 126.6 (C3), 116.8 (C2), 116.8 (C2), 98.9 (C1'), 98.9 (C1'), 72.3 (H5'), 71.8 (C3'), 70.9 (C2'), 69.4 (C5), 69.3 (C5), 69.0 (C4'), 52.8 (C13'), 25.1 (C6), 20.4 (C11'), 20.4 (C9'), 20.3 (C7'). HRMS (ESI$^+$): m/z calcd for $[C_{21}H_{26}O_{11}+Na]^+$ calcd. 477.1373 found 477.1363.

Aceto-β-glucuronic Acid Methyl Ester Para-Hydroxybenzyl Methyl Bromide (2S,3R,4S,5S,6S)-2-(4-(1-bromoethyl) phenoxy)-6-(methoxycarbonyl)tetrahydro-2H-pyran-3,4,5-triyl triacetate (35e)

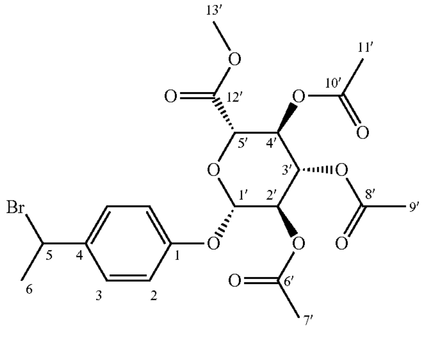 [SMILES: COC(=O)[C@H]1O[C@@H](Oc2ccc(C(C)Br)cc2)[C@H](OC(C)=O)[C@@H](OC(C)=O)[C@@H]1OC(C)=O]

(2S,3R,4S,5S,6S)-2-(4-(1-hydroxyethyl) phenoxy)-6-(methoxycarbonyl)tetrahydro-2H-pyran-3,4,5-triyl triacetate (34e) (0.249 g, 0.55 mmol, 1 eq) was dissolved in anhydrous diethyl ether (10 mL) and anhydrous dichloromethane (2 mL) at 0° C. under $N_2$. Neat $PBr_3$ (0.05 mL, 0.55 mmol, 1 eq) was added and the reaction was stirred under $N_2$ for 30 min. Thin-layer chromatography (1:1 petroleum ether:ethyl acetate) showed that some starting material remained, so additional $PBr_3$ (0.1 mL, 1.1 mmol, 2 eq) was added and the reaction stirred for 15 min. TLC then showed completion. The reaction was quenched with cold water (10 mL), extracted into DCM (3×50 mL) washed with brine (10 mL), dried (sodium sulfate), and the solvent removed in vacuo to give (2S,3R,4S,5S,6S)-2-(4-(1-bromoethyl) phenoxy)-6-(methoxy carbonyl)tetrahydro-2H-pyran-3,4,5-triyl triacetate (35e) as an off-white solid (0.341 g, 0.660 mmol, quantitative).

$^1$H NMR (400 MHz, $CDCl_3$, mixture of diastereomers) δ 7.31 (d, J=8.8 Hz, 2H. H3), 6.91 (d, J=8.7 Hz, 2H, H2), 5.37-5.19 (m, 3H, H2', H3', H4'), 5.15 (m, 2H, H1', H5), 4.27-4.14 (m, 1H, H5'), 3.66 (s, 3H, H13'), 1.98 (s, 9H, H11', H9', H7'), 1.94 (d, J=6.9 Hz, 3H, H6). $^{13}$C NMR (101 MHz, $CDCl_3$) δ 169.8 (C6'), 169.2 (C8'), 169.0 (C10'), 166.8 (C12'), 156.2 (C4), 138.2 (C1), 128.1 (C3), 116.8 (C2), 98.6 (C1'), 72.3 (C5'), 71.7 (C3'), 70.9 (C2'), 69.0 (C4'), 52.8 (C13'), 49.0 (C5), 26.7 (C6), 26.7 (C6), 20.4 (C9', $C_{11}$'), 20.3 (C7'). HRMS (ESI$^+$): m/z calcd for $[C_{21}H_{25}O_{10}Br+Na]^+$ calcd. 539.0529 found 539.0541.

Aceto-β-glucuronic Acid Methyl Ester Para-Hydroxybenzyl Methyl β-lapa-ketol (2S,3R,4S,5S,6S)-2-(4-(1-(6-hydroxy-2,2-dimethyl-5-oxo-3,4,5,6-tetrahydro-2H-benzo[h]chromen-6-yl) ethyl) phenoxy)-6-(methoxycarbonyl)tetrahydro-2H-pyran-3,4,5-triyl triacetate (36e)

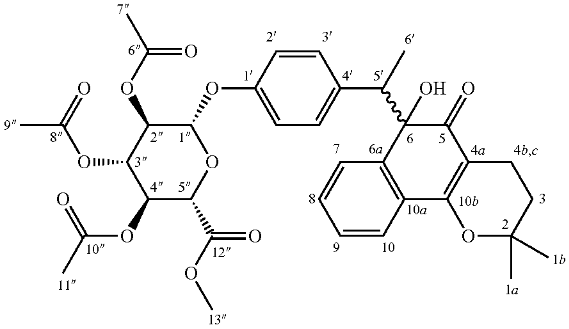 [SMILES: COC(=O)[C@H]1O[C@@H](Oc2ccc(C(C)C3(O)C(=O)C4=C(OC(C)(C)CC4)c4ccccc43)cc2)[C@H](OC(C)=O)[C@@H](OC(C)=O)[C@@H]1OC(C)=O]

(2S,3R,4S,5S,6S)-2-(4-(1-bromoethyl) phenoxy)-6-(methoxycarbonyl)tetrahydro-2H-pyran-3,4,5-triyl triacetate (35e) (0.341 g, 0.66 mmol, 1.1 eq), NaI (0.257 g, 1.7 mmol, 2.8 eq), β-lapachone (1) (0.145 g, 0.6 5989 mmol, 1 eq) and indium (0) powder (0.076 g, 0.66 mmol, 1.1 eq) were added to anhydrous dimethylformamide (3 mL). The solution was heated to 40° C. and sonicated overnight, while monitoring by thin-layer chromatography (50% ethyl acetate/petroleum ether) and LCMS. 1M HCl (~0.5 mL) was added to quench the reaction and it was extracted with ethyl acetate (3×150 mL). The organic layers were combined and washed with brine (10 mL), dried (sodium sulfate), and the solvent removed in vacuo. The product was purified by flash column chromatography on silica gel 60 (40-60% ethyl acetate/petroleum ether) to give (2S,3R,4S,5S,6S)-2-(4-(1-(6-hydroxy-2,2-dimethyl-5-oxo-3,4,5,6-tetrahydro-2H-benzo[h]chromen-6-yl)ethyl) phenoxy)-6-(methoxycarbonyl)tetrahydro-2H-pyran-3,4,5-triyl triacetate (36e) as an off-white solid (0.0168 g, 0.024 mmol, 4%).

$^1$H NMR (400 MHz, MeOD, mixture of diastereomers 1:1) δ 7.67-7.61 (m, 2H, H7, H10), 7.47 (td, J=7.5, 1.5 Hz, 1H, H8), 7.44-7.36 (m, 1H, H9), 6.66 (dd, J=8.9, 1.8 Hz, 2H, H2'), 6.37 (dd, J=8.7, 2.3 Hz, 2H, H3'), 5.41 (td, J=9.5, 2.3 Hz, 1H, H3"), 5.32 (dd, J=11.3, 7.9 Hz, 1H, H1"), 5.20-5.09 (m, 2H, H2", H4"), 4.46 (dd, J=9.9, 2.5 Hz, 1H, H5"), 3.71 (d, J=9.7 Hz, 3H, H13"), 3.10 (qd, J=7.0, 2.3 Hz, 1H, H5'), 2.34 (dq, J=16.8, 5.6 Hz, 1H, H4b,c), 2.06-1.98 (m, 9H, H7", H9", H11"), 1.92 (dddd, J=17.1, 8.6, 6.4, 2.0 Hz, 1H, H4b,c), 1.61-1.41 (m, 2H, H3), 1.33-1.26 (m, 6H, H6', H1a/H1b), 0.96 (d, J=11.5 Hz, 3H, H1a/H1b). $^{13}$C NMR (101 MHz, MeOD) δ 202.2 (C5), 202.1 (C5), 170.0 (C6"), 170.0 (C6"), 169.7 (C10"), 169.5 (C8"), 169.5 (C8"), 167.5 (C12"), 167.5 (C12"), 161.9 (C10b), 161.9 (C10b), 155.6 (C1'), 155.5 (C1'), 139.0 (C6a), 139.0 (C6a), 135.8 (C4'), 135.6 (C4'), 128.8 (C10a), 128.7 (C10a), 128.4 (C3', $C_8$), 128.3 (C3', $C_8$), 127.3 (C7/C10), 127.3 (C7/C10), 127.3 (C9), 127.2 (C9), 122.4 (C7/C10), 115.2 (C2'), 115.1 (C2'), 107.3 (C4a), 107.3 (C4a), 97.7 (C1"), 97.5 (C1"), 79.6 (C6), 77.6 (C2), 77.6 (C2), 71.9 (C3"), 71.8 (C3"), 71.5 (C5"), 71.5 (C5"), 71.0 (C2"), 69.3 (C4"), 52.6 (C5'), 52.6 (C5'), 51.9 (C13"), 51.9 (C13"), 31.0 (C3), 30.9 (C3), 26.2 (C1a/C1b), 26.0 (C1a/C1b), 25.0 (C1a/C1b), 24.8 (C1a/C1b), 19.1 (C7"/C9"/

C11"), 19.1 (C7"/C9"/C11"), 19.0 (C7"/C9"/C11"), 19.0 (C7"/C9"/C11"), 19.0 (C7"/C9"/C11"), 15.0 (C4b,c), 14.6 (C6'), 14.5 (C6'). $R_f$: 0.36 (50% EtOAc/Pet ether). HRMS ($ESI^+$): m/z calcd for $[C_{36}H_{40}O_{13}+Na]^+$ calcd. 703.2367 found 703.2363.

β-glucuronide-para-hydroxybenzyl methyl β-lapa-ketol (2S,3S,4S,5R,6S)-3,4,5-trihydroxy-6-(4-(1-(6-hydroxy-2,2-dimethyl-5-oxo-3,4,5,6-tetrahydro-2H-benzo[h]chromen-6-yl)ethyl) phenoxy)tetrahydro-2H-pyran-2-carboxylic acid (37e)

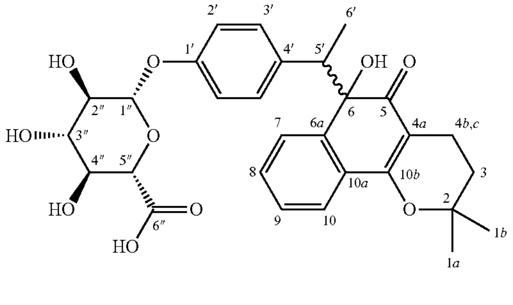 [SMILES: CC(c1ccc(O[C@@H]2O[C@H](C(=O)O)[C@@H](O)[C@H](O)[C@H]2O)cc1)C1(O)C(=O)C2=C(OC(C)(C)CC2)c2ccccc21]

The acyl-protected glucuronide β-lapachone prodrug (36e) (0.168 g, 0.025 mmol, 1 eq) was dissolved in tetrahydrofuran (2 mL) and methanol (2 mL) and stirred at 0° C. A separate solution of LiOH monohydrate (0.0063 g, 0.15 mmol, 6 eq) in water (1 mL) was prepared and added to the solution of 36e dropwise. The reaction was stirred for 1.5 hr and product formation was monitored by LCMS. After complete conversion, glacial acetic acid (8.4 μL, 0.15 mmol, 6 eq) was added and the solvent removed in vacuo. Crude product 37e was purified by semi-preparative HPLC to give (2S,3S,4S,5R,6S)-3,4,5-trihydroxy-6-(4-(1-(6-hydroxy-2,2-dimethyl-5-oxo-3,4,5,6-tetrahydro-2H-benzo[h]chromen-6-yl)ethyl) phenoxy)tetrahydro-2H-pyran-2-carboxylic acid (37e) as an orange solid after lyophilization (0.0041 g, 0.0076 mmol, 31%). HPLC Purification Method: Column=YMC Pack Pro C18 5 μm 250×10 mm 120 Å; mobile phases: A=$H_2O$+0.1% formic acid, B=ACN+0.1% formic acid; gradient: t=0-1 min 0% B, t=1-10 min 0-100% B, t=$10^{-12}$ min 100% B. Retention time of 37e=8.5 min.

$^1H$ NMR (400 MHz, MeOD, mixture of diastereomers) o 7.64 (dtd, J=7.4, 5.3, 1.4 Hz, 2H, H7, H10), 7.46 (tt, J=7.5, 2.0 Hz, 1H, H8), 7.39 (tt, J=7.5, 1.3 Hz, 1H, H9), 6.73 (t, J=8.9 Hz, 2H, H2'), 6.36 (dd, J=8.4, 5.4 Hz, 2H, H3'), 4.81 (dd, J=7.6, 3.7 Hz, 1H, H1"), 3.88 (dd, J=9.7, 2.6 Hz, 1H, H5"), 3.66-3.52 (m, 1H, H4"), 3.49-3.39 (m, 2H, H3", H2"), 3.10 (qd, J=7.1, 2.7 Hz, 1H, H5'), 2.33 (ddt, J=16.7, 10.7, 5.9 Hz, 1H, H4b,c), 2.06-1.87 (m, 1H, H4b,c), 1.62-1.42 (m, 2H, H3), 1.36-1.22 (m, 6H, H6', H1a/H1b), 1.00 (d, J=3.8 Hz, 3H, H1a/H1b). $^{13}C$ NMR (101 MHz, MeOD, mixture of diastereomers) δ 202.3 (C5), 202.2 (C5), 171.5 (C6"), 162.0 (C10b), 156.5 (C1'), 156.3 (C1'), 139.1 (C6a), 139.0 (C6a), 135.1 (C4'), 134.8 (C4'), 128.8 (C8), 128.8 (C8), 128.3 (C10a), 128.1 (C3'), 128.1 (C3'), 127.3 (C10/C7), 127.2 (C9), 122.4 (C10/C7), 115.5 (C2'), 115.2 (C2'), 107.3 (C4a), 107.3 (C4a), 100.9 (C1"), 100.4 (C1"), 79.7 (C6), 77.7 (C2), 77.7 (C2), 75.9 (C2"/C3"), 75.1 (C5"), 73.0 (C2"/C3"), 71.6 (C4"), 52.7 (C5'), 52.6 (C5'), 31.0 (C3), 30.9 (C3), 26.1 (C1a/C1b), 25.9 (C1a/C1b), 25.2 (C1a/C1b), 24.9 (C1a/C1b), 15.1 (C4b,c), 14.7 (C6'), 14.4 (C6'). HRMS ($ESI^+$): m/z calcd for $[C_{29}H_{32}O_{10}+Na]^+$ calcd. 563.1888 found 563.1885.

Aceto-β-glucuronic acid methyl ester 2,6-dimethoxy-para-hydroxybenzaldehyde (2S,3R,4S,5S,6S)-2-(4-formyl-3,5-dimethoxyphenoxy)-6-(methoxycarbonyl)tetrahydro-2H-pyran-3,4,5-triyl triacetate (33f)

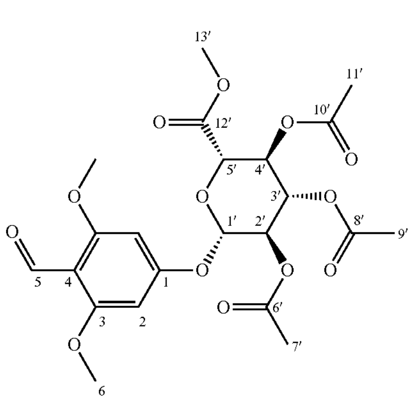 [SMILES: COC(=O)[C@H]1O[C@@H](Oc2cc(OC)c(C=O)c(OC)c2)[C@H](OC(C)=O)[C@@H](OC(C)=O)[C@@H]1OC(C)=O]

Acetobromo-α-D-glucuronic acid methyl ester (31) (0.627 g, 1.6 mmol, 1 eq) and 4-hydroxy-2,6-dimethoxybenzaldehyde (32f) (0.315 g, 1.7 mmol, 1.1 eq) were combined in anhydrous acetonitrile (10 mL) under $N_2$ in the dark and stirred for 30 min. $Ag_2O$ (0.946 g, 4.0 mmol, 2.5 eq) was added and the reaction was stirred at room temperature overnight in the dark. Thin-layer chromatography monitored reaction progress (50% ethyl acetate/petroleum ether). The reaction was filtered through celite and the solvent removed in vacuo. The residue was dissolved in ethyl acetate, washed with sat. $Na_2CO_3$ (10 mL), water (10 mL), and brine (10 mL). It was then dried (sodium sulfate), and the solvent was removed in vacuo. The product was purified by flash column chromatography on silica gel 60 (50% EtOAc/Pet ether) to give (2S,3R,4S,5S,6S)-2-(4-formyl-3,5-dimethoxyphenoxy)-6-(methoxycarbonyl)tetrahydro-2H-pyran-3,4,5-triyl triacetate (33f) as an off-white solid (0.219 g, 0.44 mmol, 28%).

$^1H$ NMR (400 MHz, $CDCl_3$) δ 10.22 (s, 1H, H5), 6.14 (s, 2H, H2), 5.33-5.21 (m, 3H, H3', H1', H4'), 5.21-5.12 (m, 1H, H2'), 4.30-4.20 (m, 1H, H5'), 3.74 (s, 6H, H6), 3.61 (s, 3H, H13'), 1.98-1.92 (m, 9H, H11', H9', H7'). $^{13}C$ NMR (101 MHz, $CDCl_3$) δ 187.6 (C5), 169.7 (C8'), 169.1 (C10'), 169.0 (C6'), 166.5 (C12'), 163.6 (C3), 162.4 (C1), 110.1 (C4), 97.6 (C1'), 92.7 (C2), 72.2 (C5'), 71.5 (C3'), 70.8 (C2'), 68.5 (C4'), 55.9 (C6), 52.8 (C13'), 20.4 (C7'), 20.3 (C9'), 20.3 (C11'). HRMS ($ESI^+$): m/z calcd for $[C_2H_{26}O_{13}+H]^+$ calcd. 498.13734 found 498.1370.

Aceto-β-glucuronic acid methyl ester 2,6-dimethoxy-para-hydroxybenzyl alcohol (2S,3R,4S,5S,6S)-2-(4-(hydroxymethyl)-3,5-dimethoxyphenoxy)-6-(methoxycarbonyl)tetrahydro-2H-pyran-3,4,5-triyl triacetate (34f)

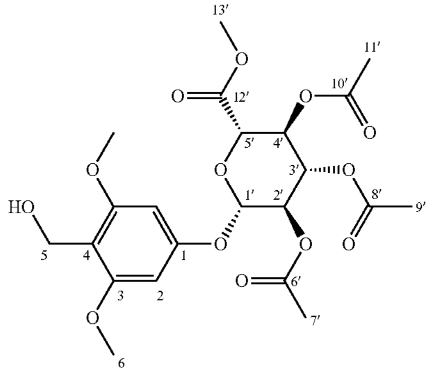 [SMILES: COC(=O)[C@H]1O[C@@H](Oc2cc(OC)c(CO)c(OC)c2)[C@H](OC(C)=O)[C@@H](OC(C)=O)[C@@H]1OC(C)=O]

Aceto-β-glucuronic acid methyl ester 2,6-dimethoxy-para-hydroxybenzaldehyde (2S,3R,4S,5S,6S)-2-(4-formyl-3,5-dimethoxyphenoxy)-6-(methoxycarbonyl)tetrahydro-2H-pyran-3,4,5-triyl triacetate (33f) (0.22 g, 0.44 mmol, 1 eq) was dissolved in chloroform (5 mL) and isopropanol (1 mL) with silica gel (0.2 g) and stirred at 0° C. under $N_2$ for 15 min. $NaBH_4$ (0.034 g, 0.88 mmol, 2 eq) was added and the reaction was stirred for 45 min. It was monitored by thin-layer chromatography (1:1 ethyl acetate:petroleum ether). The reaction was diluted with dichloromethane (10 mL), filtered over celite, and washed with dichloromethane (10 mL). The filtrate was washed with brine (10 mL), dried (magnesium sulfate), and the solvent removed in vacuo to give (2S,3R,4S,5S,6S)-2-(4-(hydroxymethyl)-3,5-dimethoxyphenoxy)-6-(methoxycarbonyl)tetrahydro-2H-pyran-3,4,5-triyl triacetate (34f) as an off-white solid (0.198 g, 0.39 mmol, 90%).

$^1$H NMR (400 MHz, $CDCl_3$) δ 6.20 (s, 2H, H2), 5.31-5.26 (m, 2H, H3', H4'), 5.19 (t, J=8.1 Hz, 1H, H2'), 5.12 (d, J=7.4 Hz, 1H, H1'), 4.61 (s, 2H, H5), 4.21-4.11 (m, 1H, H5'), 3.73 (s, 6H, H6), 3.66 (s, 3H, H13'), 2.40 (brs, 1H, OH), 2.04-1.94 (m, 9H, H11', H9', H7'). $^{13}$C NMR (101 MHz, $CDCl_3$) δ 170.0 (C6'), 169.2 (C8'), 169.1 (C10'), 166.7 (C12'), 158.9 (C3), 157.7 (C1), 112.5 (C4), 99.1 (C1'), 93.7 (C2), 72.3 (C5'), 71.8 (C3'), 71.0 (C2'), 68.8 (C4'), 55.7 (C6), 53.9 (C5), 52.8 (C13'), 20.5 (C11'), 20.4 (C9'), 20.3 (C7'). HRMS ($ESI^+$): m/z calcd for $[C_{22}H_{28}O_{13}+Na]^+$ calcd. 523.1422 found 523.1439.

Aceto-β-glucuronic acid methyl ester 2,6-dimethoxy-para-hydroxybenzyl bromide (2S,3R,4S,5S,6S)-2-(4-(bromomethyl)-3,5-dimethoxyphenoxy)-6-(methoxycarbonyl) tetrahydro-2H-pyran-3,4,5-triyl triacetate (35f)

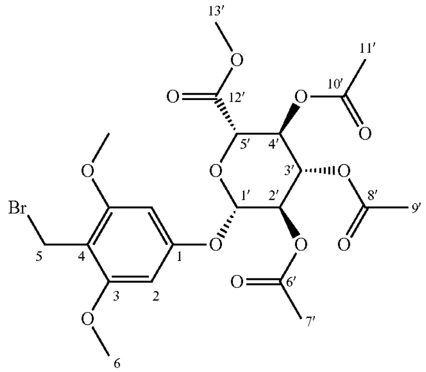 [SMILES: COC(=O)[C@H]1O[C@@H](Oc2cc(OC)c(CBr)c(OC)c2)[C@H](OC(C)=O)[C@@H](OC(C)=O)[C@@H]1OC(C)=O]

(2S,3R,4S,5S,6S)-2-(4-(hydroxymethyl)-3,5-dimethoxyphenoxy)-6-(methoxycarbonyl)tetrahydro-2H-pyran-3,4,5-triyl triacetate (34f) (0.198 g, 0.39 mmol, 1 eq) was dissolved in anhydrous diethyl ether (10 mL) and anhydrous dichloromethane (1 mL) at 0° C. under $N_2$. Neat $PBr_3$ (0.05 mL, 0.5 mmol, 1.3 eq) was added and the reaction was stirred under $N_2$ for 30 min. Thin-layer chromatography (1:1 petroleum ether:ethyl acetate) showed that some starting material remained, so additional $PBr_3$ (0.1 mL, 1.0 mmol, 2.6 eq) was added and the reaction stirred for 15 min. TLC then showed completion. The reaction was quenched with cold water (10 mL), extracted into DCM (3×50 mL) washed with brine (10 mL), dried (sodium sulfate), and the solvent removed in vacuo to give (2S,3R,4S,5S,6S)-2-(4-(bromomethyl)-3,5-dimethoxyphenoxy)-6-(methoxycarbonyl)tetrahydro-2H-pyran-3,4,5-triyl triacetate (35f) as an unstable pink solid (0.223 g, 0.39 mmol, quantitative).

$^1$H NMR (400 MHz, $CDCl_3$) δ 6.18 (s, 2H, H2), 5.36-5.27 (m, 2H, H3', H4'), 5.21-5.13 (m, 1H, H2'), 5.10 (dd, J=7.0, 4.9 Hz, 1H, H1'), 4.57 (s, 2H, H5), 4.27-4.10 (m, 1H, H5'), 3.79 (s, 6H, H6), 3.67 (s, 3H, H13'), 2.05-1.93 (m, 9H, H11', H9', H7'). $^{13}$C NMR (101 MHz, $CDCl_3$) δ 170.0 (C6'), 169.2 (C8'), 169.2 (C10'), 166.6 (C12'), 159.1 (C3), 158.6 (C1), 109.7 (C4), 98.8 (C1'), 93.5 (C2), 72.4 (C5'), 71.8 (C3'), 71.0 (C2'), 68.8 (C4'), 55.9 (C6), 52.9 (C13'), 23.8 (C5), 20.6 (C11'), 20.5 (C9'), 20.4 (C7'). HRMS could not be obtained due to compound instability.

The invention claimed is:

1. A protected ortho-quinone compound comprising a group represented by:

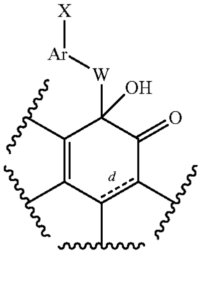

where —Ar— is a phenylene or a substituted phenylene,

—X is selected from —$NH_2$, —OH and —SH, and the protected forms of each,

—W— is a methylene or a substituted methylene, d is a double or single bond, and the ketol form of the ortho-quinone is selected from the group consisting of β-Lapachone, Rhinacanthone, Dunnione, Biflorin, Tanshinone I, Tanshinone IIA, Tanshinone IIB, Dihydrotanshinone I, Cryptotanshinone, Mansonone A, Mansonone C-G, Miltirone, Salvicine, Caryopteron A, Lantalucratin A-C, pyrroloquinolone quinone and 3-hydroxy-β-lapachone, and the salts and solvates thereof.

2. The protected ortho-quinone of claim 1, wherein —X is —$NH_2$.

3. The protected ortho-quinone of claim 1, wherein —X is the protected form of —OH, and the protecting group is a glycan.

4. The protected ortho-quinone of claim 3, wherein the glycan is a monosaccharide.

5. The protected ortho-quinone of claim 4, wherein the monosaccharide is glucuronic acid.

6. The protected ortho-quinone of claim 1, wherein —Ar— is phenylene.

7. The protected ortho-quinone of claim 1, wherein —Ar— is phenylene substituted with one to four substituent groups, with each substituent group independently selected from alkyl, alkoxy, nitro, halo, and amido.

8. The protected ortho-quinone of claim 1, wherein —W— is methylene (—$CH_2$—).

9. The protected ortho-quinone of claim 1, wherein —W— is methylene substituted with one or two groups independently selected from $C_{1-10}$ alkyl, $C_{2-10}$ alkenyl, $C_{2-10}$ alknyl, $C_{3-6}$ cycloalkyl, halogen, $C_{1-10}$ haloalkyl, $C_{1-10}$ haloalkoxy, $C_{1-10}$ aminoalkyl, $C_{1-10}$ hydroxyalkyl, $C_{1-10}$ azidoalkyl, —$NR^{W1}R^{W2}$, —$OR^{W1}$, cyano, carboxy, carbamoyl, sulfamoyl and mercapto, wherein —$R^{W1}$ and —$R^{W2}$ are independently selected from hydrogen and $C_{1-4}$ alkyl.

10. The protected ortho-quinone of claim 9, wherein —W— is methylene substituted with one group selected from $C_{2-10}$ alkenyl, $C_{1-10}$ alkylamino, $C_{1-10}$ alkylhydroxyl, $C_{1-10}$ alkylazido and carboxy.

11. A conjugate of formula:

$$Z\text{-}(L\text{-}D)_p$$

where:

—Z is a polypeptide,

-L- is a linker, p is an integer from 1 to 8,

D is a protected ortho-quinone compound according to claim 1 and the salts and solvates thereof.

12. The conjugate of claim 11, wherein -D is connected to -L- via the group —X.

13. The conjugate of claim 11, wherein -D is connected to -L- via a substituent to the group —W—, or via a substituent to the group —Ar—.

14. The conjugate of claim 11, wherein p is an integer from 1 to 4.

15. The conjugate of claim 11, wherein the linker -L- comprises one or more groups that are susceptible to enzymatic cleavage.

16. The conjugate of claim 11, wherein the linker -L- is or comprises a group of formula V:

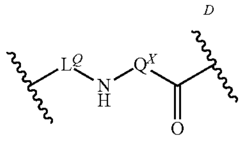

wherein:

-$L^Q$- is a selected from a bond, $C_1$-$C_{10}$ alkylene and $C_1$-$C_{10}$ alkylene containing O or NH in the backbone;

-$Q^X$- is an amino-acid residue, a dipeptide, or a tripeptide; and

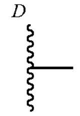

indicates the position where the group of Formula V is attached to a protected ortho-quinone, -D.

17. The conjugate of claim 16, wherein -$Q^X$- is a dipeptide.

18. The conjugate of claim 16, wherein -$Q^X$- is selected from the group consisting of:

$^{NH}$-Phe-Lys-$^{C=O}$,
$^{NH}$Val-Ala-$^{C=O}$,
$^{NH}$Val-Lys-$^{C=O}$,
$^{NH}$Ala-Lys-$^{C=O}$,
$^{NH}$-Val-Cit-$^{C=O}$,
$^{NH}$-Phe-Cit-$^{C=O}$,
$^{NH}$-Leu-Cit-$^{C=O}$,
$^{NH}$-Ile-Cit-$^{C=O}$,
$^{NH}$-Phe-Arg-$^{C=O}$, and
$^{NH}$-Trp-Cit-$^{C=O}$;

where Cit is citrulline, and NH and C=O are the amino and carboxy terminals of the amino acid residues, which are present as —N(H)— and —C(O)— in the linker of formula V.

19. The conjugate of claim 11, wherein the linker -L- is of formula:

$$\text{-}L^1\text{-}S\text{-}L^2\text{-}$$

wherein:

-$L^1$- is a polypeptide binding moiety;

-$L^2$- is a binding moiety linked to the protected ortho-quinone, D; and

—S— is a spacer.

20. The conjugate of claim 19, wherein -$L^2$- is a group of formula V:

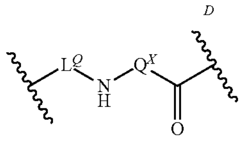

wherein:

-$L^Q$- is a selected from a bond, $C_1$-$C_{10}$ alkylene and $C_1$-$C_{10}$ alkylene containing O or NH in the backbone;

-$Q^X$- is an amino-acid residue, a dipeptide, or a tripeptide; and

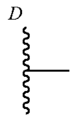

indicates the position where the group of Formula V is attached to a protected ortho-quinone, -D.

21. The conjugate of claim 19, wherein the spacer, —S—, is or comprises one or more groups selected from $C_1$-$C_{20}$ alkylene, an alkylenediamine moiety, a (poly)ethylene glycol moiety, an amino acid residue, and combinations thereof.

22. A method of treating cancer, comprising: administering to a subject a therapeutically-effective amount of a protected ortho-quinone according to claim 1 and the salts and solvates thereof.

23. The conjugate of claim 11, wherein the protected ortho-quinone compound is selected from the group consisting of β-Lapachone, Rhinacanthone, Dunnione, Biflorin, Tanshinone I, Tanshinone IIA, Tanshinone IIB, Dihydrotanshinone I, Cryptotanshinone, Mansonone A, C, D, E, F, and G, Miltirone, Salvicine, Caryopteron A, Lantalucratin A, B and C, pyrroloquinolone quinone and 3-hydroxy-β-lapachone.

24. The method of claim 22, wherein the protected ortho-quinone compound is selected from the group consisting of β-Lapachone, Rhinacanthone, Dunnione, Biflorin, Tanshinone I, Tanshinone IIA, Tanshinone IIB, Dihydrotanshinone I, Cryptotanshinone, Mansonone A, C, D, E, F, and G, Miltirone, Salvicine, Caryopteron A, Lantalucratin A, B and C, pyrroloquinolone quinone and 3-hydroxy-β-lapachone.

* * * * *